(12) United States Patent
Sahin et al.

(10) Patent No.: US 10,946,069 B2
(45) Date of Patent: *Mar. 16, 2021

(54) COMBINATION THERAPY INVOLVING ANTIBODIES AGAINST CLAUDIN 18.2 FOR TREATMENT OF PANCREATIC CANCER

(71) Applicants: ASTELLAS PHARMA INC., Tokyo (JP); TRON-Translationale Onkologie an der Universitatsmedizin der Johannes Gutenberg-Universitat Mainz gemeinnutzige GmbH, Mainz (DE)

(72) Inventors: Ugur Sahin, Mainz (DE); Ozlem Tureci, Mainz (DE); Rita Mitnacht-Kraus, Friedberg (DE); Stefan Woll, Nackenheim (DE); Stefan Jacobs, Mainz-Kastel (DE); Cornelia Heinz, Dalheim (DE)

(73) Assignees: Astellas Pharma Inc., Tokyo (JP); TRON-Translationale Onkologie an der Universitatsmedizin der Johannes Gutenberg-Universitat Mainz, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/401,931

(22) Filed: May 2, 2019

(65) Prior Publication Data
US 2019/0298803 A1    Oct. 3, 2019

Related U.S. Application Data

(60) Continuation of application No. 15/684,168, filed on Aug. 23, 2017, now Pat. No. 10,314,890, which is a division of application No. 14/769,046, filed as application No. PCT/EP2014/000433 on Feb. 18, 2014, now Pat. No. 9,770,487.

(30) Foreign Application Priority Data

Feb. 20, 2013 (WO) ................. PCT/EP2013/000505

(51) Int. Cl.
C07K 16/28 (2006.01)
C07K 16/30 (2006.01)
A61K 31/7068 (2006.01)
A61K 45/06 (2006.01)
A61K 39/00 (2006.01)
A61K 38/20 (2006.01)
A61K 39/395 (2006.01)
A61K 31/555 (2006.01)

(52) U.S. Cl.
CPC ........ *A61K 38/2013* (2013.01); *A61K 31/555* (2013.01); *A61K 31/7068* (2013.01); *A61K 39/39558* (2013.01); *A61K 45/06* (2013.01); *C07K 16/28* (2013.01); *C07K 16/30* (2013.01); *C07K 16/303* (2013.01); *A61K 2039/505* (2013.01); *C07K 2317/14* (2013.01); *C07K 2317/34* (2013.01); *C07K 2317/73* (2013.01); *C07K 2317/732* (2013.01); *C07K 2317/734* (2013.01); *C07K 2317/74* (2013.01)

(58) Field of Classification Search
None
See application file for complete search history.

(56) References Cited

U.S. PATENT DOCUMENTS

| | | |
|---|---|---|
| 2006/0035852 A1 | 2/2006 | Sahin et al. |
| 2008/0166350 A1 | 7/2008 | Tureci et al. |
| 2009/0155817 A1 | 6/2009 | Sahin et al. |
| 2009/0169547 A1 | 7/2009 | Sahin et al. |
| 2009/0208498 A1 | 8/2009 | Sahin et al. |
| 2010/0166779 A1 | 7/2010 | Sahin et al. |
| 2012/0164160 A1 | 6/2012 | Sahin et al. |
| 2012/0195830 A1 | 8/2012 | Sahin et al. |
| 2012/0258091 A1 | 10/2012 | Sahin et al. |
| 2014/0186338 A1 | 7/2014 | Sahin et al. |
| 2015/0132253 A1 | 5/2015 | Sahin et al. |
| 2015/0147763 A1 | 5/2015 | Sahin et al. |
| 2015/0157711 A1 | 6/2015 | Sahin et al. |
| 2015/0252103 A1 | 9/2015 | Sahin et al. |
| 2015/0252104 A1 | 9/2015 | Sahin et al. |
| 2015/0315287 A1 | 11/2015 | Tureci et al. |
| 2015/0337052 A1 | 11/2015 | Sahin et al. |
| 2016/0185860 A1 | 6/2016 | Sahin et al. |

FOREIGN PATENT DOCUMENTS

| | | |
|---|---|---|
| EP | 1112364 | 7/2001 |
| EP | 1119620 | 8/2001 |
| EP | 1144629 | 10/2001 |
| EP | 1165784 | 1/2002 |

(Continued)

OTHER PUBLICATIONS

Chirgwin et al. (Management of breast cancer with nanoparticle albumin-bound (nab)-paclitaxel combination regimens: A clinical review. The Breast, 20, 394-406, 2011. (Year: 2011).*

Namboodiri et al. (Differential inhibition of trastuzumab- and cetuximab-induced cytotoxicity of cancer cells by immunoglobulin G1 expressing different GM allotypes. Clin. Exp. Immunol. pp. 361-365, 2011. (Year: 2011).*

Sanchez-Rovira et al. Phase II trial of gemcitabine/doxorubicin/paclitaxel administered every other week in patients with metastatic breast cancer. Clin. Breast Cancer, 1, 226-232, 2000. (Year: 2000).*

(Continued)

*Primary Examiner* — Elly-Gerald Stoica
(74) *Attorney, Agent, or Firm* — Neal, Gerber & Eisenberg LLP; Kevin A. O'Connor

(57) ABSTRACT

The present invention provides a combination therapy for effectively treating and/or preventing diseases associated with cells expressing CLDN18.2, including cancer diseases such as pancreatic cancer and metastases thereof.

20 Claims, 54 Drawing Sheets
Specification includes a Sequence Listing.

(56) References Cited

FOREIGN PATENT DOCUMENTS

| | | |
|---|---|---|
| EP | 1208202 | 5/2002 |
| EP | 1251863 | 10/2002 |
| EP | 1255766 | 11/2002 |
| EP | 1259526 | 11/2002 |
| EP | 1259614 | 11/2002 |
| EP | 1261703 | 12/2002 |
| EP | 1328635 | 7/2003 |
| EP | 1929003 | 6/2008 |
| EP | 1934378 | 6/2008 |
| EP | 1934615 | 6/2008 |
| EP | 1983002 | 10/2008 |
| EP | 2125034 | 12/2009 |
| EP | 1315743 | 11/2012 |
| JP | 2010528075 | 8/2010 |
| RU | 2354402 C2 | 5/2009 |
| WO | WO2000012708 | 3/2000 |
| WO | WO2000015659 | 3/2000 |
| WO | WO2000020447 | 4/2000 |
| WO | WO2000058473 | 10/2000 |
| WO | WO2000078961 | 12/2000 |
| WO | WO2001016318 | 3/2001 |
| WO | WO2001048192 | 7/2001 |
| WO | WO2001054708 | 8/2001 |
| WO | WO2001055236 | 8/2001 |
| WO | WO2001055314 | 8/2001 |
| WO | WO2001055318 | 8/2001 |
| WO | WO2001055367 | 8/2001 |
| WO | WO2001068848 | 9/2001 |
| WO | WO2001075067 | 10/2001 |
| WO | WO2001090357 | 11/2001 |
| WO | WO2002014499 | 2/2002 |
| WO | WO2001218576 | 3/2002 |
| WO | WO2002018576 | 3/2002 |
| WO | WO2002020569 | 3/2002 |
| WO | WO2004032961 | 4/2004 |
| WO | WO2004063355 | 7/2004 |
| WO | WO2006024283 | 3/2006 |
| WO | WO2007027867 | 3/2007 |
| WO | WO2007035676 | 3/2007 |
| WO | WO2007035690 | 3/2007 |
| WO | WO2007059997 | 5/2007 |
| WO | WO2008013948 | 1/2008 |
| WO | WO2008013954 | 1/2008 |
| WO | WO2008095152 | 8/2008 |
| WO | WO2008145338 | 12/2008 |
| WO | WO2008152822 | 12/2008 |
| WO | WO2009037090 | 3/2009 |
| WO | WO2010141093 | 12/2010 |
| WO | WO2013174404 | 11/2013 |
| WO | WO2013174510 | 11/2013 |

OTHER PUBLICATIONS

Sanchez et al. (Results from a phase II study of Gemcitabine In combination with paclitaxel in metastatic breast cancer. Annals of Oncology, 9 (Suppl. 4), 77P, 1998. (Year: 1998).*

Alberts, et al., "Gemcitabine and oxaliplatin for patients with advanced or metastatic pancreatic cancer: a North Central cancer treatment group (NCCTG) phase I study," Annals of Oncology, 13, 553-557, 2002.

Cappella, et al., "Cell cycle effects of Gemcitabine," Int. Journal of Cancer, 93, 401-408, 2001.

Cartwright, et al., "Cancer of the Pancreas: Are We Making Progress? A Review of Studies in the US Oncology Research Network", Cancer Control, vol. 15, No. 4, Oct. 2008.

Garg, et al., Immunogenic cell death, DAMPs and anticancer therapeutics: An emerging amalgamation., Biochim. Biophys. Acta, 1805, 53-71, 2010.

Heiskala, et al., "The Roles of Claudin Superfamily Proteins in Paracellular Transport," Traffic, vol. 2, No. 2, pp. 92-98 (2001).

International Preliminary Report on Patentability for International Application No. PCT/EP2014/000433, dated Sep. 3, 2015.

Nacht, et al., "Combining Serial Analysis of Gene Expression and Array Technologies to Identify Genes Differentially Expressed in Breast Cancer," Cancer Research, vol. 59, No. 21, pp. 5464-5470 (1999).

Niimi, et al., Claudin-18, a Novel Downstream Target Gene for the T/EBP/NKX2.1 Homeodomain Transcription Factor, Encodes Lung- and Stomach-Specific Isoforms through Alternative Splicing, Molecular and Cellular Biology, Nov. 2001, p. 7380-7390.

Ross, et al., "Systematic Variation in Gene Expression Patterns in Human Cancer Cell Lines," Nature Genetics, vol. 24, No. 3, pp. 227-235 (2000).

Sahin, et al., "Claudin-18 Splice Variant 2 Is a Pan-Cancer Target Suitable for Therapeutic Antibody Development", Clinical Cancer Research 2008; 14(23), Dec. 1, 2008.

Schafer, et al., "Combined Treament of L1CAM Antibodies and Cytostatic Drugs Improve the Therapeutic Response of Pancreatic and Ovarian Carcinoma", Cancer Letters, 319, (2012), pp. 66-82.

Tanaka, "Pathologic Studies on the Lesion of Gastric Cancer and the Distribution of its Metastases The Comparative Study Between Gastrectomied and Non-Gastrectomied Cases," Journal of the Showa Medical Association, vol. 23, No. 8, pp. 40-65 (1963).

Tanaka, et al., "Claudin-18 is an Early-Stage Marker of Pancreatic Carcinogenesis", Journal of Histochemistry & Cytochemistry, 2011, 59:942, Aug. 10, 2011.

Tassone, et al., "Zoledronic acid induces antiproliferative and apoptotic effects in human pancreatic cancer cells in vitro," British Journal of Cancer, Jun. 16, 2003, vol. 88, No. 12, pp. 1971-1978.

Trojan, et al., "In vitro chemosensitivity to gemcitabine, oxaliplatin and zoledronic acid predicts treatment response in metastatic gastric cancer," Anti-Cancer Drugs, Jan. 2005, vol. 16, No. 1, pp. 87-91.

Woll, et al., "Claudin 18.2 is a Target for IMAB362 Antibody in Pancreatic Neoplasms", International Journal of Cancer, 134, pp. 731-739 (2014).

Yagi, et al., "A Case of Krukenberg's Tumor," Advances in Obstetrics and Gynecology, vol. 11, No. 4, pp. 324-326 (1959).

Lansakara-P. et al., *International Journal of Pharmaceutics*, 429: 123-134 (2012).

Mashkovskii, *Medicinal Drugs*, (Doctor's handbook) Part 1, 12$^{th}$ Edition, Revised and supplemented (1993) p. 8.

Vincent et al., "Pancreatic Cancer," *The Lancet*, 378 (9791): 607-620 (Aug. 1, 2011).

Sanada et al., (Immunohistochemical study of Claudin 18 involvement in intestinal differentiation during the progression of intraductal papillary mucinous neoplasm, *Anticancer Research*, 30: 2995-3004 (2010).

U.S. Appl. No. 10/537,002, US-2006-0035852-A1, U.S. Pat. No. 7,527,933.
U.S. Appl. No. 12/326,997, US-2009-0155817-A1, U.S. Pat. No. 8,088,588.
U.S. Appl. No. 12/423,153, US-2009-0208498-A1, U.S. Pat. No. 8,586,047.
U.S. Appl. No. 13/296,620, US-2012-0258091-A1, U.S. Pat. No. 8,637,012.
U.S. Appl. No. 14/043,109, US-2014-0186338-A1, Abandoned.
U.S. Appl. No. 14/821,411, US-2015-0337052-A1, Abandoned.
U.S. Appl. No. 15/650,092, US-2017-0320963-A1, Pending.
U.S. Appl. No. 11/596,649, US-2008-0166350-A1, U.S. Pat. No. 9,044,382.
U.S. Appl. No. 14/676,254, US-2015-0315287-A1, U.S. Pat. No. 9,775,785.
U.S. Appl. No. 15/448,831, US-2017-0240646-A1, Pending.
U.S. Appl. No. 12/094,530, US-2009-0169547-A1, U.S. Pat. No. 8,168,427.
U.S. Appl. No. 13/360,545, US-2012-0164160 A1, U.S. Pat. No. 9,499,609.
U.S. Appl. No. 13/425,538, US-2012-0195830-A1, U.S. Pat. No. 9,212,228.
U.S. Appl. No. 14/661,882, US-2015-0252104-A1, U.S. Pat. No. 9,751,934.
U.S. Appl. No. 14/661,846, US-2015-0252103-A1, U.S. Pat. No. 10,174,104.
U.S. Appl. No. 15/069,511, US-2016-0185860-A1, U.S. Pat. No. 10,017,564.

(56) References Cited

OTHER PUBLICATIONS

U.S. Appl. No. 15/710,252, US-2018/0127489-A1, Pending.
U.S. Appl. No. 12/601,488, US-2010-0166779-A1, U.S. Pat. No. 8,425,902.
U.S. Appl. No. 14/397,244, US-2015-0147763-A1, U.S. Pat. No. 9,512,232.
U.S. Appl. No. 15/227,565, US-2016-0333109-A1, U.S. Pat. No. 10,053,512.
U.S. Appl. No. 14/401,899, US-2015-0132253-A1, Abandoned.
U.S. Appl. No. 15/909,577, US-2018-0258180-A1, Pending.
U.S. Appl. No. 14/401,557, US-2015-0157711-A1, U.S. Pat. No. 9,433,675.
U.S. Appl. No. 15/231,185, US-2016-0339101-A1, U.S. Pat. No. 10,022,444.
U.S. Appl. No. 15/973,116, US-2018-0326059-A1, Pending.
U.S. Appl. No. 14/442,445, US-2016-0272711-A1, U.S. Pat. No. 10,093,736.
U.S. Appl. No. 14/769,046, US-2015-0374789-A1, U.S. Pat. No. 9,770,487.
U.S. Appl. No. 15/684,168, US-2018-0000900-A1, U.S. Pat. No. 10,314,890.
U.S. Appl. No. 14/777,231, US-2016-0008465-A1, U.S. Pat. No. 10,137,195.
U.S. Appl. No. 15/565,848, US-2018-0117174-A1, Pending.
U.S. Appl. No. 16/158,187, US-2019-0076525-A1, Pending.

\* cited by examiner

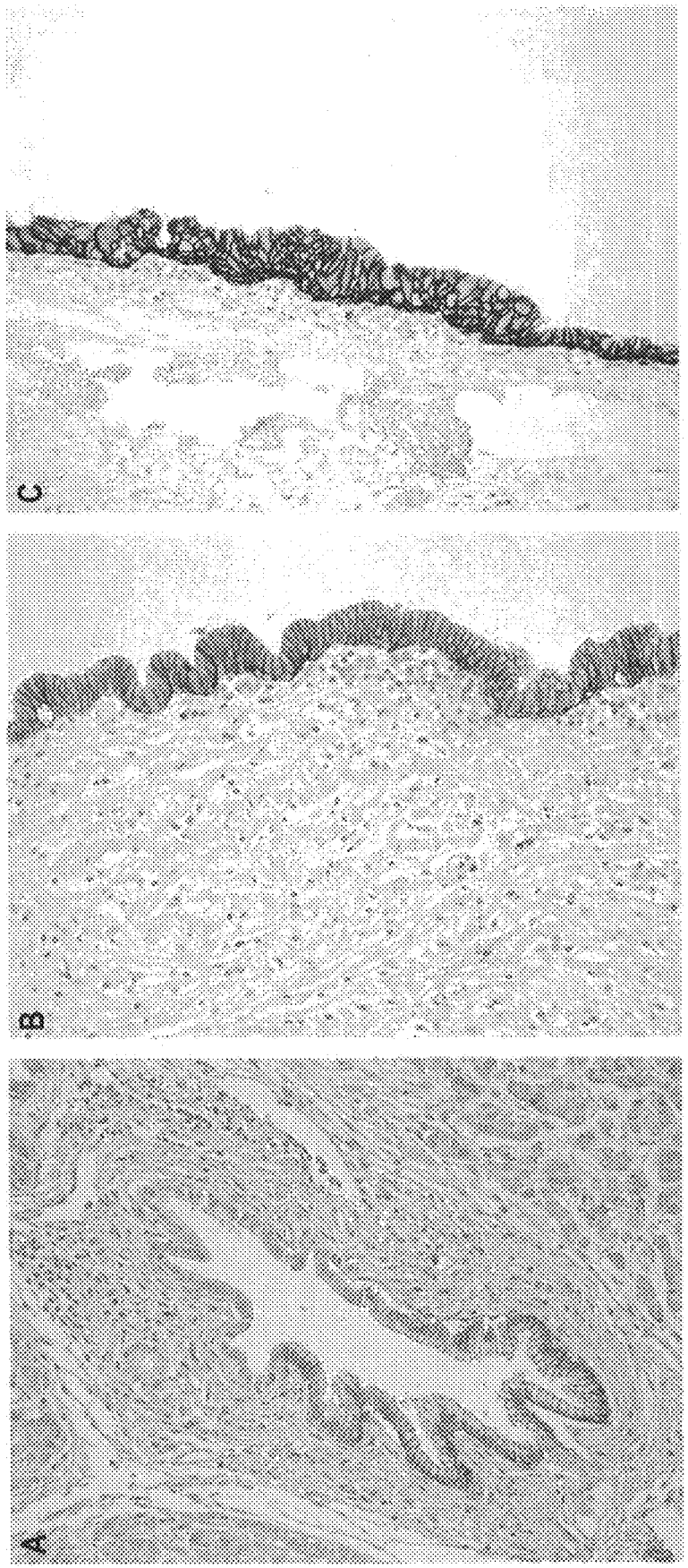

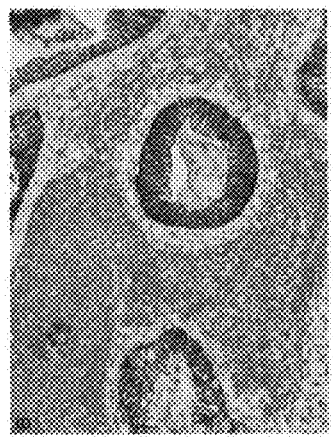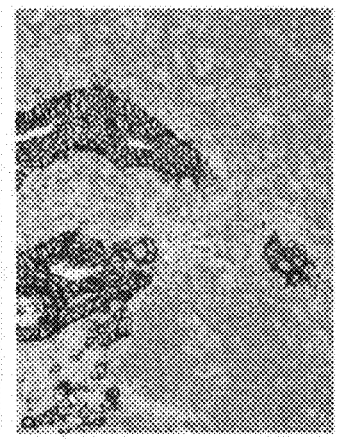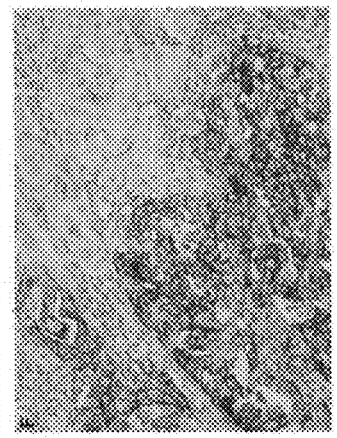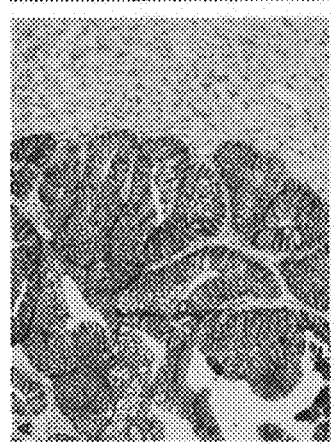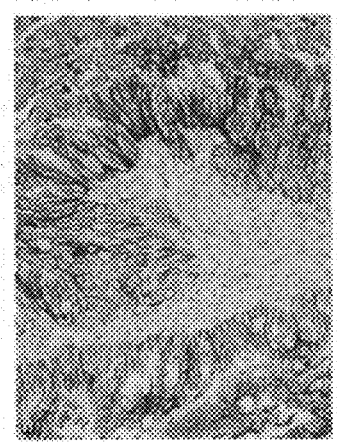

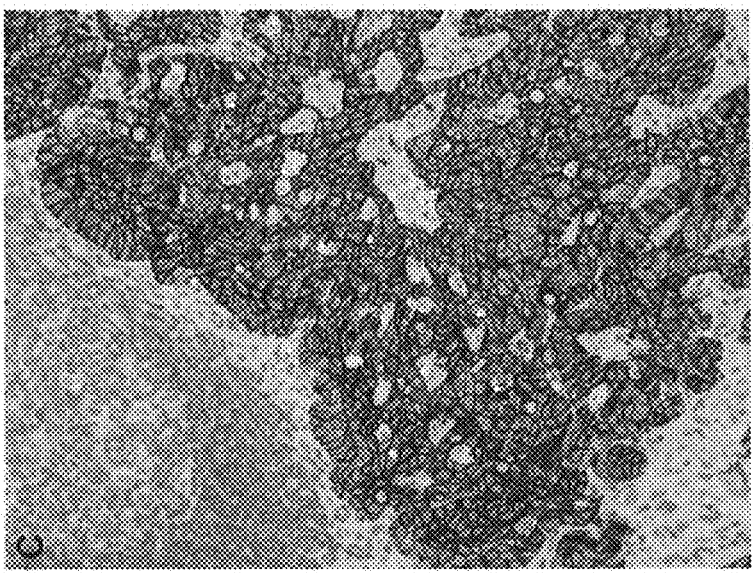
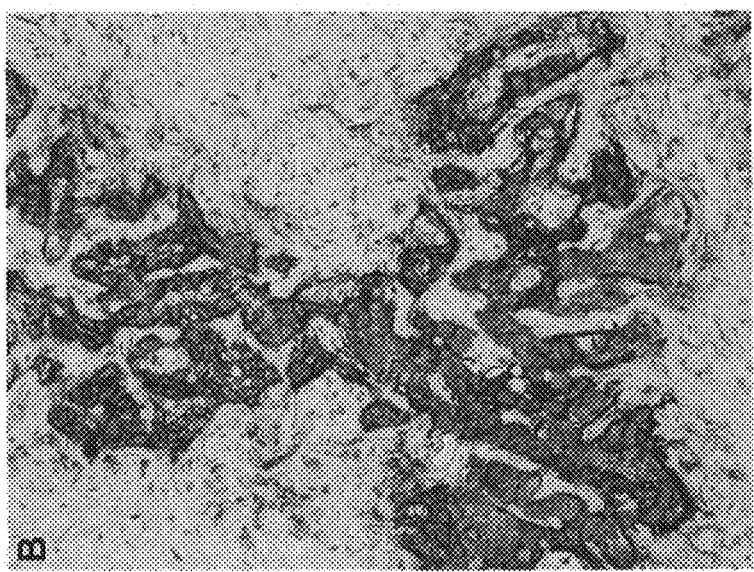
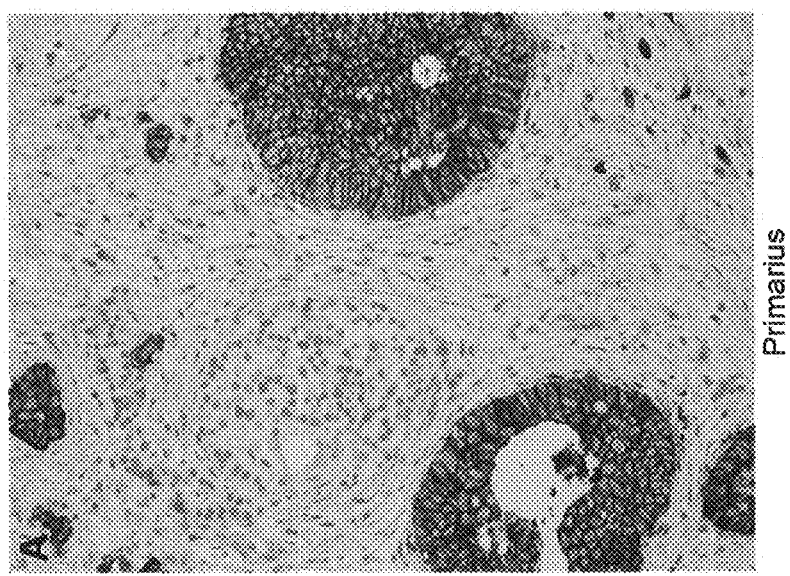

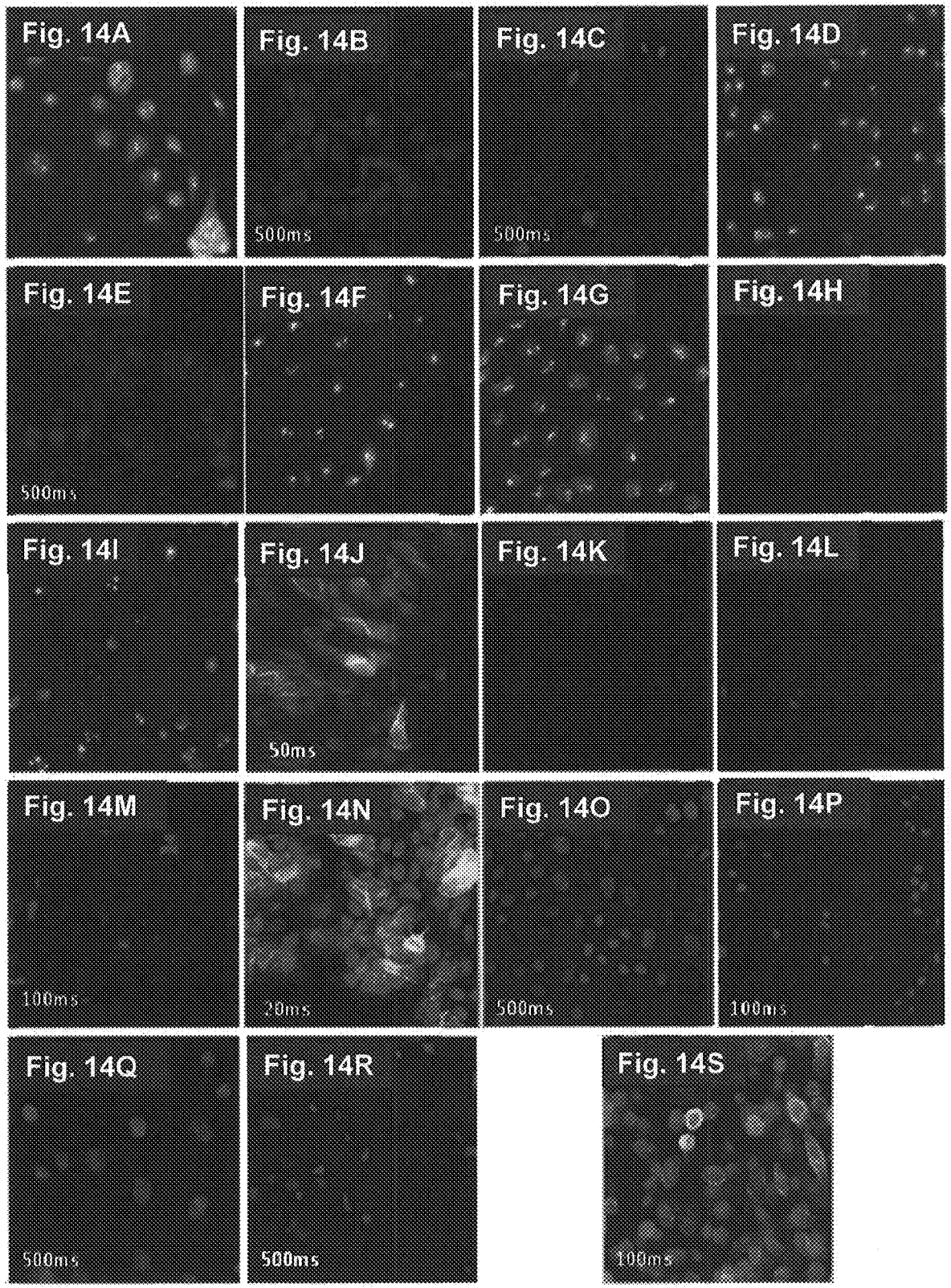

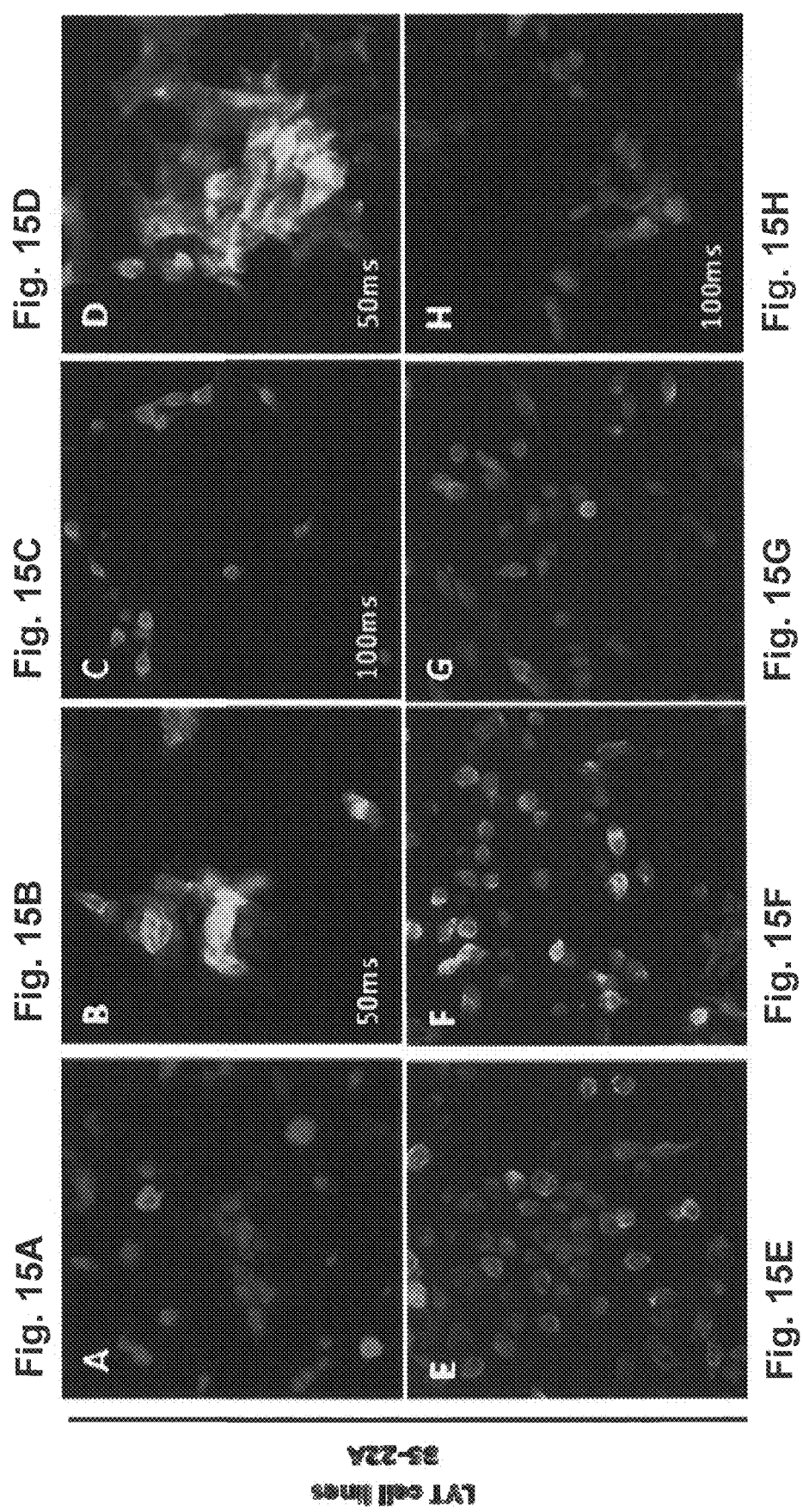

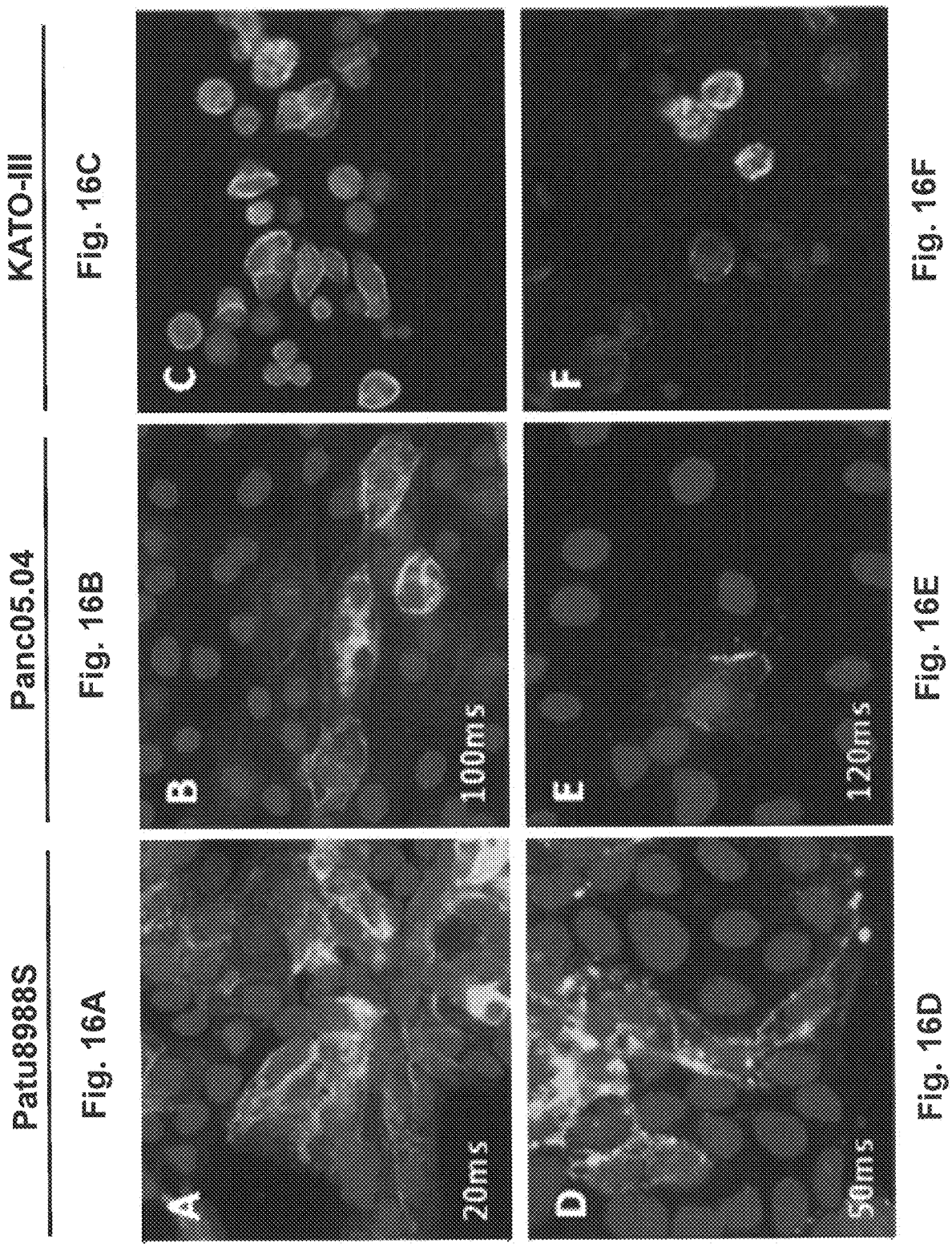

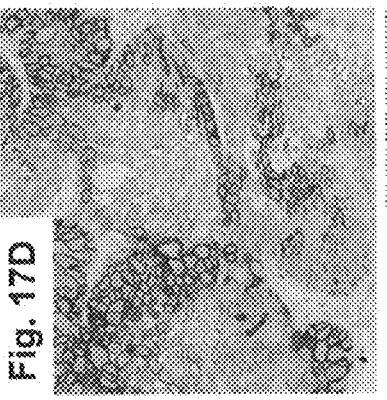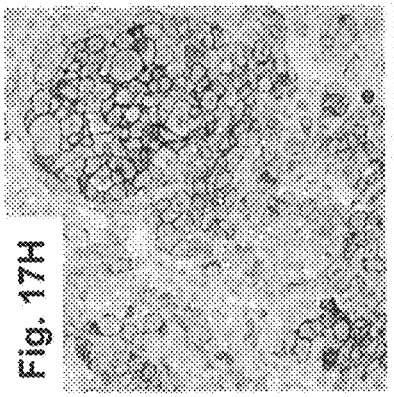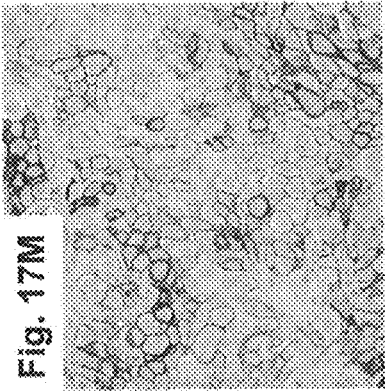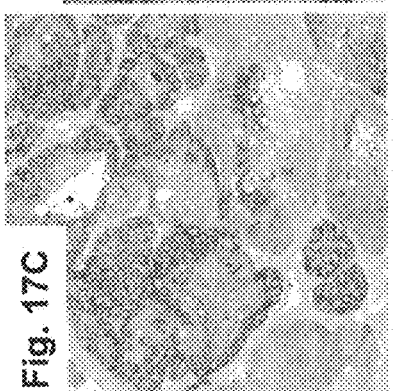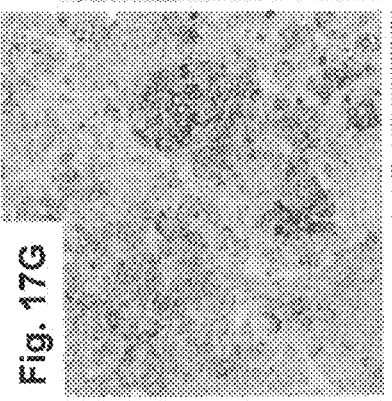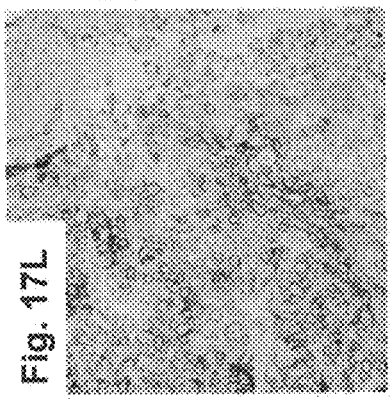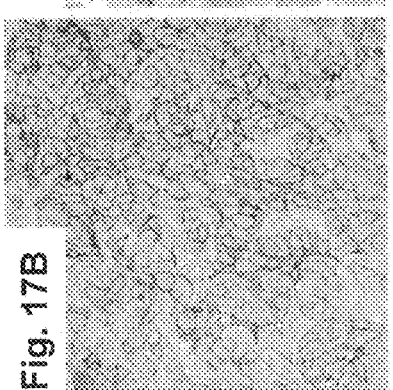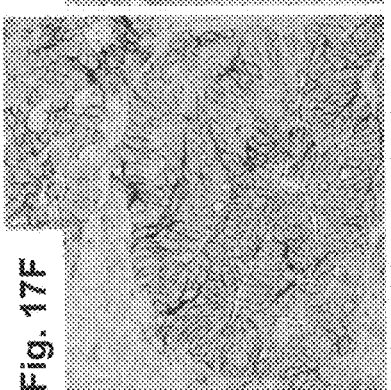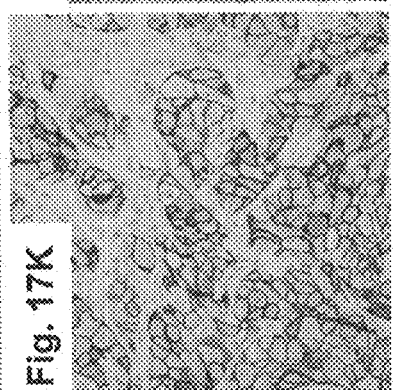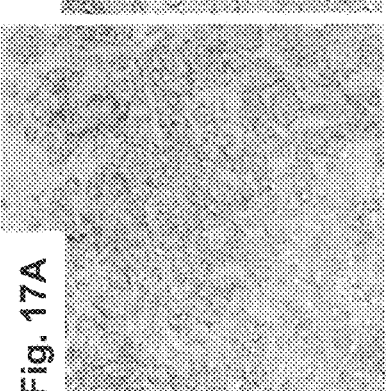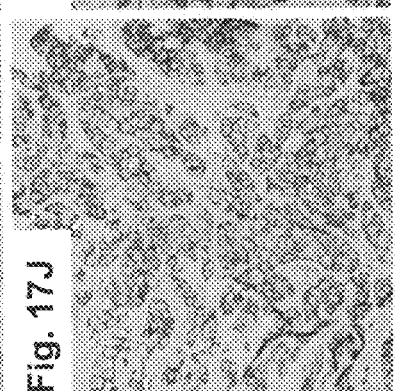

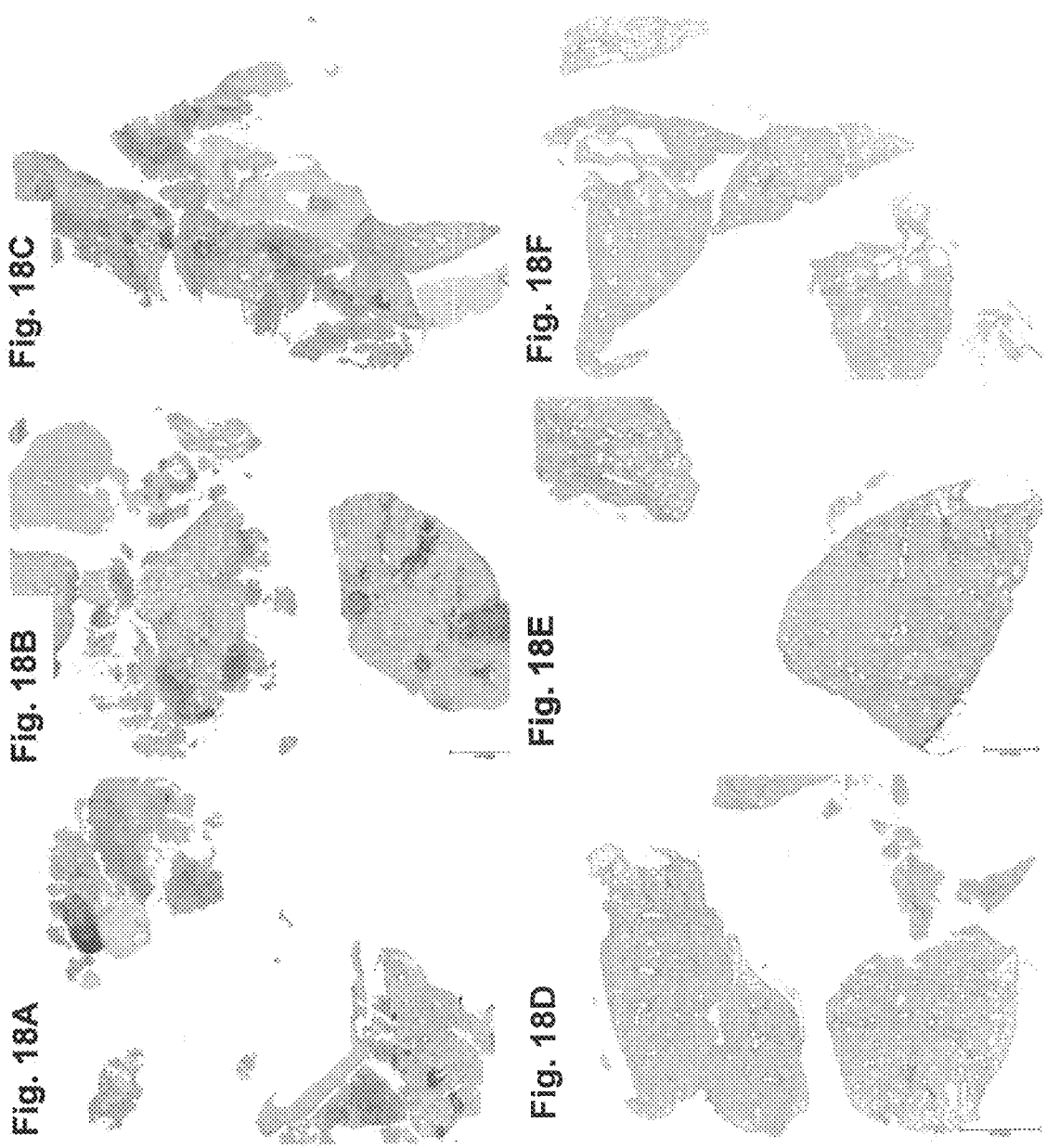

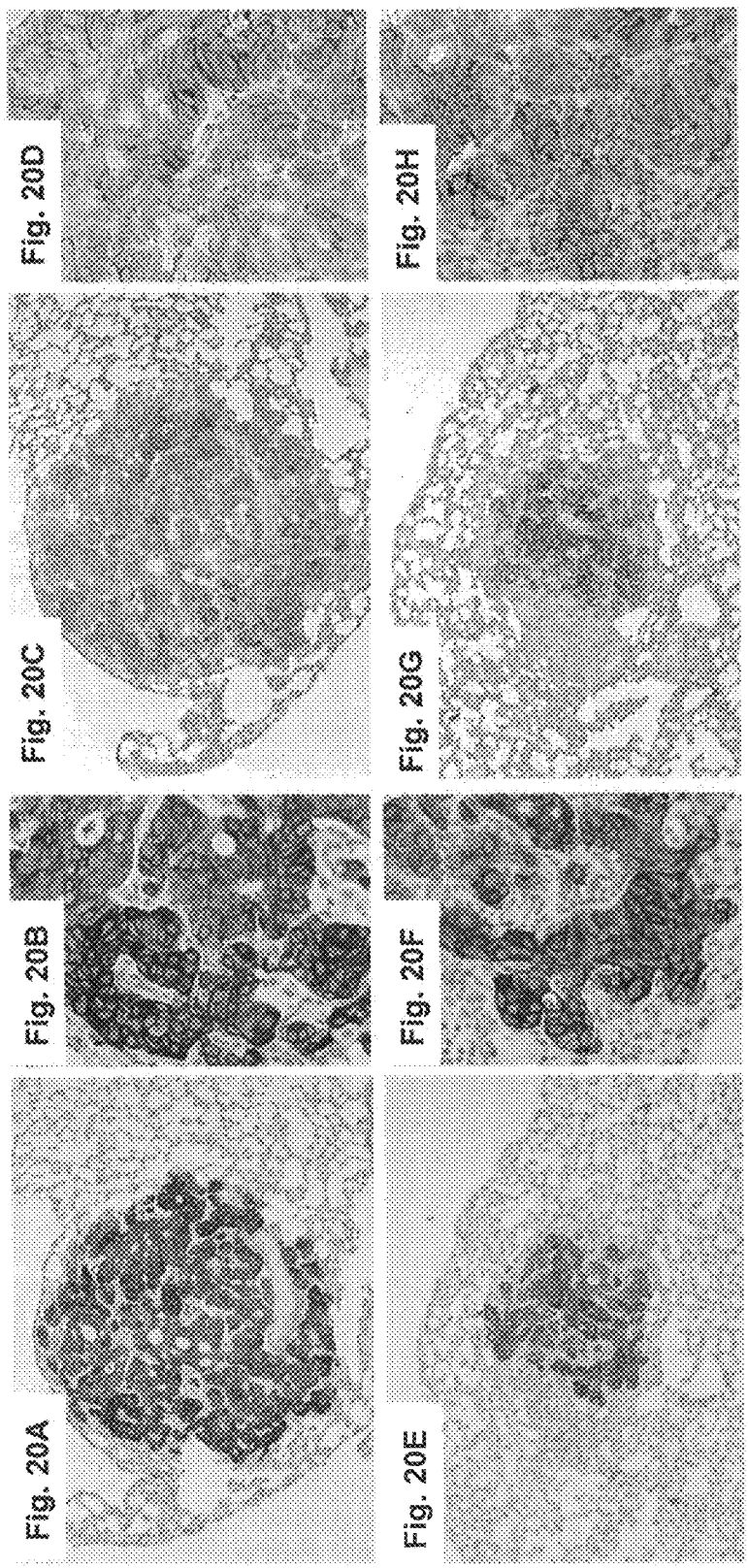

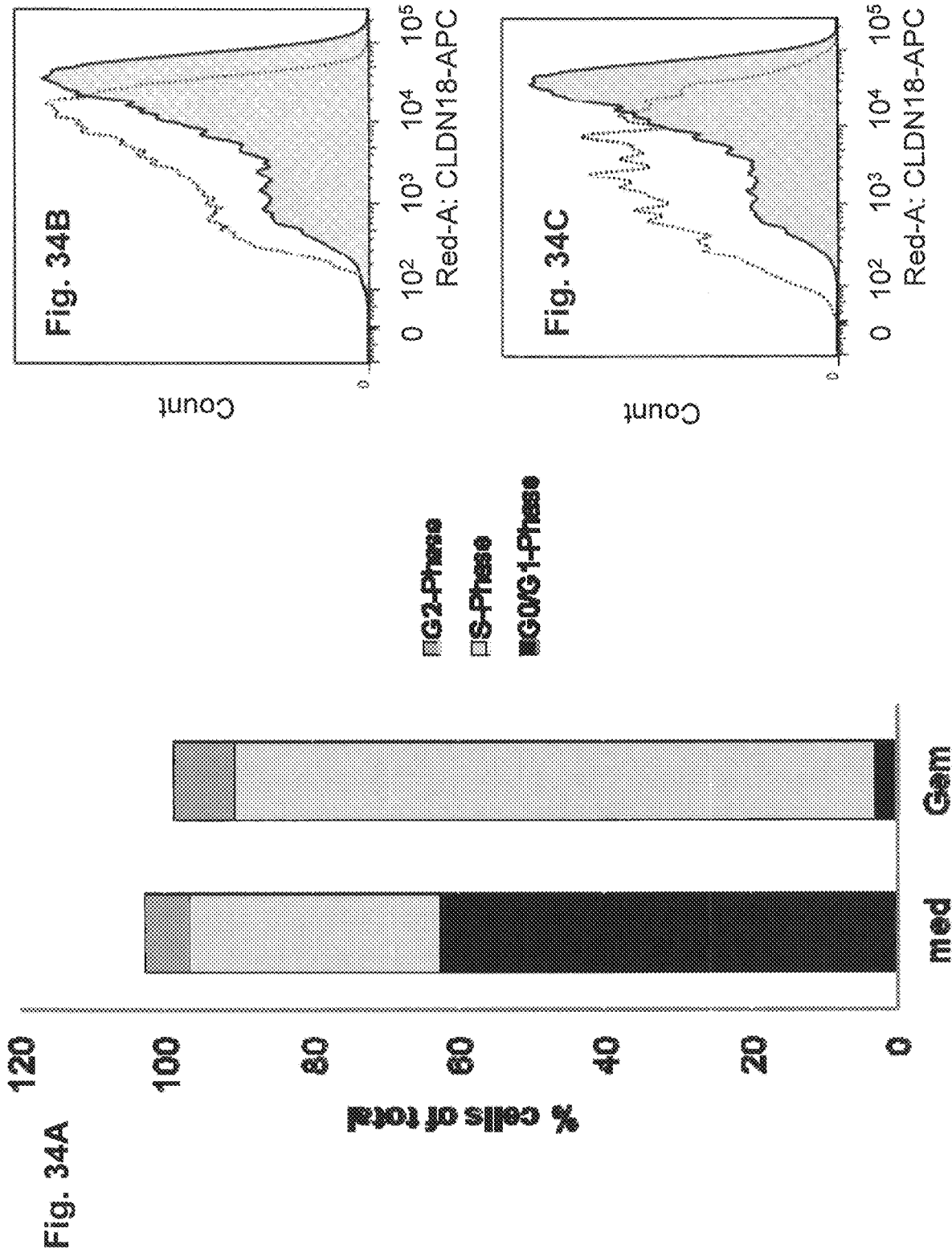

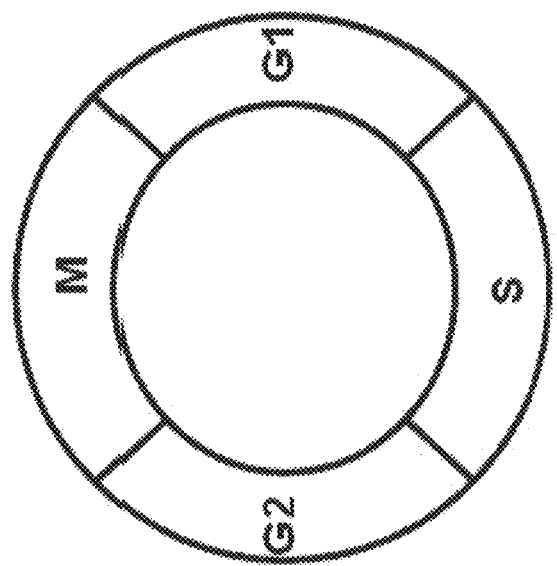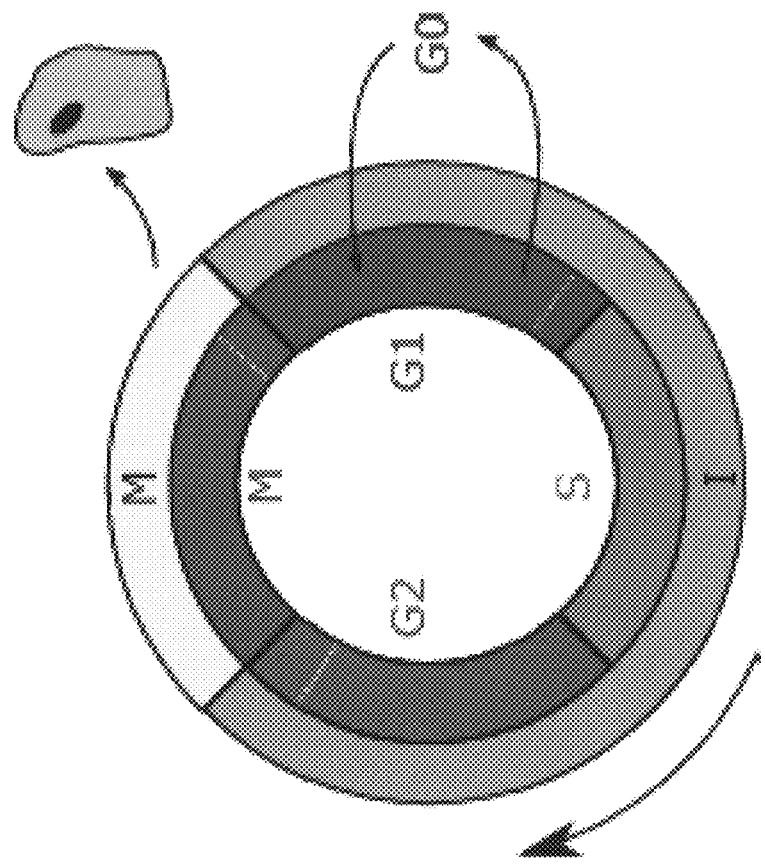
Fig. 35C

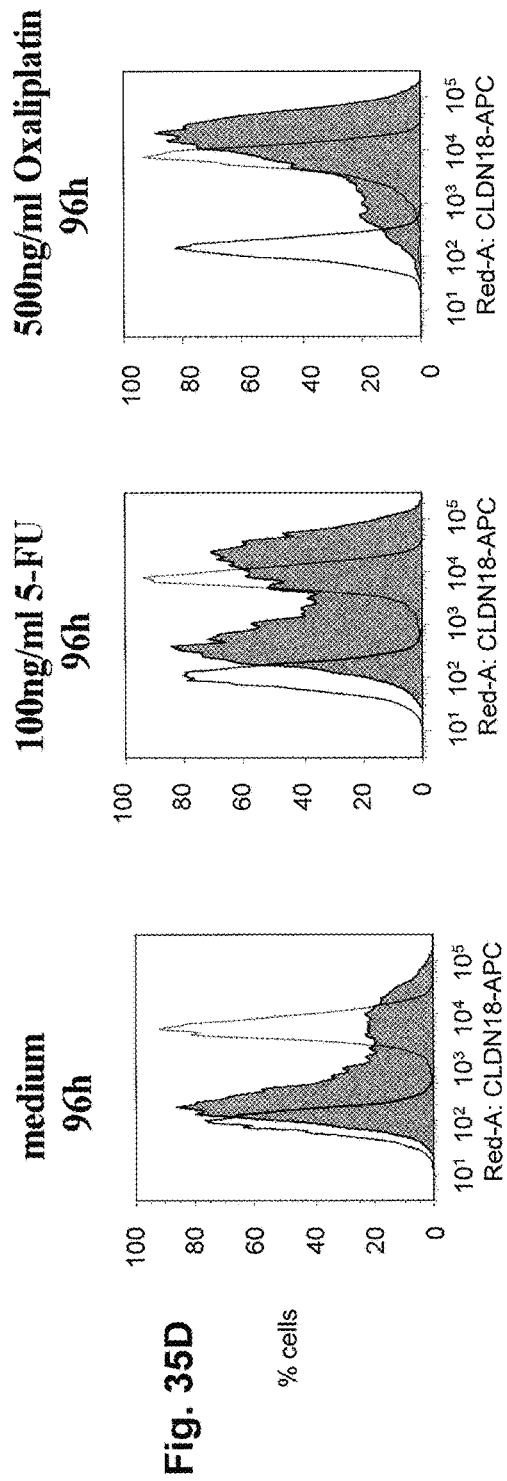

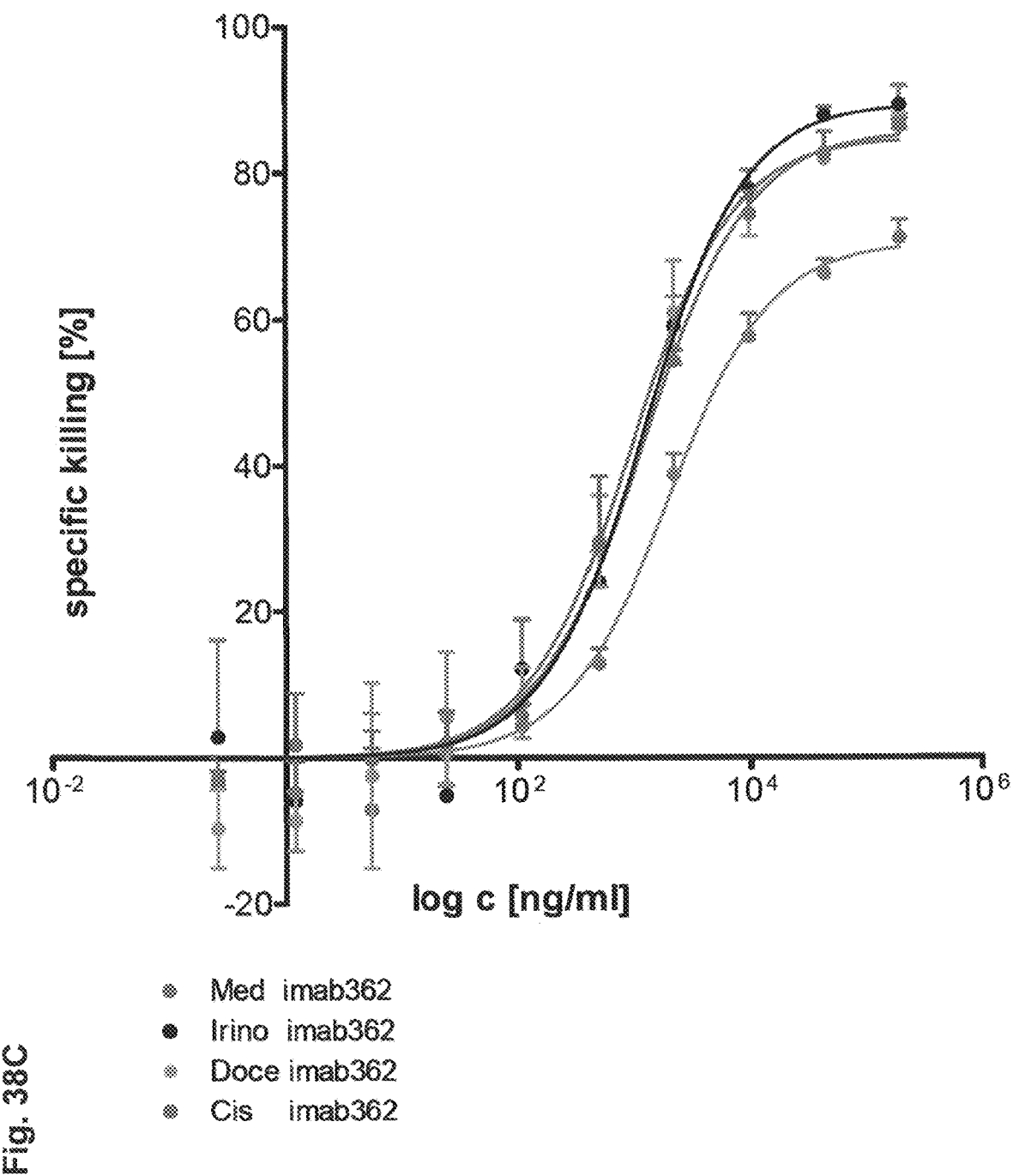

SEQUENCE LISTING

<160> NUMBER OF SEQ ID NOS: 54

<210> SEQ ID NO 1
<211> LENGTH: 261
<212> TYPE: PRT
<213> ORGANISM: Homo sapiens

<400> SEQUENCE: 1

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240
```

```
Tyr Asp Gly Gly Ala Arg Thr Glu Asp Glu Val Gln Ser Tyr Pro Ser
                245                 250                 255

Lys His Asp Tyr Val
            260

<210> SEQ ID NO 2
<211> LENGTH: 261
<212> TYPE: PRT
<213> ORGANISM: Homo sapiens

<400> SEQUENCE: 2

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 3
<211> LENGTH: 10
<212> TYPE: PRT
<213> ORGANISM: Homo sapiens

<400> SEQUENCE: 3

Asp Gln Trp Ser Thr Gln Asp Leu Tyr Asn
1               5                   10

<210> SEQ ID NO 4
```

```
<211> LENGTH: 11
<212> TYPE: PRT
<213> ORGANISM: Homo sapiens

<400> SEQUENCE: 4

Asn Asn Pro Val Thr Ala Val Phe Asn Tyr Gln
1               5                   10

<210> SEQ ID NO 5
<211> LENGTH: 14
<212> TYPE: PRT
<213> ORGANISM: Homo sapiens

<400> SEQUENCE: 5

Ser Thr Gln Asp Leu Tyr Asn Asn Pro Val Thr Ala Val Phe
1               5                   10

<210> SEQ ID NO 6
<211> LENGTH: 13
<212> TYPE: PRT
<213> ORGANISM: Homo sapiens

<400> SEQUENCE: 6

Thr Asn Phe Trp Met Ser Thr Ala Asn Met Tyr Thr Gly
1               5                   10

<210> SEQ ID NO 7
<211> LENGTH: 13
<212> TYPE: PRT
<213> ORGANISM: Homo sapiens

<400> SEQUENCE: 7

Asp Ser Ala Lys Ala Asn Met Thr Leu Thr Ser Gly Ile
1               5                   10

<210> SEQ ID NO 8
<211> LENGTH: 55
<212> TYPE: PRT
<213> ORGANISM: Homo sapiens

<400> SEQUENCE: 8

Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
                20                  25                  30

Gly Phe Thr Glu Cys Arg Gly Tyr Phe Thr Leu Leu Gly Leu Pro Ala
            35                  40                  45

Met Leu Gln Ala Val Arg Ala
        50                  55

<210> SEQ ID NO 9
<211> LENGTH: 24
<212> TYPE: PRT
<213> ORGANISM: Homo sapiens

<400> SEQUENCE: 9

Phe Ala Leu Lys Cys Ile Arg Ile Gly Ser Met Glu Asp Ser Ala Lys
1               5                   10                  15

Ala Asn Met Thr Leu Thr Ser Gly
            20

<210> SEQ ID NO 10
<211> LENGTH: 40
```

```
<212> TYPE: PRT
<213> ORGANISM: Homo sapiens

<400> SEQUENCE: 10

Ala Asn Met Leu Val Thr Asn Phe Trp Met Ser Thr Ala Asn Met Tyr
1               5                   10                  15

Thr Gly Met Gly Gly Met Val Gln Thr Val Gln Thr Arg Tyr Thr Phe
            20                  25                  30

Gly Ala Ala Leu Phe Val Gly Trp
        35                  40

<210> SEQ ID NO 11
<211> LENGTH: 153
<212> TYPE: PRT
<213> ORGANISM: Homo sapiens

<400> SEQUENCE: 11

Met Asp Gln Trp Ser Thr Gln Asp Leu Tyr Asn Asn Pro Val Thr Ala
1               5                   10                  15

Val Phe Asn Tyr Gln Gly Leu Trp Arg Ser Cys Val Arg Glu Ser Ser
            20                  25                  30

Gly Phe Thr Glu Cys Arg Gly Tyr Phe Thr Leu Leu Gly Leu Pro Ala
        35                  40                  45

Met Leu Gln Ala Val Arg Ala Leu Met Ile Val Gly Ile Val Leu Gly
    50                  55                  60

Ala Ile Gly Leu Leu Val Ser Ile Phe Ala Leu Lys Cys Ile Arg Ile
65                  70                  75                  80

Gly Ser Met Glu Asp Ser Ala Lys Ala Asn Met Thr Leu Thr Ser Gly
                85                  90                  95

Ile Met Phe Ile Val Ser Gly Leu Cys Ala Ile Ala Gly Val Ser Val
            100                 105                 110

Phe Ala Asn Met Leu Val Thr Asn Phe Trp Met Ser Thr Ala Asn Met
        115                 120                 125

Tyr Thr Gly Met Gly Gly Met Val Gln Thr Val Gln Thr Arg Tyr Thr
    130                 135                 140

Phe Gly Ala Ala Leu Phe Val Gly Trp
145                 150

<210> SEQ ID NO 12
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
```

Pro Val Thr Lys Ser Phe Asn Arg Gly Glu Cys
          100                 105

<210> SEQ ID NO 13
<211> LENGTH: 326
<212> TYPE: PRT
<213> ORGANISM: Artificial
<220> FEATURE:
<223> OTHER INFORMATION: Description of artificial sequence: Translation
      of PCR product

<400> SEQUENCE: 13

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Lys Val Glu Pro
                85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 14
<211> LENGTH: 466
<212> TYPE: PRT
<213> ORGANISM: Artificial
<220> FEATURE:
<223> OTHER INFORMATION: Description of artificial sequence: chimeric monoclonal antibody

<400> SEQUENCE: 14

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Ser Ser Tyr Trp Ile Glu Trp Val Lys Gln Arg Pro Gly His Gly Leu
    50                  55                  60

Glu Trp Ile Gly Glu Ile Leu Pro Gly Ser Gly Ser Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Tyr Asp Tyr Pro Trp Phe Ala Tyr Trp Gly Gln
        115                 120                 125

Gly Thr Leu Val Thr Val Ser Ala Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

```
Thr Leu Pro Pro Ser Arg Asp Glu Leu Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
                420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460

Gly Lys
465

<210> SEQ ID NO 15
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 15

Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Gly Phe Gly Asn Ala Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
```

```
                    245                 250                 255
Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 16
<211> LENGTH: 465
<212> TYPE: PRT
<213> ORGANISM: Artificial
<220> FEATURE:
<223> OTHER INFORMATION: Description of artificial sequence: chimeric
      monoclonal antibody

<400> SEQUENCE: 16

Met Glu Trp Ile Trp Ile Phe Leu Phe Ile Leu Ser Gly Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Asp Tyr Tyr Ile Asn Trp Val Lys Gln Arg Thr Gly Gln Gly Leu
    50                  55                  60

Glu Trp Ile Gly Glu Ile Tyr Pro Gly Ser Gly Asn Thr Tyr Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Tyr Gly Ala Phe Asp Tyr Trp Gly Gln Gly
        115                 120                 125
```

Thr Thr Leu Thr Val Ser Ser Ala Ser Thr Lys Gly Pro Ser Val Phe
            130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 17
<211> LENGTH: 467
<212> TYPE: PRT
<213> ORGANISM: Artificial
<220> FEATURE:
<223> OTHER INFORMATION: Description of artificial sequence: chimeric
      monoclonal antibody

<400> SEQUENCE: 17

Met Gly Trp Ser Cys Ile Ile Leu Phe Leu Val Ala Thr Ala Thr Gly
1               5                   10                  15

```
Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
            35                  40                  45

Thr Ser Tyr Trp Ile Asn Trp Val Lys Gln Arg Pro Gly Gln Gly Leu
        50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
            115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430
```

-continued

```
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
        450                 455                 460
Pro Gly Lys
465

<210> SEQ ID NO 18
<211> LENGTH: 466
<212> TYPE: PRT
<213> ORGANISM: Artificial
<220> FEATURE:
<223> OTHER INFORMATION: Description of artificial sequence: chimeric
      monoclonal antibody

<400> SEQUENCE: 18

Met Glu Trp Arg Ile Phe Leu Phe Ile Leu Ser Gly Thr Ala Gly Val
1               5                   10                  15
His Ser Gln Val Gln Leu Gln Gln Ser Gly Pro Glu Leu Val Lys Pro
            20                  25                  30
Gly Ala Ser Val Lys Met Ser Cys Lys Ala Ser Gly Tyr Thr Phe Thr
        35                  40                  45
Asp Tyr Val Ile Ser Trp Val Lys Gln Arg Thr Gly Gln Gly Leu Glu
    50                  55                  60
Trp Ile Gly Glu Ile Tyr Pro Gly Ser Gly Ser Thr Tyr Tyr Asn Glu
65                  70                  75                  80
Lys Phe Lys Gly Lys Ala Thr Leu Thr Ala Asp Lys Ser Ser Asn Thr
                85                  90                  95
Ala Tyr Met Gln Leu Ser Ser Leu Thr Ser Glu Asp Ser Ala Val Tyr
            100                 105                 110
Phe Cys Ala Arg Gly Val Leu Leu Arg Ala Met Asp Tyr Trp Gly Gln
        115                 120                 125
Gly Thr Ser Val Thr Val Ser Ser Ala Ser Thr Lys Gly Pro Ser Val
    130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Ser Leu Gly Thr Gln Thr Tyr Ile Cys Asn Val Asn His Lys
    210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
```

```
Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
        450                 455                 460

Gly Lys
465

<210> SEQ ID NO 19
<211> LENGTH: 469
<212> TYPE: PRT
<213> ORGANISM: Artificial
<220> FEATURE:
<223> OTHER INFORMATION: Description of artificial sequence: chimeric
      monoclonal antibody

<400> SEQUENCE: 19

Met Asp Trp Ile Trp Ile Met Leu His Leu Leu Ala Ala Ala Thr Gly
1               5                   10                  15

Ile Gln Ser Gln Val His Leu Gln Gln Ser Gly Ser Glu Leu Arg Ser
            20                  25                  30

Pro Gly Ser Ser Val Lys Leu Ser Cys Lys Asp Phe Asp Ser Glu Val
        35                  40                  45

Phe Pro Phe Ala Tyr Met Ser Trp Ile Arg Gln Lys Pro Gly His Gly
    50                  55                  60

Phe Glu Trp Ile Gly Asp Ile Leu Pro Ser Ile Gly Arg Thr Ile Tyr
65                  70                  75                  80

Gly Glu Lys Phe Glu Asp Lys Ala Thr Leu Asp Ala Asp Thr Val Ser
                85                  90                  95

Asn Thr Ala Tyr Leu Glu Leu Asn Ser Leu Thr Ser Glu Asp Ser Ala
            100                 105                 110

Ile Tyr Tyr Cys Ala Arg Gly Glu Gly Tyr Gly Ala Trp Phe Ala Tyr
        115                 120                 125

Trp Gly Gln Gly Thr Leu Val Thr Val Ser Ala Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
```

-continued

```
                195                 200                 205
Thr Val Pro Ser Ser Leu Gly Thr Gln Thr Tyr Ile Cys Asn Val
    210                 215                 220
Asn His Lys Pro Ser Asn Thr Lys Val Asp Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
            275                 280                 285
Ser His Glu Asp Pro Glu Val Lys Phe Asn Trp Tyr Val Asp Gly Val
        290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Asp Glu Leu Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 20
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 20

Met Glu Ser Gln Thr Gln Val Leu Met Ser Leu Leu Phe Trp Val Ser
1               5                   10                  15
Gly Thr Cys Gly Asp Ile Val Met Thr Gln Ser Pro Ser Ser Leu Thr
                20                  25                  30
Val Thr Ala Gly Glu Lys Val Thr Met Ser Cys Lys Ser Ser Gln Ser
            35                  40                  45
Leu Leu Asn Ser Gly Asn Gln Lys Asn Tyr Leu Thr Trp Tyr Gln Gln
        50                  55                  60
Lys Pro Gly Gln Pro Pro Lys Leu Leu Ile Tyr Trp Ala Ser Thr Arg
65                  70                  75                  80
```

```
Glu Ser Gly Val Pro Asp Arg Phe Thr Gly Ser Gly Ser Gly Thr Asp
            85                  90                  95

Phe Thr Leu Thr Ile Ser Ser Val Gln Ala Glu Asp Leu Ala Val Tyr
        100                 105                 110

Tyr Cys Gln Asn Asp Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 21
<211> LENGTH: 235
<212> TYPE: PRT
<213> ORGANISM: Artificial
<220> FEATURE:
<223> OTHER INFORMATION: Description of artificial sequence: chimeric
      monoclonal antibody

<400> SEQUENCE: 21

```
Met His Phe Gln Val Gln Ile Phe Ser Phe Leu Leu Ile Ser Ala Ser
1                   5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Pro Thr Phe Gly Gly Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205
```

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 22
<211> LENGTH: 234
<212> TYPE: PRT
<213> ORGANISM: Artificial
<220> FEATURE:
<223> OTHER INFORMATION: Description of artificial sequence: chimeric
      monoclonal antibody

<400> SEQUENCE: 22

Met Glu Phe Gln Thr Gln Val Phe Val Phe Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Ile Thr Cys Lys Ala Ser Gln Asn
        35                  40                  45

Val Arg Thr Ala Val Ala Trp Tyr Gln Gln Lys Pro Gly Gln Ser Pro
50                  55                  60

Lys Ala Leu Ile Tyr Leu Ala Ser Asn Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Leu Gln His Trp
            100                 105                 110

Asn Tyr Pro Leu Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 23
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 23

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

```
Val Ser Val Gly Glu Lys Val Thr Met Ser Cys Lys Ser Gln Ser
        35                  40                  45

Leu Leu Tyr Ser Ser Asn Gln Lys Asn Tyr Leu Ala Trp Tyr Gln Gln
50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Pro Leu Thr Phe Gly Ala Gly Thr
        115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 24
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 24

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
```

```
                145                 150                 155                 160
Leu Leu Asn Asn Phe Tyr Pro Arg Glu Ala Lys Val Gln Trp Lys Val
                    165                 170                 175

Asp Asn Ala Leu Gln Ser Gly Asn Ser Gln Glu Ser Val Thr Glu Gln
                    180                 185                 190

Asp Ser Lys Asp Ser Thr Tyr Ser Leu Ser Ser Thr Leu Thr Leu Ser
                    195                 200                 205

Lys Ala Asp Tyr Glu Lys His Lys Val Tyr Ala Cys Glu Val Thr His
                    210                 215                 220

Gln Gly Leu Ser Ser Pro Val Thr Lys Ser Phe Asn Arg Gly Glu Cys
225                 230                 235                 240

<210> SEQ ID NO 25
<211> LENGTH: 239
<212> TYPE: PRT
<213> ORGANISM: Artificial
<220> FEATURE:
<223> OTHER INFORMATION: Description of artificial sequence: chimeric
      monoclonal antibody

<400> SEQUENCE: 25

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Ala Gly Glu Lys Val Thr Met Ser Cys Lys Ser Ser Gln Ser
                35                  40                  45

Leu Leu Asn Ser Arg Thr Arg Lys Asn Tyr Leu Ala Trp Tyr Gln Gln
            50                  55                  60

Lys Pro Gly Gln Ser Pro Lys Leu Leu Ile Tyr Trp Ala Ser Thr Arg
65              70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
                100                 105                 110

Tyr Cys Lys Gln Ser Tyr Asn Leu Tyr Thr Phe Gly Gly Gly Thr Lys
                115                 120                 125

Leu Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                    165                 170                 175

Asn Ala Leu Gln Ser Gly Asn Ser Gln Glu Ser Val Thr Glu Gln Asp
                    180                 185                 190

Ser Lys Asp Ser Thr Tyr Ser Leu Ser Ser Thr Leu Thr Leu Ser Lys
                    195                 200                 205

Ala Asp Tyr Glu Lys His Lys Val Tyr Ala Cys Glu Val Thr His Gln
                    210                 215                 220

Gly Leu Ser Ser Pro Val Thr Lys Ser Phe Asn Arg Gly Glu Cys
225                 230                 235

<210> SEQ ID NO 26
<211> LENGTH: 240
<212> TYPE: PRT
<213> ORGANISM: Artificial
<220> FEATURE:
```

```
<223> OTHER INFORMATION: Description of artificial sequence: chimeric
      monoclonal antibody

<400> SEQUENCE: 26

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Ala Thr Asp
                85                  90                  95

Phe Thr Leu Thr Ile Ser Ser Val Gln Ala Glu Asp Leu Ala Asp Tyr
            100                 105                 110

His Cys Gly Gln Gly Tyr Ser Tyr Pro Tyr Thr Phe Gly Gly Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 27
<211> LENGTH: 240
<212> TYPE: PRT
<213> ORGANISM: Artificial
<220> FEATURE:
<223> OTHER INFORMATION: Description of artificial sequence: chimeric
      monoclonal antibody

<400> SEQUENCE: 27

Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95
```

```
Phe Thr Leu Thr Ile Ser Ser Val Lys Ala Glu Asp Leu Ala Val Tyr
                100                 105                 110

Tyr Cys Gln Gln Tyr Tyr Ser Tyr Pro Leu Thr Phe Gly Ala Gly Thr
            115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 28
<211> LENGTH: 234
<212> TYPE: PRT
<213> ORGANISM: Artificial
<220> FEATURE:
<223> OTHER INFORMATION: Description of artificial sequence: chimeric
      monoclonal antibody

<400> SEQUENCE: 28

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Lys Ala Glu Asp Leu Ala Val Tyr Tyr Cys Gln Gln Tyr Tyr
            100                 105                 110

Ser Tyr Pro Leu Thr Phe Gly Ala Gly Thr Lys Leu Glu Leu Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                 215                 220
```

Val Thr Lys Ser Phe Asn Arg Gly Glu Cys
225                 230

<210> SEQ ID NO 29
<211> LENGTH: 117
<212> TYPE: PRT
<213> ORGANISM: Artificial
<220> FEATURE:
<223> OTHER INFORMATION: Description of artificial sequence: Translation
      of PCR product

<400> SEQUENCE: 29

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Pro Trp Phe Ala Tyr Trp Gly Gln Gly Thr Leu
            100                 105                 110

Val Thr Val Ser Ala
        115

<210> SEQ ID NO 30
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 30

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser
        115

<210> SEQ ID NO 31
<211> LENGTH: 116
<212> TYPE: PRT
<213> ORGANISM: Artificial

```
<220> FEATURE:
<223> OTHER INFORMATION: Description of artificial sequence: Translation
      of PCR product

<400> SEQUENCE: 31

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Thr Gly Gln Gly Leu Glu Trp Ile
        35                  40                  45

Gly Glu Ile Tyr Pro Gly Ser Gly Asn Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Tyr Gly Ala Phe Asp Tyr Trp Gly Gln Gly Thr Thr Leu
            100                 105                 110

Thr Val Ser Ser
        115

<210> SEQ ID NO 32
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 32

Gln Val Gln Leu Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
        115

<210> SEQ ID NO 33
<211> LENGTH: 118
<212> TYPE: PRT
<213> ORGANISM: Artificial
<220> FEATURE:
<223> OTHER INFORMATION: Description of artificial sequence: Translation
      of PCR product

<400> SEQUENCE: 33

Gln Val Gln Leu Gln Gln Ser Gly Pro Glu Leu Val Lys Pro Gly Ala
1               5                   10                  15
```

```
Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Leu Leu Arg Ala Met Asp Tyr Trp Gly Gln Gly Thr
            100                 105                 110

Ser Val Thr Val Ser Ser
            115
```

```
<210> SEQ ID NO 34
<211> LENGTH: 120
<212> TYPE: PRT
<213> ORGANISM: Artificial
<220> FEATURE:
<223> OTHER INFORMATION: Description of artificial sequence: Translation
      of PCR product

<400> SEQUENCE: 34

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45

Ile Gly Asp Ile Leu Pro Ser Ile Gly Arg Thr Ile Tyr Gly Glu Lys
    50                  55                  60

Phe Glu Asp Lys Ala Thr Leu Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Glu Gly Tyr Gly Ala Trp Phe Ala Tyr Trp Gly Gln
            100                 105                 110

Gly Thr Leu Val Thr Val Ser Ala
            115                 120
```

```
<210> SEQ ID NO 35
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 35

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 36
<211> LENGTH: 106
<212> TYPE: PRT
<213> ORGANISM: Artificial
<220> FEATURE:
<223> OTHER INFORMATION: Description of artificial sequence: Translation
      of PCR product

<400> SEQUENCE: 36

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

<210> SEQ ID NO 37
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 37

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
                20                  25                  30

Val Ala Trp Tyr Gln Gln Lys Pro Gly Gln Ser Pro Lys Ala Leu Ile
            35                  40                  45

Tyr Leu Ala Ser Asn Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105

<210> SEQ ID NO 38
<211> LENGTH: 113
<212> TYPE: PRT

<213> ORGANISM: Artificial
<220> FEATURE:
<223> OTHER INFORMATION: Description of artificial sequence: Translation of PCR product

<400> SEQUENCE: 38

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 39
<211> LENGTH: 113
<212> TYPE: PRT
<213> ORGANISM: Artificial
<220> FEATURE:
<223> OTHER INFORMATION: Description of artificial sequence: Translation of PCR product

<400> SEQUENCE: 39

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys

<210> SEQ ID NO 40
<211> LENGTH: 112
<212> TYPE: PRT
<213> ORGANISM: Artificial
<220> FEATURE:
<223> OTHER INFORMATION: Description of artificial sequence: Translation of PCR product

<400> SEQUENCE: 40

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser

```
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Tyr Thr Phe Gly Gly Gly Thr Lys Leu Glu Ile Lys
            100                 105                 110

<210> SEQ ID NO 41
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 41

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Ala Thr Asp Phe Thr Leu Thr
65                  70                  75                  80

Ile Ser Ser Val Gln Ala Glu Asp Leu Ala Asp Tyr His Cys Gly Gln
                85                  90                  95

Gly Tyr Ser Tyr Pro Tyr Thr Phe Gly Gly Gly Thr Lys Leu Glu Ile
            100                 105                 110

Lys

<210> SEQ ID NO 42
<211> LENGTH: 113
<212> TYPE: PRT
<213> ORGANISM: Artificial
<220> FEATURE:
<223> OTHER INFORMATION: Description of artificial sequence: Translation
      of PCR product

<400> SEQUENCE: 42

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95
```

```
Tyr Tyr Ser Tyr Pro Leu Thr Phe Gly Ala Gly Thr Lys Leu Glu Leu
            100                 105                 110
Lys
```

<210> SEQ ID NO 43
<211> LENGTH: 107
<212> TYPE: PRT
<213> ORGANISM: Artificial
<220> FEATURE:
<223> OTHER INFORMATION: Description of artificial sequence: Translation
      of PCR product

<400> SEQUENCE: 43

```
Asn Ile Val Met Thr Gln Ser Pro Lys Ser Met Ser Met Ser Val Gly
1               5                   10                  15
Glu Arg Val Thr Leu Thr Cys Lys Ala Ser Glu Asn Val Val Thr Tyr
            20                  25                  30
Val Ser Trp Tyr Gln Gln Lys Pro Glu Gln Ser Pro Lys Leu Leu Ile
        35                  40                  45
Tyr Gly Ala Ser Asn Arg Tyr Thr Gly Val Pro Asp Arg Phe Thr Gly
    50                  55                  60
Ser Gly Ser Ala Thr Asp Phe Thr Leu Thr Ile Ser Ser Val Lys Ala
65                  70                  75                  80
Glu Asp Leu Ala Val Tyr Tyr Cys Gln Gln Tyr Tyr Ser Tyr Pro Leu
                85                  90                  95
Thr Phe Gly Ala Gly Thr Lys Leu Glu Leu Lys
            100                 105
```

<210> SEQ ID NO 44
<211> LENGTH: 15
<212> TYPE: PRT
<213> ORGANISM: Artificial
<220> FEATURE:
<223> OTHER INFORMATION: Epitope

<400> SEQUENCE: 44

```
Met Asp Gln Trp Ser Thr Gln Asp Leu Tyr Asn Asn Pro Val Thr
1               5                   10                  15
```

<210> SEQ ID NO 45
<211> LENGTH: 15
<212> TYPE: PRT
<213> ORGANISM: Artificial
<220> FEATURE:
<223> OTHER INFORMATION: Epitope

<400> SEQUENCE: 45

```
Ser Thr Gln Asp Leu Tyr Asn Asn Pro Val Thr Ala Val Phe Asn
1               5                   10                  15
```

<210> SEQ ID NO 46
<211> LENGTH: 15
<212> TYPE: PRT
<213> ORGANISM: Artificial
<220> FEATURE:
<223> OTHER INFORMATION: Epitope

<400> SEQUENCE: 46

```
Leu Tyr Asn Asn Pro Val Thr Ala Val Phe Asn Tyr Gln Gly Leu
1               5                   10                  15
```

<210> SEQ ID NO 47

```
<211> LENGTH: 15
<212> TYPE: PRT
<213> ORGANISM: Artificial
<220> FEATURE:
<223> OTHER INFORMATION: Epitope

<400> SEQUENCE: 47

Pro Val Thr Ala Val Phe Asn Tyr Gln Gly Leu Trp Arg Ser Cys
1               5                   10                  15

<210> SEQ ID NO 48
<211> LENGTH: 15
<212> TYPE: PRT
<213> ORGANISM: Artificial
<220> FEATURE:
<223> OTHER INFORMATION: Epitope

<400> SEQUENCE: 48

Val Phe Asn Tyr Gln Gly Leu Trp Arg Ser Cys Val Arg Glu Ser
1               5                   10                  15

<210> SEQ ID NO 49
<211> LENGTH: 15
<212> TYPE: PRT
<213> ORGANISM: Artificial
<220> FEATURE:
<223> OTHER INFORMATION: Epitope

<400> SEQUENCE: 49

Gln Gly Leu Trp Arg Ser Cys Val Arg Glu Ser Ser Gly Phe Thr
1               5                   10                  15

<210> SEQ ID NO 50
<211> LENGTH: 15
<212> TYPE: PRT
<213> ORGANISM: Artificial
<220> FEATURE:
<223> OTHER INFORMATION: Epitope

<400> SEQUENCE: 50

Arg Ser Cys Val Arg Glu Ser Ser Gly Phe Thr Glu Cys Arg Gly
1               5                   10                  15

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide

<400> SEQUENCE: 51
agagagctct ggcttcaccg agtg                                          24

<210> SEQ ID NO 52
<211> LENGTH: 26
<212> TYPE: DNA
<213> ORGANISM: Artificial Sequence
<220> FEATURE:
<223> OTHER INFORMATION: Oligonucleotide

<400> SEQUENCE: 52
ccagaagtta gtcaccagca tgttgg                                        26

<210> SEQ ID NO 53
<211> LENGTH: 25
<212> TYPE: DNA
<213> ORGANISM: Artificial Sequence
```

```
<220> FEATURE:
<223> OTHER INFORMATION: Oligonucleotide

<400> SEQUENCE: 53
gggataattt cagctgacta aacag                                              25

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide

<400> SEQUENCE: 54
ttccgtttag ttaggtgcag ttatc                                              25
```

COMBINATION THERAPY INVOLVING ANTIBODIES AGAINST CLAUDIN 18.2 FOR TREATMENT OF PANCREATIC CANCER

CROSS-REFERENCE TO RELATED APPLICATIONS

This application is a continuation application of U.S. patent application Ser. No. 15/684,168, filed on Aug. 23, 2017, which is a divisional application of U.S. patent application Ser. No. 14/769,046, filed on Aug. 19, 2015, now issued as U.S. Pat. No. 9,770,487 on Sep. 26, 2017, which is a national stage entry of international application PCT/EP2014/000433, filed on Feb. 18, 2014, which claimed priority to international application PCT/EP2013/000505, filed on Feb. 20, 2013. The entire contents of these applications are incorporated herein by reference.

BACKGROUND

Pancreatic cancer is one of the most lethal cancers. The mortality approaches 100% because of the propensity for early metastatic spread, and because the disease is highly resistant to radiation and chemotherapy. Given that 27,000 new cases are diagnosed every year in North America and 68 000 in Europe there is an urgent need to develop novel treatment strategies to reduce the mortality of pancreatic cancer patients.

The tight junction molecule Claudin 18 splice variant 2 (Claudin 18.2 (CLDN18.2)) is a member of the claudin family of tight junction proteins. CLDN18.2 is a 27.8 kDa transmembrane protein comprising four membrane spanning domains with two small extracellular loops. In normal tissues there is no detectable expression of CLDN18.2 by RT-PCR with exception of stomach. Immunohistochemistry with CLDN18.2 specific antibodies reveals stomach as the only positive tissue. CLDN18.2 is a highly selective gastric lineage antigen expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas.

The chimeric IgG1 antibody IMAB362 which is directed against CLDN18.2 has been developed by Ganymed Pharmaceuticals AG. IMAB362 recognizes the first extracellular domain (ECD1) of CLDN18.2 with high affinity and specificity. IMAB362 does not bind to any other claudin family member including the closely related splice variant 1 of Claudin 18 (CLDN18.1). IMAB362 shows precise tumor cell specificity and bundles four independent highly potent mechanisms of action. Upon target binding IMAB362 mediates cell killing by ADCC, CDC and induction of apoptosis induced by cross linking of the target at the tumor cell surface and direct inhibition of proliferation. Thus, IMAB362 lyses efficiently CLDN18.2-positive cells, including human gastric cancer cell lines in vitro and in vivo.

The toxicity and PK/TK profile of IMAB362 has been thoroughly examined in mice and cynomolgus monkeys including dose range finding studies, 28-day repeated dose toxicity studies in cynomolgus and a 3-month repeated dose toxicity study in mice. In both mice (longest treatment duration weekly administration for 3 months, highest dose levels 400 mg/kg) and cynomolgus monkeys (up to 5 weekly applications of up to 100 mg/kg) repeated doses of IMAB362 i.v. are well tolerated. No signs of systemic or local toxicity are induced. Specifically, no gastric toxicity has been observed in any toxicity study. IMAB362 does not induce immune activation and cytokine release. No adverse effects on male or female reproductive organs were recorded. IMAB362 does not bind to tissues lacking the target. Biodistribution studies in mice indicate that the reason for lack of gastric toxicity is most likely compartimentalization of tight junctions at the luminal site in healthy gastric epithelia, which appears to impair accessibility of the IMAB362 epitope profoundly.

IMAB362 is in early clinical testing. A phase I clinical study has been conducted in human. 5 dose cohorts (33 mg/m$^2$, 100 mg/m$^2$, 300 mg/m$^2$, 600 mg/m$^2$, 1000 mg/m$^2$) of 3 patients each have received a single intravenous administration of IMAB362 and have been observed for 28 days. IMAB362 was very well tolerated, with no relevant safety observation in the patients. In one patient all measured tumor markers decreased significantly within 4 weeks after treatment. In an ongoing phase IIa clinical study IMAB362 is given repetitively.

Here we present data demonstrating that chemotherapeutic agents can stabilize or increase expression of CLDN18.2 on the surface of pancreatic cancer cells resulting in an enhanced drugability of CLDN18.2 by an anti-CLDN18.2 antibody such as IMAB362. A synergistic effect of an anti-CLDN18.2 antibody such as IMAB362 with particular chemotherapeutic regimens, in particular chemotherapeutic regimens used for pancreatic cancer treatment was observed. Human cancer cells pre-treated with chemotherapy are more susceptible to antibody-induced target-specific killing. In mouse tumor models, tumor control with an anti-CLDN18.2 antibody plus chemotherapy is superior to that with an anti-CLDN18.2 antibody as single agent.

SUMMARY OF THE INVENTION

The present invention generally provides a combination therapy for effectively treating and/or preventing diseases associated with cells expressing CLDN18.2, including cancer diseases such as gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. Particularly preferred cancer diseases are pancreatic cancer and the metastases thereof.

In one aspect, the present invention provides a method of treating or preventing pancreatic cancer in a patient comprising administering to the patient (i) an antibody having the ability of binding to CLDN18.2 and (ii) an agent stabilizing or increasing expression, i.e. the level, of CLDN18.2. Expression of CLDN18.2 is preferably at the cell surface of a cancer cell. The agent stabilizing or increasing expression of CLDN18.2 may be administered prior to, simultanously with or following administration of the antibody having the ability of binding to CLDN18.2, or a combination thereof.

The agent stabilizing or increasing expression of CLDN18.2 may be a cytotoxic and/or cytostatic agent. In one embodiment, the agent stabilizing or increasing expression of CLDN18.2 comprises an agent which induces a cell cycle arrest or an accumulation of cells in one or more phases of the cell cycle, preferably in one or more phases of the cell cycle other than the G1-phase such as the S-phase, G2-phase, or a combination thereof or a combination of the S-phase or the G2-phase with the G1-phase. The agent stabilizing or increasing expression of CLDN18.2 may comprise an agent selected from the group consisting of nucleoside analogs, platinum compounds, camptothecin analogs and taxanes, prodrugs thereof, salts thereof, and combinations thereof. The nucleoside analog may be selected from the group consisting of gemcitabine, 5-fluorouracil, prodrugs thereof and salts thereof. The platinum compound may selected from the group consisting of oxaliplatin, cisplatin, prodrugs thereof and salts thereof. The camptothecin analog may be selected from the group consisting of irinotecan, topotecan, prodrugs thereof and salts thereof. The taxane may be selected from the group consisting of paclitaxel, docetaxel, prodrugs thereof and salts thereof. The agent stabilizing or increasing expression of CLDN18.2 may comprise an agent selected from the group consisting of gemcitabine, 5-fluorouracil, oxaliplatin, irinotecan, paclitaxel, prodrugs thereof, salts thereof and combinations thereof. The agent stabilizing or increasing expression of CLDN18.2 may comprise a combination of oxaliplatin and 5-fluorouracil or prodrugs thereof, a combination of cisplatin and 5-fluorouracil or prodrugs thereof, a combination of at least one taxane and oxaliplatin, a combination of at least one taxane and cisplatin, a combination of at least one taxane and 5-fluorouracil or prodrugs thereof, or a combination of at least one camptothecin analog and 5-fluorouracil or prodrugs thereof. The agent stabilizing or increasing expression of CLDN18.2 may comprise a combination of gemcitabine and oxaliplatin, a combination of gemcitabine and cisplatin, a combination of gemcitabine and carboplatin or a combination of oxaliplatin, 5-fluorouracil or prodrugs thereof and irinotecan. Accordingly, the method of the invention may comprise administering a combination of gemcitabine and oxaliplatin, a combination of gemcitabine and cisplatin, a combination of gemcitabine and carboplatin or a combination of oxaliplatin, 5-fluorouracil or prodrugs thereof and irinotecan. In one embodiment, the method of the invention comprises administering folinic acid, 5-fluorouracil or prodrugs thereof, irinotecan and oxaliplatin. The agent stabilizing or increasing expression of CLDN18.2 may comprise an agent inducing immunogenic cell death. The agent inducing immunogenic cell death may comprise oxaliplatin.

In a further aspect, the present invention provides a method of treating or preventing cancer in a patient comprising administering to the patient (i) an antibody having the ability of binding to CLDN18.2 and (ii) gemcitabine. In one embodiment, the cancer is selected from the group consisting of gastric cancer, esophageal cancer, pancreatic cancer, lung cancer, ovarian cancer, colon cancer, hepatic cancer, head-neck cancer, cancer of the gallbladder and the metastasis thereof. The cancer disease may be a Krukenberg tumor, peritoneal metastasis and/or lymph node metastasis. In one embodiment, the cancer is an adenocarcinoma, in particular an advanced adenocarcinoma. In one embodiment, the cancer is pancreatic cancer.

In one embodiment, the method of the invention further comprises administering an agent stimulating γδ T cells. In one embodiment, the γδ T cells are Vγ9Vδ2 T cells. In one embodiment, the agent stimulating γδ T cells is a bisphosphonate such as a nitrogen-containing bisphosphonate (aminobisphosphonate). In one embodiment, the agent stimulating γδ T cells is selected from the group consisting of zoledronic acid, clodronic acid, ibandronic acid, pamidronic acid, risedronic acid, minodronic acid, olpadronic acid, alendronic acid, incadronic acid and salts thereof. In one embodiment, the agent stimulating γδ T cells is administered in combination with interleukin-2.

The method of the invention may further comprise administering at least one further chemotherapeutic agent which may be a cytotoxic agent.

The antibody having the ability of binding to CLDN18.2 may bind to native epitopes of CLDN18.2 present on the surface of living cells. In one embodiment, the antibody having the ability of binding to CLDN18.2 binds to the first extracellular loop of CLDN18.2. In one embodiment, the antibody having the ability of binding to CLDN18.2 mediates cell killing by one or more of complement dependent cytotoxicity (CDC) mediated lysis, antibody dependent cellular cytotoxicity (ADCC) mediated lysis, induction of apoptosis and inhibition of proliferation. In one embodiment, the antibody having the ability of binding to CLDN18.2 is a monoclonal, chimeric or humanized antibody, or a fragment of an antibody. In one embodiment, the antibody mediates cell killing when bound to cellular CLDN18.2, in particular to CLDN18.2 expressed by cells on their cell surface, wherein the cells are preferably cancer cells, such as cells of the cancers described herein. In one embodiment, the antibody having the ability of binding to CLDN18.2 is an antibody selected from the group consisting of (i) an antibody produced by and/or obtainable from a clone deposited under the accession no. DSM ACC2737, DSM ACC2738, DSM ACC2739, DSM ACC2740, DSM ACC2741, DSM ACC2742, DSM ACC2743, DSM ACC2745, DSM ACC2746, DSM ACC2747, DSM ACC2748, DSM ACC2808, DSM ACC2809, or DSM ACC2810, (ii) an antibody which is a chimerized or humanized form of the antibody under (i), (iii) an antibody having the specificity of the antibody under (i) and (iv) an antibody comprising the antigen binding portion or antigen binding site, in particular the variable region, of the antibody under (i) and preferably having the specificity of the antibody under (i). In one embodiment, the antibody is coupled to a therapeutic agent such as a toxin, a radioisotope, a drug or a cytotoxic agent.

In one embodiment, the method of the invention comprises administering the antibody having the ability of binding to CLDN18.2 at a dose of up to 1000 mg/m$^2$. In one embodiment, the method of the invention comprises administering the antibody having the ability of binding to CLDN18.2 repeatedly at a dose of 300 to 600 mg/m$^2$.

According to the invention, CLDN18.2 preferably has the amino acid sequence according to SEQ ID NO: 1.

In one embodiment, the cancer described herein is CLDN18.2 positive. In one embodiment, cancer cells of the cancer described herein are CLDN18.2 positive. In one embodiment, cancer cells of the cancer described herein express CLDN18.2 on their cell surface.

In one embodiment, the pancreatic cancer described herein comprises primary cancer, advanced cancer or metastatic cancer, or a combination thereof such as a combination of pancreatic primary cancer and metastatic cancer. In one embodiment, the methods of the invention are for the simultaneous treatment of primary cancer and metastatic cancer such as pancreatic primary cancer and pancreatic metastatic cancer. In one embodiment, the metastatic cancer comprises metastasis to the lymph nodes, ovary, liver or lung, or a combination thereof. In one embodiment, the pancreatic cancer comprises cancer of the pancreatic duct. In one embodiment, the pancreatic cancer comprises an adenocarcinoma or carcinoma, or a combination thereof. In one embodiment, the pancreatic cancer comprises a ductal adenocarcinoma, a mucinous adenocarcinoma, a neuroendocrine carcinoma or an acinic cell carcinoma, or a combination thereof. In one embodiment, the pancreatic cancer is partially or completely refractory to gemcitabine treatment such as gemcitabine monotherapy. In one embodiment, preventing pancreatic cancer comprises preventing a recurrence of pancreatic cancer.

In one embodiment, the patient to be treated according to the invention had a surgery for pancreatic cancer. In one embodiment, the patient has a precancerous pancreatic lesion, in particular a precancerous pancreatic lesion comprising a beginning malignant histological change in the pancreatic ducts. In these embodiments, the methods of the invention preferably aim at preventing the development of malignant pancreatic cancer.

In a further aspect, the present invention provides a medical preparation for treating or preventing pancreatic cancer comprising (i) an antibody having the ability of binding to CLDN18.2 and (ii) an agent stabilizing or increasing expression of CLDN18.2. The medical preparation of the present invention may further comprise an agent stimulating γδ T cells. The antibody having the ability of binding to CLDN18.2 and the agent stabilizing or increasing expression of CLDN18.2, and optionally the agent stimulating γδ T cells, may be present in the medical preparation in a mixture or separate from each other. The medical preparation may be present in the form of a kit comprising a first container including the antibody having the ability of binding to CLDN18.2 and a second container including the agent stabilizing or increasing expression of CLDN18.2, and optionally a container including the agent stimulating γδ T cells. The medical preparation may further include printed instructions for use of the preparation for treatment or prevention of pancreatic cancer, in particular for use of the preparation in a method of the invention. Different embodiments of the medical preparation, and, in particular, of the antibody having the ability of binding to CLDN18.2, the agent stabilizing or increasing expression of CLDN18.2 and the agent stimulating γδ T cells are as described above for the methods of the invention.

In a particular aspect, the present invention provides a medical preparation comprising (i) an antibody having the ability of binding to CLDN18.2, and (ii) gemcitabine. The medical preparation of the present invention may further comprise an agent stimulating γδ T cells. The antibody having the ability of binding to CLDN18.2 and gemcitabine, and optionally the agent stimulating γδ T cells, may be present in the medical preparation in a mixture or separate from each other. The medical preparation may be for treating or preventing cancer such as pancreatic cancer. The medical preparation may be present in the form of a kit comprising a first container including the antibody having the ability of binding to CLDN18.2 and a second container including gemcitabine, and optionally a container including the agent stimulating γδ T cells. The medical preparation may further include printed instructions for use of the preparation for treatment or prevention of cancer such as pancreatic cancer, in particular for use of the preparation in a method of the invention. Different embodiments of the medical preparation, and, in particular, of the antibody having the ability of binding to CLDN18.2, the agent stabilizing or increasing expression of CLDN18.2 and the agent stimulating γδ T cells are as described above for the methods of the invention.

The present invention also provides the agents described herein such as the antibody having the ability of binding to CLDN18.2 and/or the agent stabilizing or increasing expression of CLDN18.2 for use in the methods described herein. For example, the present invention also provides the antibody having the ability of binding to CLDN18.2 for administration in conjunction with an agent stabilizing or increasing expression of CLDN18.2 such as gemcitabine, and optionally an agent stimulating γδ T cells.

Other features and advantages of the instant invention will be apparent from the following detailed description and claims.

BRIEF DESCRIPTION OF THE DRAWINGS

FIGS. 4A, 4B, and 4C show a CLDN18.2 expression in normal and precancerous pancreatic tissues. 43-14A staining of various precancerous structures (FIG. 4A) normal and PanIN1; (FIG. 4B) PanIN2; (FIG. 4C) PanIN3. Magnification 200×.

FIGS. 9A, 9B, 9C, 9D, 9E and 9F show expression of CLDN18.2 in primary and metastatic pancreatic tumor tissue. Staining of FFPE tissue sections (3 m) using the murine, monoclonal 43-14A antibody on (FIGS. 9A, 9C and 9E)

adenocarcinoma primary tumor and (FIGS. 9B, 9D and 9F) lymph node metastasis. The sections were counterstained using Mayers Haematoxylin.

Figure 10:
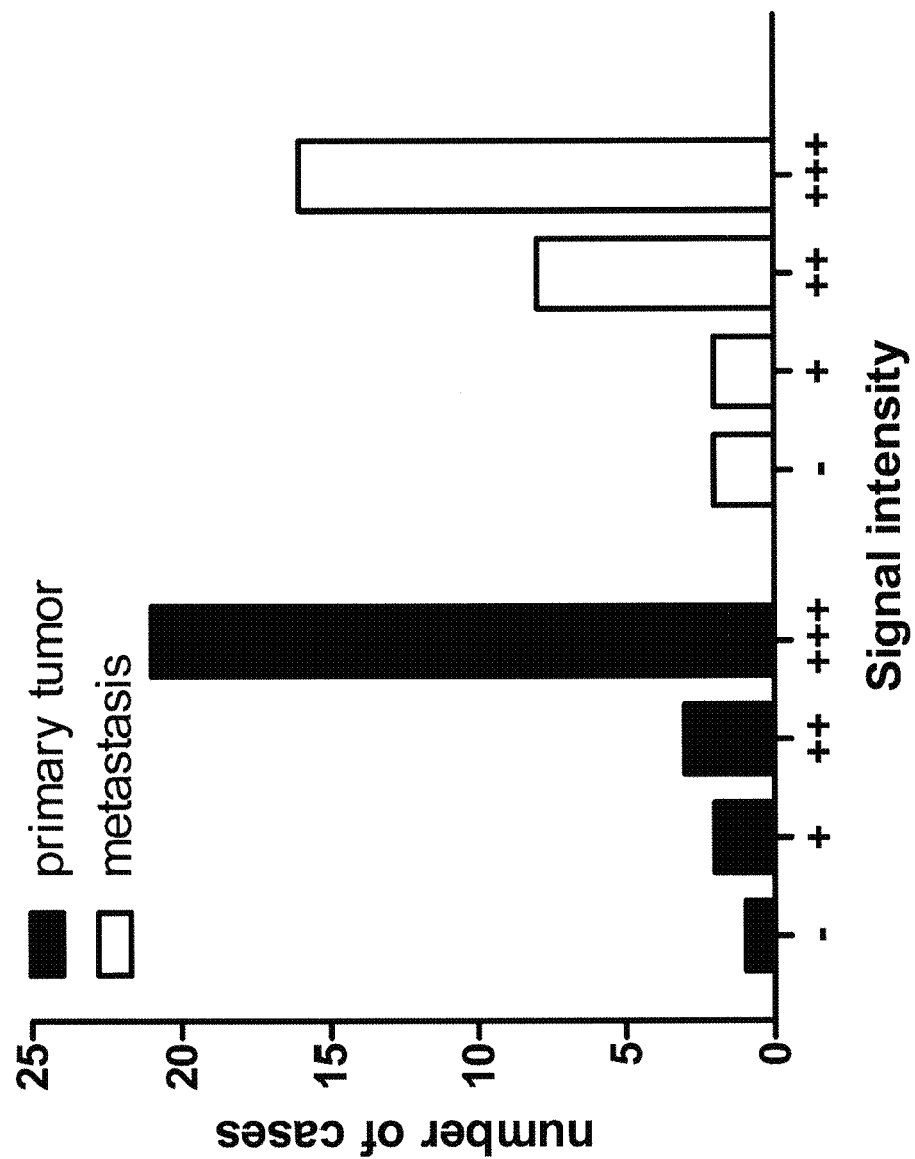

FIG. 10 shows expression of CLDN18.2 in matched pancreatic primary tumor and lymph node metastatic tissues (graphical analysis).

FIGS. 11A, 11B and 11C show expression of CLDN18.2 in matched pancreatic primary tumor and metastatic tissues. Staining of FFPE tissue sections (3 m) of (FIG. 11A) primary adenocarcinoma, (FIG. 11B) liver metastasis and (FIG. 11C) lymph node metastasis, using the murine, monoclonal 43-14A antibody. The sections were counterstained using Mayers Haematoxylin. 200× magnification.

Figure 12A:
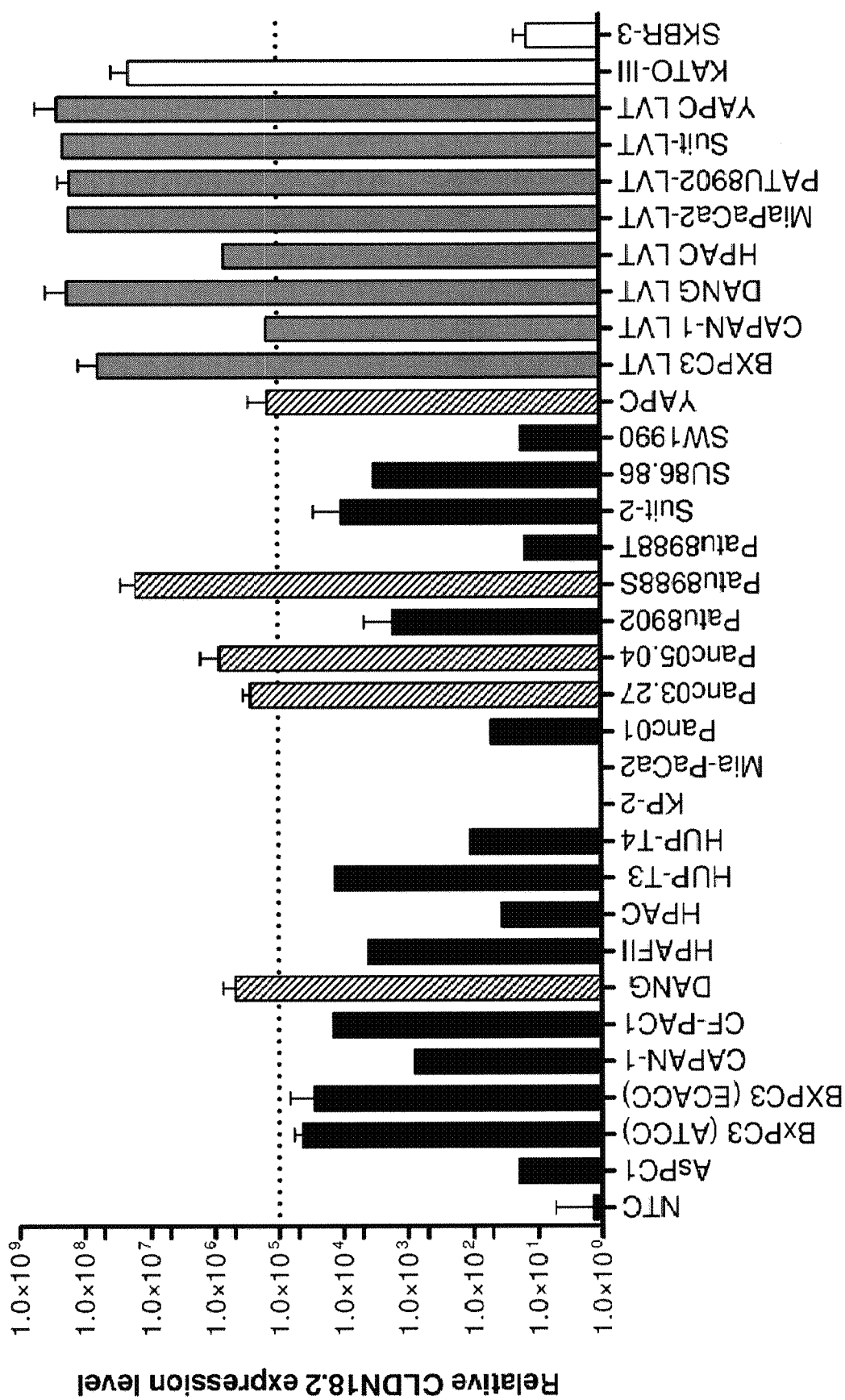
Figures 12B, 12C:
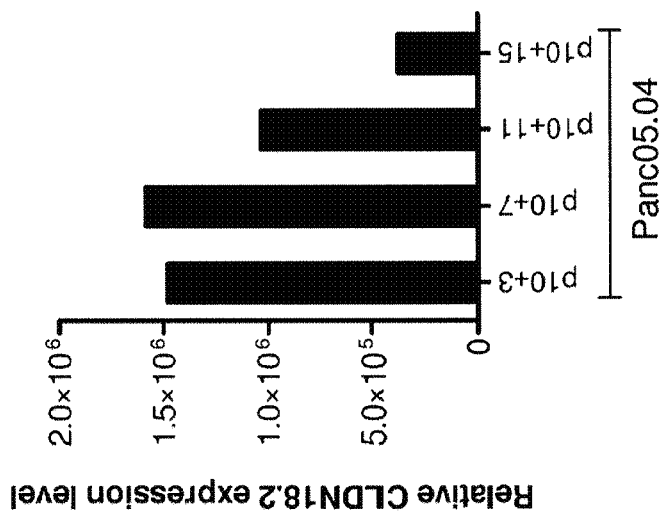
Figure 12D:
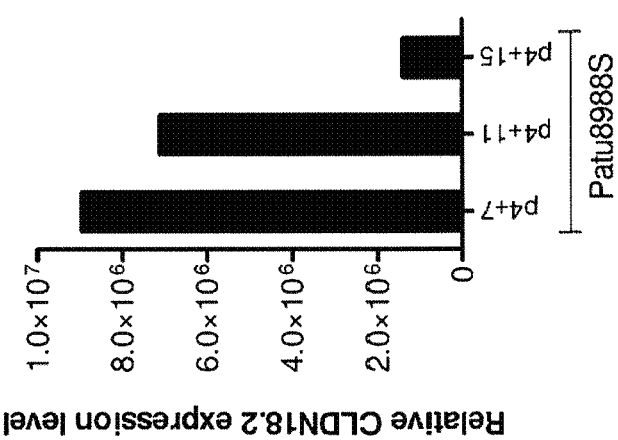

FIGS. 12A, 12B, 12C and 12D show CLDN18.2 mRNA levels in pancreatic carcinoma cell lines. FIG. 12A shows Q-PCR expression analyses of different pancreas CA cell lines, the lentivirally transduced (LVT) cell lines (gray bars), the stomach cancer cell line KATO-III (positive control) and the breast cancer cell line SKBR-3 (negative control). CLDN18.2 transcripts were amplified using gene specific primers. Endogenous cell lines showing a relative expression level above $1 \times 10^5$ were scored as CLDN18.2 positive (hatched bars). NTC: H2O control sample. Error bars: Mean+SD. (FIGS. 12B-12D) Passage-dependent CLDN18.2 expression analyses in Patu8988S (FIG. 12B), Panc05.04 (FIG. 12C) and the indicated LVT cell lines (FIG. 12D). Passage number is indicated below each bar.

Figure 13A:
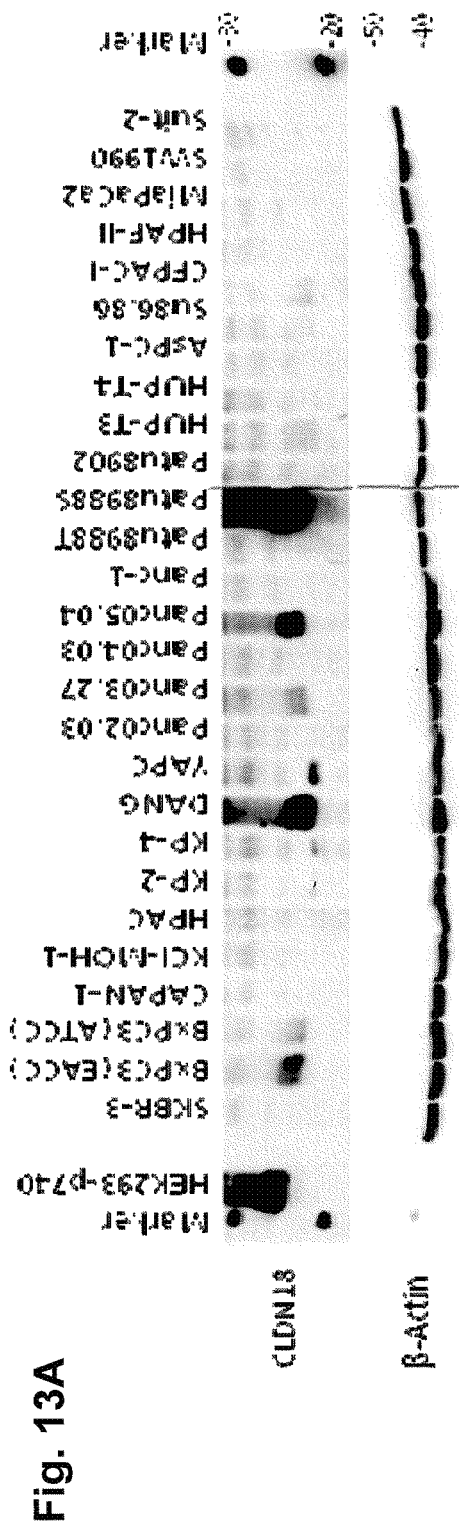
Figure 13B:
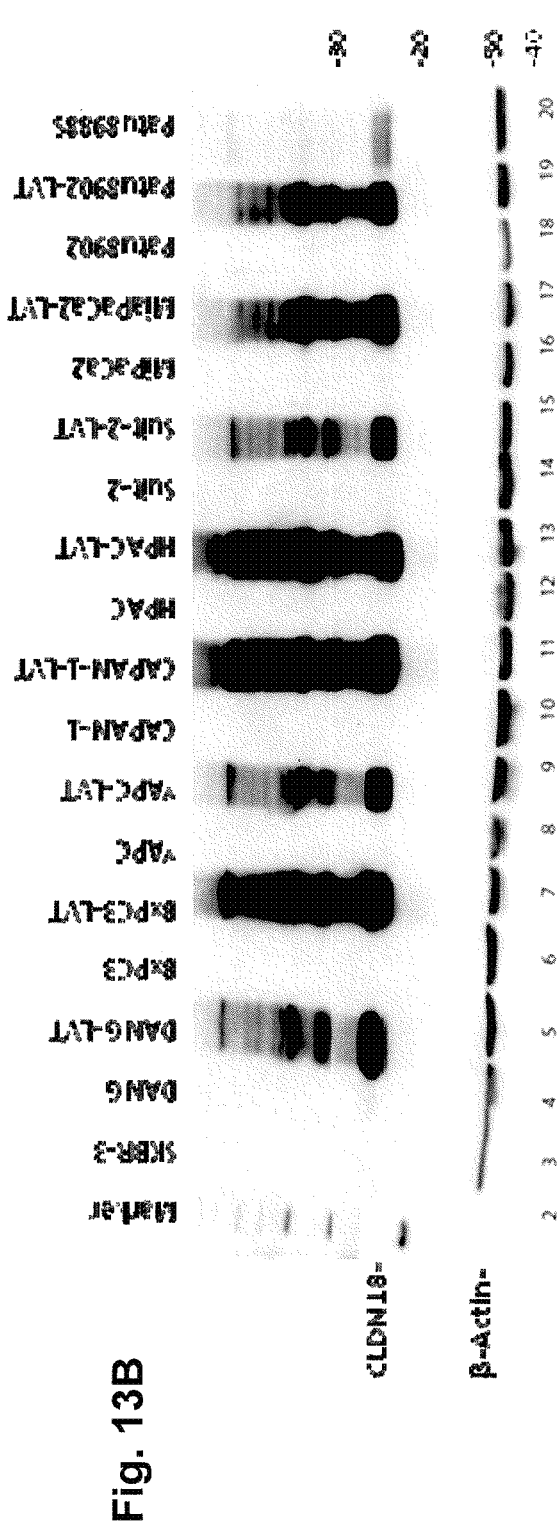

FIGS. 13A and 13B show CLDN18.2 protein levels in cell lysates of pancreatic carcinoma cell lines. Proteins were separated on a 12.5% SDS-PAGE. Western Blot analysis was performed using a CLDN18 antibody detecting the C-terminal of CLDN18.1 and CLDN18.2 (Zymed-MID) and using a loading control antibody detecting β-actin. Exposure times of 140 sec (Pierce SuperSignal West Dura) and 20 sec (Pierce SuperSignal West Pico) were used respectively. FIG. 13A shows detection of CLDN18 in pancreas cell line lysates, the positive control (HEK293-p740) and the negative control cell lysates (SKBR-3). FIG. 13B shows CLDN18.2 expression compared between non-transduced parental cell lysates and lentivirally transduced (LVT) cell line lysates. Patu8988S and SKBR-3 were added as positive and negative control, respectively.

FIGS. 14A, 14B, 14C, 14D, 14E, 14F, 14G, 14H, 14I, 14J, 14K, 14L, 14M, 14N, 14O, 14P, 14Q, 14R and 14S show detection and cellular localization of CLDN18 expression in pancreatic cancer cell lines. Staining of pancreatic cancer cell lines grown on cover slips. Antibody: 35-22A (20× magnification, the exposure time is indicated below each picture) DAPI was used to stain the nuclei (blue). (FIG. 14A: AsPC1; FIG. 14B: BxPC3; FIG. 14C: CFPAC; FIG. 14D: DANG; FIG. 14E: HPAF-II; FIG. 14F: HUP-T3; FIG. 14G: HUP-T4; FIG. 14H: KCl-MOH; FIG. 14I: Panc1; FIG. 14J: Panc05.04; FIG. 14K: Panc02.04; FIG. 14L: Panc04.03; FIG. 14M: Patu8902; FIG. 14N: Patu8988S; FIG. 14O: Su86.86: FIG. 14P: Suit-2; FIG. 14Q: SW-1990; FIG. 14R: YAPC; FIG. 14S: gastric cancer control cell line KATO-III).

FIGS. 15A, 15B, 15C, 15D, 15E, 15F, 15G and 15H show detection and cellular localization of CLDN18 expression in CLDN18.2 transduced pancreatic cancer cell lines. CLDN18 detection in the lentivirally transduced (LVT) pancreatic cancer cell lines using 35-22A antibody after fixation and permeabilization. Alexa488 or Alexa555 labeled secondary antibodies were used for detection. FIG. 15A: BxPC3-LVT; FIG. 15B: CAPAN1-LVT; FIG. 15C: DANG-LVT; FIG. 15D: HPAC-LVT; FIG. 15E: MiaPaCa2-LVT; FIG. 15F: Patu8902-LVT; FIG. 15G: Suit-2-LVT; FIG. 15H: YAPC-LVT.

Figure 16I:
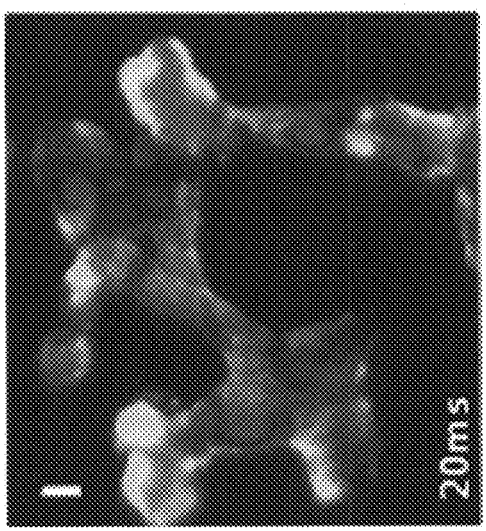
Figure 16L:
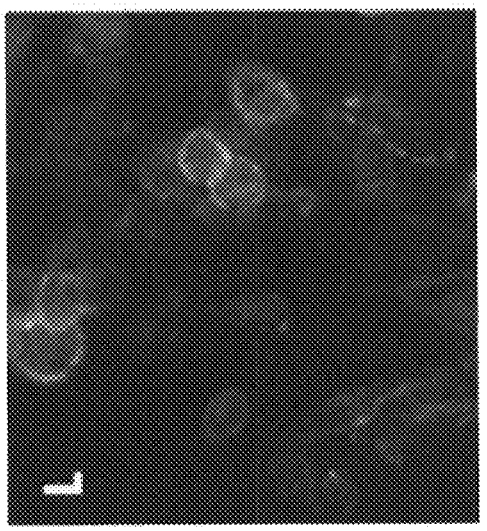
Figure 16H:
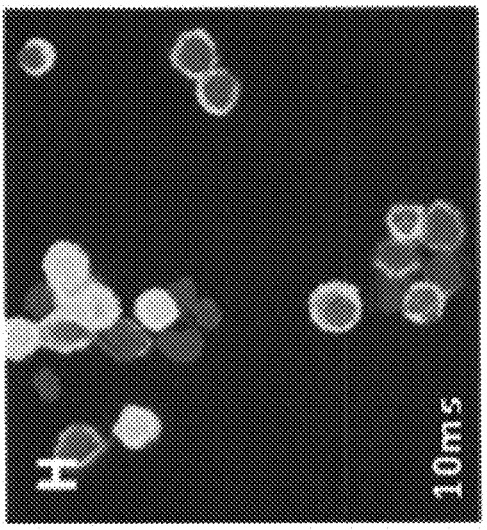
Figure 16K:
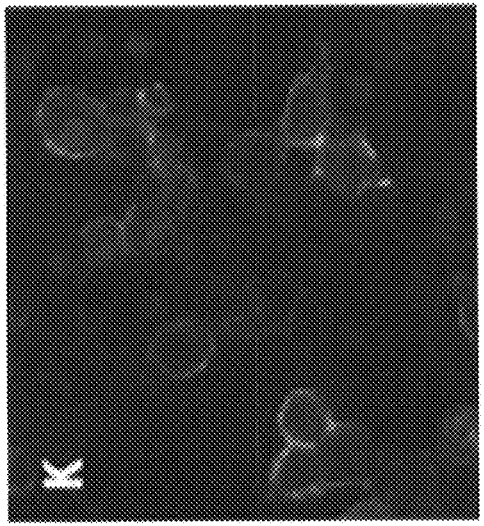
Figure 16G:
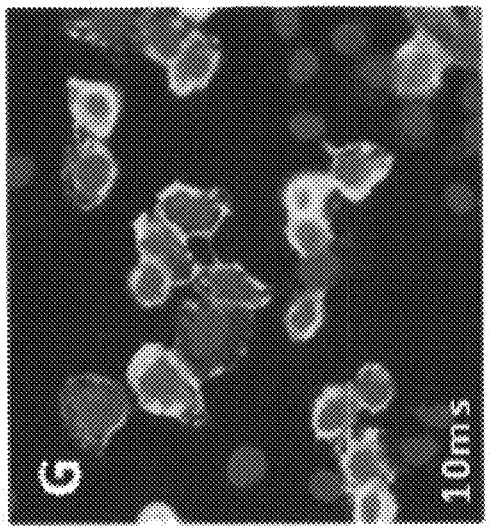
Figure 16J:
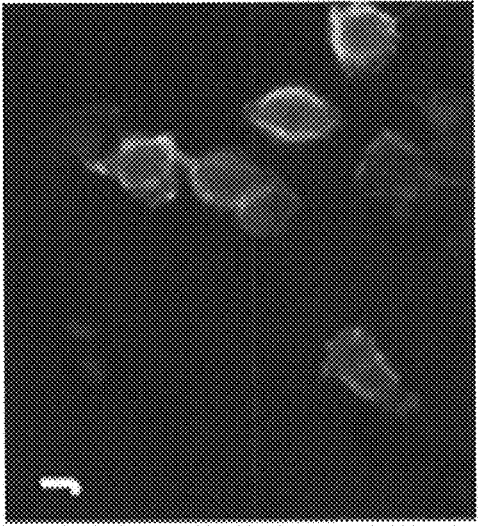

FIGS. 16A, 16B, 16C, 16D, 16E, 16F, 16G, 16H, 16I, 16J, 16K and 16L show binding of IMAB362 to the cell surface of CLDN18.2 positive pancreas CA cell lines (pharmacodynamics). IF analysis of pancreatic cancer cell lines (FIGS. 16A, 16B, 16D and 16E), lentivirally transduced pancreas cell lines (FIGS. 16G-16L) and KATO-III gastric cancer control cells (FIGS. 16C and 16F) expressing CLDN18.2. Cells were stained with IMAB362 under native conditions (FIGS. 16D-16E) and for comparison with 35-22A after fixation and permeabilization of the cells (FIGS. 16A-16C). DAPI was used to stain the nuclei. Exposure times are indicated in each panel. FIG. 16G: BxPC3-LVT; FIG. 16H: CAPAN1-LVT; FIG. 16I: DANG-LVT; FIG. 16J: MiaPaCa2-LVT; FIG. 16K: Patu8902-LVT; FIG. 16L: Suit2-LVT.

FIGS. 17A, 17B, 17C, 17D, 17E, 17F, 17G, 17H, 17J, 17K, 17L and 17M show CLDN18.2 expression in xenograft tumors of different cell lines. Expression of CLDN18.2 in CAPAN1-LVT (FIGS. 17A and 17B), BxPC3-LVT (FIGS. 17C and 17D), PATU8988S-LVT (FIGS. 17E and 17F), MiaPaCa2-LVT (FIGS. 17G and 17H), YAPC-LVT (FIGS. 17J and 17K) and DANG-LVT (FIGS. 17L and 17M) xenograft tumors. Tissue staining was performed with Zymed-MID antibody. Magnification lens 10× (FIGS. 17A, 17C, 17E, 17G, 17J and 17L) and 20× (FIGS. 17B, 17D, 17F, 17H, 17K and 17M).

FIGS. 18A, 18B, 18C, 18D, 18E and 18F show an engraftment check of Suit-2 and MiaPaCa2 pancreatic cancer cell lines. Cells were injected into the tail vein of nude mice. Animals were sacrificed 45 (FIG. 18A), 52 (FIG. 18B), 59 (FIG. 18C) days after Suit-2 (FIGS. 18A-18C) application or 59 (FIG. 18D), 66 (FIG. 18E), 73 (FIG. 18F) days after MiaPaCa2 (FIGS. 18D-18F) injection. Lungs were prepared and stained with MHC class I antibodies (anti-human MHC I, clone EPR1394Y) to detect the human cells in mouse tissues.

Figure 19B:
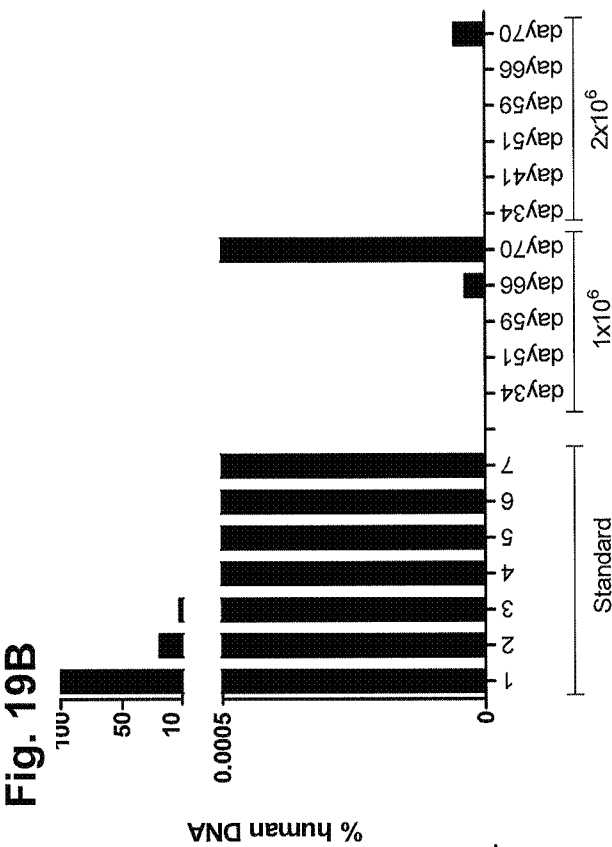
Figure 19A:
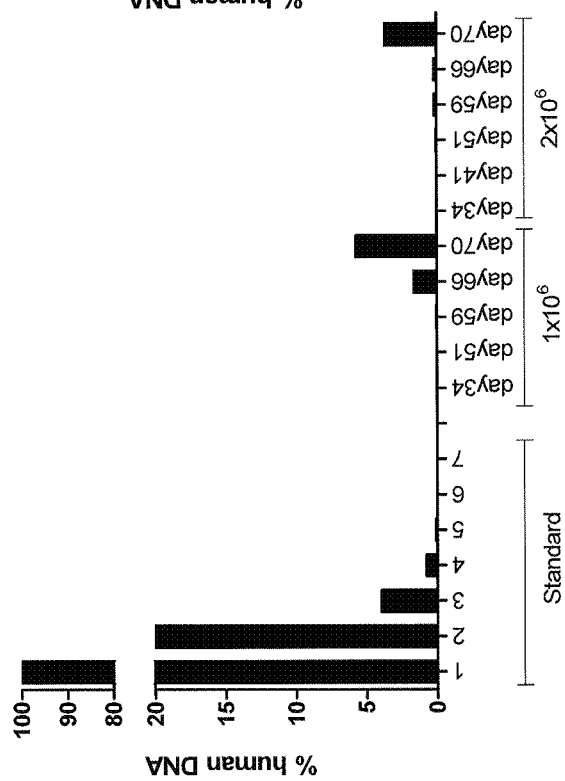

FIGS. 19A and 19B show a metastasis engraftment analysis of Patu8988S. Patu8988S cells were i.v. injected with $1 \times 10^6$ or $2 \times 10^6$ cells in Nu/Nu mice and lungs (FIG. 19A) and livers (FIG. 19B) of the mice were isolated at different time points as indicated below the x-axis. To calculate the % of human DNA present in each tissue preparation, a standard curve was prepared by mixing human and mouse DNA and preparing 7×5-fold dilutions resulting in 100% (1)-0.0064% (7) human DNA.

FIGS. 20A, 20B, 20C, 20D, 20E, 20F, 20G and 20H show an IHC analysis of Patu8988S metastasis in mouse lung tissues. Mice injected in their tail veins with Patu8988S cells were sacrificed at different time points (FIGS. 20A-20D=70 days, FIGS. 20E-20H=86 days) and lung tissues were isolated and stained with an MHC-I (EPR1394Y) antibody (FIGS. 20A, 20B, 20E and 20F) diluted 1:1000 or with anti-Claudin18 (Zymed-Mid) (FIGS. 20C, 20D, 20G and 20H) at 0.2 µg/ml. Magnifications: FIGS. 20A, 20C, 20E and 20G=10× and FIGS. 20B, 20D, 20F and 20H=20×.

Figure 21:
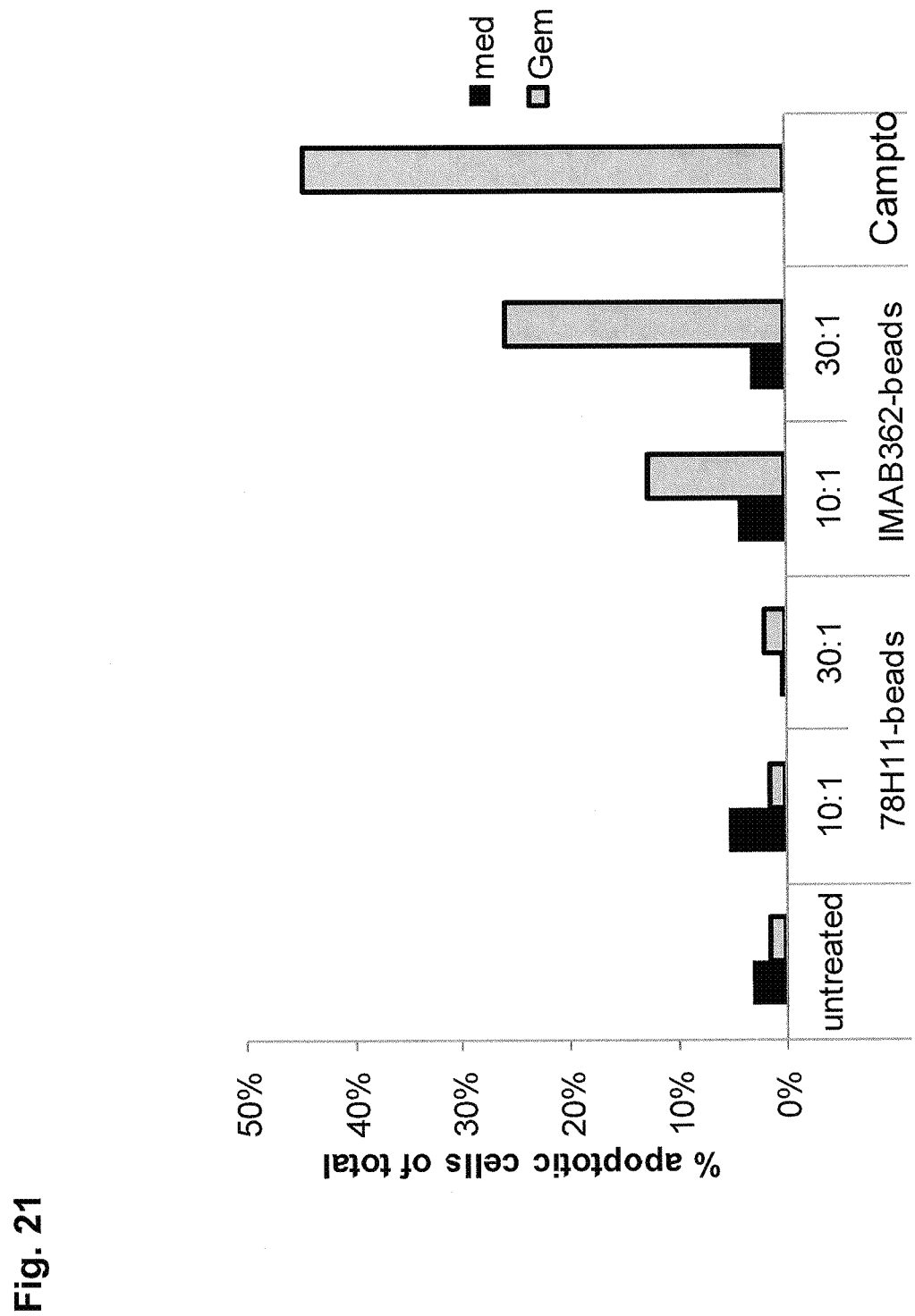

FIG. 21 shows an IMAB362 mediated apoptosis of gemcitabine treated pancreas tumor cells. Apoptosis induced by cross-linking of CLDN18.2 on BxPC3-CLDN18 after 48 hours. BxPC3-CLDN18 were cultivated in medium or medium+100 ng/ml gemcitabine. Apoptotic cell fraction of mononuclear cells were shifted. Similar shifts were obtained by incubation of tumor cells with Camptotecin.

Figure 22A:
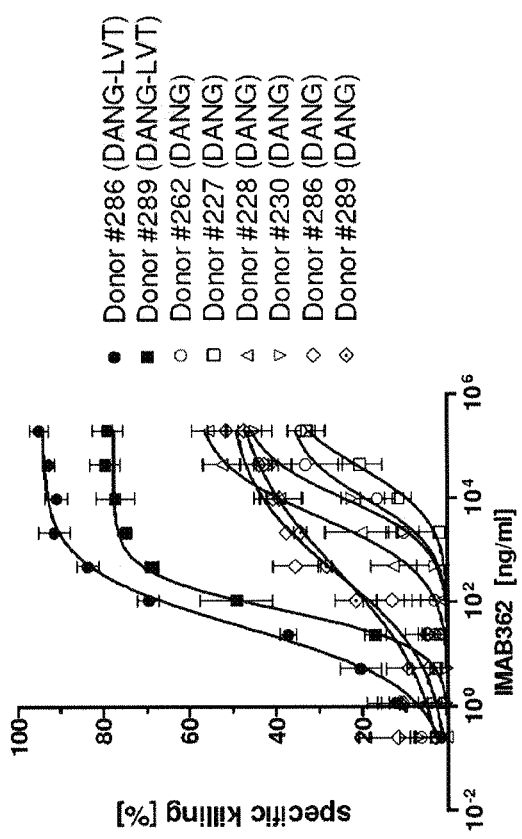
Figure 22B:
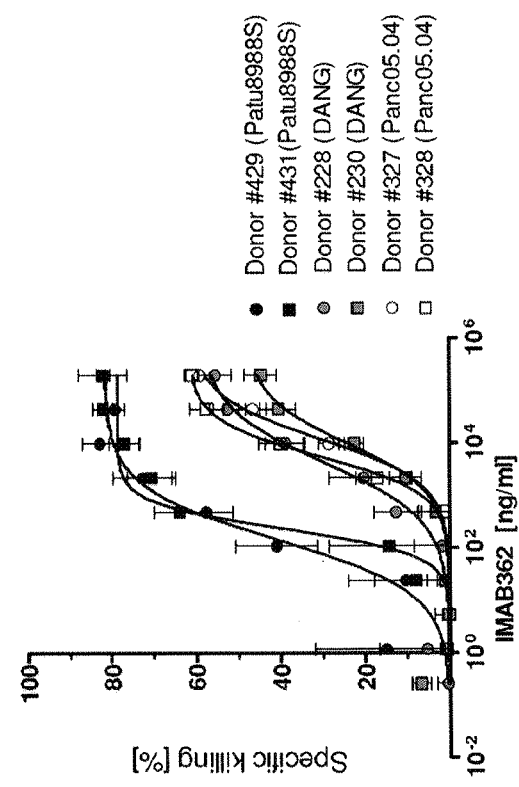
Figure 22C:
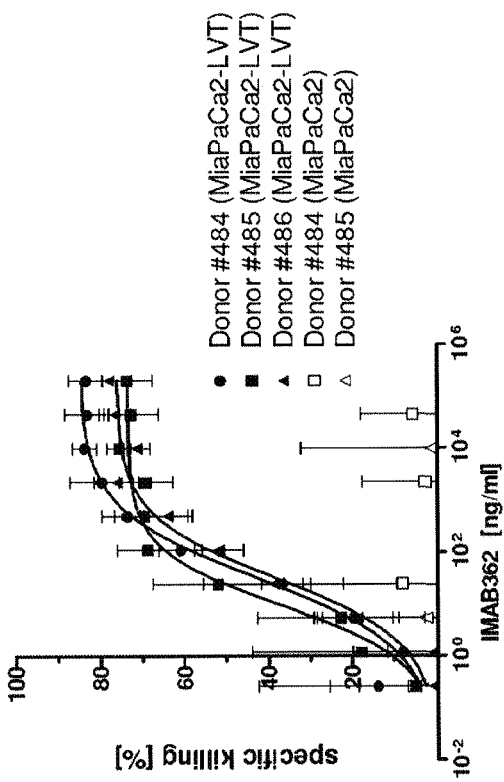
Figure 22D:
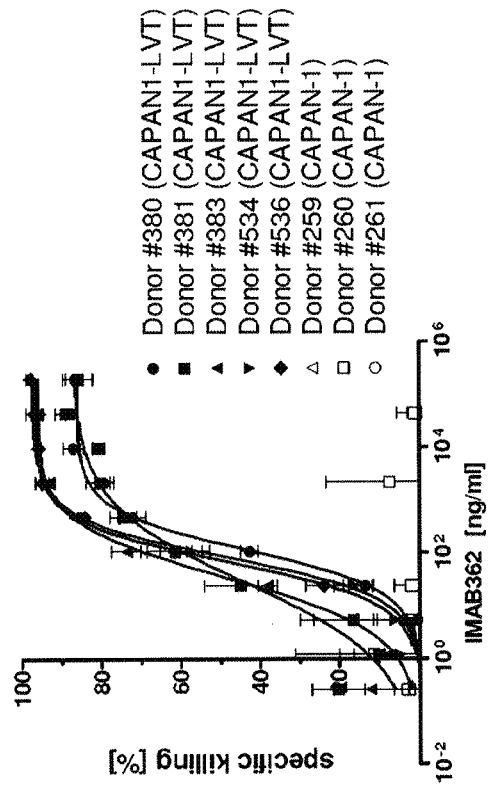
Figure 22E:
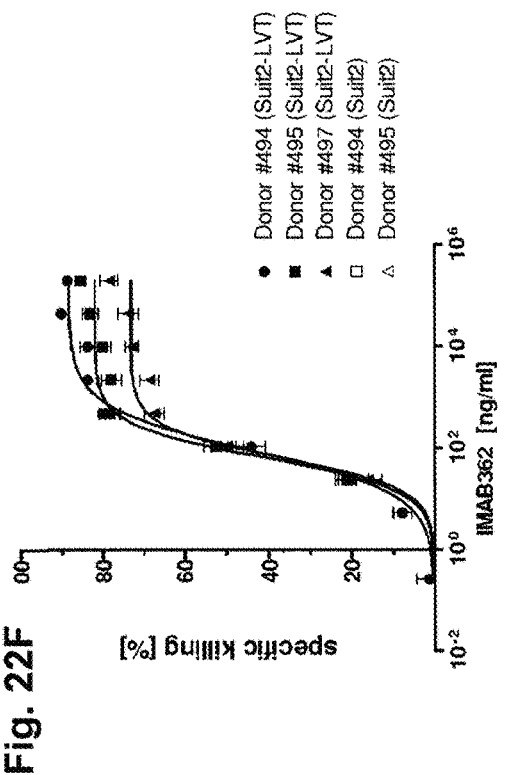
Figure 22F:
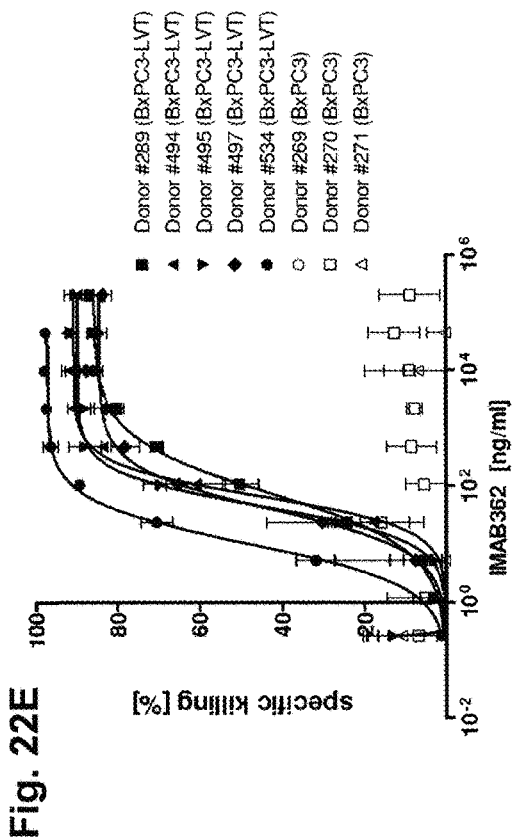
Figure 22G:
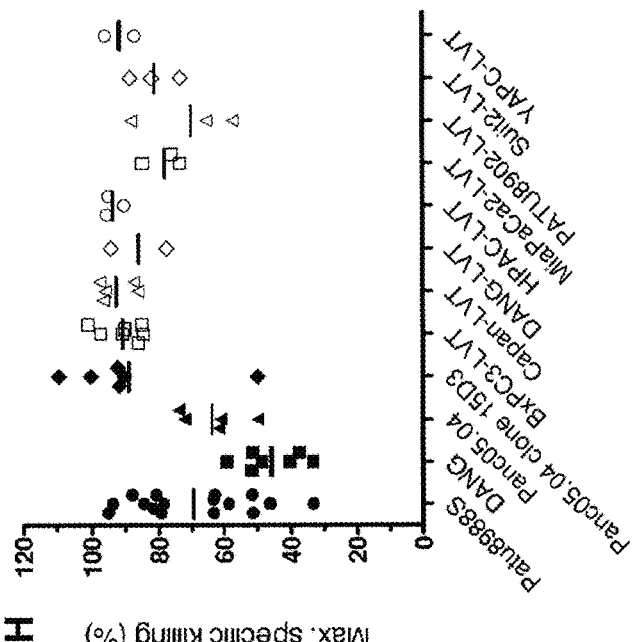

FIGS. 22A, 22B, 22C, 22D, 22E, 22F, 22G and 22H show potency of IMAB362-induced ADCC activity on pancreatic cancer cells. FIG. 22A shows ADCC performed with CLDN18.2 positive pancreatic cancer cell lines using PBMCs of different donors. FIGS. 22B-22F show ADCC performed with LVT pancreas cell lines ectopically expressing CLDN18.2 and the corresponding parental cells. FIG. 22G shows a dot plot.

Figures 23A, 23B:
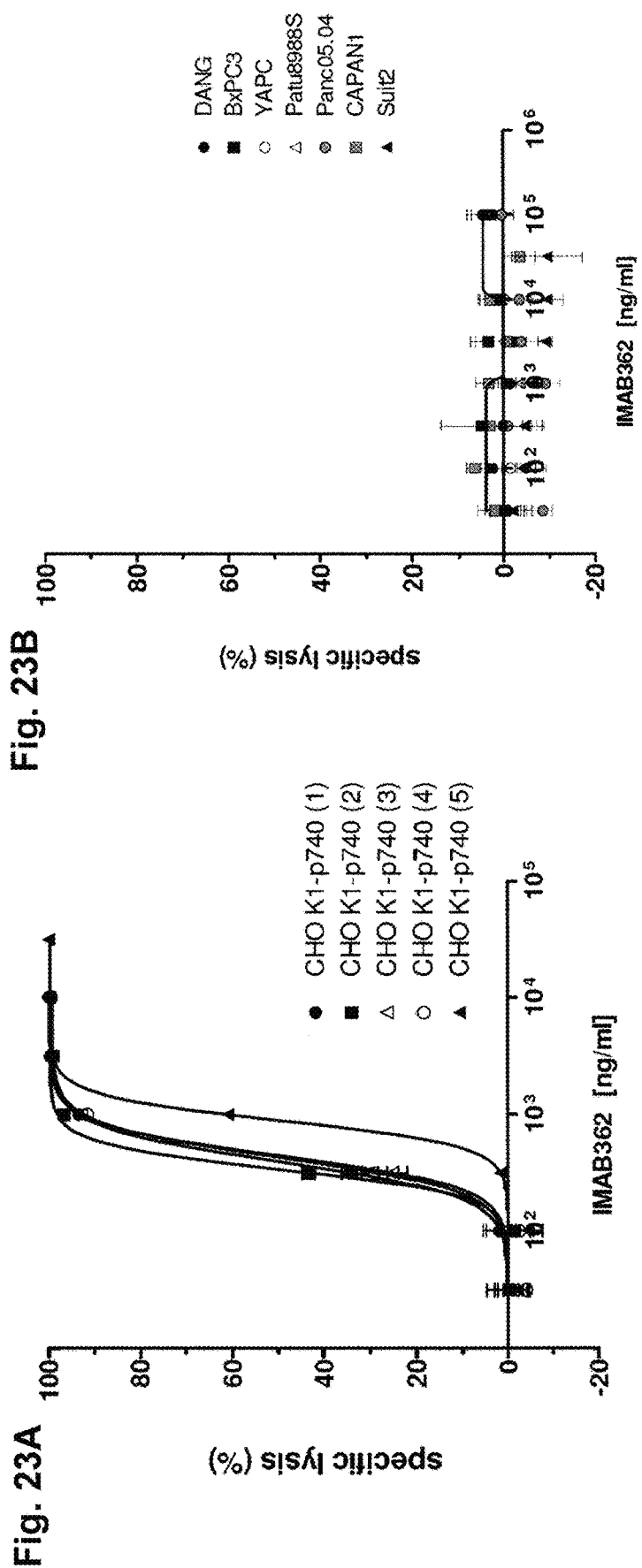
Figure 23E:
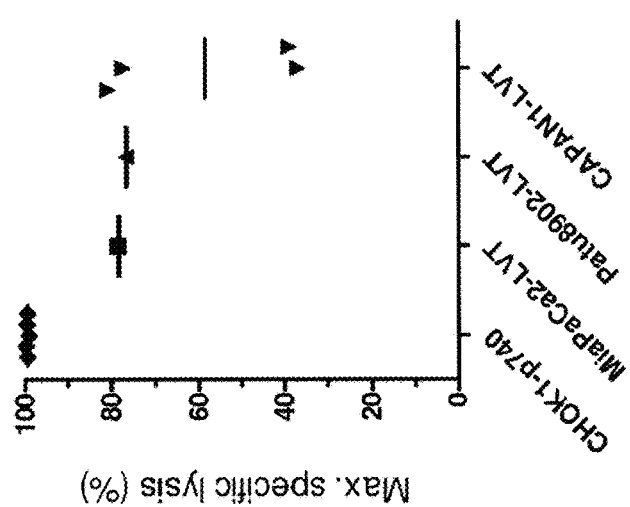
Figure 23D:
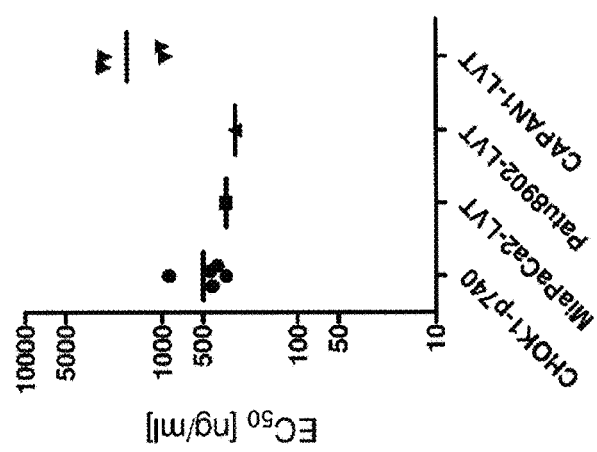
Figure 23C:
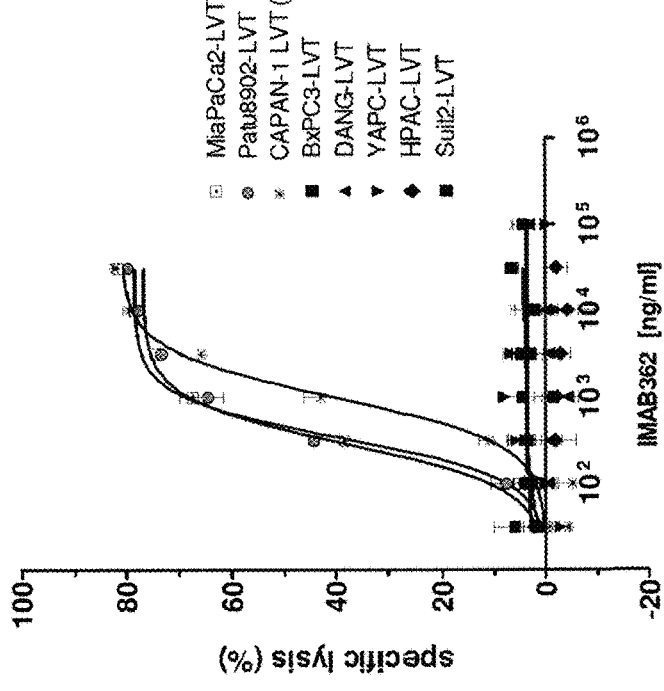

FIGS. 23A, 23B, 23C, 23D and 23E show potency of IMAB362-induced CDC activity on pancreatic cancer cells. FIG. 23A shows a CDC performed with healthy human serum pool as complement source, IMAB362 and CLDN18.2 positive pancreas CDOK1-p740 control cells in 4 independent experiments. FIG. 23B shows a CDC performed with CLDN18.2 positive (Patu8988S, DANG, Panc05.04) and CLDN18.2 negative (CAPAN1, Suit2, BxPC3, YAPC) pancreas cell lines. FIG. 23C shows a CDC with ectopically expressing LVT cell lines. FIG. 23D shows a dot plot showing IMAB362 concentration causing half maximum lysis rates (EC50) on pancreatic cancer cell lines. FIG. 23E shows maximum killing rates obtained with IMAB362 on pancreatic cancer cell lines.

Figure 24A:
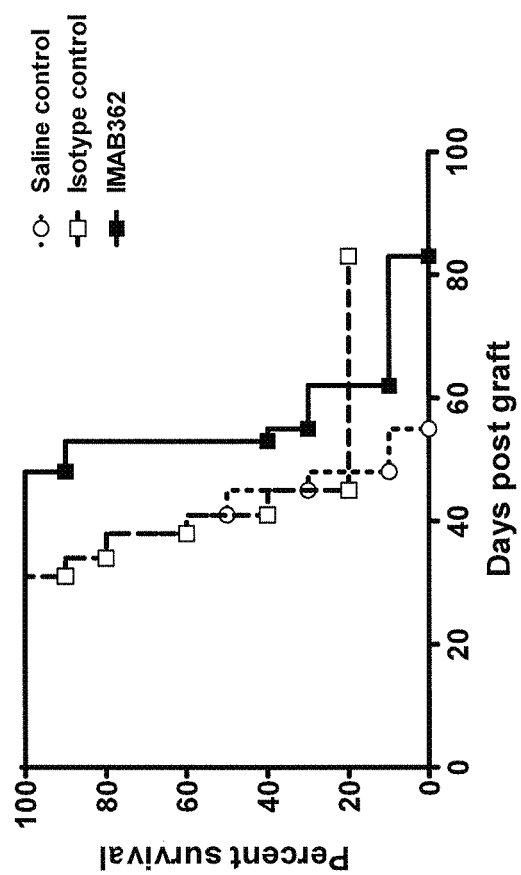
Figure 24B:
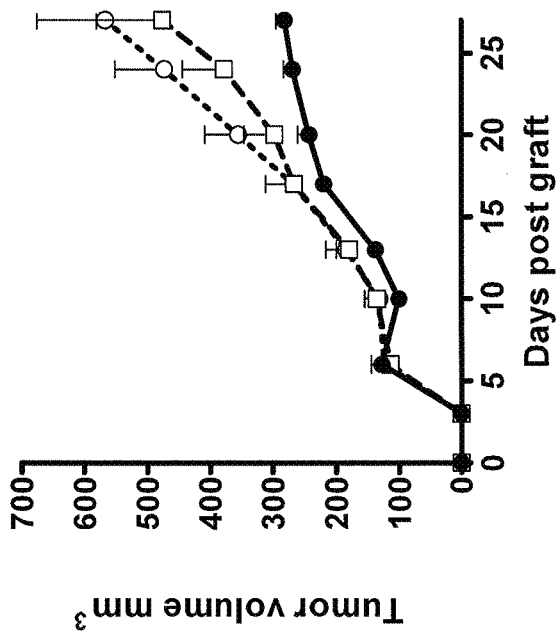

FIGS. 24A and 24B show the effect of IMAB362 treatment on subcutaneous MiaPaCa2-LVT xenografts. MiaPaCa2-LVT xenograft tumors were inoculated by injection of 1e7 MiaPaCa2-LVT cells subcutaneous into the flank of 15 female Hsd:Athymic Nude-Foxn1nu mice for each treatment group. On the third day after tumor cell injection, treatment was initiated with 200 µg IMAB362 or controls respectively. Treatment was continued semi-weekly with alternating i.p. and i.v. injection until animals were sacrificed. FIG. 24A shows the effect of IMAB362 treatment on tumor growth. The size of s.c. tumors was measured twice weekly (mean+SEM). FIG. 24B shows Kaplan-Meier survival plots. Mice were sacrificed when tumor reached a volume of 1400 mm$^3$ or tumor became ulcerous.

Figure 25A:
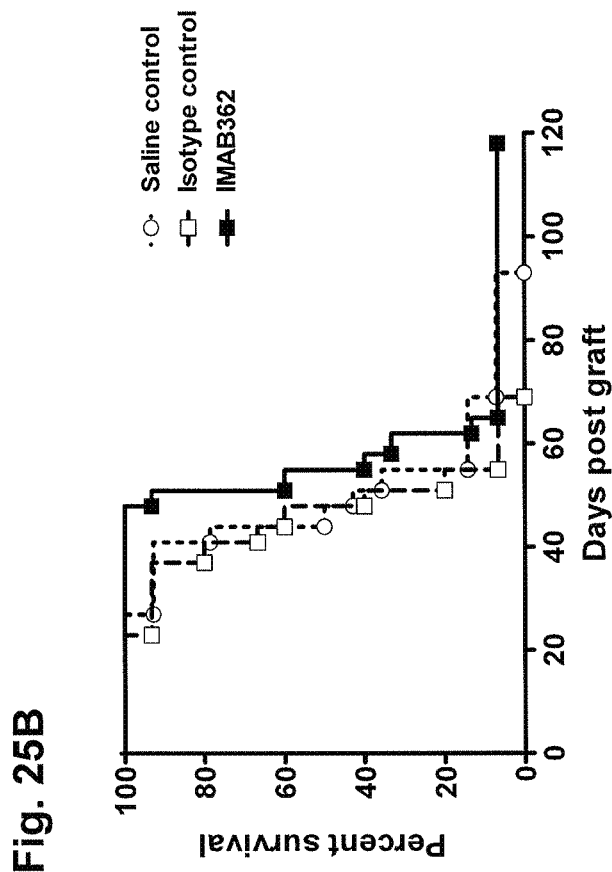
Figure 25B:
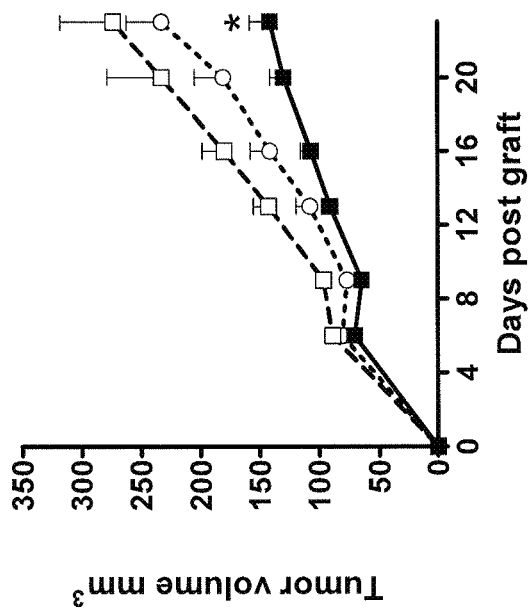

FIGS. 25A and 25B show IMAB362 treatment of subcutaneous BxPC3-LVT xenografts. BxPC3-LVT xenograft tumors were inoculated by injection of 1e7 BxPC3-LVT cells subcutaneous into the flank of 15 female Hsd:Athymic Nude-Foxn1nu mice for each treatment group. On the third day after tumor cell injection, treatment was initiated with 200 µg IMAB362 or controls respectively. Treatment was continued semi-weekly with alternating i.p. and i.v. injection until animals were sacrificed. FIG. 25A shows the effect of IMAB362 treatment on tumor growth. The size of s.c. tumors was measured twice weekly (mean+SEM, *p<0.05). FIG. 25B shows Kaplan-Meier survival plots. Mice were sacrificed, when tumor reached a volume of 1400 mm$^3$ or tumor became ulcerous.

Figure 26A:
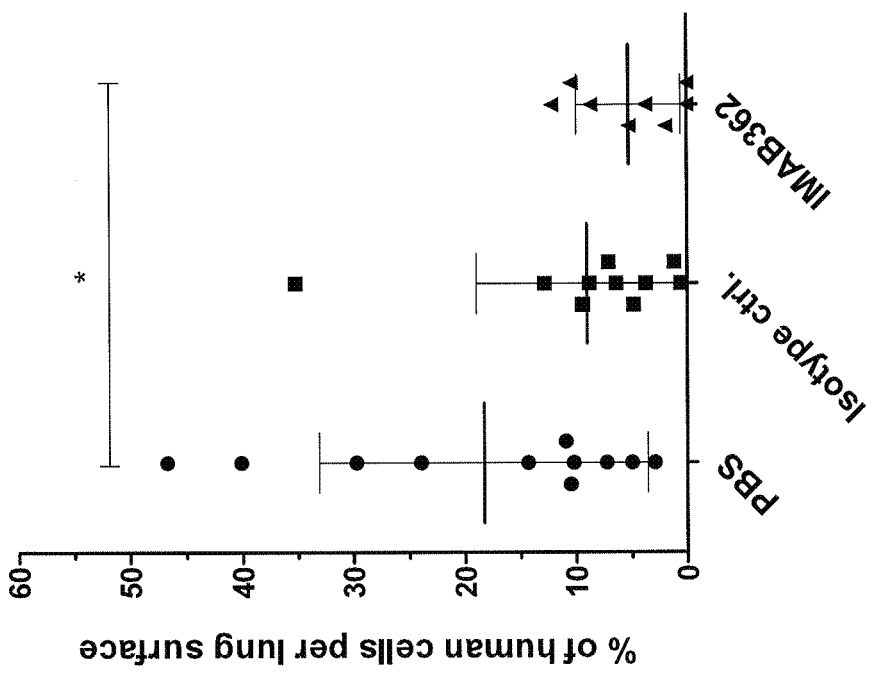
Figure 26B:
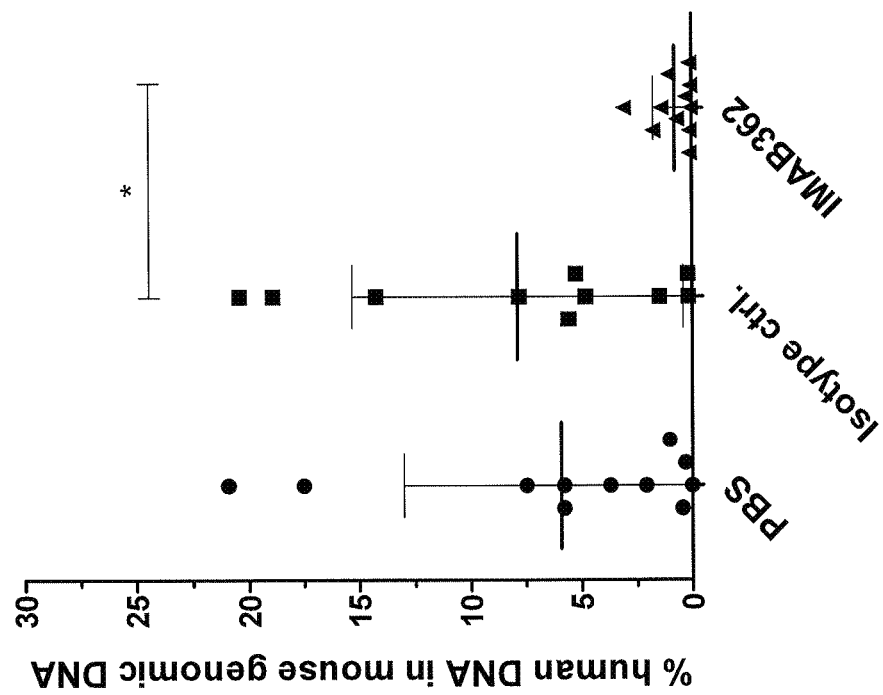

FIGS. 26A and 26B show the effect of IMAB362 treatment on growth of Suit2-LVT pancreas metastasis. 2×10$^6$ Suit2-LVT tumor cells were injected intravenously into the tail vein of 12 female Hsd:Athymic Nude-Foxn1nu mice per treatment group. On the third day after tumor cell injection, treatments were initiated with 200 µg IMAB362, 200 µg isotype control or with an equal volume of PBS. Animals were sacrificed on day 42 post graft. FIG. 26A shows a qPCR analysis (mean of 2-4 reactions per sample) determining the percentage of human DNA present in the mouse lung samples. FIG. 26B shows the percentage of human cells covering the mouse lung surface was determined by planimetry. Human cells were immunohistochemically stained in tissue sections with anti-human MHC-class I antibodies. *p<0.05 (Kruskal-Wallis test). Error bars: mean±SD.

Figure 27B:
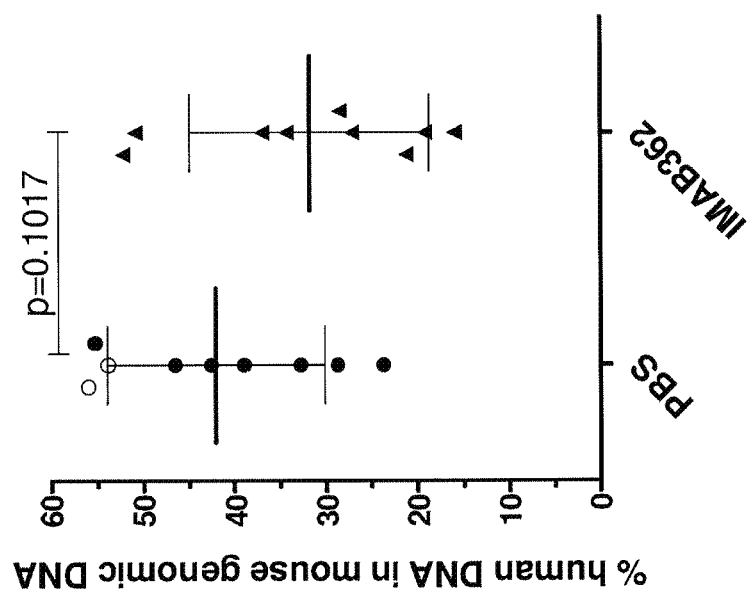
Figure 27A:
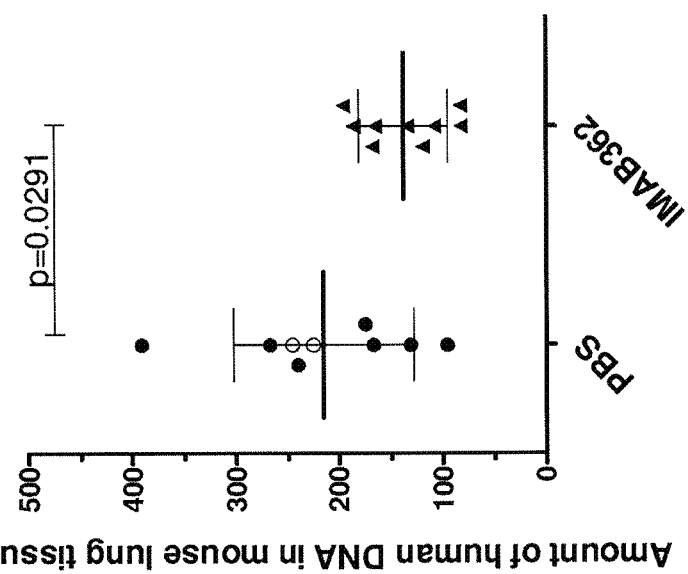
Figure 27C:
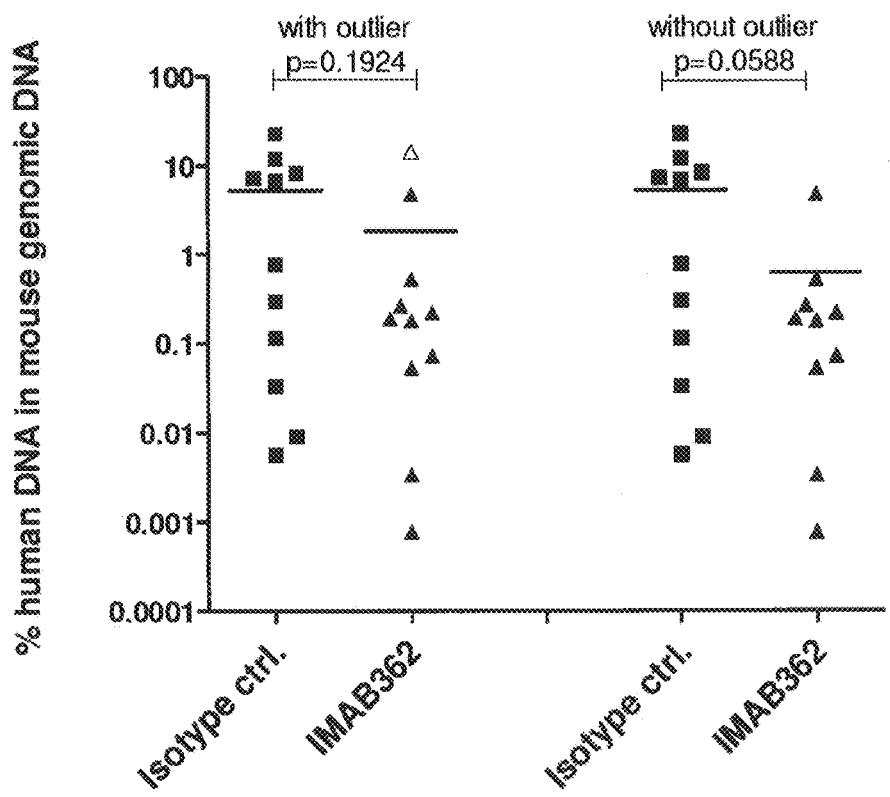
Figure 27D:
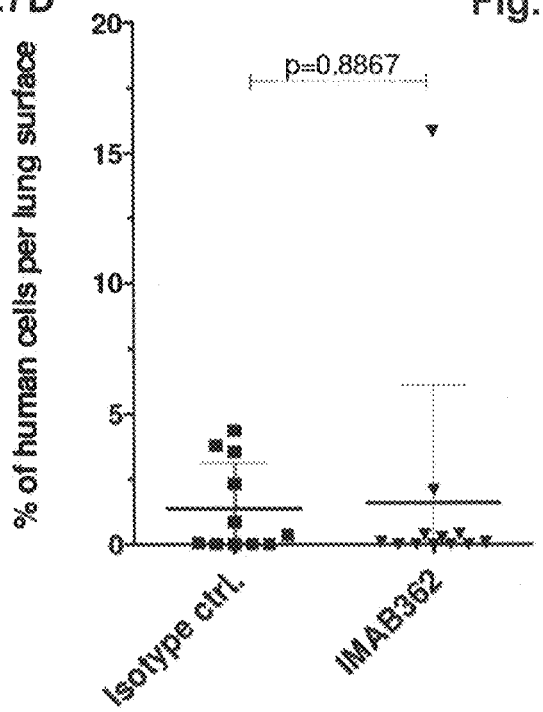
Figure 27E:
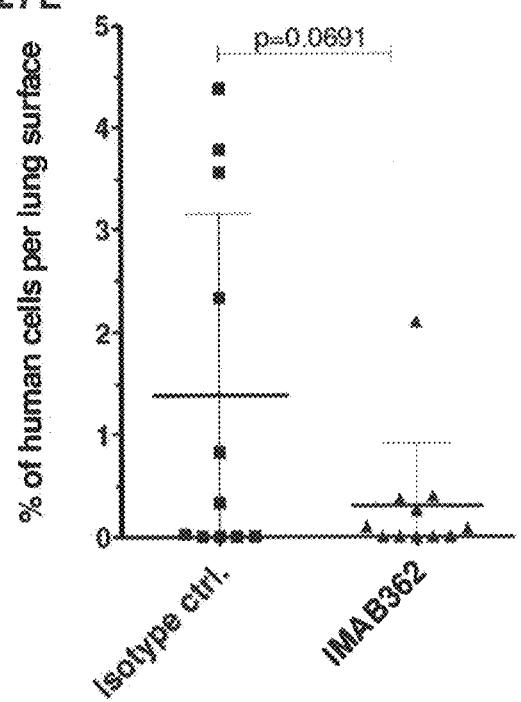

FIGS. 27A, 27B, 27C, 27D and 27E show Q-PCR and IHC analyses of Patu8988S lung metastasis. 2×10$^6$ Patu8988S cells were injected per mouse. Animals were sacrificed after 65 days. Open circles: mice sacrificed after 63 days. FIG. 27A shows mice that were treated with 200 µg IMAB362 semi-weekly or saline control. Amount of human DNA (ng) detected in with Q-PCR, which was calculated from the Ct values. FIG. 27B shows a Q-PCR experiment repeat as described in Figure A. Here the percentage of human DNA present in mouse DNA was calculated from the Ct values. FIG. 27C shows mice that were treated with IMAB362 and isotype control antibody (rituximab). The percentage of human DNA present in the mouse lungs was calculated from the Ct values. For the IMAB362 group, one outlier was detected (open triangle). The significance is indicated by including or excluding the outlier values. (FIGS. 27D and 27E) same experiment as in FIG. 27C. Here surface of the metastasis was determined using the Image J program. Dot plots show the significance of IMAB362 inhibition including (FIG. 27D) or excluding (FIG. 27E) the outlier value. P-value: unpaired t-test. Error bars±SD.

Figure 28:
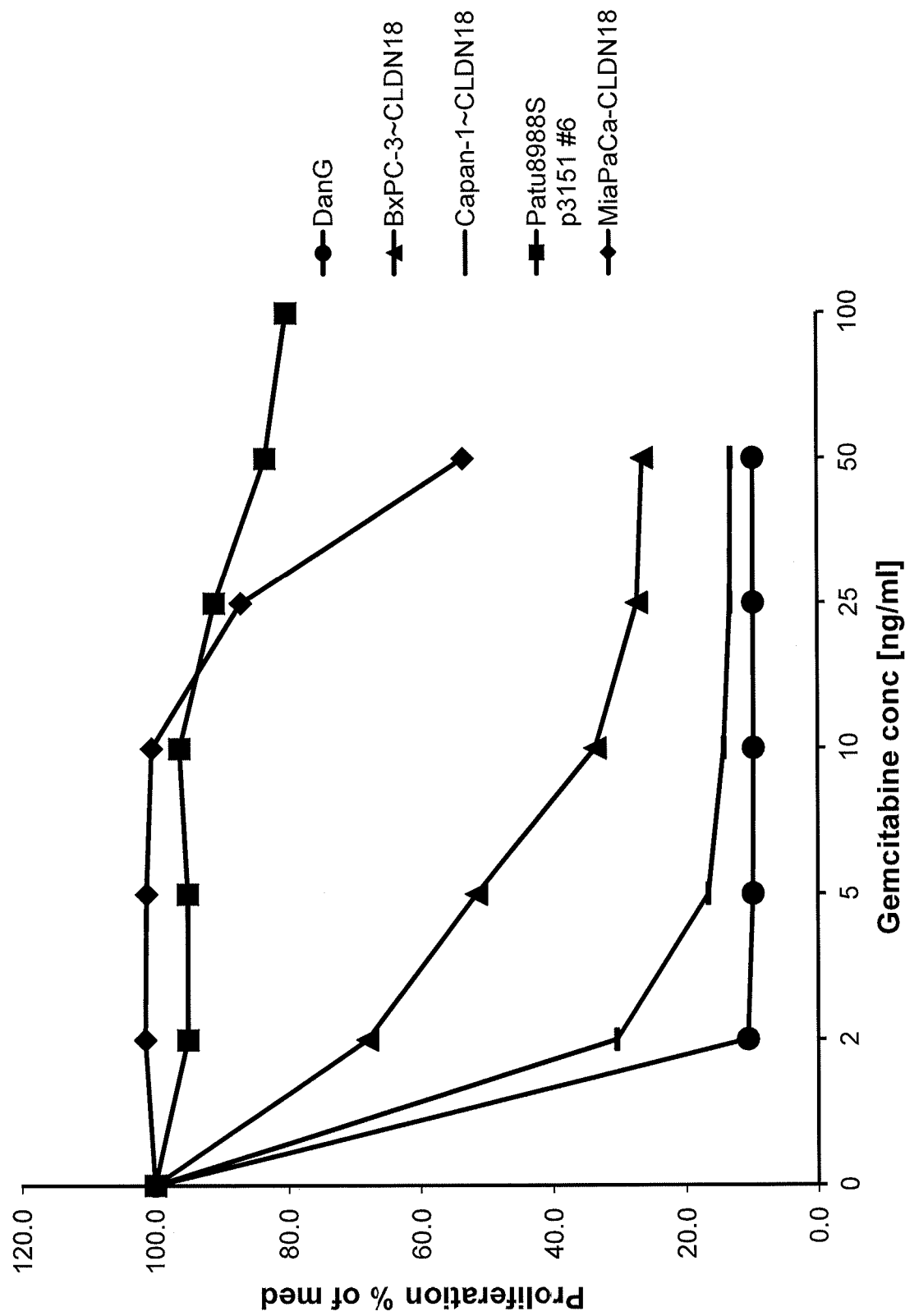

FIG. 28 shows dose response curves for gemcitabine. Pancreas cancer cell lines show very different sensitivity for gemcitabine. Cell lines were exposed for 4 days with different concentrations of gemcitabine and inhibition of proliferation analysed via viability assay.

Figure 29:
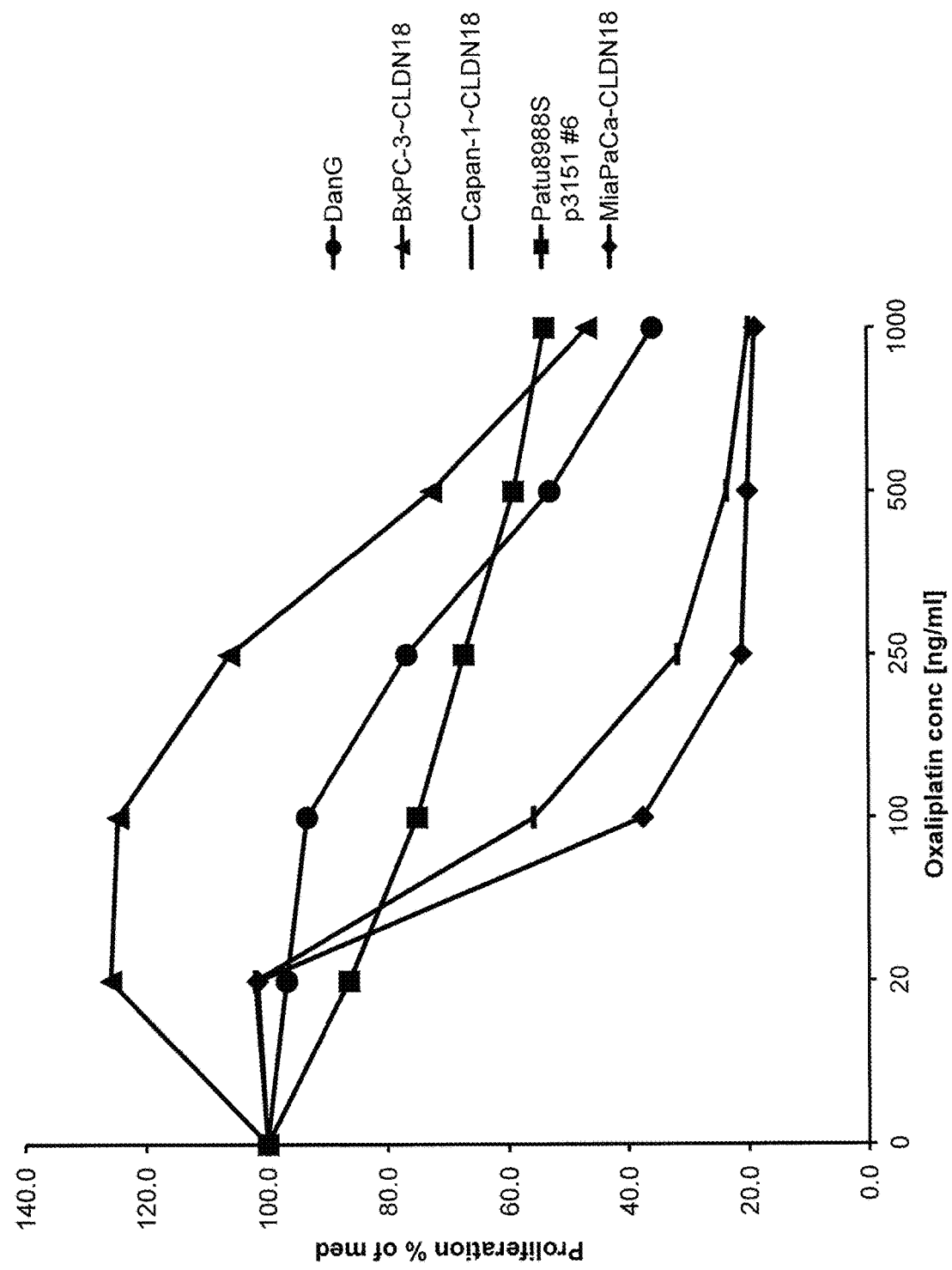

FIG. 29 shows dose response curves for oxaliplatin. Pancreas cancer cell lines show very different sensitivity for oxaliplatin. Cell lines were exposed for 4 days with different concentrations of oxaliplatin and inhibition of proliferation analysed via viability assay.

Figure 30B:
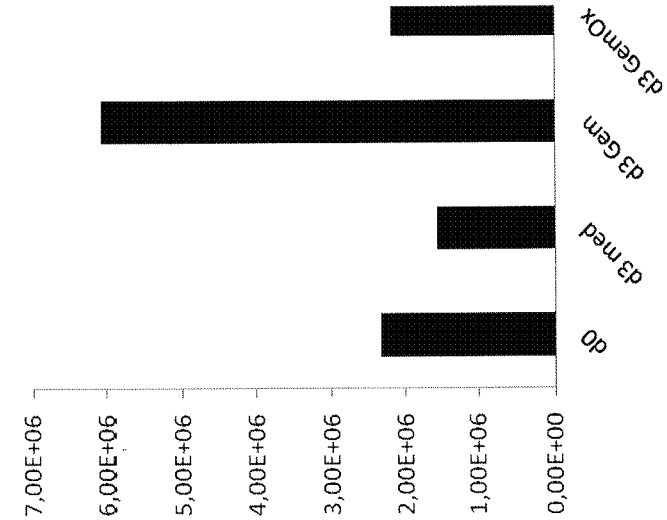
Figure 30A:
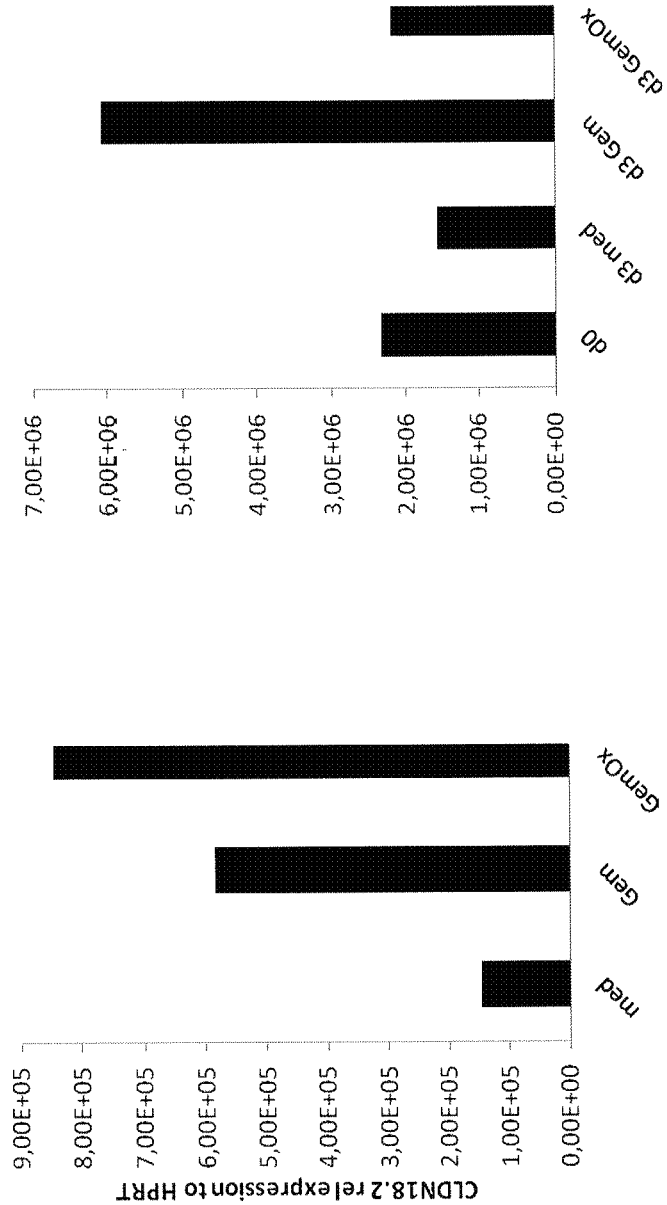

FIGS. 30A and 30B show the effect of treatment wih chemotherapeutic agents on CLDN18.2 expression (RNA). RNA of untreated, Gem (1 ng/ml) or GemOx (Gem 1 ng/ml+Ox 10 ng/ml) pretreated DANG (2 days) (FIG. 30A) or Patu8988S (FIG. 30B) cells 3 days pretreated with Gem (10 ng/ml or GemOx (Gem 10 ng/ml+Ox 100 ng/ml). RNA was converted to cDNA. CLDN18.2 transcript level was analyzed in quantitative real-time PCR. Results are shown as relative units in comparison to transcript level of house keeping gene HPRT.

Figure 31:
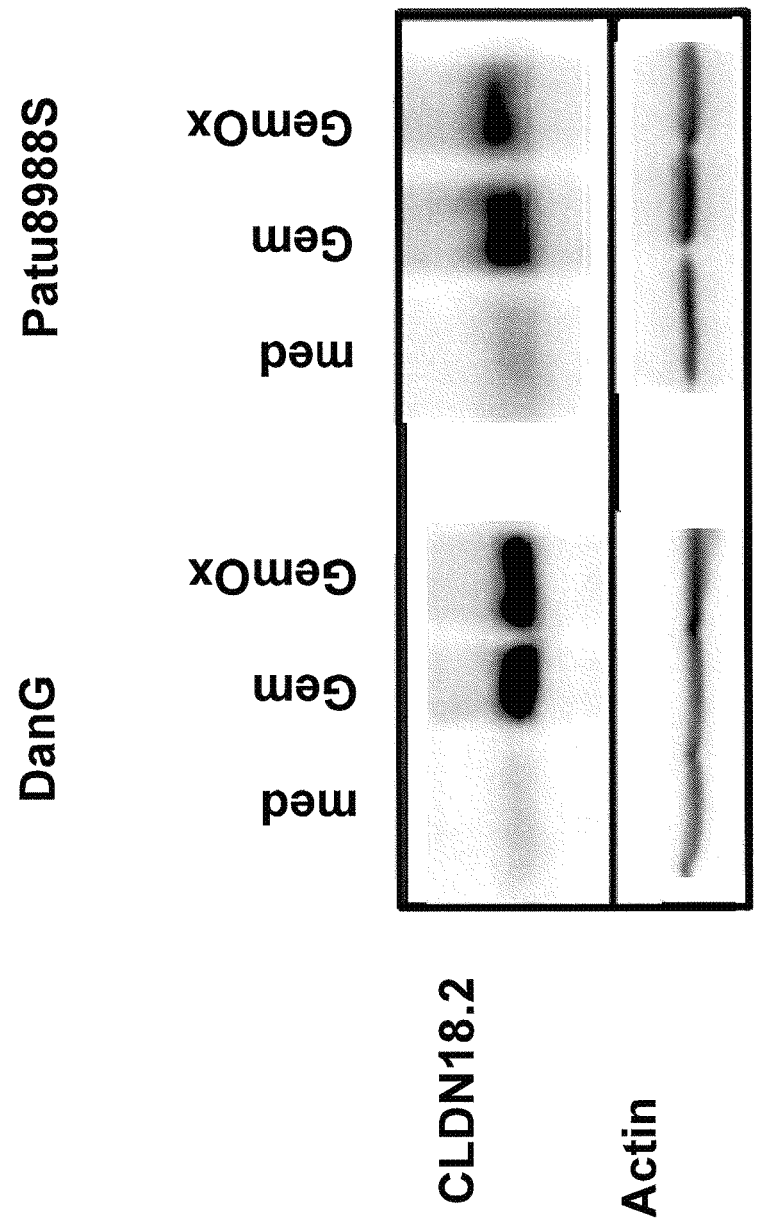

FIG. 31 shows effect of chemotherapy on CLDN18.2 protein level in pancreatic carcinoma cells. Protein from total cell lysates of untreated (med), Gem (1 ng/ml) or GemOx (Gem 1 ng/ml+Ox 10 ng/ml) pretreated DANG (A) or Patu8988S (B) cells were analyzed for CLDN18.2 expression detected with Zymed C-term polyclonal antisera. Actin was used to show equal loading of proteins.

Figure 32:
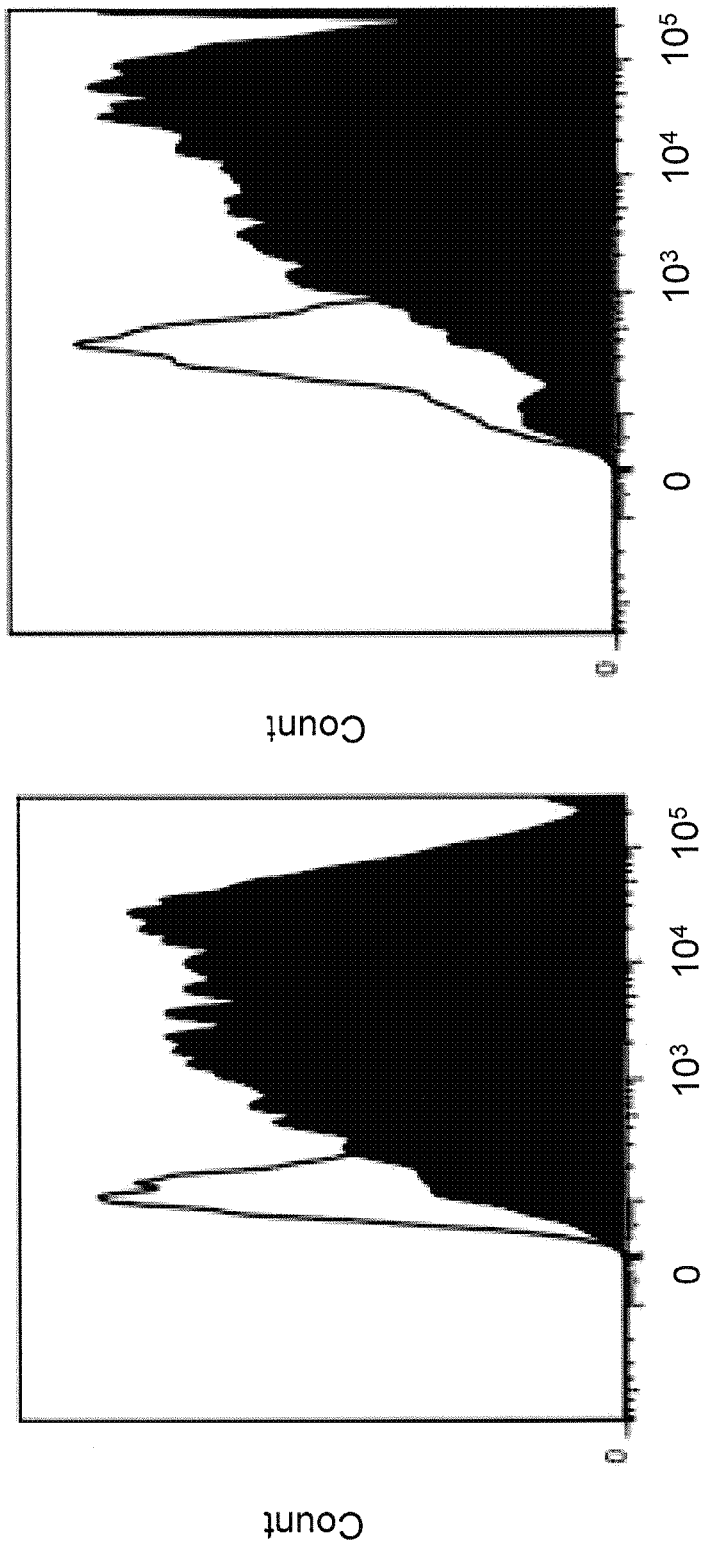

FIG. 32 shows FACS analysis of CLDN18.2 cell surface expression. CLDN18 expression (filled histogram) of medium cultivated (left) and Gem treated (right) Patu8988S is shown in an overlay compared to Isotyp Co. Patu8988S are treated with gemcitabine (10 ng/ml)) for 3 days.

Figure 33B:
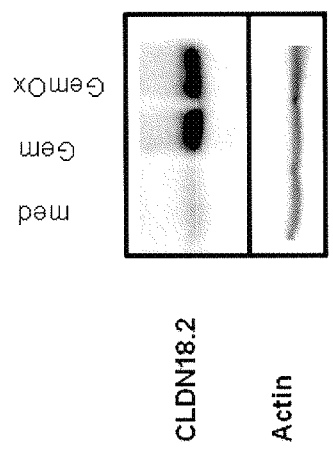
Figure 33A:
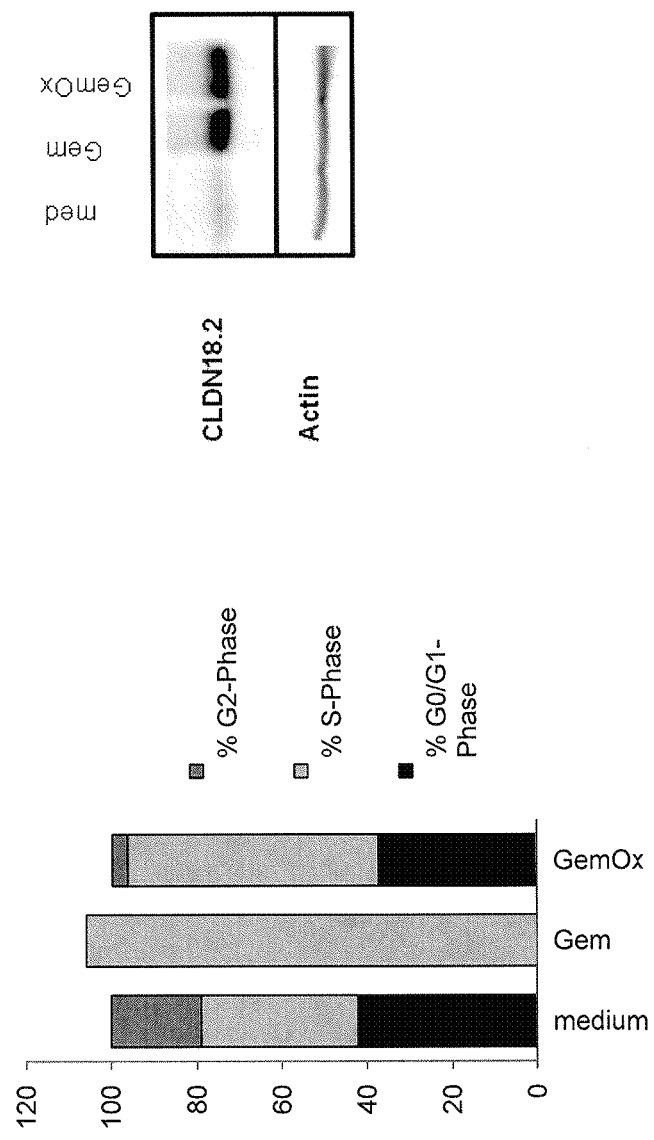

FIGS. 33A and 33B shows cell cycle analyses of DANG cells treated or not with either gemcitabine (Gem; 2 ng/ml) or gemcitabine+oxaliplatin (GemOx; 1 ng/ml+10 ng/ml) for two days. (33A) Gemcitabine treatment leads to cell cycle arrest of cells in S-Phase. The area of each bar is divided to indicate the percentage of cells in G0/G1, S and G2 phase. (33B) Western blot analyses showed upregulation of CLDN18 after treatment with Gem.

FIGS. 34A, 34B and 34C show influence of gemcitabine on cell cycle (FIG. 34A) and CLDN18.2 expression (FIGS. 34B and 34C) in Patu8988S cells. Patu8988S cells were either untreated or treated with gemcitabine (10 ng/ml) for 2 days. In FIG. 34A, the area of each bar is divided to indicate the percentage of cells in G0/G1, S and G2 phase. The density of CLDN18.2 (x-axis) was plotted against the cell number (y-axis). In FIG. 34B, CLDN18.2 expression of untreated (dotted line) versus Gem treated (solid line) is blotted. In FIG. 34C, CLDN18.2 expression of gem treated Patu8988S cells in G0/G1 phase (dotted line) versus cells in S phase (solid line) is shown.

Figure 35B:
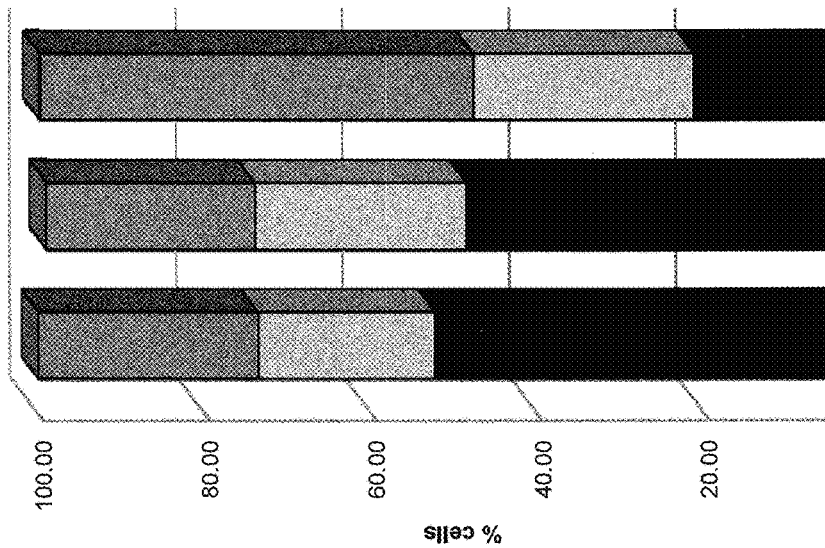

FIGS. 35A, 35B, 35C, 35D and 35E show effect of chemotherapy on gastric cancer cells. Cultivation of Kato III cells for 96 hours leads to a cell cycle arrest in the G0/G1-phase (FIGS. 35A and 35C) and downregulation of CLDN18.2 (FIG. 35D). Cytostatic compounds resulting in a cell cycle arrest in different phases of the cell cycle stabilize CLDN18.2-expression (FIG. 35D).

Figure 36:
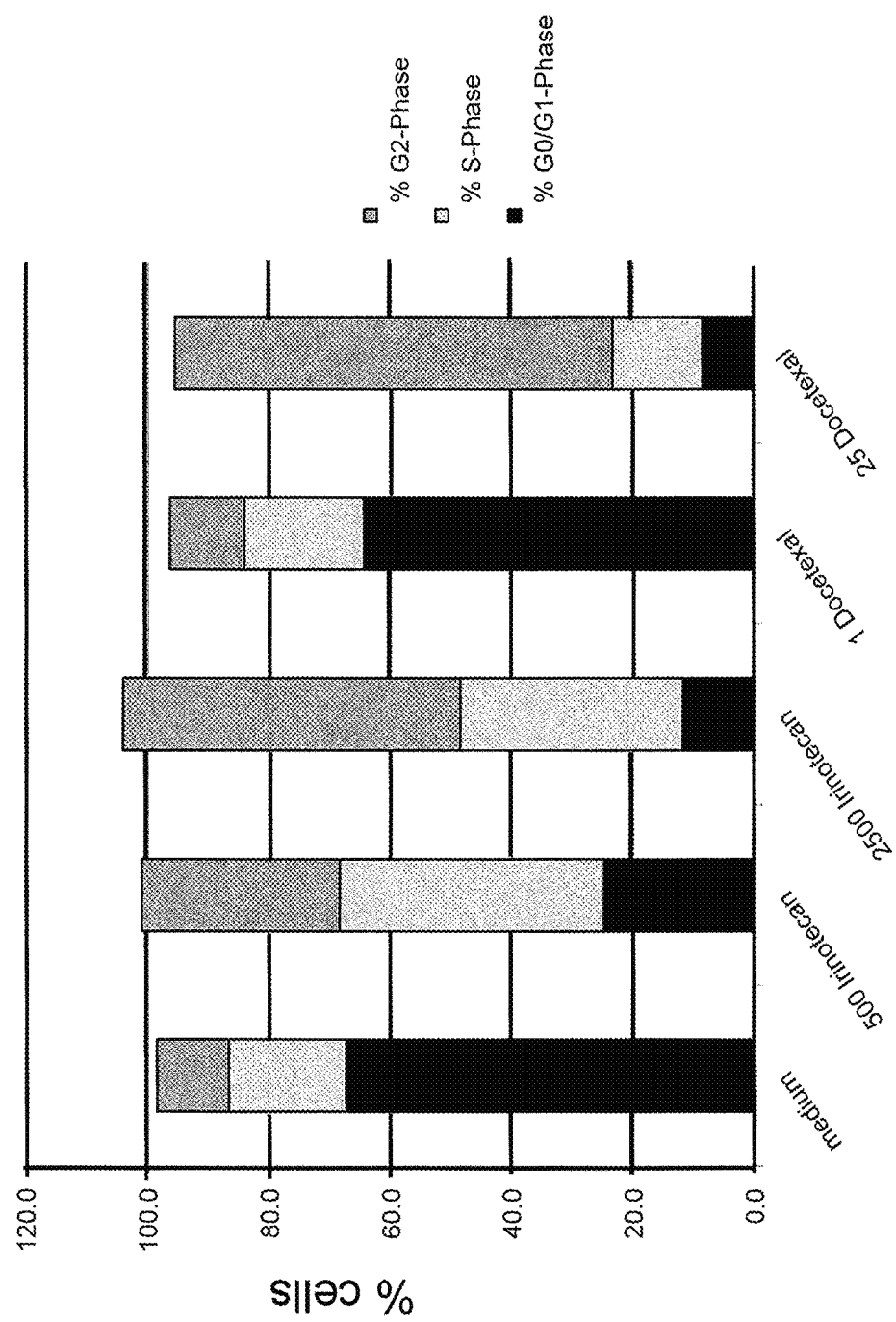

FIG. 36 shows effect of chemotherapy on gastric cancer cells. Cytostatic compounds resulting in a cell cycle arrest in different phases of the cell cycle (S/G2-phase (Irinotecan) or G2-phase (Docetaxel)). The area of each bar is divided to indicate the percentage of cells in G0/G1, S and G2 phase.

Figure 37A:
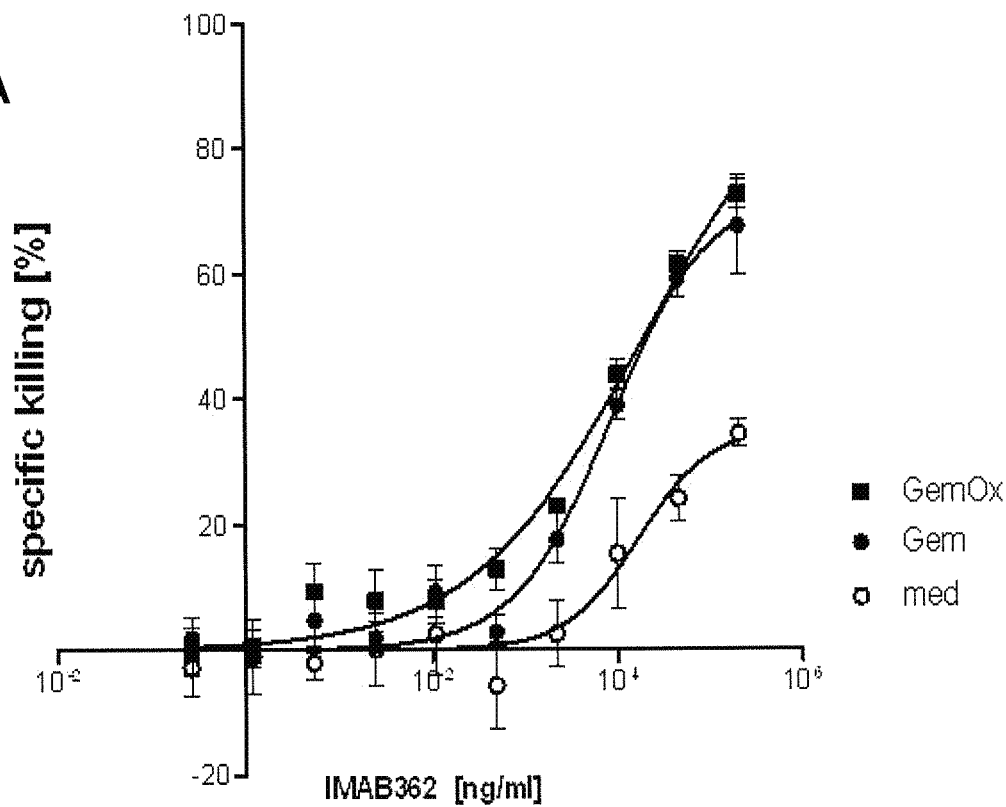
Figure 37B:
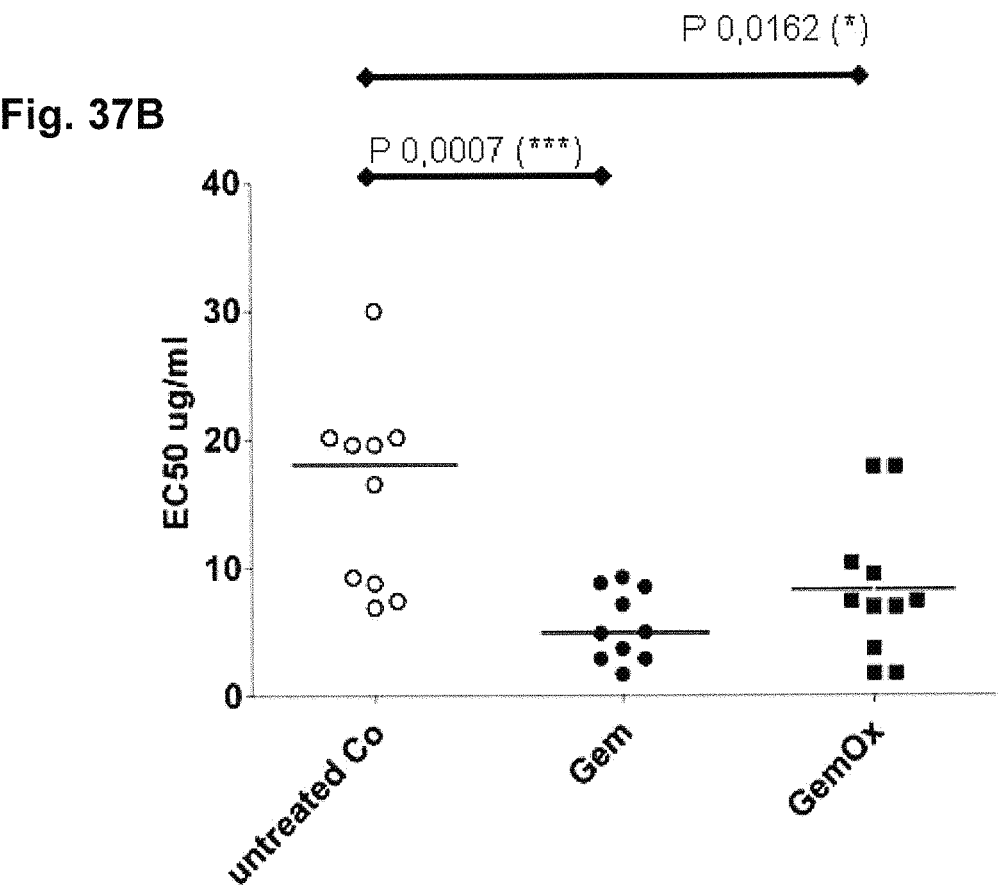

FIGS. 37A and 37B show dose response curves for IMAB362 mediated ADCC after chemotherapy treatment of DANG. FIG. 37A shows dose response curves of one representary donor after pretreatment of DANG pancreas cancer cells with Gem or GemOx for 40 h. FIG. 37B shows EC50 values (mean) for IMAB362 mediated ADCC. P-values: unpaired t-test.

Figure 38A:
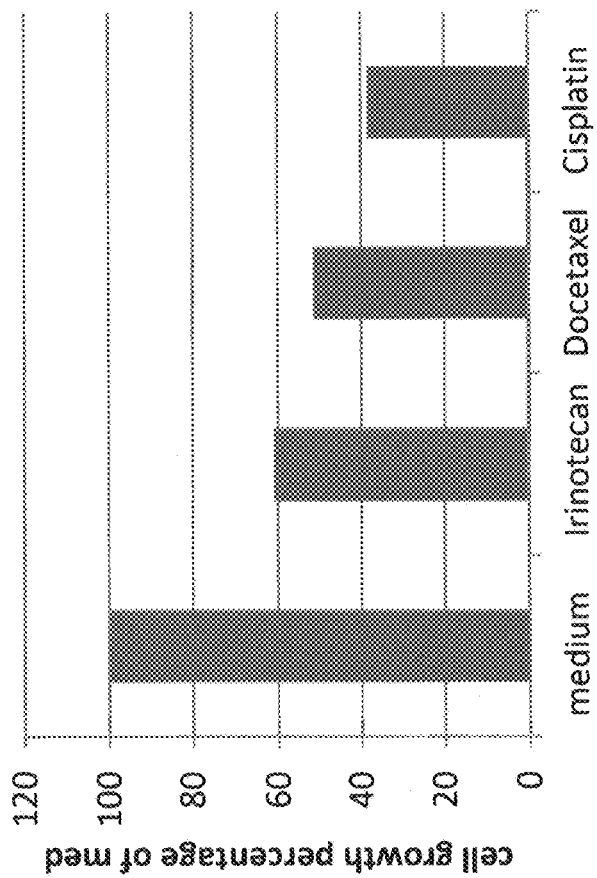
Figure 38B:
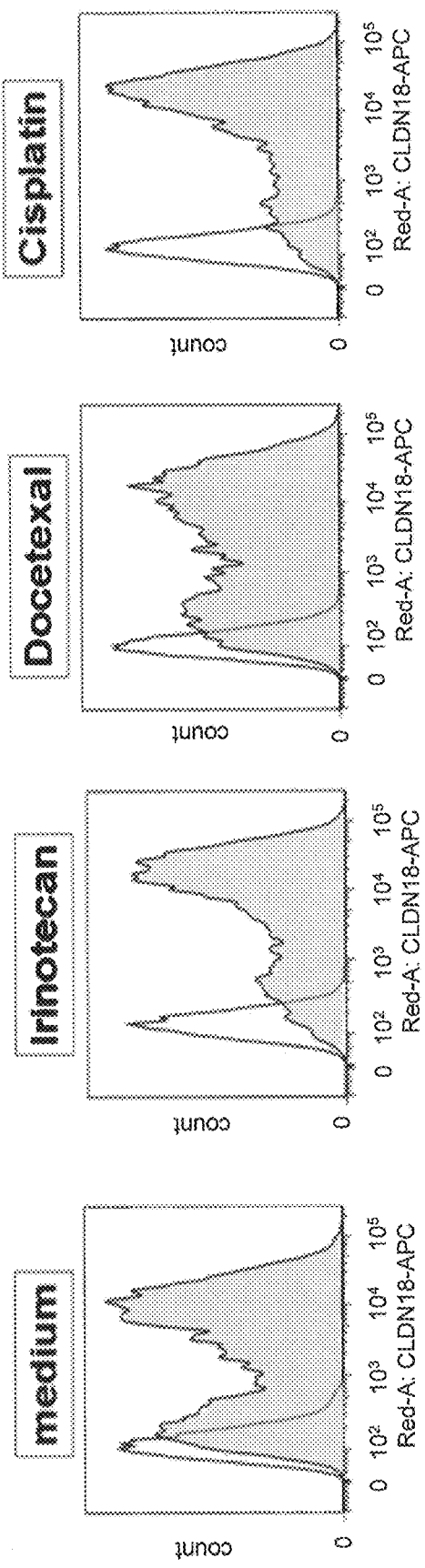
Figure 38D:
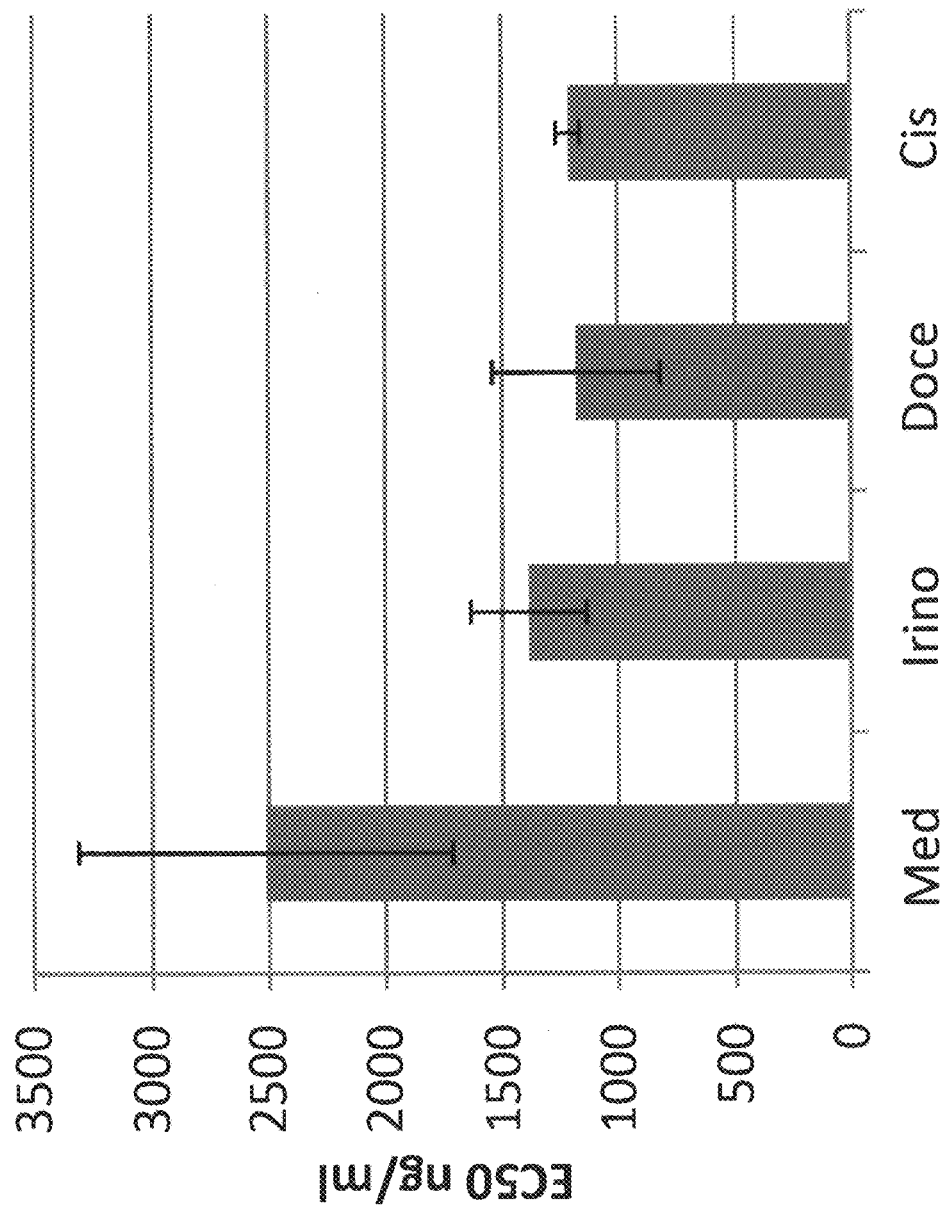

FIGS. 38A, 38B, 38C and 38D show effect of chemotherapy on gastric cancer cells. In FIG. 38A, cells treated with Irinotecan, Docetaxel or Cisplatin exhibit a lower level of viable cells compared to medium cultivated target cells. In FIG. 38B, CLDN18.2 expression in cells treated with Irinotecan, Docetaxel or Cisplatin is increased compared to medium cultivated cells. In FIGS. 38C and 38D, treatment of cells with Irinotecan, Docetaxel or Cisplatin augments the potency of IMAB362 to induce ADCC.

Figure 39:
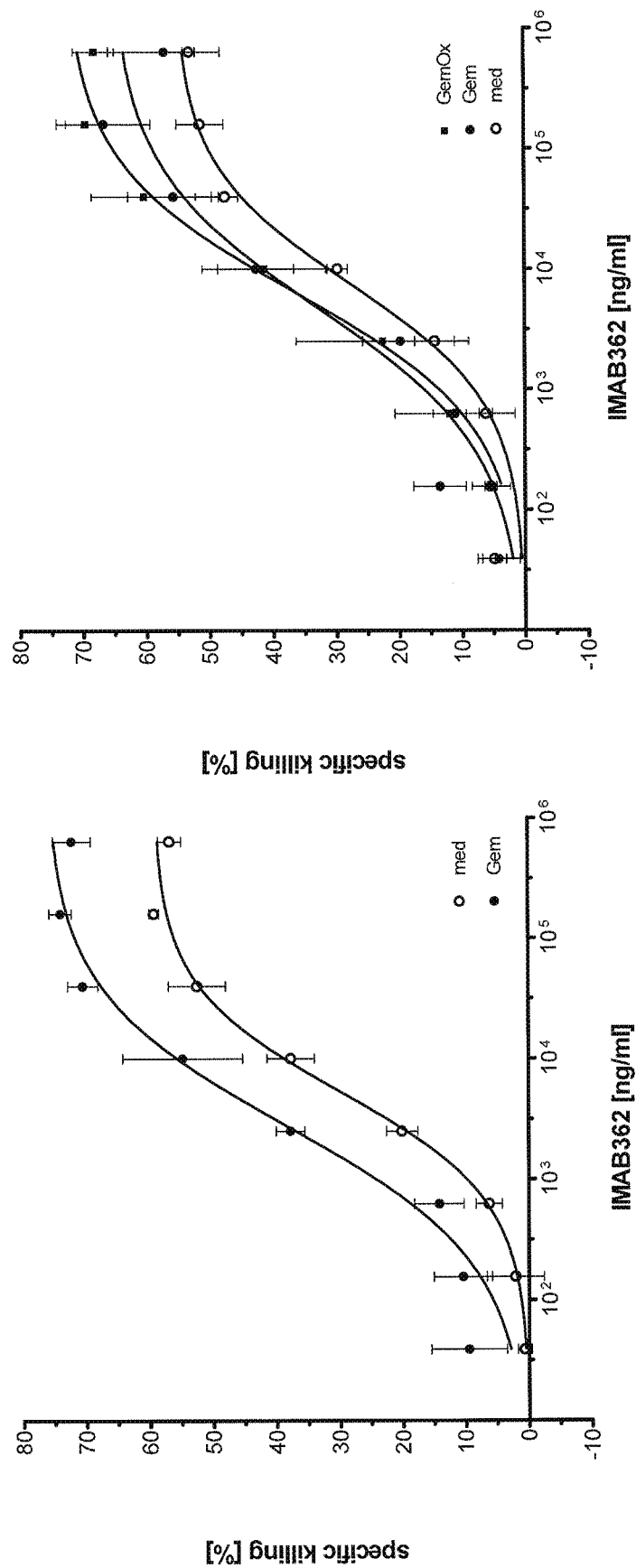

FIG. 39 shows the influence of chemotherapeutic agents on IMAB362 mediated CDC of MiaPaCa2-LVT cells. Dose response curves of 2 independent assays. MiaPaCa2-LVT were cultivated in medium, Gem (10 ng/ml) or GemOx (10 ng/ml Gem+100 ng/ml Ox) for 70 h.

Figure 40:
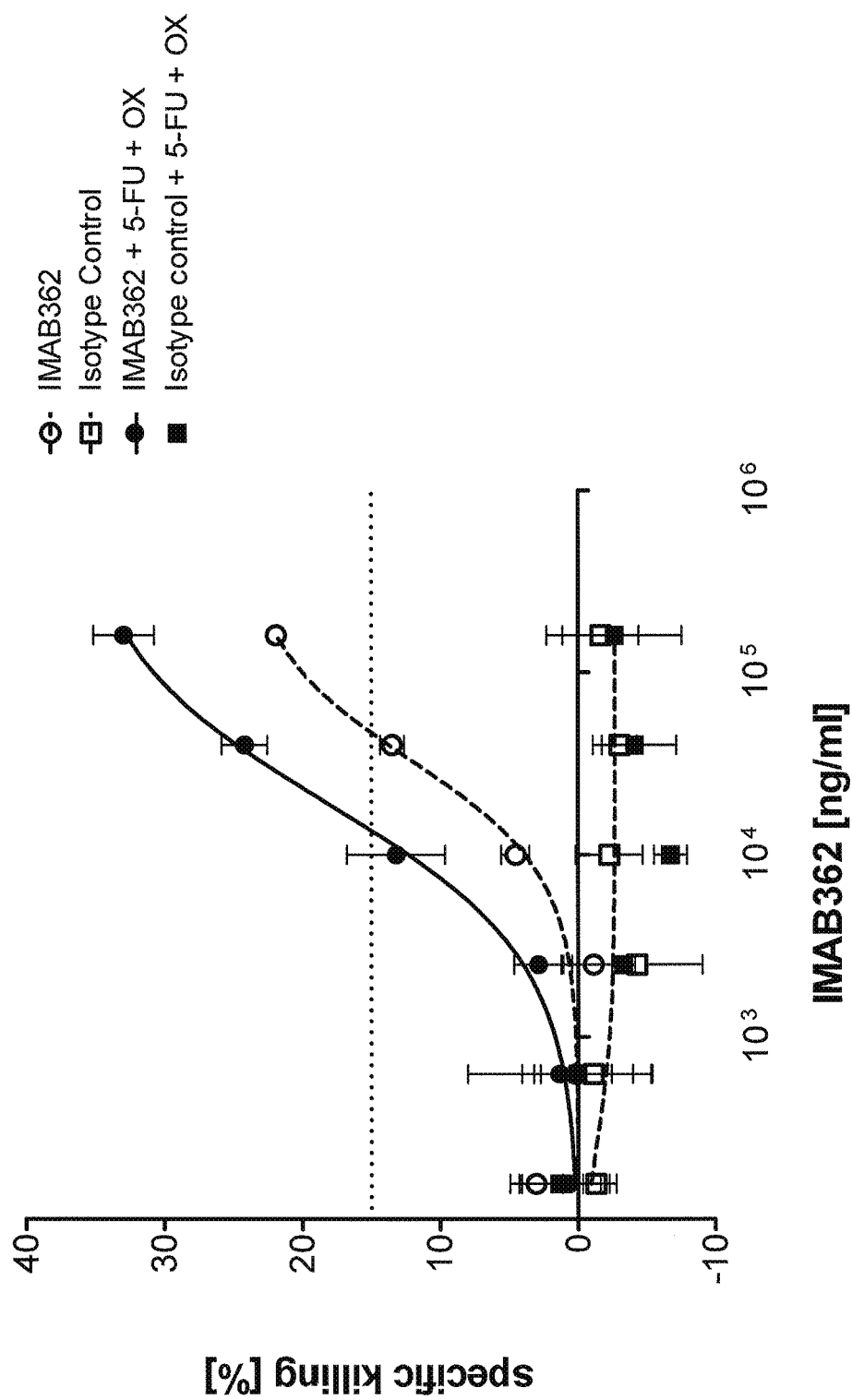
Figure 41A:
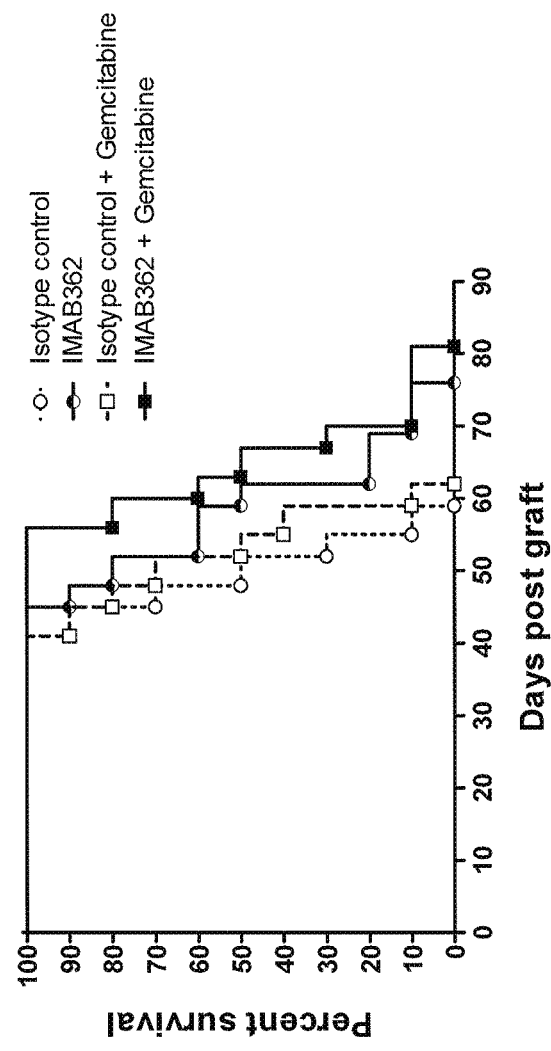
Figure 41B:
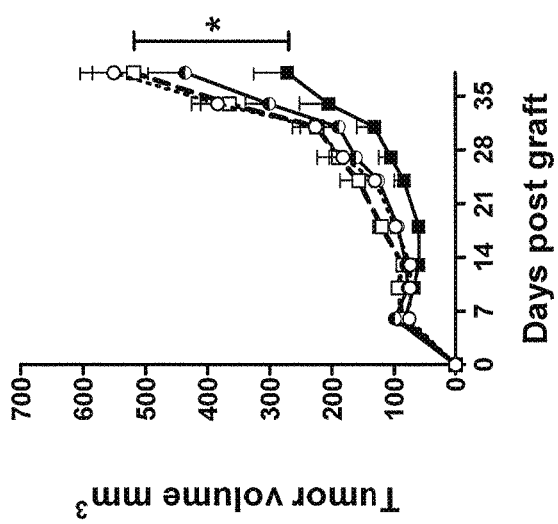

FIG. 40 shows the effects of chemotherapy on IMAB362-induced CDC FIGS. 41A and 41B show the effect of IMAB362 treatment combined with Gem or GemOx on BxPC3-LVT xenografts. BxPC3-LVT xenograft tumors were inoculated by injection of 8.5e6 BxPC3-LVT cells subcutaneous into the flank of 10 female Hsd:Athymic Nude-Foxn1nu mice for each treatment group. On the third day after tumor cell injection, treatment was initiated with chemotherapy (50 mg/kg gemcitabine i.p., respectively 50 mg/kg gemcitabine plus 5 mg/kg oxaliplatin i.p.) and were continued weekly for six weeks. 24 h after injection of chemotherapeutic agents, 800 µg IMAB362 or controls were applied intravenous into the tail vein. IMAB362 treatment was continued weekly until mice were sacrificed. FIG. 41A shows growth curves of subcutaneous BxPC3-LVT xenografts. The size of s.c. tumors was measured twice weekly (mean+SEM). FIG. 41B shows Kaplan-Meier survival curves. Mice were sacrificed when tumors reached a volume of 1400 mm3 or tumors became ulcerous.

Figure 42A:
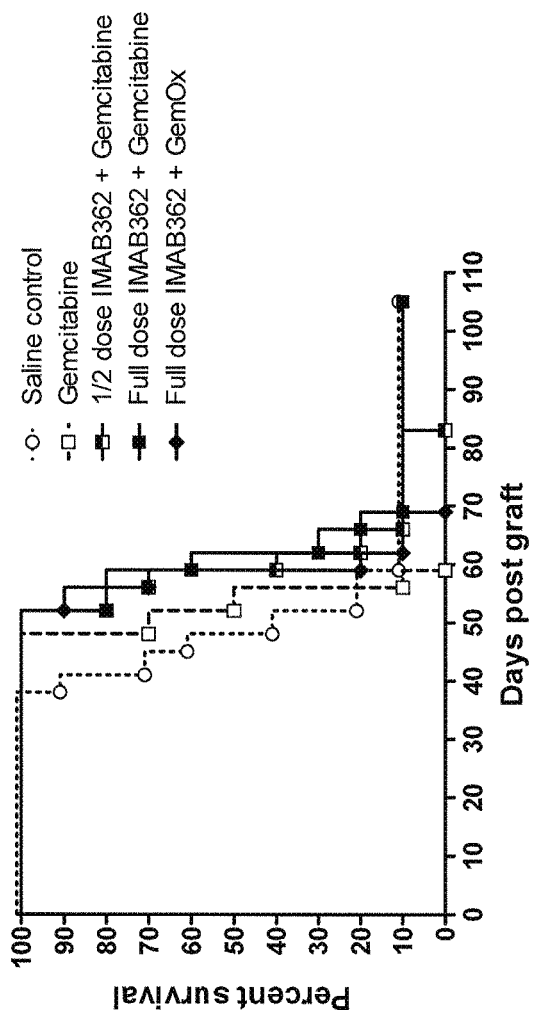
Figure 42B:
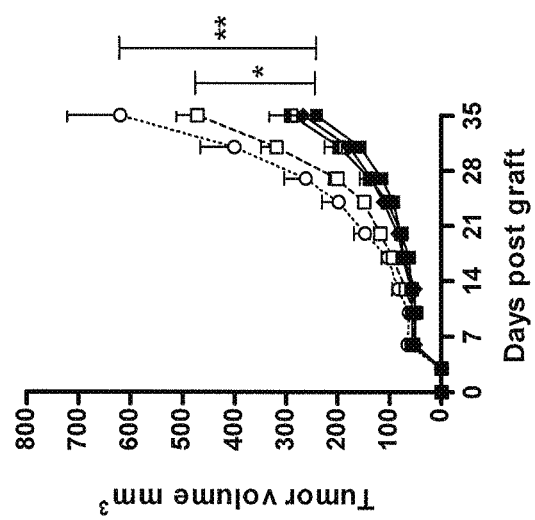

FIGS. 42A and 42B show enhancement of antitumoral efficacy by combination of gemcitabine regimen with IMAB362. BxPC3-LVT xenograft tumors were inoculated by injection of 8.5e6 BxPC3-LVT cells subcutaneous into the flanks of 10 female Hsd:Athymic Nude-Foxn1nu mice for each treatment group. On the third day after tumor cell injection, treatments were initiated with chemotherapy (100 mg/kg gemcitabine i.p., or 100 mg/kg gemcitabine plus 5 mg/kg oxaliplatin i.p.) and were continued weekly for six weeks. 24 h after injection of chemotherapeutic agents, 200 µg (½ dose) or 400 µg (full dose) IMAB362 were applied intravenous into the tail vein. IMAB362 treatment was continued semi-weekly with i.p. and i.v. injections alternating until mice were sacrificed. FIG. 42A shows growth curves of subcutaneous BxPC3-LVT xenografts. The size of s.c. tumors was measured twice weekly (mean+SEM). FIG. 42B shows Kaplan-Meier survival curves. Mice were sacrificed when tumors reached a volume of 1400 $mm^3$ or tumors became ulcerous.

Figure 43A:
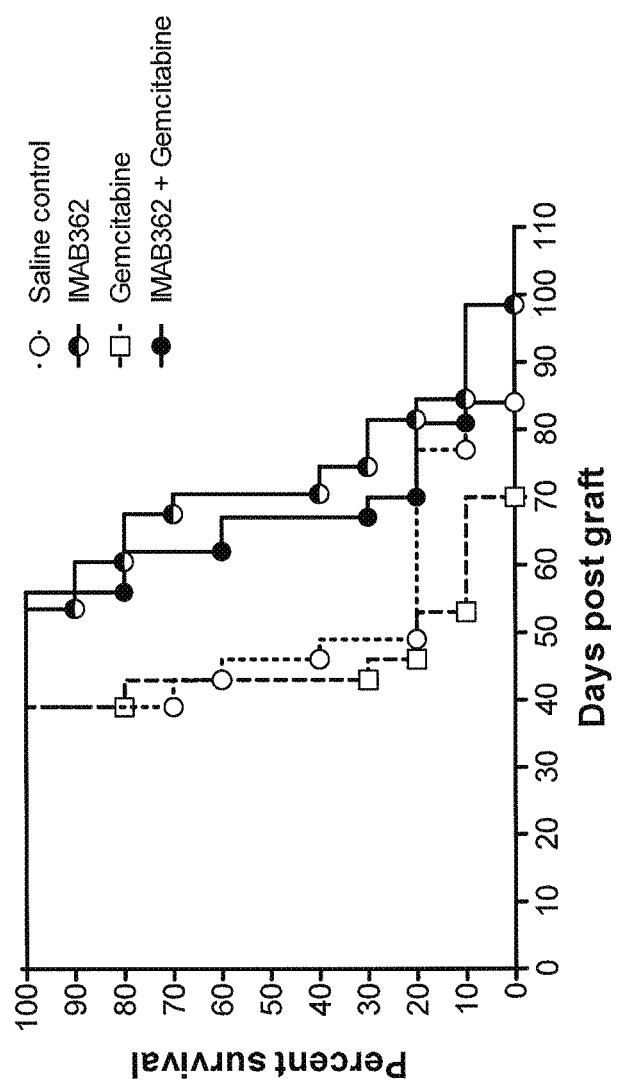
Figure 43B:
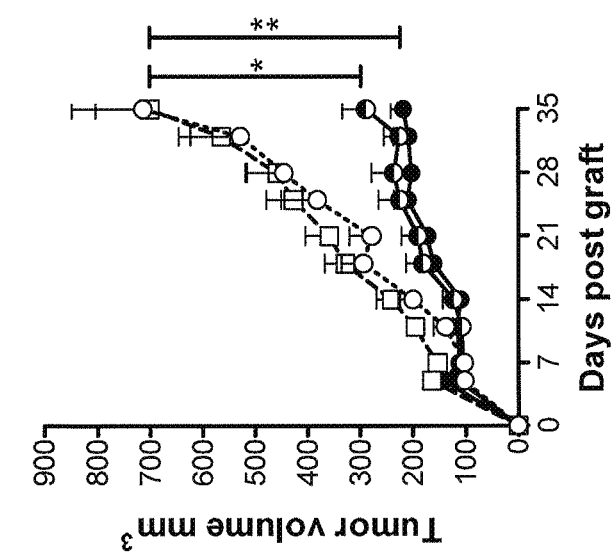

FIGS. 43A and 43B show effect of IMAB362 treatment combined with gemcitabine on MiaPaCa2-LVT xenografts. MiaPaCa2-LVT xenograft tumors were inoculated by injection of 5e6 MiaPaCa2-LVT cells subcutaneous into the flank of 10 female Hsd:Athymic Nude-Foxn1nu mice for each treatment group. 4 days after tumor cell injection, treatment was initiated with chemotherapy (50 mg/kg gemcitabine i.p) and were continued weekly for six weeks. 24 h after injection of chemotherapeutic agents, 200 µg IMAB362 or controls were applied intravenous into the tail vein. IMAB362 treatment was continued semi-weekly with i.p. and i.v. injections alternating until mice were sacrificed. FIG. 43A shows growth of subcutaneous xenografts. The size of tumors was measured twice weekly (mean+SEM). FIG. 43B shows Kaplan-Meier survival curves. Mice were sacrificed when tumors reached a volume of 1400 $mm^3$ or tumors became ulcerous.

Figure 44A:
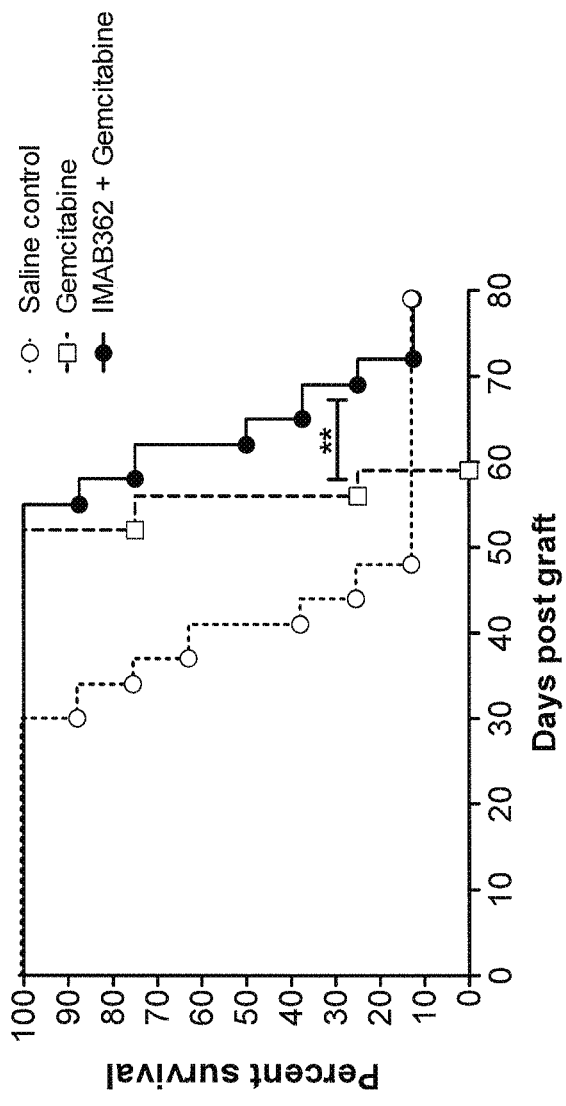
Figure 44B:
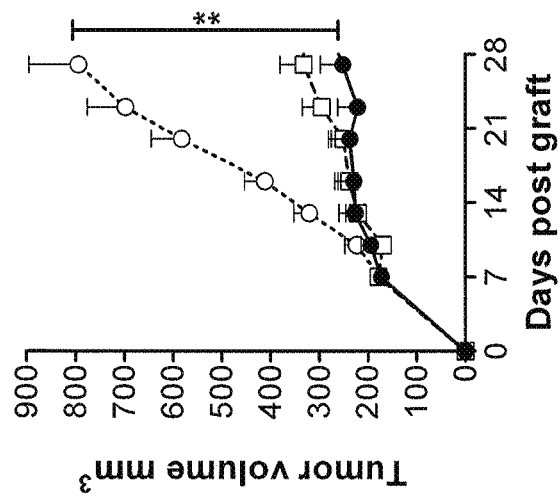

FIGS. 44A and 44B show effect of IMAB362 treatment combined with gemcitabine on established MiaPaCa2-LVT xenograft tumors. MiaPaCa2-LVT xenograft tumors were inoculated by injection of 1e7 MiaPaCa2-LVT cells subcutaneous into the flank of female Hsd:Athymic Nude-Foxn1$^{nu}$ mice. 9 days after subcutaneous tumor inoculation, tumor bearing mice reorganised in homogenous treatment groups with 8 animals per group and treatment was initiated. Mice were treated with 150 mg/kg gemcitabine semi-weekly for 4 weeks i.p. 24 h after gemcitabine injection, 200 µg IMAB362 or controls were applied intravenous into the tail vein. Treatment with 200 µg IMAB362 was continued semi-weekly with i.p. and i.v. injections alternating until mice were sacrificed. In FIG. 44A, the size of subcutaneous tumors was measured twice weekly (mean+SEM; =p<0.01). FIG. 44B shows Kaplan-Meier survival curves. Mice were sacrificed when tumor reached a volume of 1400 $mm^3$ or tumor became ulcerous (Log-rank (Mantel-Cox) test; =p<0.01).

Figure 45A:
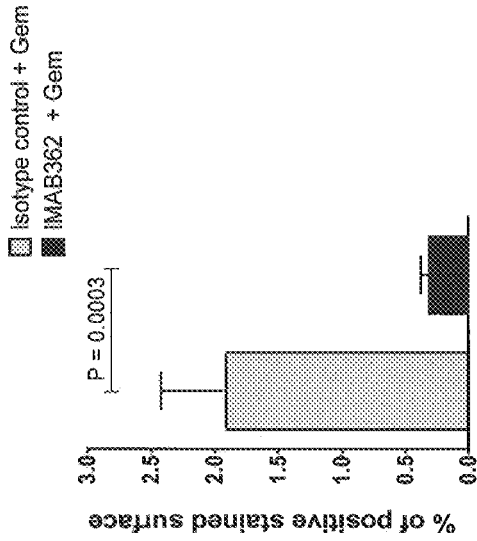
Figure 45B:
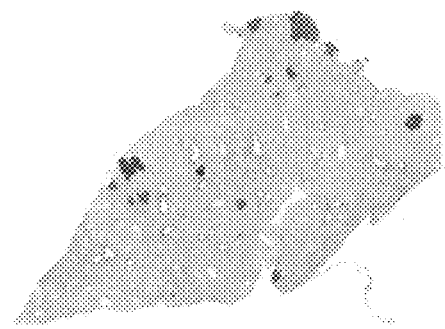
Figure 45C:
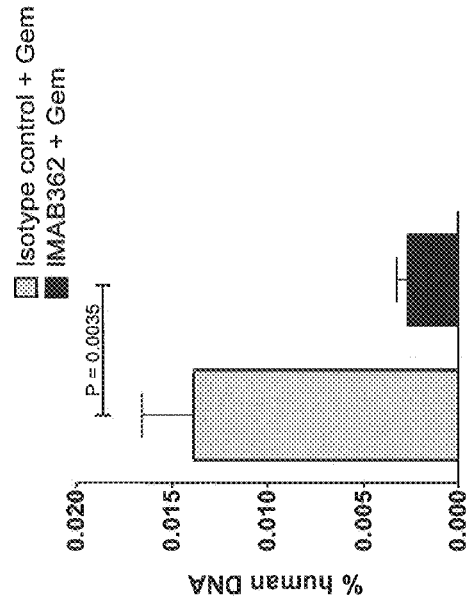
Figure 45D:
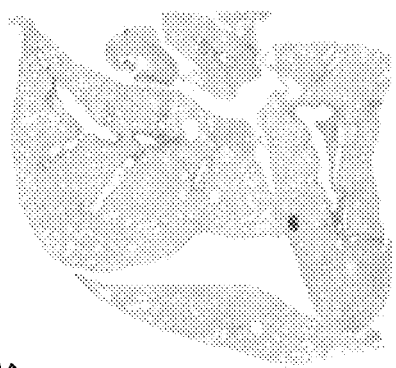

FIGS. 45A, 45B, 45C and 45D show effect of IMAB362 in combination with gemcitabine on lung metastases in Patu8988S xenograft model. 2×10$^6$ Patu8988S tumor cells were injected intravenously into the tail vein of 12 female Hsd:Athymic Nude-Foxn1$^{nu}$ mice per treatment group. Two weeks after intraveneous tumor cell injection treatment was initiated with maintenance treatment of 200 µg IMAB362 semi-weekly (i.v./i.p.) combined with administration of 100 mg/kg gemcitabine i.p. semi-weekly for 4 weeks. Control group was treated with 200 µg isotype control antibody combined with 100 mg/kg gemcitabine semi-weekly. Animals were sacrificed on day 70 post graft. FIG. 45A shows a quantitative PCR analysis (mean of 3 reactions per sample) of human DNA in lung samples of IMAB362 and isotype antibody treated mice. Significant difference (P=0.0035, Mann Whitney test) versus isotype control. In FIG. 45B, the percentage of stained human cells covering the mouse lung surface was determined by computer-based analysis. Immunohistological staining was performed with anti human MHC-I antibody (clone EPR1394Y) on paraffin embedded lung tissues (Mean+SEM; P=0.0003, Mann Whitney test). FIGS. 45C and 45D show examples for immunohistological stainings with anti MHC-I antibody on Patu8988s lung metastases in IMAB362+ gemcitabine (45C) or isotype antibody+ gemcitabine treated mice (45D).

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence.

The term "CLDN18.1" preferably relates to human CLDN18.1, and, in particular, to a protein comprising, preferably consisting of the amino acid sequence according to SEQ ID NO: 2 of the sequence listing or a variant of said amino acid sequence.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the invention, the term "CLDN18.2 positive cancer" means a cancer involving cancer cells expressing CLDN18.2, preferably on the surface of said cancer cells.

"Cell surface" is used in accordance with its normal meaning in the art, and thus includes the outside of the cell which is accessible to binding by proteins and other molecules. For example, a transmembrane protein having one or more extracellular portions is considered as being expressed on the cell surface.

CLDN18.2 is expressed on the surface of cells if it is located at the surface of said cells and is accessible to binding by CLDN18.2-specific antibodies added to the cells.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

According to the invention, the term "disease" refers to any pathological state, including cancer, in particular those forms of cancer described herein. Any reference herein to cancer or particular forms of cancer also includes cancer metastasis thereof. In a preferred embodiment, a disease to be treated according to the present application involves cells expressing CLDN18.2.

"Diseases associated with cells expressing CLDN18.2" or similar expressions means according to the invention that CLDN18.2 is expressed in cells of a diseased tissue or organ. In one embodiment, expression of CLDN18.2 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a corresponding healthy tissue is repressed. For example, CLDN18.2 is expressed in pancreatic cancer tissue while expression is not detectable in non-cancerous pancreatic tissue. According to the invention, diseases associated with cells expressing CLDN18.2 include cancer diseases. Furthermore, according to the invention, cancer diseases preferably are those wherein the cancer cells express CLDN18.2.

As used herein, a "cancer disease" or "cancer" includes a disease characterized by aberrantly regulated cellular growth, proliferation, differentiation, adhesion, and/or migration. By "cancer cell" is meant an abnormal cell that grows by a rapid, uncontrolled cellular proliferation and continues to grow after the stimuli that initiated the new growth cease. Preferably, a "cancer disease" is characterized by cells expressing CLDN18.2 and a cancer cell expresses CLDN18.2. A cell expressing CLDN18.2 preferably is a cancer cell, preferably of the cancers described herein.

According to the invention, a "carcinoma" is a malignant tumor derived from epithelial cells.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so.

The pancreas, an organ of endodermal derivation, is the key regulator of protein and carbohydrate digestion and glucose homeostasis. The exocrine pancreas (80% of the tissue mass of the organ) is composed of a branching network of acinar and duct cells that produce and deliver digestive enzymes into the gastrointestinal tract. The acinar cells, which are organized in functional units along the duct network, synthesize and secrete enzymes into the ductal lumen in response to cues from the stomach and duodenum. Within the acinar units near the ducts are centroacinar cells. The endocrine pancreas, which regulates metabolism and glucose homeostasis through the secretion of hormones into the bloodstream, is composed of four specialized endocrine cell types gathered together into clusters called Islets of Langerhans.

Pancreatic cancer is a malignant neoplasm originating from transformed cells arising in tissues forming the pancreas. Pancreatic cancer is the fourth most common cause of cancer-related deaths in the United States and the eighth worldwide. Early pancreatic cancer often does not cause symptoms, and the later symptoms are usually nonspecific and varied. Therefore, pancreatic cancer is often not diagnosed until it is advanced. Pancreatic cancer has a poor prognosis: for all stages combined, the 1- and 5-year relative survival rates are 25% and 6%, respectively. For local disease the 5-year survival is approximately 20% while the median survival for locally advanced and for metastatic disease, which collectively represent over 80% of individuals, is about 10 and 6 months respectively.

Pancreatic cancer includes adenocarcinomas (tumors exhibiting glandular architecture) arising within the exocrine component of the pancreas and neuroendocrine carcinomas arising from islet cells.

The most common form of pancreatic cancer, ductal adenocarcinoma, is typically characterized by moderately to poorly differentiated glandular structures on microscopic examination. Pancreatic ductal adenocarcinoma (PDAC) commonly arises in the head of the pancreas with infiltration into surrounding tissues including lymphatics, spleen, and peritoneal cavity, and with metastasis to the liver and lungs. PDAC primarily exhibits a glandular pattern with duct-like structures and varying degrees of cellular atypia and differentiation. Less common subtypes of PDAC include colloid, adenosquamous, or sarcomatoid histology. Often within an individual tumor, there are regional differences in histology, tumor grade, and degree of differentiation. Even the smallest primary lesions commonly exhibit perineural and lymphovascular invasion, suggesting a propensity for early distant spread.

The second most common type of exocrine pancreas cancer is mucinous. Mucinous adenocarcinoma produces a large volume of mucin that results in a cystic appearance on imaging studies.

Pancreatic neuroendocrine tumors form in hormone-making cells (islet cells) of the pancreas. Acinic cell neoplasms arise from the acinar cells of the pancreas.

According to the invention, the term "cancer" also includes cancer metastasis of a primary tumor such as primary pancreatic cancer. Thus, if reference is made, for example, to pancreatic cancer, this also includes metastasis of the pancreatic cancer, for example metastasis to the lung, liver and/or lymph nodes.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis. One particular form of metastasis which is treatable using the therapy of the invention is metastasis originating from pancreatic cancer as primary site. In preferred embodiments such pancreatic cancer metastasis is metastasis into lymph nodes, metastasis into lung and/or metastasis into liver.

Krukenberg tumor is an uncommon metastatic tumor of the ovary accounting for 1% to 2% of all ovarian tumors. Krukenberg tumor is a metastatic signet ring cell adenocarcinoma of the ovary. Stomach is the primary site in most Krukenberg tumor cases (70%). Carcinomas of colon, appendix, and breast (mainly invasive lobular carcinoma) are the next most common primary sites. Rare cases of Krukenberg tumor originating from carcinomas of the gallbladder, biliary tract, pancreas, small intestine, ampulla of Vater, cervix, and urinary bladder/urachus have been reported.

A refractory cancer is a malignancy for which a particular treatment is ineffective, which is either initially unresponsive to treatment, or which becomes unresponsive over time.

By "treat" is meant to administer a compound or composition or a combination of compounds or compositions to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

The term "patient" means according to the invention a subject for treatment, in particular a diseased subject, including human beings, nonhuman primates or another animals, in particular mammals such as cows, horses, pigs, sheeps, goats, dogs, cats or rodents such as mice and rats. In a particularly preferred embodiment, a patient is a human being.

The term "agent stabilizing or increasing expression of CLDN18.2" refers to an agent or a combination of agents the provision of which to cells results in increased RNA and/or protein levels of CLDN18.2 in said cells, preferably in increased levels of CLDN18.2 protein on the cell surface, compared to the situation where the cells are not provided with the agent or the combination of agents. Preferably, the cells are cancer cells, in particular cancer cells expressing CLDN18.2 and thus are a target for CLDN18.2 binding antibodies, such as cells of the cancer types described herein, in particular pancreatic cancer. The term "agent stabilizing or increasing expression of CLDN18.2" refers, in particular, to an agent or a combination of agents the provision of which to cells results in a higher density of CLDN18.2 on the surface of said cells compared to the situation where the cells are not provided with the agent or the combination of agents. "Stabilizing expression of CLDN18.2" includes, in particular, the situation where the agent or the combination of agents prevents a decrease or reduces a decrease in expression of CLDN18.2, e.g. expression of CLDN18.2 would decrease without provision of the agent or the combination of agents and provision of the agent or the combination of agents prevents said decrease or reduces said decrease of CLDN18.2 expression. "Increasing expression of CLDN18.2" includes, in particular, the situation where the agent or the combination of agents increases expression of CLDN18.2, e.g. expression of CLDN18.2 would decrease, remain essentially constant or increase without provision of the agent or the combination of agents and provision of the agent or the combination of agents increases CLDN18.2 expression compared to the situation without provision of the agent or the combination of agents so that the resulting expression is higher compared to the situation where expression of CLDN18.2 would decrease, remain essentially constant or increase without provision of the agent or the combination of agents.

According to the invention, the term "agent stabilizing or increasing expression of CLDN18.2" includes chemotherapeutic agents or combinations of chemotherapeutic agents such as cytostatic agents. Chemotherapeutic agents may affect cells in one of the following ways: (1) damage the DNA of the cells so they can no longer reproduce, (2) inhibit the synthesis of new DNA strands so that no cell replication is possible, (3) stop the mitotic processes of the cells so that the cells cannot divide into two cells.

According to the invention, the term "agent stabilizing or increasing expression of CLDN18.2" preferably relates to an agent or a combination of agents such a cytostatic compound or a combination of cytostatic compounds the provision of which to cells, in particular cancer cells, results in the cells being arrested in or accumulating in one or more phases of the cell cycle, preferably in one or more phases of the cell cycle other than the G1- and G0-phases, preferably other than the G1-phase, preferably in one or more of the G2- or S-phase of the cell cycle such as the G1/G2-, S/G2-, G2- or S-phase of the cell cycle. The term "cells being arrested in or accumulating in one or more phases of the cell cycle" means that the percentage of cells which are in said one or more phases of the cell cycle increases. Each cell goes through a cycle comprising four phases in order to replicate itself. The first phase called G1 is when the cell prepares to replicate its chromosomes. The second stage is called S, and in this phase DNA synthesis occurs and the DNA is duplicated. The next phase is the G2 phase, when the RNA and protein duplicate. The final stage is the M stage, which is the stage of actual cell division. In this final stage, the duplicated DNA and RNA split and move to separate ends of the cell, and the cell actually divides into two identical, functional cells. Chemotherapeutic agents which are DNA damaging agents usually result in an accumulation of cells in the G1 and/or G2 phase. Chemotherapeutic agents which block cell growth by interfering with DNA synthesis such as antimetabolites usually result in an accumulation of cells in the S-phase. Examples of these drugs are gemcitabine, 6-mercaptopurine and 5-fluorouracil.

According to the invention, the term "agent stabilizing or increasing expression of CLDN18.2" includes nucleoside analogs such as gemcitabine, 5-fluorouracil or prodrugs thereof, platinum compounds such as oxaliplatin and cisplatin, taxanes such as paclitaxel and docetaxel, and camptothecin analogs such as irinotecan and topotecan, and combinations of drugs such as combinations of drugs comprising one or more of gemcitabine, oxaliplatin and 5-fluorouracil such as a combination of drugs comprising gemcitabine and oxaliplatin, gemcitabine and 5-fluorouracil, oxaliplatin and 5-fluorouracil or other drug combinations described herein. According to the invention a reference to an agent stabilizing or increasing expression of CLDN18.2, such as a reference to a nucleoside analog, a platinum compound, a camptothecin analog or a taxane, for example, a reference to gemcitabine, 5-fluorouracil, oxaliplatin, irinotecan or paclitaxel is to include any prodrug such as ester, salt or derivative such as conjugate of said agent. Examples are conjugates of said agent with a carrier substance, e.g. protein-bound paclitaxel such as albumin-bound paclitaxel. Preferably, salts of said agent are pharmaceutically acceptable.

In one preferred embodiment, an "agent stabilizing or increasing expression of CLDN18.2" is or comprises an "agent inducing immunogenic cell death".

In specific circumstances, cancer cells can enter a lethal stress pathway linked to the emission of a spatiotemporally defined combination of signals that is decoded by the immune system to activate tumor-specific immune responses (Zitvogel L. et al. (2010) Cell 140: 798-804). In such scenario cancer cells are triggered to emit signals that are sensed by innate immune effectors such as dendritic cells to trigger a cognate immune response that involves CD8+ T cells and IFN-γ signalling so that tumor cell death may elicit a productive anticancer immune response. These signals include the pre-apoptotic exposure of the endoplasmic reticulum (ER) chaperon calreticulin (CRT) at the cell surface, the pre-apoptotic secretion of ATP, and the post-apoptotic release of the nuclear protein HMGB1. Together, these processes constitute the molecular determinants of immunogenic cell death (ICD). Anthracyclines, oxaliplatin, and γ irradiation are able to induce all signals that define ICD, while cisplatin, for example, which is deficient in inducing CRT translocation from the ER to the surface of dying cells—a process requiring ER stress—requires complementation by thapsigargin, an ER stress inducer.

According to the invention, the term "agent inducing immunogenic cell death" refers to an agent or a combination of agents which when provided to cells, in particular cancer cells, is capable of inducing the cells to enter a lethal stress pathway which finally results in tumor-specific immune responses. In particular, an agent inducing immunogenic cell death when provided to cells induces the cells to emit a spatiotemporally defined combination of signals, including, in particular, the pre-apoptotic exposure of the endoplasmic reticulum (ER) chaperon calreticulin (CRT) at the cell surface, the pre-apoptotic secretion of ATP, and the post-apoptotic release of the nuclear protein HMGB1.

According to the invention, the term "agent inducing immunogenic cell death" includes anthracyclines and oxaliplatin.

The term "nucleoside analog" refers to a structural analog of a nucleoside, a category that includes both purine analogs and pyrimidine analogs.

The term "gemcitabine" is a compound which is a nucleoside analog of the following formula:

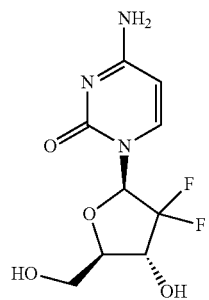 [SMILES: Nc1ccn([C@@H]2O[C@H](CO)[C@@H](O)C2(F)F)c(=O)n1]

In particular, the term refers to the compound 4-amino-1-(2-deoxy-2,2-difluoro-β-D-erythro-pentofuranosyl)pyrimidin-2(1H)-one or 4-amino-1-[(2R,4R,5R)-3,3-difluoro-4-hydroxy-5-(hydroxymethyl)oxolan-2-yl]-1,2-dihydropyrimidin-2-one.

According to the invention, gemcitabine is preferably administered by the intravenous route. Preferably, gemcitabine is administered in dose ranges of 0.5 to 2 $g/m^2$, preferably 0.8 to 1.5 $g/m^2$, more preferably 1 to 1.2 $g/m^2$ of body surface area. For example, gemcitabine may be given at a dose of 1000 mg per square meter weekly for 7 of 8 weeks and then weekly for 3 of 4 weeks.

The term "nucleoside analog" includes fluoropyrimidine derivatives such as fluorouracil and prodrugs thereof. The term "fluorouracil" or "5-fluorouracil" (5-FU or f5U) (sold under the brand names Adrucil, Carac, Efudix, Efudex and Fluoroplex) is a compound which is a pyrimidine analog of the following formula:

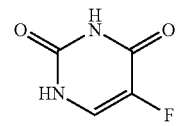

In particular, the term refers to the compound 5-fluoro-1H-pyrimidine-2,4-dione.

The term "capecitabine" (Xeloda, Roche) refers to a chemotherapeutic agent that is a prodrug that is converted into 5-FU in the tissues. Capecitabine which may be orally administered has the following formula:

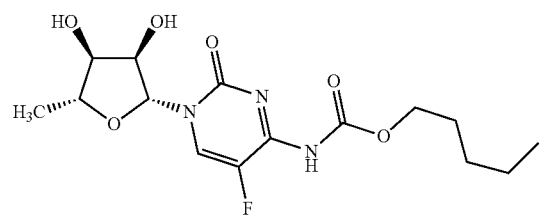 [SMILES: CCCCCOC(=O)Nc1nc(=O)n([C@@H]2O[C@H](C)[C@@H](O)[C@H]2O)cc1F]

In particular, the term refers to the compound pentyl [1-(3,4-dihydroxy-5-methyltetrahydrofuran-2-yl)-5-fluoro-2-oxo-1H-pyrimidin-4-yl]carbamate.

According to the invention, the term "platinum compound" refers to compounds containing platinum in their structure such as platinum complexes and includes compounds such as cisplatin, carboplatin and oxaliplatin.

The term "cisplatin" or "cisplatinum" refers to the compound cis-diamminedichloroplatinum(II) (CDDP) of the following formula:

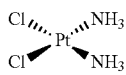

The term "carboplatin" refers to the compound cis-diammine(1,1-cyclobutanedicarboxylato)platinum(II) of the following formula:

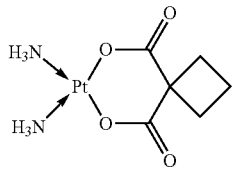

The term "oxaliplatin" refers to a compound which is a platinum compound that is complexed to a diaminocyclohexane carrier ligand of the following formula:

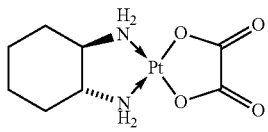

In particular, the term "oxaliplatin" refers to the compound [(1R,2R)-cyclohexane-1,2-diamine](ethanedioato-O,O')platinum(II). Oxaliplatin for injection is also marketed under the trade name Eloxatine.

Taxanes are a class of diterpene compounds that were first derived from natural sources such as plants of the genus *Taxus*, but some have been synthesized artificially. The principal mechanism of action of the taxane class of drugs is the disruption of microtubule function, thereby inhibiting the process of cell division. Taxanes include docetaxel (Taxotere) and paclitaxel (Taxol).

According to the invention, the term "docetaxel" refers to a compound having the following formula:

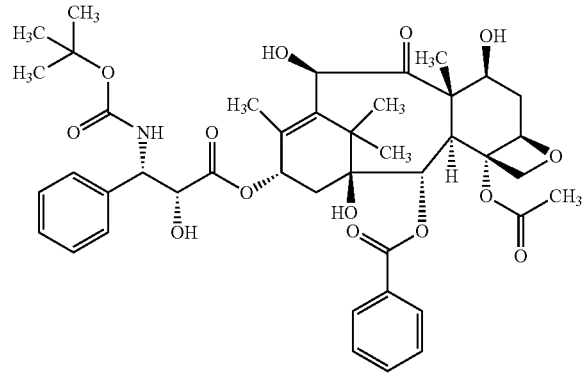 [SMILES: CC(=O)O[C@@]12CO[C@@H]1C[C@H](O)[C@@]1(C)C(=O)[C@H](O)C3=C(C)[C@@H](OC(=O)[C@H](O)[C@@H](NC(=O)OC(C)(C)C)c4ccccc4)C[C@@](O)([C@@H](OC(=O)c4ccccc4)[C@H]21)C3(C)C]

In particular, the term "docetaxel" refers to the compound 1,7β,10β-trihydroxy-9-oxo-5β,20-epoxytax-11-ene-2α,4,13α-triyl 4-acetate 2-benzoate 13-{(2R,3 S)-3-[(tert-butoxycarbonyl)-amino]-2-hydroxy-3-phenylpropanoate}.

According to the invention, the term "paclitaxel" refers to a compound having the following formula:

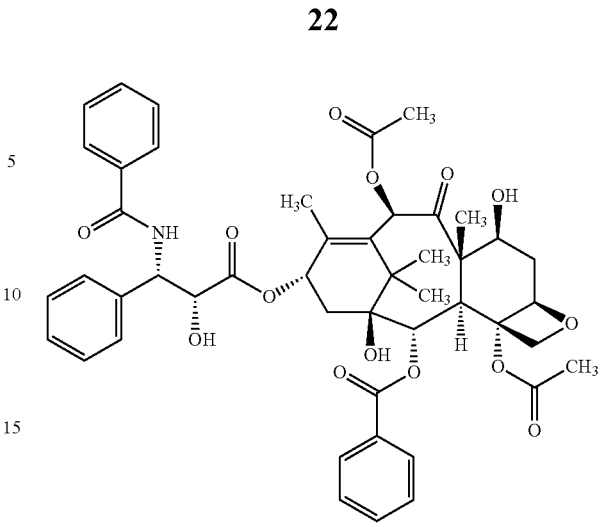

In particular, the term "paclitaxel" refers to the compound (2α,4α,5β,7β,10β,13α)-4,10-bis-(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate.

According to the invention, the term "camptothecin analog" refers to derivatives of the compound camptothecin (CPT; (S)-4-ethyl-4-hydroxy-1H-pyrano[3',4':6,7]indolizino[1,2-b]quinoline-3,14-(4H,12H)-dione). Preferably, the term "camptothecin analog" refers to compounds comprising the following structure:

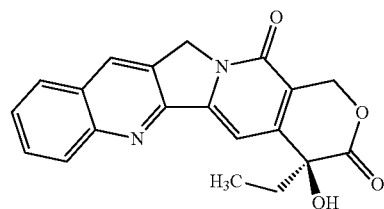 [SMILES: CC[C@@]1(O)C(=O)OCc2c1cc1n(c2=O)Cc2cc3ccccc3nc2-1]

According to the invention, preferred camptothecin analogs are inhibitors of DNA enzyme topoisomerase I (topo I). Preferred camptothecin analogs according to the invention are irinotecan and topotecan.

Irinotecan is a drug preventing DNA from unwinding by inhibition of topoisomerase I. In chemical terms, it is a semisynthetic analogue of the natural alkaloid camptothecin having the following formula:

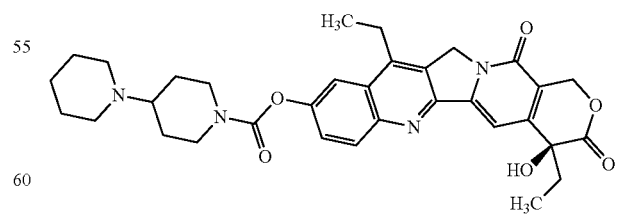

In particular, the term "irinotecan" refers to the compound (S)-4,11-diethyl-3,4,12,14-tetrahydro-4-hydroxy-3,14-dioxo1H-pyrano[3',4':6,7]-indolizino[1,2-b]quinolin-9-yl-[1,4'-bipiperidine]-1'-carboxylate.

Topotecan is a topoisomerase inhibitor of the formula:

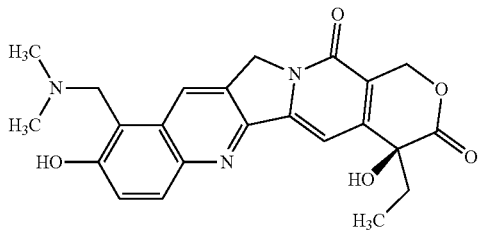 [SMILES: CC[C@@]1(O)C(=O)OCc2c1cc1n(c2=O)Cc2cc3c(CN(C)C)c(O)ccc3nc2-1]

In particular, the term "topotecan" refers to the compound (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride.

Anthracyclines are a class of drugs commonly used in cancer chemotherapy that are also antibiotics. Structurally, all anthracyclines share a common four-ringed 7,8,9,10-tetrahydrotetracene-5,12-quinone structure and usually require glycosylation at specific sites.

Anthracyclines preferably bring about one or more of the following mechanisms of action: 1. Inhibiting DNA and RNA synthesis by intercalating between base pairs of the DNA/RNA strand, thus preventing the replication of rapidly-growing cancer cells. 2. Inhibiting topoisomerase II enzyme, preventing the relaxing of supercoiled DNA and thus blocking DNA transcription and replication. 3. Creating iron-mediated free oxygen radicals that damage the DNA and cell membranes.

According to the invention, the term "anthracycline" preferably relates to an agent, preferably an anticancer agent for inducing apoptosis, preferably by inhibiting the rebinding of DNA in topoisomerase II.

Preferably, according to the invention, the term "anthracycline" generally refers to a class of compounds having the following ring structure

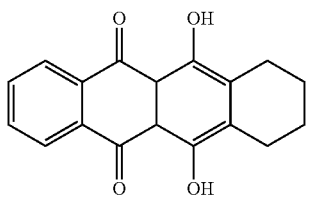 [SMILES: O=C1c2ccccc2C(=O)C2C(O)=C3CCCCC3=C(O)C12]

including analogs and derivatives, pharmaceutical salts, hydrates, esters, conjugates and prodrugs thereof.

Examples of anthracyclines and anthracycline analogs include, but are not limited to, daunorubicin (daunomycin), doxorubicin (adriamycin), epirubicin, idarubicin, rhodomycin, pyrarubicin, valrubicin, N-trifluoro-acetyl doxorubicin-14-valerate, aclacinomycin, morpholinodoxorubicin (morpholino-DOX), cyanomorpholino-doxorubicin (cyanomorpholino-DOX), 2-pyrrolino-doxorubicin (2-PDOX), 5-iminodaunomycin, mitoxantrone and aclacinomycin A (aclarubicin). Mitoxantrone is a member of the anthracendione class of compounds, which are anthracycline analogs that lack the sugar moiety of the anthracyclines but retain the planar polycylic aromatic ring structure that permits intercalation into DNA.

Particularly preferred as anthracyline according to the invention is a compound of the following formula:

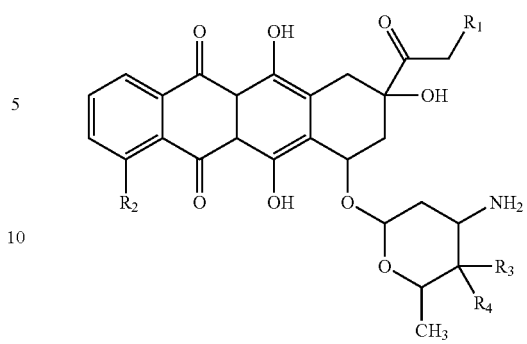

wherein
$R_1$ is selected from the group consisting of H and OH, $R_2$ is selected from the group consisting of H and OMe, $R_3$ is selected from the group consisting of H and OH, and $R_4$ is selected from the group consisting of H and OH.

In one embodiment, $R_1$ is H, $R_2$ is OMe, $R_3$ is H, and $R_4$ is OH. In another embodiment, $R_1$ is OH, $R_2$ is OMe, $R_3$ is H, and $R_4$ is OH. In another embodiment, $R_1$ is OH, $R_2$ is OMe, $R_3$ is OH, and $R_4$ is H. In another embodiment, $R_1$ is H, $R_2$ is H, $R_3$ is H, and $R_4$ is OH.

Specifically contemplated as anthracycline in the context of the present invention is epirubicin. Epirubicin is an anthracycline drug which has the following formula:

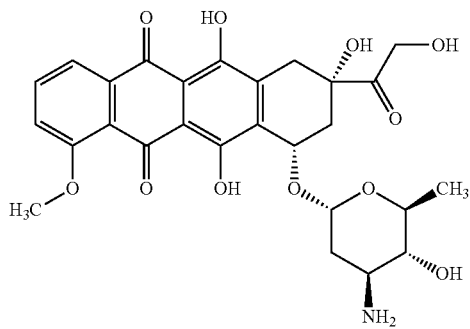 [SMILES: COc1cccc2c1C(=O)c1c(O)c3c(c(O)c1C2=O)C[C@@](O)(C(=O)CO)C[C@@H]3O[C@H]1C[C@H](N)[C@@H](O)[C@H](C)O1]

and is marketed under the trade name Ellence in the US and Pharmorubicin or Epirubicin Ebewe elsewhere. In particular, the term "epirubicin" refers to the compound (8R,10S)-10-[(2S,4S,5R,6S)-4-amino-5-hydroxy-6-methyl-oxan-2-yl]oxy-6,11-dihydroxy-8-(2-hydroxyacetyl)-1-methoxy-8-methyl-9,10-dihydro-7H-tetracen-5,12-dion. Epirubicin is favoured over doxorubicin, the most popular anthracycline, in some chemotherapy regimens as it appears to cause fewer side-effects.

According to the invention, an agent stabilizing or increasing expression of CLDN18.2 may be a chemotherapeutic agent, in particular a chemotherapeutic agent established in cancer treatment and may be part of a combination of drugs such as a combination of drugs established for use in cancer treatment. Such combination of drugs may be a drug combination used in chemotherapy, and may be a drug combination as used in the FOLFIRINOX chemotherapeutic regimen.

The drug combination used in FOLFIRINOX chemotherapy comprises of leucovorin, fluorouracil, irinotecan (such as irinotecan hydrochloride) and oxaliplatin. Oxaliplatin may be given at 85 mg per square meter of body-surface area; irinotecan at 180 mg per square meter; leucovorin at 400 mg per square meter; and fluorouracil at 400 mg per square meter given as a bolus followed by 5-fluorouracil at 2400 mg per square meter given as a continuous infusion of preferably 46-hours, preferably every 2 weeks).

The term "folinic acid" or "leucovorin" refers to a compound useful in synergistic combination with the chemotherapy agent 5-fluorouracil. Thus, if reference is made herein to the administration of 5-fluorouracil or a prodrug thereof, said administration in one embodiment may comprise an administration in conjunction with folinic acid. Folinic acid has the following formula:

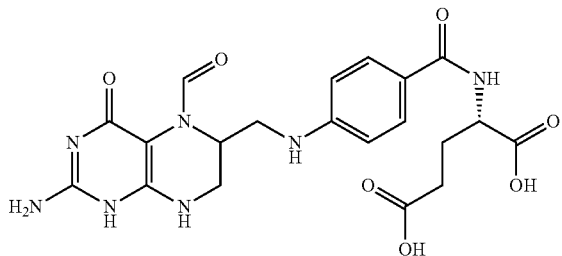 [SMILES: Nc1nc(=O)c2c([nH]1)NCC(CNc1ccc(C(=O)N[C@@H](CCC(=O)O)C(=O)O)cc1)N2C=O]

In particular, the term refers to the compound (2S)-2-{[4-[(2-amino-5-formyl-4-oxo-5,6,7,8-tetrahydro-1H-pteridin-6-yl)methylamino]benzoyl]amino}pentanedioic acid.

γδ T cells (gamma delta T cells) represent a small subset of T cells that possess a distinct T cell receptor (TCR) on their surface. A majority of T cells have a TCR composed of two glycoprotein chains called α- and β-TCR chains. In contrast, in γδ T cells, the TCR is made up of one γ-chain and one δ-chain. This group of T cells is usually much less common than αβ T cells. Human γδ T cells play an important role in stress-surveillance responses like infectious diseases and autoimmunity. Transformation-induced changes in tumors are also suggested to cause stress-surveillance responses mediated by γδ T cells and enhance antitumor immunity. Importantly, after antigen engagement, activated γδ T cells at lesional sites provide cytokines (e.g. INFγ, TNFα) and/or chemokines mediating recruitment of other effector cells and show immediate effector functions such as cytotoxicity (via death receptor and cytolytic granules pathways) and ADCC.

The majority of γδ T cells in peripheral blood express the Vγ9Vδ2 T cell receptor (TCRγδ). Vγ9Vδ2 T cells are unique to humans and primates and are assumed to play an early and essential role in sensing "danger" by invading pathogens as they expand dramatically in many acute infections and may exceed all other lymphocytes within a few days, e.g. in tuberculosis, salmonellosis, ehrlichiosis, brucellosis, tularemia, listeriosis, toxoplasmosis, and malaria. γδ T cells respond to small non-peptidic phosphorylated antigens (phosphoantigens) such as pyrophosphates synthesized in bacteria and isopentenyl pyrophosphate (IPP) produced in mammalian cells through the mevalonate pathway. Whereas IPP production in normal cells is not sufficient for activation of γδ T cells, dysregulation of the mevalonate pathway in tumor cells leads to accumulation of IPP and γδ T cell activation. IPPs can also be therapeutically increased by aminobisphosphonates, which inhibit the mevalonate pathway enzyme farnesyl pyrophosphate synthase (FPPS). Among others, zoledronic acid (ZA, zoledronate, Zometa™, Novartis) represents such an aminobiphosphonate, which is already clinically administered to patients for the treatment of osteoporosis and metastasic bone disease. Upon treatment of PBMCs in vitro, ZA is taken up especially by monocytes.

IPP accumulates in the monocytes and they differentiate to antigen-presenting cells stimulating development of γδ T cells. In this setting, the addition of interleukin-2 (IL-2) is preferred as growth and survival factor for activated γδ T cells. Finally, certain alkylated amines have been described to activate Vγ9Vδ2 T cells in vitro, however only at millimolar concentrations.

According to the invention, the term "agent stimulating γδ T cells" relates to compounds stimulating development of γδ T cells, in particular Vγ9Vδ2 T cells, in vitro and/or in vivo, in particular by inducing activation and expansion of γδ T cells. Preferably, the term relates to compounds which in vitro and/or in vivo increase isopentenyl pyrophosphate (IPP) produced in mammalian cells, preferably by inhibiting the mevalonate pathway enzyme farnesyl pyrophosphate synthase (FPPS).

One particular group of compounds stimulating γδ T cells are bisphosphonates, in particular nitrogen-containing bisphosphonates (N-bisphosphonates; aminobisphosphonates).

For example, suitable bisphosphonates for use in the invention may include one or more of the following compounds including analogs and derivatives, pharmaceutical salts, hydrates, esters, conjugates and prodrugs thereof:
[1-hydroxy-2-(1H-imidazol-1-yl)ethane-1,1-diyl]bis(phosphonic acid), zoledronic acid, e.g. zoledronate; (dichlorophosphono-methyl)phosphonic acid, e.g. clodronate
{1-hydroxy-3-[methyl(pentyl)amino]propane-1,1-diyl}bis (phosphonic acid), ibandronic acid, e.g. ibandronate
(3-amino-1-hydroxypropane-1,1-diyl)bis(phosphonic acid), pamidronic acid, e.g. pamidronate;
(1-hydroxy-1-phosphono-2-pyridin-3-yl-ethyl)phosphonic acid, risedronic acid, e.g. risedronate;
(1-Hydroxy-2-imidazo[1,2-a]pyridin-3-yl-1-phosphonoethyl)phosphonic acid, minodronic acid;
[3-(dimethylamino)-1-hydroxypropane-1,1-diyl]bis(phosphonic acid), olpadronic acid.
[4-amino-1-hydroxy-1-(hydroxy-oxido-phosphoryl)-butyl] phosphonic acid, alendronic acid, e.g. alendronate;
[(Cycloheptylamino)methylene]bis(phosphonic acid), incadronic acid;
(1-hydroxyethan-1,1-diyl)bis(phosphonic acid), etidronic acid, e.g. etidronate; and
{[(4-chlorophenyl)thio]methylene}bis(phosphonic acid), tiludronic acid.

According to the invention, zoledronic acid (INN) or zoledronate (marketed by Novartis under the trade names Zometa, Zomera, Aclasta and Reclast) is a particularly preferred bisphosphonate. Zometa is used to prevent skeletal fractures in patients with cancers such as multiple myeloma and prostate cancer, as well as for treating osteoporosis. It can also be used to treat hypercalcemia of malignancy and can be helpful for treating pain from bone metastases.

In one particularly preferred embodiment, an agent stimulating γδ T cells according to the invention is administered in combination with IL-2. Such combination has been shown to be particularly effective in mediating expansion and activation of γ9δ2 T cells.

Interleukin-2 (IL-2) is an interleukin, a type of cytokine signaling molecule in the immune system. It is a protein that attracts lymphocytes and is part of the body's natural response to microbial infection, and in discriminating between foreign (non-self) and self. IL-2 mediates its effects by binding to IL-2 receptors, which are expressed by lymphocytes.

The IL-2 used according to the invention may be any IL-2 supporting or enabling the stimulation of γδ T cells and may be derived from any species, preferably human. 11-2 may be isolated, recombinantly produced or synthetic IL-2 and may be naturally occurring or modified IL-2.

The term "antigen" relates to an agent such as a protein or peptide comprising an epitope against which an immune response is directed and/or is to be directed. In a preferred embodiment, an antigen is a tumor-associated antigen, such as CLDN18.2, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" preferably relates to proteins that are under normal conditions specifically expressed in a limited number of tissues and/or organs or in specific developmental stages and are expressed or aberrantly expressed in one or more tumor or cancer tissues. In the context of the present invention, the tumor-associated antigen is preferably associated with the cell surface of a cancer cell and is preferably not or only rarely expressed in normal tissues.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as CLDN18.2 preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives of antibodies, including, without limitation, human antibodies, humanized antibodies, chimeric antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The antibodies described herein may be human antibodies. The term "human antibody", as used herein, is intended to include antibodies having variable and constant regions derived from human germline immunoglobulin sequences. The human antibodies described herein may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g., modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "bispecific molecule" is intended to include any agent, e.g., a protein, peptide, or protein or peptide complex, which has two different binding specificities. For example, the molecule may bind to, or interact with (a) a cell surface antigen, and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CLDN18.2, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

An antibody may be conjugated to a therapeutic moiety or agent, such as a cytotoxin, a drug (e.g., an immunosuppressant) or a radioisotope. A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Suitable therapeutic agents for forming antibody conjugates include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

Antibodies also can be conjugated to a radioisotope, e.g., iodine-131, yttrium-90 or indium-111, to generate cytotoxic radiopharmaceuticals.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982).

As used herein, an antibody is "derived from" a particular germline sequence if the antibody is obtained from a system by immunizing an animal or by screening an immunoglobulin gene library, and wherein the selected antibody is at least 90%, more preferably at least 95%, even more preferably at least 96%, 97%, 98%, or 99% identical in amino acid sequence to the amino acid sequence encoded by the germline immunoglobulin gene. Typically, an antibody derived from a particular germline sequence will display no more than 10 amino acid differences, more preferably, no more than 5, or even more preferably, no more than 4, 3, 2, or 1 amino acid difference from the amino acid sequence encoded by the germline immunoglobulin gene.

As used herein, the term "heteroantibodies" refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

The antibodies described herein may be monoclonal antibodies. The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The antibodies described herein may be recombinant antibodies. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

Antibodies described herein may be derived from different species, including but not limited to mouse, rat, rabbit, guinea pig and human.

Antibodies described herein include polyclonal and monoclonal antibodies and include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The antibodies described herein are preferably isolated. An "isolated antibody" as used herein, is intended to refer to an antibody which is substantially free of other antibodies having different antigenic specificities (e.g., an isolated antibody that specifically binds to CLDN18.2 is substantially free of antibodies that specifically bind antigens other than CLDN18.2). An isolated antibody that specifically binds to an epitope, isoform or variant of human CLDN18.2 may, however, have cross-reactivity to other related antigens, e.g., from other species (e.g., CLDN18.2 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

The term "binding" according to the invention preferably relates to a specific binding.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{11}$ M or lower, or $10^{-12}$ M or lower.

An antibody is not (substantially) capable of binding to a target if it has no significant affinity for said target and does not bind significantly, in particular does not bind detectably, to said target in standard assays. Preferably, the antibody does not detectably bind to said target if present in a concentration of up to 2, preferably 10, more preferably 20, in particular 50 or 100 μg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$ M.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN18.2 if it is capable of binding to CLDN18.2 but is not (substantially) capable of binding to other targets. Preferably, an antibody is specific for CLDN18.2 if the affinity for and the binding to such other targets does not significantly exceed the affinity for or binding to CLDN18.2-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N.Y. (1984), Kuby, Janis Immunology, W. H. Freeman and Company New York, N.Y. (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

According to the invention an antibody having the ability of binding to CLDN18.2 is an antibody capable of binding to an epitope present in CLDN18.2, preferably an epitope located within the extracellular domains of CLDN18.2, in particular the first extracellular domain, preferably amino acid positions 29 to 78 of CLDN18.2. In particular embodiments, an antibody having the ability of binding to CLDN18.2 is an antibody capable of binding to (i) an epitope on CLDN18.2 which is not present on CLDN18.1, preferably SEQ ID NO: 3, 4, and 5, (ii) an epitope localized on the CLDN18.2-loop1, preferably SEQ ID NO: 8, (iii) an epitope localized on the CLDN18.2-loop2, preferably SEQ ID NO: 10, (iv) an epitope localized on the CLDN18.2-loopD3, preferably SEQ ID NO: 11, (v) an epitope, which encompass CLDN18.2-loop1 and CLDN18.2-loopD3, or (vi) a non-glycosylated epitope localized on the CLDN18.2-loopD3, preferably SEQ ID NO: 9.

According to the invention an antibody having the ability of binding to CLDN18.2 preferably is an antibody having the ability of binding to CLDN18.2 but not to CLDN18.1. Preferably, an antibody having the ability of binding to CLDN18.2 is specific for CLDN18.2. Preferably, an antibody having the ability of binding to CLDN18.2 preferably is an antibody having the ability of binding to CLDN18.2 expressed on the cell surface. In particular preferred embodiments, an antibody having the ability of binding to CLDN18.2 binds to native epitopes of CLDN18.2 present on the surface of living cells. Preferably, an antibody having the ability of binding to CLDN18.2 binds to one or more peptides selected from the group consisting of SEQ ID NOs: 1, 3-11, 44, 46, and 48-50. Preferably, an antibody having the ability of binding to CLDN18.2 is specific for the aforementioned proteins, peptides or immunogenic fragments or derivatives thereof. An antibody having the ability of binding to CLDN18.2 may be obtained by a method comprising the step of immunizing an animal with a protein or peptide comprising an amino acid sequence selected from the group consisting of SEQ ID NOs: 1, 3-11, 44, 46, and 48-50, or a nucleic acid or host cell expressing said protein or peptide. Preferably, the antibody binds to cancer cells, in particular cells of the cancer types mentioned above and, preferably, does not bind substantially to non-cancerous cells.

Preferably, binding of an antibody having the ability of binding to CLDN18.2 to cells expressing CLDN18.2 induces or mediates killing of cells expressing CLDN18.2. The cells expressing CLDN18.2 are preferably cancer cells and are, in particular, selected from the group consisting of tumorigenic gastric, esophageal, pancreatic, lung, ovarian, colon, hepatic, head-neck, and gallbladder cancer cells. Preferably, the antibody induces or mediates killing of cells by inducing one or more of complement dependent cytotoxicity (CDC) mediated lysis, antibody dependent cellular cytotoxicity (ADCC) mediated lysis, apoptosis, and inhibition of proliferation of cells expressing CLDN18.2. Preferably, ADCC mediated lysis of cells takes place in the presence of effector cells, which in particular embodiments are selected from the group consisting of monocytes, mononuclear cells, NK cells and PMNs. Inhibiting proliferation of cells can be measured in vitro by determining proliferation of cells in an assay using bromodeoxyuridine (5-bromo-2-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

In preferred embodiments, antibodies described herein can be characterized by one or more of the following properties:
a) specificity for CLDN18.2;
b) a binding affinity to CLDN18.2 of about 100 nM or less, preferably, about 5-10 nM or less and, more preferably, about 1-3 nM or less,
c) the ability to induce or mediate CDC on CLDN18.2 positive cells;
d) the ability to induce or mediate ADCC on CLDN18.2 positive cells;
e) the ability to inhibit the growth of CLDN18.2 positive cells;
f) the ability to induce apoptosis of CLDN18.2 positive cells.

In a particularly preferred embodiment, an antibody having the ability of binding to CLDN18.2 is produced by a hybridoma deposited at the DSMZ (Mascheroder Weg 1b, 31824 Braunschweig, Germany; new address: Inhoffenstr. 7B, 31824 Braunschweig, Germany) and having the following designation and accession number:
a. 182-D1106-055, accession no. DSM ACC2737, deposited on Oct. 19, 2005
b. 182-D1106-056, accession no. DSM ACC2738, deposited on Oct. 19, 2005
c. 182-D1106-057, accession no. DSM ACC2739, deposited on Oct. 19, 2005
d. 182-D1106-058, accession no. DSM ACC2740, deposited on Oct. 19, 2005
e. 182-D1106-059, accession no. DSM ACC2741, deposited on Oct. 19, 2005 f. 182-D1106-062, accession no. DSM ACC2742, deposited on Oct. 19, 2005, g. 182-D1106-067, accession no. DSM ACC2743, deposited on Oct. 19, 2005 h. 182-D758-035, accession no. DSM ACC2745, deposited on Nov. 17, 2005 i. 182-D758-036, accession no. DSM ACC2746, deposited on Nov. 17, 2005 j. 182-D758-040, accession no. DSM ACC2747, deposited on Nov. 17, 2005 k. 182-D1106-061, accession no. DSM ACC2748, deposited on Nov. 17, 2005 l. 182-D1106-279, accession no. DSM ACC2808, deposited on Oct. 26, 2006 m. 182-D1106-294, accession no. DSM ACC2809, deposited on Oct. 26, 2006, n. 182-D1106-362, accession no. DSM ACC2810, deposited on Oct. 26, 2006.

Preferred antibodies according to the invention are those produced by and obtainable from the above-described hybridomas; i.e. 37G11 in the case of 182-D1106-055, 37H8 in the case of 182-D1106-056, 38G5 in the case of 182-D1106-057, 38H3 in the case of 182-D1106-058, 39F11 in the case of 182-D1106-059, 43A11 in the case of 182-D1106-062, 61C2 in the case of 182-D1106-067, 26B5 in the case of 182-D758-035, 26D12 in the case of 182-D758-036, 28D10 in the case of 182-D758-040, 42E12 in the case of 182-D1106-061, 125E1 in the case of 182-D1106-279, 163E12 in the case of 182-D1106-294, and 175D10 in the case of 182-D1106-362; and the chimerized and humanized forms thereof.

Preferred chimerized antibodies and their sequences are shown in the following table.

prise a CH comprising an amino acid sequence derived from a human CH such as the amino acid sequence represented by SEQ ID NO: 13 or a fragment thereof and which comprise a CL comprising an amino acid sequence derived from a human CL such as the amino acid sequence represented by SEQ ID NO: 12 or a fragment thereof.

In one embodiment, an antibody having the ability of binding to CLDN18.2 is a chimeric mouse/human IgG1 monoclonal antibody comprising kappa, murine variable light chain, human kappa light chain constant region allotype Km(3), murine heavy chain variable region, human IgG1 constant region, allotype G1m(3).

In certain preferred embodiments, chimerised forms of antibodies include antibodies comprising a heavy chain comprising an amino acid sequence selected from the group consisting of SEQ ID NOs: 14, 15, 16, 17, 18, 19, and a fragment thereof and/or comprising a light chain comprising an amino acid sequence selected from the group consisting of SEQ ID NOs: 20, 21, 22, 23, 24, 25, 26, 27, 28, and a fragment thereof.

In certain preferred embodiments, chimerised forms of antibodies include antibodies comprising a combination of heavy chains and light chains selected from the following possibilities (i) to (ix):

(i) the heavy chain comprises an amino acid sequence represented by SEQ ID NO: 14 or a fragment thereof and the light chain comprises an amino acid sequence represented by SEQ ID NO: 21 or a fragment thereof, (ii) the heavy chain comprises an amino acid sequence represented by SEQ ID NO: 15 or a fragment thereof and the light chain comprises an amino acid sequence represented by SEQ ID NO: 20 or a fragment thereof,

|  | clone | mAb | Isotype | variable region | chimerized antibody |
|---|---|---|---|---|---|
| heavy chain | 43A11 | 182-D1106-062 | IgG2a | SEQ ID NO: 29 | SEQ ID NO: 14 |
|  | 163E12 | 182-D1106-294 | IgG3 | SEQ ID NO: 30 | SEQ ID NO: 15 |
|  | 125E1 | 182-D1106-279 | IgG2a | SEQ ID NO: 31 | SEQ ID NO: 16 |
|  | 166E2 | 182-D1106-308 | IgG3 | SEQ ID NO: 33 | SEQ ID NO: 18 |
|  | 175D10 | 182-D1106-362 | IgG1 | SEQ ID NO: 32 | SEQ ID NO: 17 |
|  | 45C1 | 182-D758-187 | IgG2a | SEQ ID NO: 34 | SEQ ID NO: 19 |
| light chain | 43A11 | 182-D1106-062 | IgK | SEQ ID NO: 36 | SEQ ID NO: 21 |
|  | 163E12 | 182-D1106-294 | IgK | SEQ ID NO: 35 | SEQ ID NO: 20 |
|  | 125E1 | 182-D1106-279 | IgK | SEQ ID NO: 37 | SEQ ID NO: 22 |
|  | 166E2 | 182-D1106-308 | IgK | SEQ ID NO: 40 | SEQ ID NO: 25 |
|  | 175D10 | 182-D1106-362 | IgK | SEQ ID NO: 39 | SEQ ID NO: 24 |
|  | 45C1 | 182-D758-187 | IgK | SEQ ID NO: 38 | SEQ ID NO: 23 |
|  | 45C1 | 182-D758-187 | IgK | SEQ ID NO: 41 | SEQ ID NO: 26 |
|  | 45C1 | 182-D758-187 | IgK | SEQ ID NO: 42 | SEQ ID NO: 27 |
|  | 45C1 | 182-D758-187 | IgK | SEQ ID NO: 43 | SEQ ID NO: 28 |

In preferred embodiments, antibodies, in particular chimerised forms of antibodies according to the invention include antibodies comprising a heavy chain constant region (CH) comprising an amino acid sequence derived from a human heavy chain constant region such as the amino acid sequence represented by SEQ ID NO: 13 or a fragment thereof. In further preferred embodiments, antibodies, in particular chimerised forms of antibodies according to the invention include antibodies comprising a light chain constant region (CL) comprising an amino acid sequence derived from a human light chain constant region such as the amino acid sequence represented by SEQ ID NO: 12 or a fragment thereof. In a particular preferred embodiment, antibodies, in particular chimerised forms of antibodies according to the invention include antibodies which com- (iii) the heavy chain comprises an amino acid sequence represented by SEQ ID NO: 16 or a fragment thereof and the light chain comprises an amino acid sequence represented by SEQ ID NO: 22 or a fragment thereof, (iv) the heavy chain comprises an amino acid sequence represented by SEQ ID NO: 18 or a fragment thereof and the light chain comprises an amino acid sequence represented by SEQ ID NO: 25 or a fragment thereof, (v) the heavy chain comprises an amino acid sequence represented by SEQ ID NO: 17 or a fragment thereof and the light chain comprises an amino acid sequence represented by SEQ ID NO: 24 or a fragment thereof, (vi) the heavy chain comprises an amino acid sequence represented by SEQ ID NO: 19 or a fragment thereof and the light chain comprises an amino acid sequence represented by SEQ ID NO: 23 or a fragment thereof, (vii) the heavy chain comprises an amino acid sequence represented by SEQ ID NO: 19 or a fragment thereof and the light chain comprises an amino acid sequence represented by SEQ ID NO: 26 or a fragment thereof, (viii) the heavy chain comprises an amino acid sequence represented by SEQ ID NO: 19 or a fragment thereof and the light chain comprises an amino acid sequence represented by SEQ ID NO: 27 or a fragment thereof, and (ix) the heavy chain comprises an amino acid sequence represented by SEQ ID NO: 19 or a fragment thereof and the light chain comprises an amino acid sequence represented by SEQ ID NO: 28 or a fragment thereof.

"Fragment" or "fragment of an amino acid sequence" as used above relates to a part of an antibody sequence, i.e. a sequence which represents the antibody sequence shortened at the N- and/or C-terminus, which when it replaces said antibody sequence in an antibody retains binding of said antibody to CLDN18.2 and preferably functions of said antibody as described herein, e.g. CDC mediated lysis or ADCC mediated lysis. Preferably, a fragment of an amino acid sequence comprises at least 80%, preferably at least 90%, 95%, 96%, 97%, 98%, or 99% of the amino acid residues from said amino acid sequence. A fragment of an amino acid sequence selected from the group consisting of SEQ ID NOs: 14, 15, 16, 17, 18, 19, 20, 21, 22, 23, 24, 25, 26, 27, and 28 preferably relates to said sequence wherein 17, 18, 19, 20, 21, 22 or 23 amino acids at the N-terminus are removed.

In a preferred embodiment, an antibody having the ability of binding to CLDN18.2 comprises a heavy chain variable region (VH) comprising an amino acid sequence selected from the group consisting of SEQ ID NOs: 29, 30, 31, 32, 33, 34, and a fragment thereof.

In a preferred embodiment, an antibody having the ability of binding to CLDN18.2 comprises a light chain variable region (VL) comprising an amino acid sequence selected from the group consisting of SEQ ID NO: 35, 36, 37, 38, 39, 40, 41, 42, 43, and a fragment thereof.

In certain preferred embodiments, an antibody having the ability of binding to CLDN18.2 comprises a combination of heavy chain variable region (VH) and light chain variable region (VL) selected from the following possibilities (i) to (ix):

(i) the VH comprises an amino acid sequence represented by SEQ ID NO: 29 or a fragment thereof and the VL comprises an amino acid sequence represented by SEQ ID NO: 36 or a fragment thereof, (ii) the VH comprises an amino acid sequence represented by SEQ ID NO: 30 or a fragment thereof and the VL comprises an amino acid sequence represented by SEQ ID NO: 35 or a fragment thereof, (iii) the VH comprises an amino acid sequence represented by SEQ ID NO: 31 or a fragment thereof and the VL comprises an amino acid sequence represented by SEQ ID NO: 37 or a fragment thereof, (iv) the VH comprises an amino acid sequence represented by SEQ ID NO: 33 or a fragment thereof and the VL comprises an amino acid sequence represented by SEQ ID NO: 40 or a fragment thereof, (v) the VH comprises an amino acid sequence represented by SEQ ID NO: 32 or a fragment thereof and the VL comprises an amino acid sequence represented by SEQ ID NO: 39 or a fragment thereof, (vi) the VH comprises an amino acid sequence represented by SEQ ID NO: 34 or a fragment thereof and the VL comprises an amino acid sequence represented by SEQ ID NO: 38 or a fragment thereof, (vii) the VH comprises an amino acid sequence represented by SEQ ID NO: 34 or a fragment thereof and the VL comprises an amino acid sequence represented by SEQ ID NO: 41 or a fragment thereof, (viii) the VH comprises an amino acid sequence represented by SEQ ID NO: 34 or a fragment thereof and the VL comprises an amino acid sequence represented by SEQ ID NO: 42 or a fragment thereof, (ix) the VH comprises an amino acid sequence represented by SEQ ID NO: 34 or a fragment thereof and the VL comprises an amino acid sequence represented by SEQ ID NO: 43 or a fragment thereof.

In a preferred embodiment, an antibody having the ability of binding to CLDN18.2 comprises a VH comprising a set of complementarity-determining regions CDR1, CDR2 and CDR3 selected from the following embodiments (i) to (vi):

(i) CDR1: positions 45-52 of SEQ ID NO: 14, CDR2: positions 70-77 of SEQ ID NO: 14, CDR3: positions 116-125 of SEQ ID NO: 14, (ii) CDR1: positions 45-52 of SEQ ID NO: 15, CDR2: positions 70-77 of SEQ ID NO: 15, CDR3: positions 116-126 of SEQ ID NO: 15, (iii) CDR1: positions 45-52 of SEQ ID NO: 16, CDR2: positions 70-77 of SEQ ID NO: 16, CDR3: positions 116-124 of SEQ ID NO: 16, (iv) CDR1: positions 45-52 of SEQ ID NO: 17, CDR2: positions 70-77 of SEQ ID NO: 17, CDR3: positions 116-126 of SEQ ID NO: 17, (v) CDR1: positions 44-51 of SEQ ID NO: 18, CDR2: positions 69-76 of SEQ ID NO: 18, CDR3: positions 115-125 of SEQ ID NO: 18, and (vi) CDR1: positions 45-53 of SEQ ID NO: 19, CDR2: positions 71-78 of SEQ ID NO: 19, CDR3: positions 117-128 of SEQ ID NO: 19.

In a preferred embodiment, an antibody having the ability of binding to CLDN18.2 comprises a VL comprising a set of complementarity-determining regions CDR1, CDR2 and CDR3 selected from the following embodiments (i) to (ix):

(i) CDR1: positions 47-58 of SEQ ID NO: 20, CDR2: positions 76-78 of SEQ ID NO: 20, CDR3: positions 115-123 of SEQ ID NO: 20, (ii) CDR1: positions 49-53 of SEQ ID NO: 21, CDR2: positions 71-73 of SEQ ID NO: 21, CDR3: positions 110-118 of SEQ ID NO: 21, (iii) CDR1: positions 47-52 of SEQ ID NO: 22, CDR2: positions 70-72 of SEQ ID NO: 22, CDR3: positions 109-117 of SEQ ID NO: 22, (iv) CDR1: positions 47-58 of SEQ ID NO: 23, CDR2: positions 76-78 of SEQ ID NO: 23, CDR3: positions 115-123 of SEQ ID NO: 23, (v) CDR1: positions 47-58 of SEQ ID NO: 24, CDR2: positions 76-78 of SEQ ID NO: 24, CDR3: positions 115-123 of SEQ ID NO: 24, (vi) CDR1: positions 47-58 of SEQ ID NO: 25, CDR2: positions 76-78 of SEQ ID NO: 25, CDR3: positions 115-122 of SEQ ID NO: 25, (vii) CDR1: positions 47-58 of SEQ ID NO: 26, CDR2: positions 76-78 of SEQ ID NO: 26, CDR3: positions 115-123 of SEQ ID NO: 26, (viii) CDR1: positions 47-58 of SEQ ID NO: 27, CDR2: positions 76-78 of SEQ ID NO: 27, CDR3: positions 115-123 of SEQ ID NO: 27, and (ix) CDR1: positions 47-52 of SEQ ID NO: 28, CDR2: positions 70-72 of SEQ ID NO: 28, CDR3: positions 109-117 of SEQ ID NO: 28.

In a preferred embodiment, an antibody having the ability of binding to CLDN18.2 comprises a combination of VH and VL each comprising a set of complementarity-determining regions CDR1, CDR2 and CDR3 selected from the following embodiments (i) to (ix):

(i) VH: CDR1: positions 45-52 of SEQ ID NO: 14, CDR2: positions 70-77 of SEQ ID NO: 14, CDR3: positions 116-125 of SEQ ID NO: 14, VL: CDR1: positions 49-53 of SEQ ID NO: 21, CDR2: positions 71-73 of SEQ ID NO: 21, CDR3: positions 110-118 of SEQ ID NO: 21, (ii) VH: CDR1: positions 45-52 of SEQ ID NO: 15, CDR2: positions 70-77 of SEQ ID NO: 15, CDR3: positions 116-126 of SEQ ID NO: 15, VL: CDR1: positions 47-58 of SEQ ID NO: 20, CDR2: positions 76-78 of SEQ ID NO: 20, CDR3: positions 115-123 of SEQ ID NO: 20, (iii) VH: CDR1: positions 45-52 of SEQ ID NO: 16, CDR2: positions 70-77 of SEQ ID NO: 16, CDR3: positions 116-124 of SEQ ID NO: 16, VL: CDR1: positions 47-52 of SEQ ID NO: 22, CDR2: positions 70-72 of SEQ ID NO: 22, CDR3: positions 109-117 of SEQ ID NO: 22, (iv) VH: CDR1: positions 44-51 of SEQ ID NO: 18, CDR2: positions 69-76 of SEQ ID NO: 18, CDR3: positions 115-125 of SEQ ID NO: 18, VL: CDR1: positions 47-58 of SEQ ID NO: 25, CDR2: positions 76-78 of SEQ ID NO: 25, CDR3: positions 115-122 of SEQ ID NO: 25, (v) VH: CDR1: positions 45-52 of SEQ ID NO: 17, CDR2: positions 70-77 of SEQ ID NO: 17, CDR3: positions 116-126 of SEQ ID NO: 17, VL: CDR1: positions 47-58 of SEQ ID NO: 24, CDR2: positions 76-78 of SEQ ID NO: 24, CDR3: positions 115-123 of SEQ ID NO: 24, (vi) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 23, CDR2: positions 76-78 of SEQ ID NO: 23, CDR3: positions 115-123 of SEQ ID NO: 23, (vii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 26, CDR2: positions 76-78 of SEQ ID NO: 26, CDR3: positions 115-123 of SEQ ID NO: 26, (viii) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-58 of SEQ ID NO: 27, CDR2: positions 76-78 of SEQ ID NO: 27, CDR3: positions 115-123 of SEQ ID NO: 27, and (ix) VH: CDR1: positions 45-53 of SEQ ID NO: 19, CDR2: positions 71-78 of SEQ ID NO: 19, CDR3: positions 117-128 of SEQ ID NO: 19, VL: CDR1: positions 47-52 of SEQ ID NO: 28, CDR2: positions 70-72 of SEQ ID NO: 28, CDR3: positions 109-117 of SEQ ID NO: 28.

In further preferred embodiments, an antibody having the ability of binding to CLDN18.2 preferably comprises one or more of the complementarity-determining regions (CDRs), preferably at least the CDR3 variable region, of the heavy chain variable region (VH) and/or of the light chain variable region (VL) of a monoclonal antibody against CLDN18.2, preferably of a monoclonal antibody against CLDN18.2 described herein, and preferably comprises one or more of the complementarity-determining regions (CDRs), preferably at least the CDR3 variable region, of the heavy chain variable regions (VH) and/or light chain variable regions (VL) described herein. In one embodiment said one or more of the complementarity-determining regions (CDRs) are selected from a set of complementarity-determining regions CDR1, CDR2 and CDR3 described herein. In a particularly preferred embodiment, an antibody having the ability of binding to CLDN18.2 preferably comprises the complementarity-determining regions CDR1, CDR2 and CDR3 of the heavy chain variable region (VH) and/or of the light chain variable region (VL) of a monoclonal antibody against CLDN18.2, preferably of a monoclonal antibody against CLDN18.2 described herein, and preferably comprises the complementarity-determining regions CDR1, CDR2 and CDR3 of the heavy chain variable regions (VH) and/or light chain variable regions (VL) described herein.

In one embodiment an antibody comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of antibodies made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment an antibody comprising one or more CDRs, a set of CDRs or a combination of sets of CDRs as described herein comprises said CDRs in a human antibody framework.

Reference herein to an antibody comprising with respect to the heavy chain thereof a particular chain, or a particular region or sequence preferably relates to the situation wherein all heavy chains of said antibody comprise said particular chain, region or sequence. This applies correspondingly to the light chain of an antibody.

The term "nucleic acid", as used herein, is intended to include DNA and RNA. A nucleic acid may be single-stranded or double-stranded, but preferably is double-stranded DNA.

According to the invention, the term "expression" is used in its most general meaning and comprises the production of RNA or of RNA and protein/peptide. It also comprises partial expression of nucleic acids. Furthermore, expression may be carried out transiently or stably.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding of an antibody to its target or to sustain effector functions of an antibody. Preferably, a sequence which is a variant with respect to a specific sequence, when it replaces the specific sequence in an antibody retains binding of said antibody to CLDN18.2 and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind CLDN18.2. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The term "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN18.2 antibodies when immunized with CLDN18.2 antigen and/or cells expressing CLDN18.2. The human heavy chain transgene can be integrated into the chromosomal DNA of the mouse, as is the case for transgenic mice, e.g., HuMAb mice, such as HCo7 or HCol2 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN18.2 (e.g., IgG, IgA and/or IgE) by undergoing V-D-J recombination and isotype switching.

"Reduce", "decrease" or "inhibit" as used herein means an overall decrease or the ability to cause an overall decrease, preferably of 5% or greater, 10% or greater, 20% or greater, more preferably of 50% or greater, and most preferably of 75% or greater, in the level, e.g. in the level of expression or in the level of proliferation of cells.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

Mechanisms of mAb Action

Although the following provides considerations regarding the mechanism underlying the therapeutic efficacy of antibodies of the invention it is not to be considered as limiting to the invention in any way.

The antibodies described herein preferably interact with components of the immune system, preferably through ADCC or CDC. Antibodies described herein can also be used to target payloads (e.g., radioisotopes, drugs or toxins) to directly kill tumor cells or can be used synergistically with traditional chemotherapeutic agents, attacking tumors through complementary mechanisms of action that may include anti-tumor immune responses that may have been compromised owing to a chemotherapeutic's cytotoxic side effects on T lymphocytes. However, antibodies described herein may also exert an effect simply by binding to CLDN18.2 on the cell surface, thus, e.g. blocking proliferation of the cells.

Antibody-Dependent Cell-Mediated Cytotoxicity

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-Dependent Cytotoxicity

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell.

Production and Testing of Antibodies

Antibodies described herein can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined specificity e.g. see Babcock et al., 1996; A novel strategy for generating monoclonal antibodies from single, isolated lymphocytes producing antibodies of defined specificities. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitonealy or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

Antibodies also can be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. E. coli. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Chimerization

Murine monoclonal antibodies can be used as therapeutic antibodies in humans when labeled with toxins or radioactive isotopes. Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment chimeric antibodies are generated by joining human kappa-light chain constant region to murine light chain variable region. In an also preferred embodiment chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region.

The ability of antibodies to bind an antigen can be determined using standard binding assays (e.g., ELISA, Western Blot, Immunofluorescence and flow cytometric analysis).

To purify antibodies, selected hybridomas can be grown in two-liter spinner-flasks for monoclonal antibody purification. Alternatively, antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected monoclonal antibodies bind to unique epitopes, site-directed or multi-site directed mutagenesis can be used.

To determine the isotype of antibodies, isotype ELISAs with various commercial kits (e.g. Zymed, Roche Diagnostics) can be performed. Wells of microtiter plates can be coated with anti-mouse Ig. After blocking, the plates are reacted with monoclonal antibodies or purified isotype controls, at ambient temperature for two hours. The wells can then be reacted with either mouse IgG1, IgG2a, IgG2b or IgG3, IgA or mouse IgM-specific peroxidase-conjugated probes. After washing, the plates can be developed with ABTS substrate (1 mg/ml) and analyzed at OD of 405-650. Alternatively, the IsoStrip Mouse Monoclonal Antibody Isotyping Kit (Roche, Cat. No. 1493027) may be used as described by the manufacturer.

In order to demonstrate presence of antibodies in sera of immunized mice or binding of monoclonal antibodies to living cells expressing antigen, flow cytometry can be used. Cell lines expressing naturally or after transfection antigen and negative controls lacking antigen expression (grown under standard growth conditions) can be mixed with various concentrations of monoclonal antibodies in hybridoma supernatants or in PBS containing 1% FBS, and can be incubated at 4° C. for 30 min. After washing, the APC- or Alexa647-labeled anti IgG antibody can bind to antigen-bound monoclonal antibody under the same conditions as the primary antibody staining. The samples can be analyzed by flow cytometry with a FACS instrument using light and side scatter properties to gate on single, living cells. In order to distinguish antigen-specific monoclonal antibodies from non-specific binders in a single measurement, the method of co-transfection can be employed. Cells transiently transfected with plasmids encoding antigen and a fluorescent marker can be stained as described above. Transfected cells can be detected in a different fluorescence channel than antibody-stained cells. As the majority of transfected cells express both transgenes, antigen-specific monoclonal antibodies bind preferentially to fluorescence marker expressing cells, whereas non-specific antibodies bind in a comparable ratio to non-transfected cells. An alternative assay using fluorescence microscopy may be used in addition to or instead of the flow cytometry assay. Cells can be stained exactly as described above and examined by fluorescence microscopy.

In order to demonstrate presence of antibodies in sera of immunized mice or binding of monoclonal antibodies to living cells expressing antigen, immunofluorescence microscopy analysis can be used. For example, cell lines expressing either spontaneously or after transfection antigen and negative controls lacking antigen expression are grown in chamber slides under standard growth conditions in DMEM/F12 medium, supplemented with 10% fetal calf serum (FCS), 2 mM L-glutamine, 100 IU/ml penicillin and 100 µg/ml streptomycin. Cells can then be fixed with methanol or paraformaldehyde or left untreated. Cells can then be reacted with monoclonal antibodies against the antigen for 30 min. at 25° C. After washing, cells can be reacted with an Alexa555-labelled anti-mouse IgG secondary antibody (Molecular Probes) under the same conditions. Cells can then be examined by fluorescence microscopy.

Cell extracts from cells expressing antigen and appropriate negative controls can be prepared and subjected to sodium dodecyl sulfate (SDS) polyacrylamide gel electrophoresis. After electrophoresis, the separated antigens will be transferred to nitrocellulose membranes, blocked, and probed with the monoclonal antibodies to be tested. IgG binding can be detected using anti-mouse IgG peroxidase and developed with ECL substrate.

Antibodies can be further tested for reactivity with antigen by Immunohistochemistry in a manner well known to the skilled person, e.g. using paraformaldehyde or acetone fixed cryosections or paraffin embedded tissue sections fixed with paraformaldehyde from non-cancer tissue or cancer tissue samples obtained from patients during routine surgical procedures or from mice carrying xenografted tumors inoculated with cell lines expressing spontaneously or after transfection antigen. For immunostaining, antibodies reactive to antigen can be incubated followed by horseradish-peroxidase conjugated goat anti-mouse or goat anti-rabbit antibodies (DAKO) according to the vendors instructions.

Antibodies can be tested for their ability to mediate phagocytosis and killing of cells expressing CLDN18.2. The testing of monoclonal antibody activity in vitro will provide an initial screening prior to testing in vivo models.

Antibody Dependent Cell-Mediated Cytotoxicity (ADCC)

Briefly, polymorphonuclear cells (PMNs), NK cells, monocytes, mononuclear cells or other effector cells, from healthy donors can be purified by Ficoll Hypaque density centrifugation, followed by lysis of contaminating erythrocytes. Washed effector cells can be suspended in RPMI supplemented with 10% heat-inactivated fetal calf serum or, alternatively with 5% heat-inactivated human serum and mixed with $^{51}$Cr labeled target cells expressing CLDN18.2, at various ratios of effector cells to target cells. Alternatively, the target cells may be labeled with a fluorescence enhancing ligand (BATDA). A highly fluorescent chelate of Europium with the enhancing ligand which is released from dead cells can be measured by a fluorometer. Another alternative technique may utilize the transfection of target cells with luciferase. Added lucifer yellow may then be oxidated by viable cells only. Purified anti-CLDN18.2 IgGs can then be added at various concentrations. Irrelevant human IgG can be used as negative control. Assays can be carried out for 4 to 20 hours at 37° C. depending on the effector cell type used. Samples can be assayed for cytolysis by measuring $^{51}$Cr release or the presence of the EuTDA chelate in the culture supernatant. Alternatively, luminescence resulting from the oxidation of lucifer yellow can be a measure of viable cells.

Anti-CLDN18.2 monoclonal antibodies can also be tested in various combinations to determine whether cytolysis is enhanced with multiple monoclonal antibodies.

Complement Dependent Cytotoxicity (CDC)

Monoclonal anti-CLDN18.2 antibodies can be tested for their ability to mediate CDC using a variety of known techniques. For example, serum for complement can be obtained from blood in a manner known to the skilled person. To determine the CDC activity of mAbs, different methods can be used. $^{51}$Cr release can for example be measured or elevated membrane permeability can be assessed using a propidium iodide (PI) exclusion assay. Briefly, target cells can be washed and $5\times10^5$/ml can be incubated with various concentrations of mAb for 10-30 min. at room temperature or at 37° C. Serum or plasma can then be added to a final concentration of 20% (v/v) and the cells incubated at 37° C. for 20-30 min. All cells from each sample can be added to the PI solution in a FACS tube. The mixture can then be analyzed immediately by flow cytometry analysis using FACSArray.

In an alternative assay, induction of CDC can be determined on adherent cells. In one embodiment of this assay, cells are seeded 24 h before the assay with a density of $3\times10^4$/well in tissue-culture flat-bottom microtiter plates. The next day growth medium is removed and the cells are incubated in triplicates with antibodies. Control cells are incubated with growth medium or growth medium containing 0.2% saponin for the determination of background lysis and maximal lysis, respectively. After incubation for 20 min. at room temperature supernatant is removed and 20% (v/v) human plasma or serum in DMEM (prewarmed to 37° C.) is added to the cells and incubated for another 20 min. at 37° C. All cells from each sample are added to propidium iodide solution (10 µg/ml). Then, supernatants are replaced by PBS containing 2.5 g/ml ethidium bromide and fluorescence emission upon excitation at 520 nm is measured at 600 nm using a Tecan Safire. The percentage specific lysis is calculated as follows: % specific lysis=(fluorescence sample-fluorescence background)/(fluorescence maximal lysis-fluorescence background)×100.

Induction of Apoptosis and Inhibition of Cell Proliferation by Monoclonal Antibodies To test for the ability to initiate apoptosis, monoclonal anti-CLDN18.2 antibodies can, for example, be incubated with CLDN18.2 positive tumor cells, e.g., SNU-16, DAN-G, KATO-III or CLDN18.2 transfected tumor cells at 37° C. for about 20 hours. The cells can be harvested, washed in Annexin-V binding buffer (BD biosciences), and incubated with Annexin V conjugated with FITC or APC (BD biosciences) for 15 min. in the dark. All cells from each sample can be added to PI solution (10 µg/ml in PBS) in a FACS tube and assessed immediately by flow cytometry (as above). Alternatively, a general inhibition of cell-proliferation by monoclonal antibodies can be detected with commercially available kits. The DELFIA Cell Proliferation Kit (Perkin-Elmer, Cat. No. AD0200) is a non-isotopic immunoassay based on the measurement of 5-bromo-2'-deoxyuridine (BrdU) incorporation during DNA synthesis of proliferating cells in microplates. Incorporated BrdU is detected using europium labelled monoclonal antibody. To allow antibody detection, cells are fixed and DNA denatured using Fix solution. Unbound antibody is washed away and DELFIA inducer is added to dissociate europium ions from the labelled antibody into solution, where they form highly fluorescent chelates with components of the DELFIA Inducer. The fluorescence measured—utilizing time-resolved fluorometry in the detection—is proportional to the DNA synthesis in the cell of each well.

Preclinical Studies

Monoclonal antibodies which bind to CLDN18.2 also can be tested in an in vivo model (e.g. in immune deficient mice carrying xenografted tumors inoculated with cell lines expressing CLDN18.2, e.g. DAN-G, SNU-16, or KATO-III, or after transfection, e.g. HEK293) to determine their efficacy in controlling growth of CLDN18.2-expressing tumor cells.

In vivo studies after xenografting CLDN18.2 expressing tumor cells into immunocompromised mice or other animals can be performed using antibodies described herein. Antibodies can be administered to tumor free mice followed by injection of tumor cells to measure the effects of the antibodies to prevent formation of tumors or tumor-related symptoms. Antibodies can be administered to tumor-bearing mice to determine the therapeutic efficacy of respective antibodies to reduce tumor growth, metastasis or tumor related symptoms. Antibody application can be combined with application of other substances as cystostatic drugs, growth factor inhibitors, cell cycle blockers, angiogenesis inhibitors or other antibodies to determine synergistic efficacy and potential toxicity of combinations. To analyze toxic side effects mediated by antibodies animals can be inoculated with antibodies or control reagents and thoroughly investigated for symptoms possibly related to CLDN18.2-antibody therapy. Possible side effects of in vivo application of CLDN18.2 antibodies particularly include toxicity at CLDN18.2 expressing tissues including stomach. Antibodies recognizing CLDN18.2 in human and in other species, e.g. mice, are particularly useful to predict potential side effects mediated by application of monoclonal CLDN18.2-antibodies in humans.

Mapping of epitopes recognized by antibodies can be performed as described in detail in "Epitope Mapping Protocols (Methods in Molecular Biology) by Glenn E. Morris ISBN-089603-375-9 and in "Epitope Mapping: A Practical Approach" Practical Approach Series, 248 by Olwyn M. R. Westwood, Frank C. Hay.

The compounds and agents described herein may be administered in the form of any suitable pharmaceutical composition.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectible formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by an altered expression pattern of CLDN18.2.

For example, in one embodiment, antibodies described herein can be used to treat a patient with a cancer disease, e.g., a cancer disease such as described herein characterized by the presence of cancer cells expressing CLDN18.2.

The pharmaceutical compositions and methods of treatment described according to the invention may also be used for immunization or vaccination to prevent a disease described herein.

The present invention is further illustrated by the following examples which are not be construed as limiting the scope of the invention.

EXAMPLES

Example 1: Material and Methods

1. Antibodies

TABLE 1

Antibodies used herein

| Antibody | Provider (Cat. #) | Target | Binding site | Clonality | Species | Applications |
|---|---|---|---|---|---|---|
| IMAB362 | Ganymed | CLDN18.2 | N-Term | monoclonal | chimeric | ADCC, CDC, IF |
| anti Claudin18 (MID) | Zymed #38-8100 | CLDN18.1 CLDN18.2 | C-term aa220-246 | polyclonal | rabbit | IF, IHC |
| anti Claudin18 (C-term) | Zymed #38-800 | CLDN18.1 CLDN18.2 | C-term aa240-262 | polyclonal | rabbit | WB |
| 43-14A | Ganymed | CLDN18.2 | C-term aa248-262 | monoclonal | mouse | IHC |
| 35-22A | Ganymed | CLDN18.2 | C-term aa248-262 | monoclonal | mouse | IF, IHC |
| anti human EPR1394Y | Antibody online | human MHC-I | — | monoclonal | rabbit | IHC |
| β-Actin | SIGMA | Actin | | monoclonal | mouse | WB |

2. Immunhistochemistry (IHC)

Tissue sections (4 μm thickness) were stored at 2-8° C. until use.

Prior to the deparaffinization process the sections were incubated at 58-60° C. in a drying oven for 1 hour to melt the paraffin and to quantitatively remove water, thereby improving adherence of the tissues to the glass slides ("baking").

Deparaffinization

After melting and drying, the slides were deparaffinized using two xylol steps (5 minutes) and rehydrated using a descending alcohol array (at an ambient temperature of 20-27° C.):

5 (±1) minutes in a xylene bath;
this step was repeated once in a fresh bath;
excess liquid;
5 (±1) minutes in absolute ethanol;
repeat this step once with a fresh bath;
remove excess liquid;
5 (±1) minutes in 96% ethanol;
repeat this step once with a fresh bath;
remove excess liquid;
5 (±1) minutes in 80% ethanol;
remove excess liquid;
5 (±1) minutes in 70% ethanol;
remove excess liquid;
5 minutes in distilled or deionized water;

Epitope Retrieval and Quenching

Following the paraffin removal the target epitopes were retrieved by using a heat induced epitope retrieval procedure. Therefore the slides were put in staining jars filled with 200 ml of retrieval buffer (10 mM Citric buffer; 0.05% Tween-20; pH 6) and incubated in a pressure cooker (PASCAL, Dako) at 120° C. for 10 minutes. Afterwards the jars were removed from the cooker and allowed to cool in the Epitope Retrieval Solution for 10 (±1) min at room temperature. The slides were rinsed in Wash Buffer (1×PBS).

After cooling the sections were moved into staining jars filled with 200 ml quenching solution (0.3% Peroxidase in 1×PBS) and incubated for 15 min at room temperature, followed by 2×5 minutes washing steps in fresh wash buffer.

Blocking and Antibody Incubation

The excess wash buffer was removed, the slides were covered with 200 μl blocking buffer (10% goat serum in 1×PBS) and incubated at RT for 30 minutes. The blocking buffer was removed and replaced by 200 μl diluted antibody solution (dilution in blocking buffer). The slides were incubated with the primary antibody overnight at 2-8° C.

TABLE 2

Dilution of primary antibodies for histology analysis-stock concentration and final concentration of the antibodies used in histological assays
Primary antibody dilution

| Antibody | Stock conc. | subtype | epitope | epitope sequence | Final conc. |
|---|---|---|---|---|---|
| mumAb 43-14A | 1 mg/ml | IgG2b | CLDN18 c-term. | TEDEVQSYPSKHDYV | 0.5 μg/mL |
| mumAb 35-22A | 1 mg/ml | IgG2b | CLDN18 c-term. | TEDEVQSYPSKHDYV | 0.2 μg/mL |

On the next day the primary antibody solution was removed and the sections were washed for 3×5 min with washing buffer. Afterwards the excess wash buffer was removed and 200 μl of the ready-to-use secondary antibody solution was added (Power Vision HRP goat-α-mouse; Immunologic; NL). The slides were incubated for 30 min at RT. The excess liquid was removed and the slides washed for 3×5 min in fresh washing buffer.

Substrate Reaction and Counterstaining

After removal of excess washing buffer the sections were covered with approx. 50-150 μL of the freshly prepared substrate-chromogen solution (VectorRed; Vector Labs) for 2 min. The excess substrate was removed and the slides were incubated in jars with deionized water for 1-5 min. Subsequently, a counterstain of the tissue was performed by immersing the sections in jars containing 200 ml of Mayer's haematoxylin for 2 min. Afterwards the sections were placed in tap water for 5-10 min for the blueing of the nuclei.

Dehydration and Mounting

After performing the counterstaining, the sections were dehydrated using an ascending alcohol array:
dipping in 70% ethanol (approx. 5-10 sec)
dipping in 80% ethanol (approx. 5-10 sec)
dipping in 96% ethanol (approx. 5-10 sec)
dipping in 96% ethanol (approx. 5-10 sec)
dipping in absolute ethanol (approx. 5-10 sec)
5 min in xylene
5 min in xylene For the mounting of the samples a non-aqueous mounting medium (X-TRA-Kit, Medite) was used. The slides were mounted directly from the last xylene filled jar and air dried at RT.

TABLE 3

Tissue micro arrays for histology analysis

| TMA ID | distributer | number of cases | number of cores | core size | thickness |
|---|---|---|---|---|---|
| PA961; Pancreatic carcinoma and normal tissue microarray | Biocat | 96 | 96 | 1.5 mm | 5 μm |
| PA802; Multiple pancreatic carcinoma tissue array, single core per case | Biocat | 78 | 80 | 1.5 mm | 5 μm |
| BIC14011; Pancreas intraepithelial neoplasia tissue microarray | Biocat | 24 | 48 | 1.5 mm | 5 μm |

3. Cell Culture

All pancreatic cancer cell lines and additional control cell lines used for experiments presented herein are cultivated in media according to data sheets of origin and following standard tissue culture procedures. Conditions are summarized in Table 4. For all newly obtained cell lines, cells were tested for mycoplasm contamination and a master cell bank was prepared.

TABLE 4

Cell culture conditions for human pancreatic cancer and control cell lines

| Cell line[1] | Flask/dish | Medium | Incubation | Seeding density 2 days[2] | 3 days[2] |
|---|---|---|---|---|---|
| AsPC-1 | T150 | RPMI + 10% FCS | 5% $CO_2$, 37° C. | 1e7 | 8e6 |
| BxPC3 (ATCC) | T150 | RPMI + 10 mM HEPES + 1 mM sodium pyruvate + 4.5 g/L glucose (total) + 10% FCS Gold | 5% $CO_2$, 37° C. | 8e6 | 7e6 |
| BxPC3-LVT (ECACC) | T150 | RPMI + 10 mM HEPES + 1 mM sodium pyruvate + 1x sodium bicarbonate + 4.5 g/L glucose + 10% FCS + 1% Pen/Strep + 0.5 μg/ml (fresh) Blasticidin | 5% $CO_2$, 37° C. | 1e7 | 8e6 |
| BxPC3-LVT-Luciferase | T150 | RPMI + 10 mM HEPES + 1 mM sodium pyruvate + 1x sodium bicarbonate + 4.5 g/L glucose + 10% FCS + 1% Pen/Strep + 0.5 μg/ml Blasticidin (fresh) + 40 μg/ml Hygromycin (fresh) | 5% $CO_2$, 37° C. | 1e7 | 8e6 |
| CAPAN1 | T150 | RPMI + 20% FCS | 5% $CO_2$, 37° C. | 8e6 | 8e6 |
| CAPAN1-LVT | T150 | RPMI + 20% FCS + 1% Pen/Strep + 2.5 μg/ml Blasticidin (fresh) | 5% $CO_2$, 37° C. | 1e7 | 8e6 |
| CAPAN1-LVT- | T150 | RPMI + 20% FCS + 1% Pen/Strep + 2.5 μg/ml Blasticidin (fresh) + 40 μg/ml Hygromycin | 5% $CO_2$, 37° C. | 1e7 | 8e6 |
| CHO-K1p740 MACS/FACS (24H5) Luci #2A5 | 15 cm | DMEM:F12 + 1% Pen/Strep + 10% FCS + 1.5 mg/mL Geneticin (G-418) | 7.5% $CO_2$, 37° C. | 1.6e6 | 7e5 |
| CFPAC-1 | T150 | Iscove's MDM + 10% FCS | 5% $CO_2$, 37° C. | 5e6 | 3e6 |
| DANG 1C5F2 | 15 cm | RPMI + 1% Pen/Strep + 10% FCS | 5% $CO_2$, 37° C. | 4e6 | 2e6 |
| DANG 1C5F2 LVT | 15 cm | RPMI + 1% Pen/Strep + 10% FCS + 1 μg/ml Blasticidin (fresh) | 5% $CO_2$, 37° C. | 4e6 | 2e6 |
| HEK293p740#A5 | 15 cm | DMEM:F12 + 1% Pen/Strep + 10% FCS + 1.5 mg/mL Geneticin (G-418) | 7.5% $CO_2$, 37° C. | 8e6 | 5e6 |
| HPAC | T150 | DMEM:F12 + 15 mM HEPES + 0.002 mg/ml human Insulin + 10 ng/mL EGF + 5% FCS | 5% $CO_2$, 37° C. | 6e6 | 4e6 |
| HPAC-LVT | T150 | DMEM:F12 + 15 mM HEPES + 0.002 mg/ml human Insulin + 10 ng/mL EGF + 5% FCS + 1% Pen/Strep + 3.5 μg/ml Blasiticidin (fresh) | 5% $CO_2$, 37° C. | 6e6 | 4e6 |

TABLE 4-continued

Cell culture conditions for human pancreatic cancer and control cell lines

| Cell line[1] | Flask/dish | Medium | Incubation | Seeding density 2 days[2] | 3 days[2] |
|---|---|---|---|---|---|
| HPAF-II | T150 | MEM + 10% FCS | 5% $CO_2$, 37° C. | 5e6 | 5e6 |
| HUP-T3 | T150 | MEM + 1x MEM NEAA + 1 mM sodium pyruvate + 10% FCS | 5% $CO_2$, 37° C. | 6e6 | 3e6 |
| HUP-T4 | T150 | MEM + 1x MEM NEAA + 1 mM sodium pyruvate + 20% FCS | 5% $CO_2$, 37° C. | 6e6 | 4e6 |
| KATO III FGF-BP #12 adM[3] | T150 | RPMI + 1% Pen/Strep + 4 mM Glutamax (total) + 20% FCS | 7.5% $CO_2$, 37° C. | 8e6 | 5e6 |
| KP-2 | T150 | RPMI + 10% FCS | 5% $CO_2$, 37° C. | 8e6 | 6e6 |
| MiaPaCa-2 | T150 | MEM + 10% FCS | 5% $CO_2$, 37° C. | 1e7 | 8e6 |
| MiaPaCa-2-LVT | T150 | MEM + 10% FCS + 1% Pen/Strep + 1.5 µg/ml Blasticidin | 5% $CO_2$, 37° C. | 1e7 | 8e6 |
| NUGC-4 sub 10cH11 subE10 Luci#2 | T150 | RPMI + 1% Pen/Strep + 10% FCS | 5% $CO_2$, 37° C. | 8e6 C | 5e6 C |
| Panc-1 | T150 | DMEM + 10% FCS | 5% $CO_2$, 37° C. | 6e6 C | 4e6 C |
| Panc03.27 | T150 | RPMI + 10 mM HEPES + 1 mM sodium pyruvate + 4.5 g/L glucose + 0.01 mg/mL Insulin + 15% FCS | 5% $CO_2$, 37° C. | 6e6 C | 4e6 C |
| Panc05.04 | T150 | RPMI + 10 mM HEPES + 1 mM sodium pyruvate + 4.5 g/L glucose + 0.01 mg/mL Insulin + 15% FCS | 5% $CO_2$, 37° C. | 6e6 C | 4e6 C |
| Panc05.04 subclones | T150 | RPMI + 10 mM HEPES + 1 mM sodium pyruvate + 4.5 g/L glucose + 0.01 mg/ml Insulin + 15% FCS | 5% $CO_2$, 37° C. | 7e6 C | 5e6 C |
| Patu8902 | T150 | DMEM + 10% FCS | 5% $CO_2$, 37° C. | 5e6 C | 4e6 C |
| Patu8902-LVT | T150 | DMEM + 10% FCS + 1% Pen/Strep + 9 µg/ml Blasticidin (fresh) | 5% $CO_2$, 37° C. | 5e6 C | 4e6 C |
| Patu8988T | T150 | DMEM + 5% horse serum + 5% FCS | 5% $CO_2$, 37° C. | 3e6 C | 1e6 C |
| Patu8988S | T150 | DMEM + 5% horse serum + 5% FCS | 5-7.5% $CO_2$, 37° C. | 1.5e7 | 1e7 |
| Su86.86 | T150 | RPMI + 10 mM HEPES + 1 mM sodium pyruvate + 4.5 g/L glucose + 10% FCS | 5% $CO_2$, 37° C. | 5e6 | 3e6 |
| Suit-2 | T150 | RPMI + 10% FCS (use new flask for each split) | 5% $CO_2$, 37° C. | 1.5e7 | 1.2e7 |
| Suit-2-LVT | T150 | RPMI + 10% FCS + 1% Pen/Strep + 5 µg/ml Blasticidin (fresh) (use new flask for each split) | 5% $CO_2$, 37° C. | 1.5e7 | 1.2e7 |
| SW1990 | T150 | Leibovitz's L-15 + 10% FCS | 37° C. | 4e6 | 3e6 |
| YAPC | T150 | RPMI + 10% FCS Gold | 5% $CO_2$, 37° C. | 1.5e7 | 1e7 |
| YAPC-LVT | T150 | RPMI + 10% FCS Gold + 1% Pen/Strep + 0.5 µg/ml Blasticidin (fresh) | 5% $CO_2$, 37° C. | 1.5e7 | 1e7 |

[1]LVT refers to cell lines stably transduced with lentivirus for expression of CLDN18.2.
[2]Seeding density in the mentioned flask or dish for cultivation of cells for 2 or 3 days.
[3]adM: Cells are-recultivated from subcutaneous tumors 4. Luciferase Transfection of Pancreas Cell Lines For ADCC assays pancreatic cancer cell lines were transiently transfected with luciferase RNA. This luciferase RNA (pST1-luc2mut-2hBgUTR-A121-EciI vector (pST1-109)) was produced with an ARCA cap and dissolved in $H_2O$. RNA was stored in 22 µl aliquots at −80° C. For all pancreas cell lines the optimal electroporation conditions were determined resulting in highest transfection rates and viability of the cells. In each assay cells were detached with PBS/5 mM EDTA and 2.5×10$^6$ cells dissolved in 250 µl X-Vivo were mixed in ice-cold cuvettes with 10 µg RNA. Cells were immediately electroporated (GenePulser Xcell, Biorad) and resuspended in pre-warmed Assay-medium adjusting the cells to 5×10$^5$ cells/ml. Tested electroporation conditions were for all cell lines:

EP1: 250V, 475 µF
EP2: 200 V, 300 µF
EP3: 150V, 300 µF
EP4: 200 V, 400 µF
EP5: 250 V, 950 µF
Control: 0 V, 0 µF The viability of the cells was determined directly after electroporation using CASY or by staining cells with Trypan blue and determining the percentage of dead cells in the Neubauer chamber. Cells were seeded in quadruplicates in white 96-well plates (2.5×10$^4$ cells/well) and incubated for 24 h. Subsequently, luciferase activity was measured in a luminometer (Tecan Infinite200) after addition of luciferin mix for 90 min. Transfection was successful and consequently ADCC measurable, if RLU values>1.000 were obtained.

5. Quantitative Real-Time PCR (Q-PCR)

For RNA isolation from pancreatic cancer cell lines, cells were seeded in 10 cm dishes and grown for 2-3 days until 80% confluent. RNA was isolated according to instructions supplied with the RNeasy® Mini Kit (Qiagen). cDNA preparation was performed following manufacturers instructions provided with the SuperScript® III First Strand kit (Invitrogen). RNA and cDNA samples were stored at −80° C.

Quantitative analysis of CLDN18.2 transcripts was performed by amplifying oligo(dT)-primed cDNAs in a 40 cycle PCR reaction using PCR primers #5054s (5'-AGAGAGCTCTGGCTTCACCGAGTG-3') and #5060as (5'-CCAGAAGTTAGTCACCAGCATGTTGG-3') differentiating between CLDN18.1 and CLDN18.2 isoforms. The reaction was prepared with SYBR Green (QuantiTect SYBR Green PCR Kit, Qiagen), which intercalates in double stranded DNA. The reactions and measurements were performed using the ABI-PRISM7900 Sequence Detection System instrument and software (Applied Biosystems).

The relative expression levels of CLDN18 transcripts was computed using ΔΔCT calculation with respect to the house keeping gene HPRT.

6. Western Blot Analysis

For isolation of proteins of pancreatic cancer cell lines, cells were seeded in 10 cm dishes and grown for 2-3 days until 80% confluent. Cells were lysed by addition of 800 µl 4×SDS sample buffer (34% glycin, 250 mM Tris pH6.8, 5% β-mercaptoethanol, 8.2% SDS). To disintegrate the genomic DNA, the protein samples were sonified under following conditions: Output Control: level 1, Duty Cycle: 70% for 20-25 sec. Protein concentration was measured in a spectrophotometer (Absorption at 280 nm) and samples were stored at −80° C. until use.

To detect CLDN18.2 expression in Western blots, a 12.5% poly acrylamide gel for separation (for 2 small gels 4.1 ml 29:1 acrylamide/bis-acrylamide, 100 µl 10% SDS, 2.5 ml Tris pH8.8, 3.2 ml $H_2O$, 100 µl APS, 10 µl TEMED) was prepared between two fixed glass plates. After polymerization the gel was overlaid with a stacking gel (1.5 ml 29:1 acrylamide/bis-acrylamide, 100 µl 10% SDS, 2.5 ml Tris pH6.8, 5.8 ml $H_2O$, 100 µl APS, 10 µl TEMED) and a gel comb was placed between the glass plates. After polymerization the gel was loaded with 75 µg of each protein sample prepared by addition of (1:20) 4×SDS-sample buffer (250 mM Tris-HCL, 34% Glycerine, 8.2% SDS, pH 6.8) and 7.5 µl of a size marker-mix (1.5 µl Magic Mark XP Western Standard mixed with 6 µl SeaBlue Plus2 Prestained Standard). Gels were run in 1×SDS running buffer (25 mM Tris, 0.192 M Glycin, 0.1% SDS) at 80 V for 30 min and 180 V for 60 min. Semi-dry blotting of the gel on a nitrocellulose membrane was performed for 90 min at 160 mA in 1× transfer buffer (25 mM Tris, 0.192 mM glycin, 20% MeOH). Blots were first blocked in 5% milk powder/PBS and primary antibodies (0.25 µg/ml anti-Claudin18 (C-term) or 0.1 µg/ml anti-β-actin) were added in a solution of 1% milk powder/PBS. Blots were incubated over night at 4° C., washed 3 times 10 min in 1×PBS/0.05% Tween20 and then incubated for 1 h with labelled secondary antibodies at room temperature in 1% milk powder/PBS (goat-anti-rabbit IgG (FC) diluted 1:1000). Blots were washed again 3 times 10 min in 1×PBS/0.05% Tween20 and detection was performed by addition of 1-3 ml detection solution (Pico and Dura Detection System (Pierce) for 1 min and scanning of the blots in a LAS-3000 detection box (Increment: 10 sec, Interval Time: 10 sec, Sensitivity: high) according to GA_056_Chemolumineszenzentwickler LAS3000.

7. Flowcytometry (FACS)

Cells were harvested with PBS/5 mM EDTA or Trypsin/EDTA from an exponentially growing culture at 70-85% confluency. Cells were counted, centrifuged for 5 min (468 g) and the pellet was resuspended in FACS buffer (2% FCS, 0.1% sodium azide in PBS) adjusting the concentration to $2\times10^6$/ml. 100 µl cells were plated in round bottom 96-well plates and again centrifuged (5 min, 468 g). IMAB362 (or isotype control Rituximab) was serially diluted 0.1-200 µg/ml (11 dilution steps+no antibody control) in 50 µl FACS-buffer and added to the cells for 30 min at 4° C. Then, 200 µl FACS buffer was added to each well and plates were centrifuged (5 min, 468 g). The supernatant was removed and washing was repeated. Secondary goat anti-human antibodies (FC specific, F(ab')2 conjugated with APC (Dianova)) were diluted (1:100) in FACS buffer and 30 µl was added to each well. Plates were incubated for 30 min at 4° C. After incubation plates were washed again two times with 200 µl FACS buffer and the pellet was finally resuspended in 100 µl FACS buffer for measurement FACS Array Bioanalyzer (BD) according to GA_018_BD FACS Array bioanalyzer.

8. Lentiviral Transduction

Figure 1:
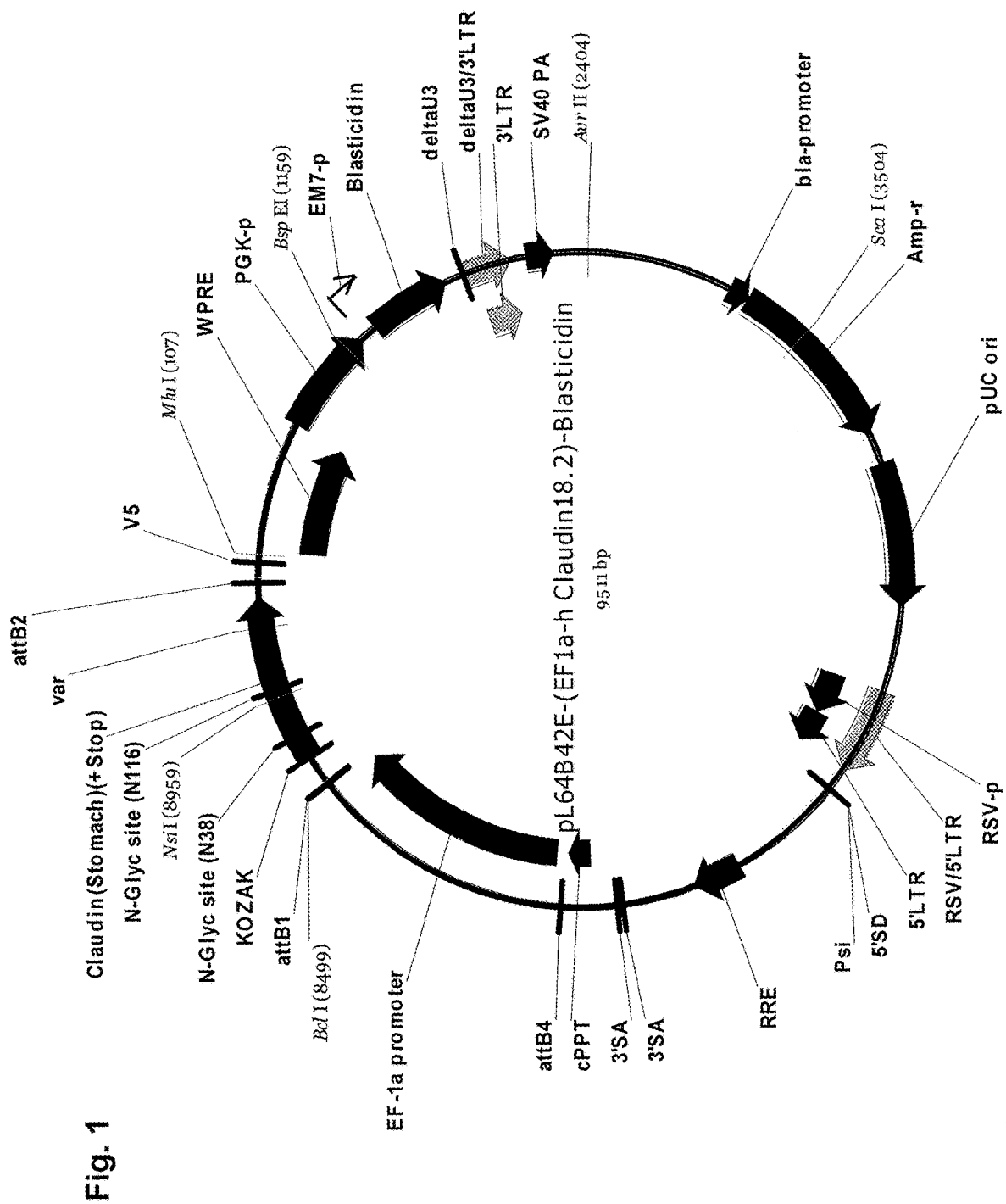
FIG. 1 shows a lentiviral vector used for transduction of pancreas cancer cell lines. Human CLDN18.2 was cloned downstream of the EF1α promoter. The expression cassette is integrated between the long terminal repeats (5' and 3'-LTR) which enable packaging and reverse transcription of the viral mRNA. RSV: rous sarcoma virus allows Tat independent production of viral mRNA. Amp: Ampicillin resistance gene. PGKp: Promotor of blasticidin. WPRE: woodchuck posttranscriptional regulatory element; enhances transgene expression. LTR: long terminal repeat, allows viral packaging. SV40A allows transcriptional termination and polyadenylation of mRNA. pUC: bacterial vector backbone. Bla: promoter of ampicillin.

Lentiviral Vector Construction:

Lentiviruses belong to the RNA viruses, which stably integrate into human genomic DNA of both dividing and non-dividing cells. Vector pLenti6.4 (Invitrogen) was used as backbone. It contains a Blasticidin gene for selection of positively transduced cells. CLDN18.2 fused to the EF1α promoter was cloned into the recombination region of the vector generating pL64B42E (EF1α-hCLaudin18.2)-Blasticidin (FIG. 1).

Selection of Cell Lines:

Cell lines were selected according to literature data or, which were previously tested in vivo. Selection criteria included homogenous subcutaneous growth in nude mice and a therapeutic window of 20-100 days. Three cell lines (DANG, YAPC and BxPC3) were integrated that already showed weak expression of CLDN18.2 mRNA and three (MiaPaCa-2, Patu8902 and Suit-2) that are able to metastasize according to literature. Two other cell lines (known to grow as homogenous subcutaneous tumors in vivo) were selected randomly (HPAC, CAPAN1).

Determination of Blasticidin Selection Conditions:

For all cell lines the blasticidin concentration required for selection of cells after lentiviral transduction was determined before transduction was performed. Pancreatic cancer cells were seeded in 6 well plates at a high density, resulting in 80-90% confluence after 24 h. Blasticidin (Stock: 10 mg/ml, Invitrogen) was added to the wells in increasing concentrations ranging from 0.5-12 µg/ml (5 dilution steps+ no blasticidin control). The medium was exchanged every 3-4 days and cells were analyzed in a microscope before removing the medium. The amount of dead cells and the condition of the living cells was documented. Cells were cultivated for 14 days. The lowest blasticidin concentration causing 100% apoptotic cells after 14 days was preferred for selection of lentivirally transduced cells. The required blasticidin concentrations for each of the established LVT cell lines are indicated in Table 4.

Envelope Selection:

For lentiviral transduction, GFP-lentiviral control vector pL64B42E-(EF1a-GFP)-blast was packaged into different envelope particles (VSV-G, GALV, RD114, Mokola-G and Rabies-G). Depending on the proteins present in the envelope and the composition of the cellular membrane, attachment to the target cancer cells is more or less efficient. For all pancreatic cancer cell lines the VSV-G envelope showed highest transduction efficiency (68.5-91.2%) (Table 5). Consequently, the CLDN18.2 expression vector pL64B42E (EF1α-hCLaudin18.2)-Blasticidin was packaged into VSV-G envelopes. Producer cells were infected and the viruses were isolated from the medium at high titers ($3.86\times10^7$ particles/ml). Viral supernatants were stored at −80° C.

TABLE 5

Generation of CLDN18.2 over-expressing pancreatic cancer cell lines by lentiviral transduction

| Cell line | Envelope test (GFP control viral vector) | | | | | Transduction efficiency of pL64B42E (EF1α-hCLaudin18.2)[1] |
|---|---|---|---|---|---|---|
| | VSV-G | GALV | RD114a | Mokola-G | Rabies-G | |
| BxPC3-LVT | 91.1 | 29.5 | 21.4 | 61.4 | 57.1 | 92.8% |
| CAPAN1-LVT | 83.7 | 12.3 | 31.7 | 24.3 | 23.1 | 89.6% |
| DANG-LVT | 91.2 | 41.3 | 13.8 | 33.7 | 41.4 | 87.5% |
| HPAC-LVT | 77.7 | 38.4 | 49.6 | 72.8 | 61.5 | 97.3% |
| MiaPaCa-2-LVT | n.d. | n.d. | n.d. | n.d. | n.d. | 96.3% |
| Patu8902-LVT | n.d. | n.d. | n.d. | n.d. | n.d. | 93.0% |
| Suit2-LVT | n.d. | n.d. | n.d. | n.d. | n.d. | 92.2% |
| YAPC-LVT | 68.5 | 41.3 | 13.8 | 33.7 | 41.4 | 82.2% |

[1]Efficiencies obtained by packaging of the vector in VSV-G envelope particles, measured 2 days after infection.

Lentiviral Transduction of Pancreatic Cancer Cell Lines:

For infection of the pancreatic cancer target cell lines, a 24-well plate was coated with 200 µl 1× Retronectin® (20 µg/ml, Takara Inc.) and the plate was sealed with Parafilm® and incubated for 3-16 h at 4° C. Plates were washed with 200 ml PBS and blocked with PBS/2% BSA for 30 min at RT. Plates were washed again and loaded with 300 µl viral supernatant by centrifugation for 25 min at 2500 rpm at 15° C. The supernatant was removed and loading was repeated 3 times. The plates were finally washed once with PBS and target cells at low passage were seeded in each well. For all pancreatic cancer cell lines, $5\times10^5$-$1\times10^7$ cells per 24 well were seeded. Plates were incubated for 2 days at 37° C. Subsequently cells were detached and transduction efficiency was determined by FACS using a FITC-labeled IMAB362 antibody. Cells were expanded and a master cell bank was prepared for each cell line.

9. ADCC Assay

Pancreatic cancer target cells were seeded two days in advance in flasks to obtain 80-90% confluent cultures on the day ADCC started. Pancreatic cancer cells were transfected with luciferase RNA and were seeded in white 96 well plates at a density of $1\times10^4$ cells per well in 50 µl assay medium (culture medium as described in Table 4 with 20 mM HEPES). NUGC-4 sub 10cH11 subE10 Luci #2 cells (8000 cells/well) were seeded in addition as positive controls in all assays. Cells were cultivated for 4-6 h before addition of antibody and purified PBMCs.

PBMCs were prepared from fresh human buffy coat obtained from healthy donors. About 3×20-25 ml blood was diluted (1:2) with PBS and carefully layered on 4×15 ml Ficol-Paque Plus (GE Healthcare) in 50 ml Falcon tubes. Gradients were centrifuged (25 min, 700 g). After centrifugation, peripheral blood mononuclear cells (PBMC) were collected from the interphase, washed in PBS/2 mM EDTA, centrifuged (5 min, 468 g), again resuspended in PBS/2 mM EDTA and centrifuged (10 min, 208 g) to remove the platelets. The pellets were resuspended in 50 ml PBS/2 mM EDTA and cells were counted. PBMCs were centrifuged (5 min, 468 g) and resuspended in X-Vivo-15 culture medium at a concentration of $1.6\times10^7$ cells/ml for addition to the pancreas cells and $1.28\times10^7$ cells/ml for addition to the NUGC-4 sub 10cH11 subE10 Luci #2 cells.

Antibodies (IMAB362 and the isotype control antibody ch78H11 1H6) were serially diluted (4.5 fold) 10 times resulting in a concentration range of 200 µg/ml-0.26 ng/ml. Of each dilution 25 µl was added in quadruplicates to the target cells. PBS without antibodies was added in the medium and lysis control wells. Subsequently, 25 µl PBMCs were added to each well (E:T ratio=40:1) and plates were incubated for 24 h+1 h at 37° C., 5% $CO_2$.

The next day, 10 µl 8% Triton X100/PBS solution was added to the lysis control wells and 10 µl PBS in all other wells. Finally, 50 µl freshly prepared luciferin stock solution was added (160 mM HEPES, 1×PBS, 3.84 mg/ml D-Luciferin (BD Biosciences)) to each well and plates were incubated for 80 min at RT in the dark. Luminescence resulting from the oxidation of lucifer yellow by the luciferase of viable cells was measured using a microplate-reader (Infinite200, Tecan, Switzerland). Percentage of cellular cytotoxicity was calculated using the following formula:

Specific killing (%)=100−[($RLU_{sample}$−$RLU_{triton}$)/($RLU_{medium\ ctrl}$−$RLU_{triton}$)×100]

10. CDC

CDC was performed as follows.

Target cells (CHO-K1 p740 MACS/FACS (24H5) p3151 Luci #2A5) were seeded in 50 µl assay medium in 96-well white assay plates (10,000 cells/well) and grown for 24 h+20 min at 37° C., 7.5% CO2 und 95% rH before addition of the samples. Each 96-well assay plate comprised a total number of 3 different negative controls (heat inactivated serum, serum with and without IMAB362 and serum with an isotype control antibody (Rituximab)) and a positive control of healthy human serum pool (lot #31032011) with 500 ng/ml IMAB362. An additional positive control was generated at the end of the reaction by addition of 0.8% Triton X100 to a second medium control well causing total lysis. One of the 96-well assay plates comprised a functional positive control generated by 7 serial 3.16 fold dilutions of IMAB362 (10 000-31.8 ng/ml). This control resulted in a sigmoid dose-dependent lysis of target cells. All samples were prepared (200 µl each) at the same time in a 96 well deepwell dilution plate. Samples were taken 3 times from each well by reverse pipetting to generate the triplicates in the assay plates. After addition of 50 µl of each test and control item to the assay plates, plates were incubated for 80+5 min at 37° C., 7.5% CO2 und 95% rH.

To each well 10 µl PBS was added, except in the Triton-Lysis control wells. To each Triton-Lysis control well, 10 µl 0.8% Triton/PBS solution was added. Luciferin substrate solution was prepared (6114 µl Aqua bidest, 2496 µl HEPES (1M), 1998 µl 1×DPBS, 4992 µl D-Luciferin Stock solution (12 mg/ml)). To each well 50 µl Luciferin substrate solution was added. Plates were incubated at 37° C., 7.5% CO2 und 95% rH for 45 min. Plates will be measured in a microplate reader.

Complement-dependent lysis was calculated using formula:

Specific lysis (%)=100−[(RLUsample−RLUtriton)/ (RLUHSCM−RLUtriton)×100]

Modifications for testing the pancreatic cancer cell lines:
Pancreatic cancer cells were transfected with luciferase RNA using optimized conditions. For each cell line tested, 1.5×104 cells were seeded per well.

Since most pancreatic cancer cell lines are difficult to detach and to singularize, trypsin was used on day 1.

Pancreatic cancer cells in assay plates were cultured at 37° C., 5% CO2.

CDC assays with chemotherapeutic agents pretreated cells was done with following IMAB362 or as isotype control antibody ch78H11 1H6 antibody concentrations: 640000, 160000, 40000, 10000, 2500, 625, 156 and 39 ng/ml.

11. Inhibition of Proliferation

To analyze dose-response curves of each chemotherapeutic agent, a proliferation assay was performed.

TABLE 6

Pancreas cancer cell lines to analyze efficacy of gemcitabine or oxaliplatin Inhibition of proliferation after applying gemcitabine or oxaliplatin in different concentrations for each pancreas cancer cell line was analyzed.

| cell line | cells seeded/well |
| --- | --- |
| BxPC3-LVT | 5000 |
| BxPC3 | 5000 |
| Panc05.04 | 5000 |
| BxPC3-LVT | 5000 |
| CAPAN1-LVT | 5000 |
| DANG | 2000 |
| MiaPaCa-2-LVT | 7000 |
| Patu8988S | 10000 |
| Patu8988Sp3151#6 | 15000 |

Cells were seeded in 96 well plates and after 4-6 hours gemcitabine or oxaliplatin was added in following concentrations: 1000, 500, 250, 100 and 20 ng/ml. The proliferation assay was incubated for 4 days at 37° C. and 5% CO2. 50 µl XTT complete reagent (50 parts XTT+1 part coupl. reagent mixed) was added and incubated at 37° C. Measurement of absorbance (cells plus supernatant) was done with the Tecan Safire after 3 h and 4 h. Inhibition of proliferation was calculated compared to medium values set as 100%. $EC_{50}$ values for gemcitabine and oxaliplatin were calculated in the GraphPad Prism program.

12. Cultivation of Pancreas Cancer Cell Lines with Chemotherapeutic Drugs for ADCC or CDC For DANG 4 to 6E+06 cells were seeded and cultivated for 2 days in medium or medium+1 ng/ml gemcitabine or 1 ng/ml gemcitabine+10 ng/ml oxaliplatin. 1-1.4E+07 Patu8988S were seeded and cultivated without or with 10 ng/ml gemcitabine or 10 ng/ml gemcitabine in combination with oxaliplatin 100 ng/ml.

On the day ADCC started, the protocol described above was followed and cell surface expression of CLDN18 was determined in FACS analysis as described above.

13. Cell Cycle Analyses

Cells were plated in six-well plates, and 5-6 hours later chemotherapeutic agents were added for either 24 h 48 h or 3 days. Cells floating in the medium were combined with the adherent cell layer, which was trypsinized. Cells were washed. Either cell cycle analysis was started directly or cell surface staining was done before as described above. Cells are resuspended in 1 ml PBS and added to 3 ml 4% PFA. After 15 min fixation of cells at room temperature cells are pelleted and washed. For RNAse treatment cells were resuspended in 200 µl RNAse (10000 U/ml) plus 0.05% Triton X-100 and incubated for 30 min at 37° C. 1 ml PBS was added and samples were centrifuged and resuspended in 200 µl PBS/PJ 50 µg/ml. At least 30 min later samples were ready to be analyzed by flow cytometry. Cell cycle phase distribution was determined using FlowJo software to analyze DNA content histograms.

14. Apoptose Assay

Following the indicated treatments, apoptosis was measured by annexin V binding (detection kit I) or by a DNA fragmentation assay (Apo-Direct) as recommended by the manufacturer (PharMingen, San Diego, Calif.). Briefly, cells floating in the supernatant were combined with the adherent fraction, which was trypsinized and then washed. An aliquot of 5E+05 cells was incubated with annexin V-APC and PI for 15 min at room temperature in the dark. Cells were immediately analyzed by flow cytometry. Viable cells exclude both annexin V-APC and PI. Early apoptotic cells are annexin V-APC-positive and PI-negative, whereas cells that are no longer viable due to apoptotic or necrotic cell death are positively stained by both annexin V and PI. Percentage of stained cells in each quadrant was quantified using FlowJo software (BD Biosciences, Franklin Lakes, N.J.).

The apoptotic assay based on DNA fragmentation was performed as follows. Treated cells (adherent and floating) were fixed in 70% icecold EtOH overnight. After washing, $10^6$ fixed cells were incubated with terminal deoxynucleotidyl transferase enzyme (TdT) and FITC-dUTP for 90 min at 37° C. to label DNA breaks. Cells were rinsed, incubated in RNase A/propidium iodide in the dark for 30 min at room temperature to stain total DNA, then analyzed by flow cytometry. Cell doublets and clumps were eliminated from the analysis by gating.

15. In Vivo Studies

All in vivo experiments were carried out in compliance with the national regulations and ethical guidelines for experimental animal studies.

15.1 Treatment of Xenografts

Xenograft tumors were inoculated by subcutaneous injection of tumor cells in 200 µl PBS into the flanks of female Hsd:Athymic Nude-Foxn1$^{nu}$ mice. Tumor bearing mice were treated with 0 µg, 200 µg, 400 µg or 800 µg antibody injected i.v. weekly or alternating i.v./i.p. semi-weekly. Chemotherapeutic agents were applied i.p. weekly or semi-weekly. Tumor sizes and animal health were monitored semi-weekly. At the end of chemotherapy treatment, antibody applications were continued until tumors reached a volume of >1400 mm$^3$ or until tumors became ulcerous. Tumor samples were cryo conserved or fixed in 4% formalin for subsequent analysis.

15.2 Metastasis Assay

Different pancreatic cancer cell lines were first analyzed for their ability to form metastasis after i.v. application of the cells in nude mice. For these engraftment analyses a group of 5-10 mice were injected with 1×10$^6$ and/or 2×10$^6$ cells and single mice were sacrificed at different time points to find the time point of metastasis engraftment and growth.

Metastasis treatments were performed with 10-12 Hsd: Athymic Nude-Foxn1$^{nu}$ mice per treatment group. They were injected with 2×10$^6$ cells (Patu8988S or Suit2-LVT) intravenously. All mice were sacrificed at the same time point, as soon as the first symptoms of metastasis disease appeared (loss of weight, weakness, shortness of breath), or the first mouse died.

Figure 2:
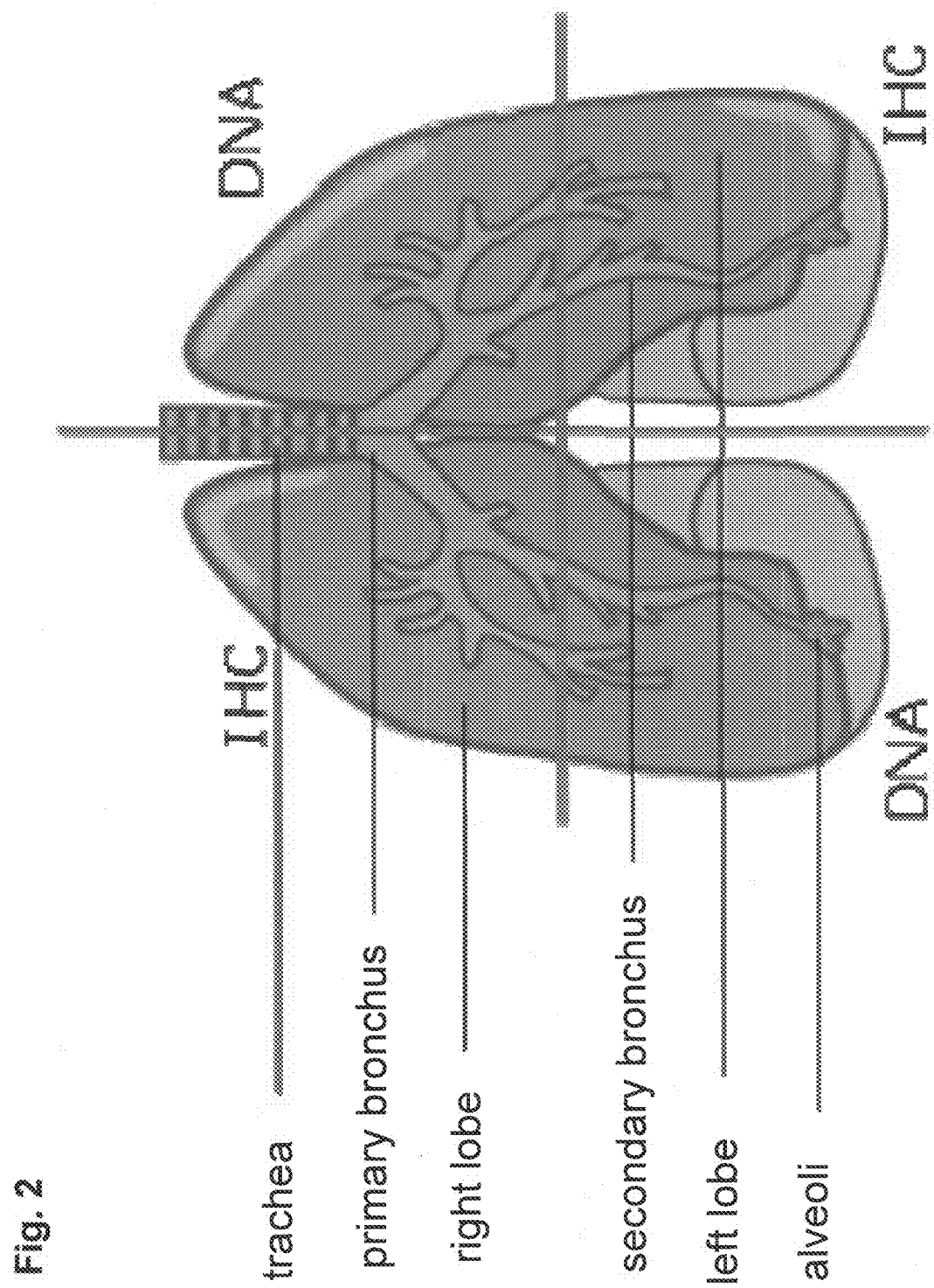
FIG. 2 shows a metastasis analysis of pancreas cells in mouse lung. Dissection scheme of mouse lungs after i.v. injection of mice with pancreas cancer cells.

Preparation of Tissue:

For engraftment studies mice were sacrificed at different time points, or as soon as mice showed clear physiological signs of metastatic disease (loss of weight, weakness, shortness of breath). All their organs were macroscopically analyzed for metastasis. Only for Patu8988S and Suit-2 cells, lungs and lungs/livers displayed macroscopically visible metastasis, respectively. These organs were dissected into 4 equal peaces, two (lung: upper right and lower left lobe), which were stored for genomic DNA isolation. The other two peaces were formalin fixed and stored for IHC analysis (FIG. 2).

Preparation of Genomic DNA and Q-PCR Strategy:

Genomic DNA was extracted from lung or liver tissue. As controls, genomic DNA was also isolated from human pancreatic cancer cells Patu8988S as well as of a non-injected negative control mouse.

The Q-PCR strategy is based on the amplification of human DNA present in the metastases. The relative detection level of human DNA in the mouse lung sample correlates directly with the amount and/or size of the metastases. Since this method is biased by the fact that the metastases do not spread evenly in the lung and sometimes one lobe is more affected than the other, two different regions of the lungs were mixed in one DNA preparation (FIG. 2).

The Q-PCR reaction was performed with primer pair #5861 5'-GGGATAATTTCAGCTGACTAAACAG-3' (SEQ ID NO: 53) and #5862 5'-TTCCGTTTAGT-TAGGTGCAGTTATC-3' (SEQ ID NO: 54) specifically amplifying the alpha-satellite DNA present in human chromosome 17, but not in mouse DNA. To generate a standard curve and as positive control, Patu8988S DNA was mixed with mouse DNA and 5 fold dilutions were prepared, resulting in 100%, 20%, 4%, 0.8%, 0.16%, $0.0^{32}$% and $0.00^{64}$% human DNA in mouse DNA. The curve was used to calculate (linear regression) the amount of human metastasis DNA present in mouse lung tissue. Q-PCR reactions were performed in 50 µl final volume comprised of 20 µl (200 ng) mouse lung DNA, 25 µl Sybr Green (Qiagen), 1.6 µl sense primer (10 µM) and 1.6 µl anti-sense primer and 1.8 µl H$_2$O.

Example 2: CLDN18.2 Expression in Normal and Neoplastic Human Pancreas Tissues

Figure 3B:
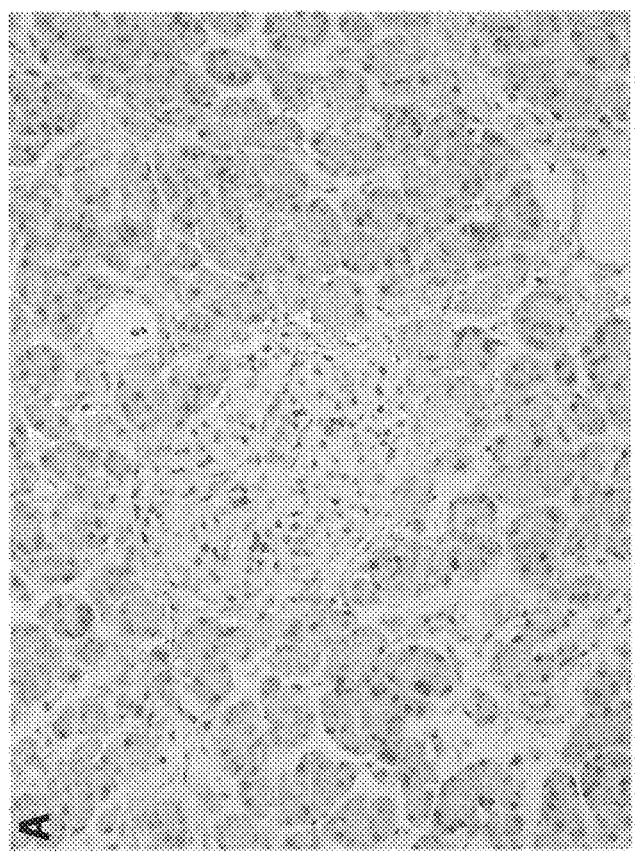
FIGS. 3A and 3B show a CLDN18.2 expression in normal and cancerous pancreatic tissues. Staining of normal pancreas formalin fixed paraffin embedded (FFPE) tissue (FIG. 3A) and pancreas adenocarcinoma tissue (FIG. 3B) with the monoclonal murine 35-22A antibody (0.2 µg/ml). Haematoxylin counterstaining (2:00 min). Magnification 200×.
Figure 3A:
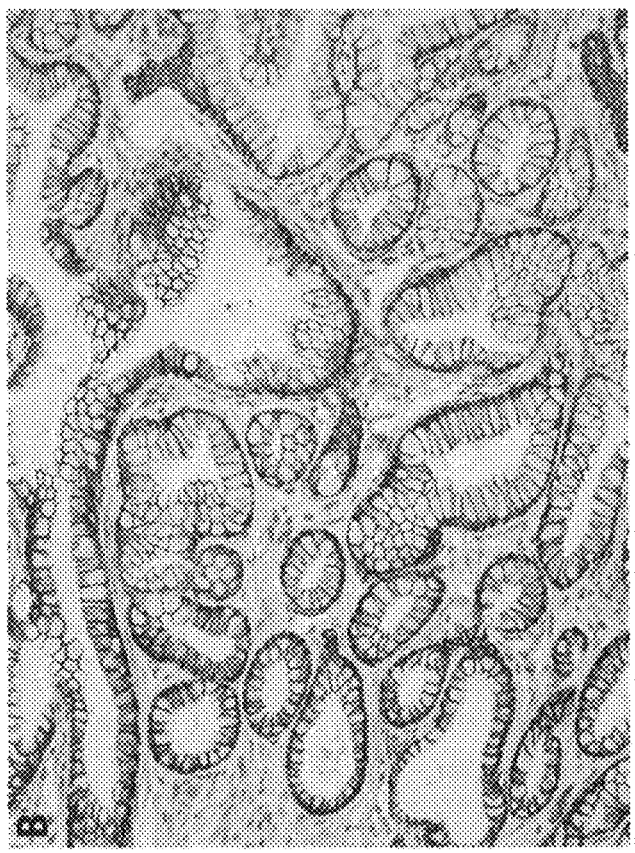

To analyze the expression level and pattern of CLDN18.2 in normal and pancreatic tumor tissues histological staining of FFPE sections was carried out with two murine monoclonal antibody reagents (FIG. 3).

Exploratory pilot experiments were performed by using the prototype antibody 35-22A on tissue microarrays (TMAs). A major disadvantage of TMAs is the variable quality of the spotted tissues and the small size and thus non-representative character of the samples. This together with the not fully optimized staining protocol may have resulted in an underestimation of positive cases.

The main experiments were performed with the antibody 43-14A. These stainings were conducted on tissue sections, which (compared to the TMAs) were larger and pre-assessed for presence of tumor cells.

The precancerous lesions, which origin from the pancreas ducts can be ranked according to the international pancreas intraepithelial neoplasia (PanIN) system (PanIN-1A, -1B, -2, -3 subtype). PanIN-1 lesions (FIG. 4A) are flat, composed of tall columnar cells with basally located nuclei and abundant supranuclear mucin. The nuclei are small and round to oval in shape and are oriented perpendicular to the basement membrane. There is histological overlap between non-neoplastic flat hyperplastic lesions and flat neoplastic lesions without atypia.

The lesions of the subtype PanIN-1B have a papillary, micropapillary or basally pseudostratified architecture and are otherwise identical to PanIN-1A. (Hruban et al. Am J Surg Pathol. 2001 May; 25(5):579-86.)

PanIN-2 lesions (FIG. 4B) are flat or papillary, have typical nuclear abnormalities, including some loss of polarity, nuclear crowding, enlarged nuclei, pseudo-stratification and hyperchromatism. Mitoses are rare, but when present are non-luminal (not apical) and not atypical. (Hruban et al. Am J Surg Pathol. 2001 May; 25(5):579-86.)

PanIN-3 lesions (FIG. 4C) are usually papillary or micropapillary, however, they may rarely be flat. True cribriforming, budding off of small clusters of epithelial cells into the lumen and luminal necroses suggest the diagnosis of PanIN-3. Lesions are characterized by a loss of nuclear polarity, dystrophic goblet cells (goblet cells with nuclei oriented towards the lumen and mucinous cytoplasm oriented toward the basement membrane), mitoses which may occasionally be abnormal, nuclear irregularities and prominent (macro) nucleoli. (Hruban et al. Am J Surg Pathol. 2001 May; 25(5):579-86.)

The expression of CLDN18.2 in precancerous tissues was analyzed with the 43-14A antibody using tissue samples of various sources.

CLDN18.2 was detected frequently in PanIN structures of the subtypes PanIN-1, -2 and -3 demonstrating an early expression of CLDN18.2 in precancerous lesions (FIG. 4), which is conserved in the later stages. In contrast, no expression was observed in normal pancreas tissue samples including the ductal structures of the pancreas.

In conclusion, CLDN18.2 is an early marker of beginning malignant histological changes in the pancreatic ducts.

Two studies were performed to assess expression of CLDN18.2 in primary pancreatic cancer.

For the pilot study several TMAs with a total of 141 primary pancreatic cancer cases were stained with the monoclonal CLDNA18.2 specific antibody 35-22A. The overall quality of the analyzed TMA was unsatisfying. Many spots were partially lost during the retrieval and inhomogenous counterstaining with haematoxylin was suggestive for suboptimal tissue processing of FFPE tissues.

Figure 6B:
FIGS. 6A and 6B show expression of CLDN18.2 in primary and metastatic pancreatic tumor tissue (pilot study). Staining of FFPE tissue sections (3 m) using the murine, monoclonal 35-22A antibody of (FIG. 6A) adenocarcinoma primary tumor and (FIG. 6B) lymph node metastasis. Haematoxylin (Mayers) counterstained.
Figure 6A:

Overall >48.9% of the stained cases were positive for CLDN18.2, including 49.2% ($^{65}$/132) ductal adenocarcinomas, 50% (½) acinic cell carcinoma and 3 of 7 neuroendocrine carcinomas (Table 7). The tumor cell membrane was stained without any background on other cell types (FIG. 6).

Figure 5:
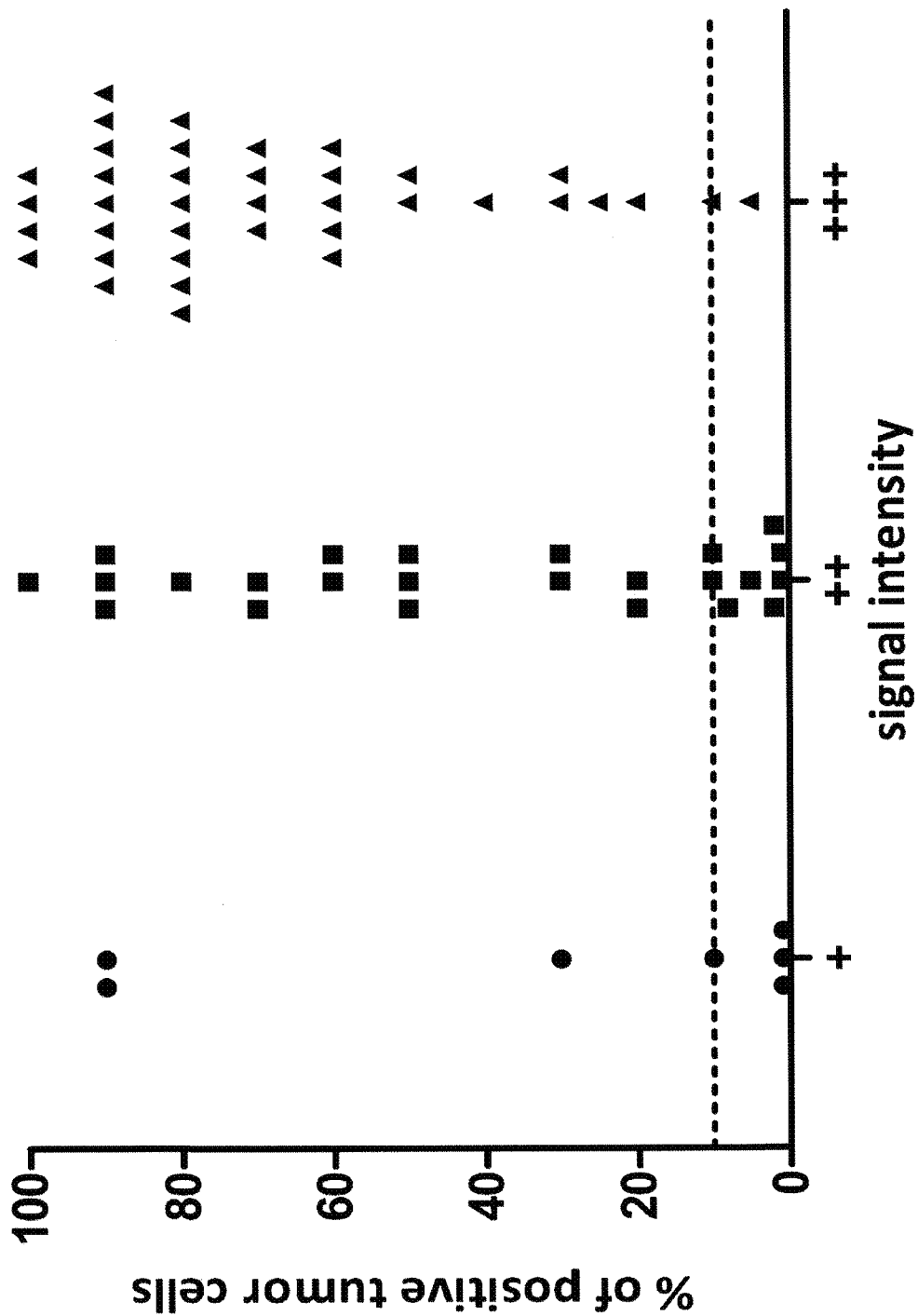
FIG. 5 shows the correlation between CLDN18.2 signal intensity and amount of positive tumor cells for the analyzed pancreas primary tumors (pilot study). Each dot represents a pancreatic primary cancer case analyzed by staining FFPE sections using the monoclonal, murine 35-22A antibody (0.2 g/ml). The dashed line marks the 10% value.

Moreover, we observed a correlation between CLDN18.2 expression intensity and the fraction of stained tumor cells within the tumor (Table 8, FIG. 5).

TABLE 7

Pilot study: Number of CLDN18.2 positive cases divided in the pancreas cancer subtypes. Tissues were stained using the monoclonal, murine 35-22A (0.2 µg/ml) antibody and reviewed for CLDN18.2 positive tumor cells.

| primary pancreas CA | total | positive fraction ≥1% [%] | staining intensity ≥2+ [%] |
|---|---|---|---|
| total | 141 | 69 [48.9] | 62 [43.9] |
| ductal adenocarcinoma (PDAC) | 132 | 65 [49.2] | 58 [44.3] |

TABLE 7-continued

Pilot study: Number of CLDN18.2 positive cases divided in the pancreas cancer subtypes. Tissues were stained using the monoclonal, murine 35-22A (0.2 µg/ml) antibody and reviewed for CLDN18.2 positive tumor cells.

| primary pancreas CA | total | positive fraction ≥1% [%] | staining intensity ≥2+ [%] |
|---|---|---|---|
| acinic cell carcinoma | 2 | 1 [50.0] | 1 [50.0] |
| neuroendocrine carcinoma | 7 | 3 [42.8] | 3 [42.8] |

TABLE 8

Pilot study: Correlation between CLDN18.2 signal intensity and amount of positive tumor cells for the analyzed pancreas primary tumors. Percentage of positive primary tumor cases correlated to the staining intensity. The cases were grouped in six fractions depending on the amount of positive tumor cells for a better visualization.

| | signal Intensity | | | |
|---|---|---|---|---|
| % of pos. cells | + | ++ | +++ | Total |
| any positivity | 7 | 24 | 38 | 69 |
| 1-9% | 3 [42.8] | 6 [25.0] | 1 [2.6] | 10 [14.5] |
| 10-39% | 2 [28.6] | 6 [25.0] | 5 [13.2] | 13 [18.8] |
| 40-49% | 0 | 0 | 1 [2.6] | 1 [1.4] |
| 50-59% | 0 | 3 [12.5] | 2 [5.3] | 5 [7.3] |
| 60-69% | 0 | 2 [8.3] | 5 [13.2] | 7 [10.2] |
| 70-100% | 2 [28.6] | 7 [29.2] | 24 [63.1] | 33 [47.8] |

TABLE 9

Pilot study: Grading of the CLDN18.2 positive tumor cases. The grading of the tumor cells describes the cell appearance and the level of cell differentiation. Whereat grade 1 describes well differentiated cells; grade 2 moderately differentiated cells and grade 3 poor differentiated.

| grade | total cases | positive fraction ≥1% [%] | staining intensity ≥2+ [%] |
|---|---|---|---|
| 1 | 15 | 13 [86.7] | 12 [80.0] |
| 2 | 71 | 39 [54.9] | 36 [50.7] |
| 3 | 35 | 9 [25.7] | 7 [20.0] |

A second study was conducted with an optimized staining protocol with the highly sensitive antibody 43-14A using quality controlled tissue sections.

TABLE 10

Main study - number of CLDN18.2 positive cases grouped in pancreas cancer subtypes. Tissues were stained using the murine, monoclonal 43-14A (0.2 µg/ml) antibody and reviewed for CLDN18.2 positive tumor cells.

Table A

| primary CA | total cases | positive fraction ≥1% [%] | staining intensity ≥2+ [%] |
|---|---|---|---|
| total | 61 | 40 [65.6] | 39 [63.9] |
| ductal adenocarcinoma (PDAC) | 42 | 38 [90.5] | 37 [88.1] |
| acinic cell carcinoma | 1 | 0 | 0 |
| neuroendocrine | 18 | 2 [11.1] | 2 [11.1] |

TABLE 10-continued

Main study - number of CLDN18.2 positive cases grouped in pancreas cancer subtypes. Tissues were stained using the murine, monoclonal 43-14A (0.2 µg/ml) antibody and reviewed for CLDN18.2 positive tumor cells.

Table B

| primary cholangio CA | total | positive | % pos. |
|---|---|---|---|
| cholangio carcinoma | 15 | 9 | 60 |

Figure 7:
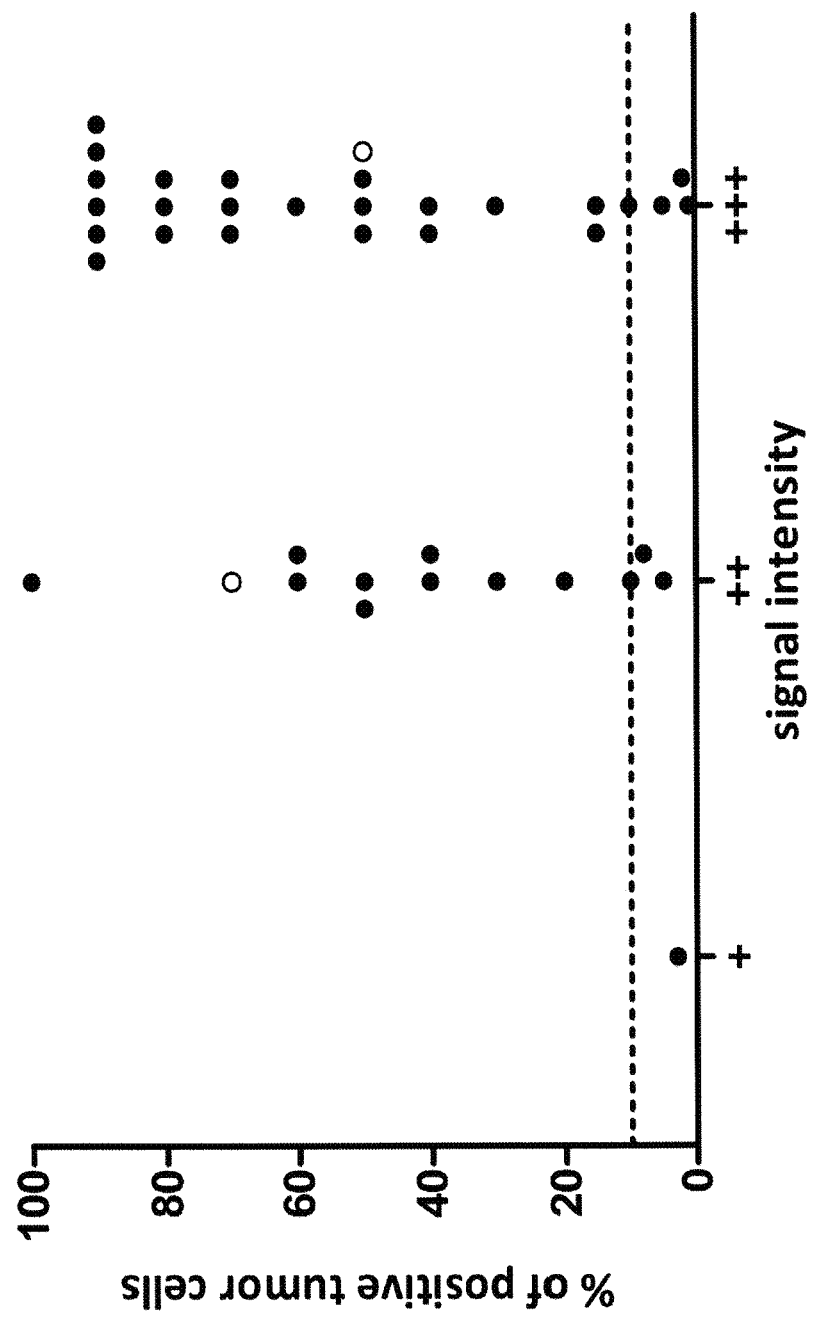
FIG. 7 shows the correlation between CLDN18.2 signal intensity and amount of positive tumor cells for the analyzed pancreas primary tumors (main study). Each dot represents a pancreatic ductal adenocarcinoma primary tumor (filled circle) or a neuroendocrine primary tumor (open circle) case analyzed by staining FFPE sections using monoclonal murine 43-14A antibody (0.2 µg/ml).

In total 42 primary ductal pancreatic cancer samples were analyzed. About 90% (38 of 42 cases) of these were positive for CLDN18.2 (Table 10), most of which (>60%) showed a strong signal intensity of +++(FIG. 7, Table 11). Also here a correlation between the CLDN18.2 expression level and the fraction of positive tumor cells was observed. Most of the analyzed cases (62%) were grade 3 tumors (Table 12).

TABLE 11

Main study: Correlation between CLDN18.2 signal intensity and amount of positive tumor cells for the analyzed pancreas primary tumors. Percentage of positive primary tumor cases correlated to the staining intensity. The cases were grouped in six fractions depending on the amount of positive tumor cells for a better visualization.

| | signal intensity | | | |
|---|---|---|---|---|
| % of pos. cells | + | ++ | +++ | Total |
| any positivity | 1 | 13 | 26 | 40 |
| 1-9% | 1 | 2 [15.4] | 3 [11.5] | 6 [15.0] |
| 10-39% | 0 | 3 [23.0] | 4 [15.4] | 7 [17.5] |
| 40-49% | 0 | 2 [15.4] | 2 [7.7] | 4 [10.0] |
| 50-59% | 0 | 2 [15.4] | 4 [15.4] | 6 [15.0] |
| 60-69% | 0 | 2 [15.4] | 1 [3.8] | 3 [7.5] |
| 70-100% | 0 | 2 [15.4] | 12 [46.2] | 14 [35.0] |

TABLE 12

Main study - Grading of the CLDN18.2 positive tumor cases. For most of the analyzed tumor cases a grading done by the corresponding pathologist was available. The grading of the tumor cells measures the cell appearance and the level of cell differentiation. Whereat grade 1 describes well differentiated cells; grade 2 moderately differentiated cells and grade 3 poorly differentiated.

| grade | total cases | positive fraction ≥1% [%] | staining intensity ≥2+ [%] |
|---|---|---|---|
| 1 | 7 | 1 [14.3] | 1 [14.3] |
| 2 | 25 | 15 [60.0] | 15 [60.0] |
| 3 | 28 | 24 [85.7] | 23 [82.1] |

Pancreas cancer is diagnosed in most patients in an advanced stage. Patients tumors have already metastasized in lymph nodes and other organs, in particular into the liver. In the main study 79 FFPE tissue samples of lymph node and liver metastases of pancreatic cancer were analyzed in an immunohistochemical assay, using the CLDN18.2 specific 43-14A antibody.

Figure 8:
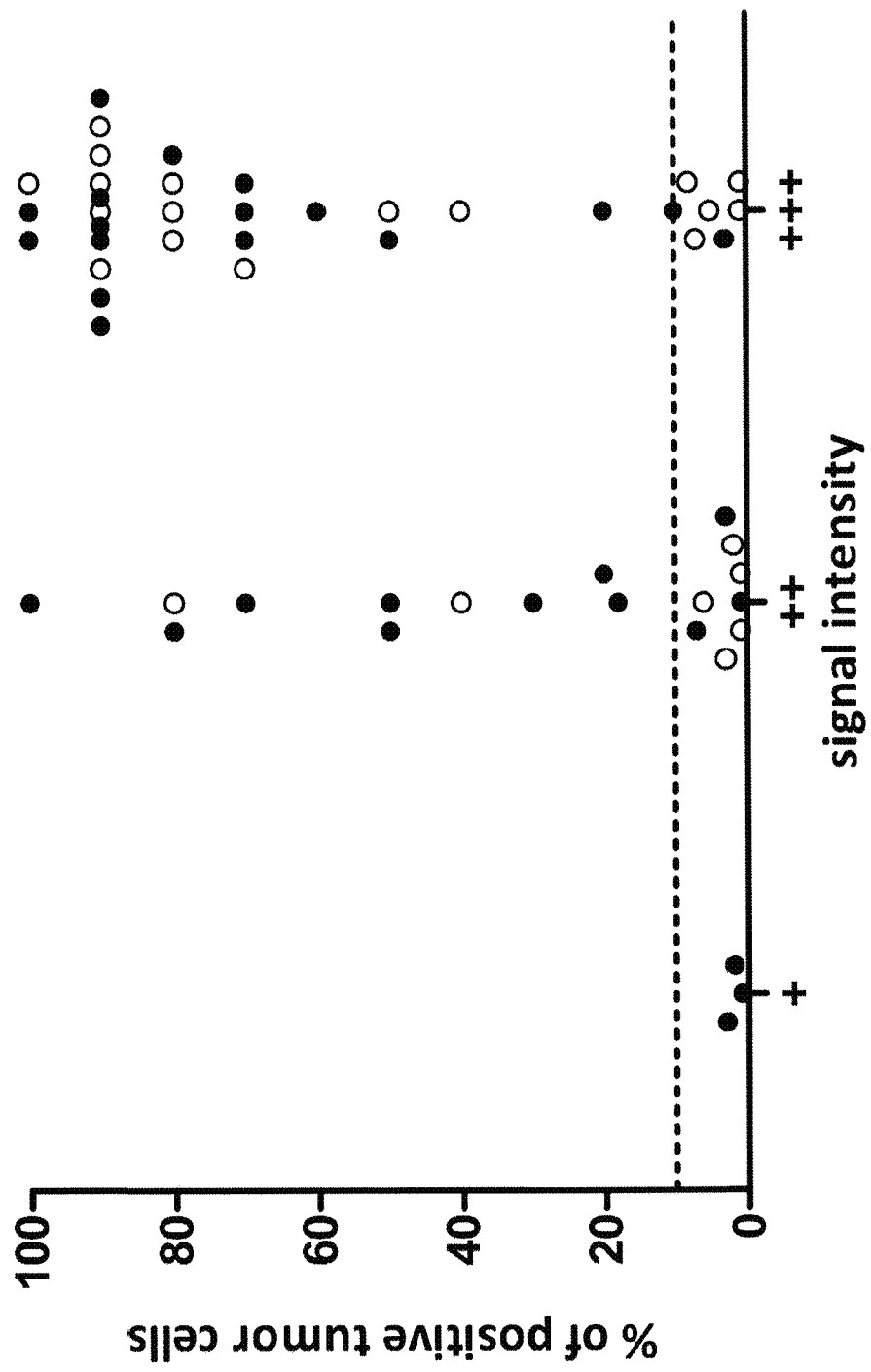
FIG. 8 shows the correlation between CLDN18.2 signal intensity and amount of positive tumor cells for the analyzed pancreas metastases. Each dot represents a pancreatic lymph node (filled circle) or liver (open circle) metastasis case analyzed by staining FFPE sections using the monoclonal, murine 43-14A antibody (0.2 µg/ml). The dashed line marks the 10% value.

70.5% of the lymph node metastases (31/44 cases) and 68.6% of the distant liver metastases (24/35 cases) demonstrated clear tumor cell staining for CLDN18.2 (Table 13). The staining pattern of the positive tumor cells was membranous, in some cases with additional weaker cytoplasmic signals (FIG. 9). In accordance with the results of the primary tumor analysis, a correlation was found between the CLDN18.2 expression level and the fraction of CLDN18.2 positive tumor cells in the metastatic samples (FIG. 8).

No correlation was found between grading of the analyzed tumors and expression level of CLDN18.2 or fraction of positive tumor cells.

TABLE 13

Number of CLDN18.2 positive metastases cases grouped by target organ. Tissues were stained using the monoclonal, murine 43-14A (0.2 µg/ml) antibody and reviewed for CLDN18.2 positive tumor cells.

| metastasis | total | positive fraction ≥1% [%] | staining intensity ≥2+ [%] |
|---|---|---|---|
| total | 79 | 55 [69.6] | 52 [65.8] |
| pancreas to lymph node | 44 | 31 [70.5] | 28 [63.6] |
| pancreas to liver | 35 | 24 [68.6] | 24 [68.6] |

To test whether the CLDN18.2 expression of positive primary tumor cases is conserved in metastases of the same patient, matched primary cancer/lymph node metastases doublets were screened using antibody 43-14A.

TABLE 14

CLDN18.2 expression in matched pancreas primary and lymph node metastatic tumor samples - Matched samples of primary adenocarcinoma and lymph node (LN) metastasis were analyzed for the expression of CLDN18.2 in tumor cells.

| Patient ID | Primary TU | LN met. |
|---|---|---|
| H/2011/775 3S & 8D | +++ (15%) | +++ (25%) |
| H/2011/2247 7C & 7G | +++ (10%) | ++ (25%) |
| H/2011/12675 4B & 4L | +++ (10%) | ++ (5%)% |
| H/2010/15941 6SS & 8H | +++ (90%) | +++ (90%) |
| H/2010/2986 2E & 2G | +++ (5%) | +++ (40%) |
| H/2010/6709 9B &9 F | +++ (70%) | +++ (10%) |
| H/2010/11569 5A & 5G | +++ (80%) | ++ (5%) |
| H/2008/380 4A & 4G | +++ (60%) | +++ (90%) |
| H/2009/13538 5B & 5E | + (20%) | + (10%) |
| H/2009/11847 7C & 7F | +++ (15%) | ++ (15%) |
| H/2009/23108 4A & 4J | +++ (5%) | +++ (70%) |
| H/2009/4917 8E & 8S | +++ (70%) | +++ (25%) |
| H/2009/214183C & 3L | +++ (55%) | ++ (70%) |
| H/2009/20336 2D & 2F | +++ (80%) | +++ (90%) |
| H/2009/17768 2C & 2E | ++ (35%) | ++ (20%) |
| H/2008/13194 3A & 3J | +++ (35%) | +++ (10%) |
| H/2008/13074 3B & 3C | +++ (50%) | +++ (50%) |
| H/2008/12082 6D & 6G | +++ (1%) | – |
| H/2008/11178 5B & 1SS | +++ (80%) | +++ (90%) |
| H/2008/28150 4B& 4C | ++ (15%) | ++ (30%) |
| H/2007/5478 4A & 4J | +++ (90%) | +++ (90%) |
| H/2007/6216 3B & 3C | +++ (50%) | +++ (60%) |
| H/2007/9047 1B & 1J | +++ (70%) | +++ (35%) |
| H/2007/13983 6C & 6J | ++ (15%) | ++ (1%) |
| H/2007/14400 6C & 6J | – | – |
| H/2006/5616 3J & 3D | +++ (35%) | +++ (5%) |
| H/2006/9779 3D & 3K | + (5%) | + (15%) |

In 25 (92.5%) of the 27 analyzed paired cases both primary tumor and lymph node pairs were positive for CLDN18.2. In a single case both tissues were negative and in one other case the primary tumor was positive for CLDN18.2, whereas the metastasis was negative.

In 21 of 26 (80.7%) positive tested doublets the signal intensity of the primary tumor and metastatic tumor cells was identical. In 5 cases the signal intensity declined from +++ to ++. In 11 of 25 (44%) paired tissues the number of positive tumor cells was lower in the metastases as compared to the primary tumor (Table 14).

In summary, the CLDN18.2 expression appears to be conserved when primary tumor cells advance to the metastatic stage. The overall intensity and the fraction of positive tumor cells in lymph node metastases was only slightly lower as compared to the primary tumor (FIG. 10).

For a small number of patients tissue samples derived from the primary tumor, the lymph node metastasis and the liver metastasis were available. These matched triplets were stained, to test the conservation of CLDN18.2 expression in distant metastases. Six matched triplets were analyzed with antibody 43-14A.

TABLE 15

CLDN18.2 expression in matched pancreas primary and metastatic tumor samples - Matched samples of primary adenocarcinoma, liver metastasis and lymph node (LN) metastasis were analyzed for the expression of CLDN18.2 in tumor cells.

| patient ID | primary tumor | lymph node metastasis | liver metastasis |
|---|---|---|---|
| H/2011/17191-VA-VI-ISS | +++ (60%) | +++ (70%) | +++ (1%) |
| H/2010/14296 XA | +++ (5-10%) | – | – |
| H/2010/4157 VII A | ++ (60%) | ++ (30%) | +++ (90%) |
| H/2009/23598 VII B | +++ (40%) | – | – |
| H/2011/3590-III SS-VIIC-I | ++ (20%) | – | – |
| H/2008/10701 | +++ (90%) | +++ (100%) | +++ (90%) |

In 3 of 6 triplets, all three tissues specimen were comparable with regard to their positivity score for CLDN18.2 (FIG. 11). In three cases a fraction of the tumor cells was CLDN18.2 positive in the primary lesion, whereas the metastatic lesions showed no CLDN18.2 staining (Table 15).

Example 3: Target Expression in Human Pancreatic Cancer Cell Lines Used for In Vitro and in Vivo Models and Pancreatic Cancer Models Source of Cell Lines A primary aim of this pre-clinical evaluation study was to analyze the inhibitory effects of IMAB362 treatment in suitable model systems. To identify CLDN18.2-positive cell lines that can be used for in vitro and in vivo characterization of IMAB362 effects, a set of 26 commercially available pancreatic cancer cell lines was screened for CLDN18.2 expression and characterized in detail. A cell bank for experimental use was prepared immediately upon arrival for each of the cell lines. They were derived from primary pancreatic adenocarcinomas (10 of which 6 mucinous adenocarcinomas), primary carcinomas (4), pancreatic adenocarcinomas metastases into liver (5) or spleen (1), or isolated from ascites (5) (see Table 16). Several of these cell lines (8) were lentivirally transduced to express CLDN18.2.

TABLE 16

Published origin and cellular characteristics of pancreas cell lines.

| | | | In vivo growth: | | |
|---|---|---|---|---|---|
| Cell line | Supplier[1] | Human Origin[2] | s.c. tumors | metastasis | Additional information |
| AsPC1 | ATCC | AS, ADCA | yes | Only after orthotopic | Orthotopic: metastasis in gut, kidney and peritoneum. |

TABLE 16-continued

Published origin and cellular characteristics of pancreas cell lines.

| Cell line | Source | Origin | Tumorigenic | Metastatic | Characteristics |
|---|---|---|---|---|---|
| | | | | transplantation or intrasplenic injection in SCID and NOG | Intrasplenic: Liver metastasis |
| BxPC3 | ATCC | PT, ADCA | yes | Only after intrasplenic injection NOG, not in Nu/Nu, NOD/SCID | Negative for cystic fibrosis transmembrane conductance regulator (CFTR) negative. |
| BxPC3 (ECACC) | ECACC | PT, ADCA | yes | | Tumorigenic in nude mice generating moderately well to poorly differentiated tumors comparable to primary adenocarcinoma. |
| CAPAN1 | DSMZ | LM, D-ADCA | yes | After intrasplenic injection in NOG | Positive for cystic fibrosis transmembrane conductance regulator (CFTR). Resistant to 5-FU |
| CFPAC1 | ATCC | LM, D-ADCA, cystic fibrosis | yes | After orthotopic transplantation in Nu/Nu | Express product of the CF gene (cytic fibrosis). Cells have the most common form of the CF mutation. No effect of cAMP agonists, adenyl cyclase stimulators or phosphodiesterase inhibitors. Respond to Ca++ ionophores. Capecitabine and cyclopamine sensitive |
| DANG | DSMZ | CA | yes | No | |
| HPAFII | ATCC | AS, ADCA | yes | Low metastatic after orthotopic transplantation in SCID | IL22-R positive (inhibits NK cell action via IL10 and TGF-β1) |
| HPAC | ATCC | ADCA | yes | Low metastatic after orthotopic transplantation in SCID | Derived from pancreas head. Tumors in nude mice histologically similar to tumor of origin. Growth stimulated with insulin, IGF-I, EGF and TGFα. Growth suppressed by dexamethasone and glucocotricoids. |
| HUP-T3 | DSMZ | AS, CA | | | From poorly differentiated ADCA |
| HUP-T4 | DSMZ | AS, CA | | | From well-differentiated papillotubular ADCA |
| KCI-MOH | DSMZ | PT-ADCA | Yes (SCID) | | Derived from pancreas head. Moderately differentiated, tubular. |
| KP-2 | JCRB | D-ADCA | yes | (minimally) | Moderately differentiated. Transplantable to nude mice histologically similar to tumor of origin. Minimally metastatic. |
| KP-4 | JCRB | D-CA | yes | highly | |
| MiaPaCa2 | JCRB | PT-CA | yes | no | Undifferentiated, sensitive to asparaginase. |
| Panc01 | ATCC | PT, D-E-CA | Yes (NOD/SCID, NOG) | Yes, after intrasplenic injection in NOG | |
| Panc02.03 | ATCC | PT, ADCA | Yes (nude/SCID) | | Derived from pancreas head. K-ras oncogene mutation |
| Panc03.27 | ATCC | PT, ADCA | Yes (nude/SCID) | | Derived from pancreas head. Wild-type K-ras |
| Panc04.03 | ATCC | PT, ADCA | Yes (nude/SCID) | | Derived from pancreas head. K-ras oncogene mutation |
| Panc05.04 | ATCC | PT, ADCA | only if transplanted in matrigel | | Derived from pancreas head. K-ras oncogene mutation. S.c. tumors sensitive for cyclopamine. |
| Patu8902 | DSMZ | PT, D-ADCA | yes | yes | Grade II, |
| Patu8988S | ATCC | LM, ADCA | yes | Lung only | Undifferentiated solid tumors in mice. |
| Patu8988T | ATCC | LM, ADCA | yes | no | Differentiated tumors in mice with tubular structures (sister cell line of Patu8988S), non-metastatic in mice. |
| Suit2 | HSRRB | LM, T-ADCA | yes | highly | Moderately differentiated tubular, epithelial-like. Highly metastatic in nude mice |
| Su86.86 | ATCC | LM, D-ADCA | Yes (orthothopic) | | Cells can be lysed by LAK cells in presence of IL-2 but not by NK cells |
| SW1990 | ATCC | SM, ADCA | Yes | | Grade II, derived from exocrine pancreas, epithelial, tumors in nude mice resemble original tumor, ductal morphology |

TABLE 16-continued

Published origin and cellular characteristics of pancreas cell lines.

| | | | | | |
|---|---|---|---|---|---|
| YPAC | DSMZ | AS, CA | Yes | Yes | Forms tumors in nude mice with functional characteristics of original tumor. |

| Cell line | Cellular products[3] | References |
|---|---|---|
| AsPC1 | CEA, pancreas cancer associated antigen, pancreas specific antigen, mucin | Chen WH et al. In Vitro: 18: 24-34 (1982) Tan and Chu et al., 1985 Tumor Biol 6: 89-98 |
| BxPC3 | CEA, pancreas cancer associated antigen, pancreas specific antigen, mucin | Tan MH et al. Cancer Invest. 4: 15-23 (1986) Suemizu et al. Int. J. Oncol. 31: 741-2007 |
| BxPC3 (ECACC) | Mucin, CEA, pancreas cancer associated antigen, pancreas specific antigen | Tan MH et al. Cancer Invest. 4: 15-23 (1986) |
| CAPAN1 | | Fogh et al. J. Natl. Cancer Inst. 58: 209-214 (1977). Suemizu et al. Int. J. Oncol. 31: 741-2007 |
| CFPAC1 | CEA, pancreatic oncofetal antigen, adenocarcinoma associated antigen, Ca19-9, epithelial keratins | Schoumacher RA et al. Proc Natl. Acad Sci. USA 87: 4012-4016 (1990). Lee et al., Oncogene 2010, 29: 56-67. Thayer et al., Nature 2003 425: 851 |
| DANG | | Not published |
| HPAFII | Mucin1 and Mucin 4 | Kim YW et al. Pancreas 4: 353-362, 1989. Curd et al., clin. Exp. Immunol.168 (2012) |
| HPAC | EGF, functional glucocorticoid receptor, keratin, pancreatic ductal epithelium marker (DU-PAN-2), antigens (HMFG1, AUA1) tumor-associated antigens (CEA, CA-125, CA19-9) | Gower W J et al. In vitro Cell Dev Biol 30A: 151-161 (1994) |
| HUP-T3 | Small amounts of CEA, TGFβ2 | Nishimura et al. Int. J. Pancreatol 13: 31-41 (1993) |
| HUP-T4 | Large amounts of CEA and CA19-9, TGFβ2 | Nishimura et al. Int. J. Pancreatol 13: 31-41 (1993) Schlingensiepen et al. Antisense Pharma GmbH |
| KCI-MOH | Cytokeratins | Mohammad et al., Pancreas 16: 19-25 (1998) |
| KP-2 | | Ikeda et al., J Cancer Res. 81: 987-993 (1990) |
| KP-4 | Parathyroid hormone-related peptide (PTHrP) | Nishi et al., Int. J. Oncol. 5: 33-39 (1994) |
| MiaPaCa2 | | Yunis et al., Int. J. Cancer 19: 218-235 (1977) |
| PancOl | | Suemizu et al. Int. J. Oncol. 31: 741-2007 |
| Panc02.03 | Cytokeratins | Jaffee et al., Cancer J. Sci. Am. 4: 194-203 (1998) |
| Panc03.27 | Cytokeratins | Jaffee et al., Cancer J. Sci. Am. 4: 194-203 (1998) |
| Panc04.03 | Cytokeratins | Jaffee et al., Cancer J. Sci. Am. 4: 194-203 (1998) |
| Panc05.04 | Cytokeratins | Jaffee et al., Cancer J. Sci. Am. 4: 194-203 (1998). Thayer et al., Nature 2003 425: 851 |
| Patu8902 | Secretes protinases and cathepsin B, expression of TGFβ2 | Elsasser et al., Virchows Arch B Cell Pathol Incl Mol Pathol, 64: 1993, 201 |

TABLE 16-continued

Published origin and cellular characteristics of pancreas cell lines.

| | | |
|---|---|---|
| Patu8988S | Cytokeratins, no mucin | Elsasser et al., Virchows Arch B Cell Pathol Incl Mol Pathol 61: 295-306 (1992) |
| Patu8988T | High mucin secretion, Cytokeratins | Elsasser et al., Virchows Arch B Cell Pathol Incl Mol Pathol 61: 295-306 (1992) |
| Suit2 | CEA, CA19-9 | Ywamura T. et al |
| Su86.86 | CEA | Drucker B J et al., In vitro Cell Dev Biol. 24: 1179-1187, 1988 |
| SW1990 | Mucin, CEA | Kyriazis A P et al., Cancer Res. 43: 4393-4401 (1983) |
| YPAC | Secrete inflammatory cytokines, IL1α (autocrine), IL6, IL8 | Yamada et al., Int J Cancer, 76: 1998, 141, |

[1]ATCC: American Type Culture Collection; HSRRB: Health Science Research Resources Bank, DSMZ: Deutsche Sammlung von Mikroorganismen und Zellkulturen.
[2]PT: primary tumor, AS: ascites, LM: liver metastasis, SM: spleen metastasis, ADCA: adenocarcioma, D: ductal, T: tubular, E: epitheloid, CA: pancreas carcinoma
[3]CEA: carcinoembryonic antigen, CA: carbohydrate antigen, IL: interleukin CLDN18.2 Transcript Expression in Human Pancreatic Cancer Cell Lines To identify CLDN18.2-expressing pancreas cell lines, transcript levels were determined with quantitative real-time PCR (RT-PCR) using a forward primer binding to exon 1 of CLDN18.2 and a reverse primer binding to exon 3 of CLDN18. The endogenously CLDN18.2 expressing human gastric carcinoma cell line KATO-III and the CLDN18.2 negative breast cancer cell line SKBR-3 were included as positive and negative controls, respectively. The RT-PCR revealed clear endogenous CLDN18.2 expression in the pancreatic cancer cell lines DANG, Panc03.27, Panc05.04, Patu8988S and YAPC with relative levels exceeding $1 \times 10^5$. Interestingly, Patu8988S cells showed CLDN18.2 expression levels (~$1 \times 10^8$) comparable to stomach CA KATO-III cells (FIG. 12A). In conclusion, we detected robust CLDN18.2 expression in 5 out of 22 pancreatic cancer cell lines.

In addition to the endogenous cell lines, the LVT cell lines ectopically expressing CLDN18.2 were analyzed on the transcript level (FIG. 12A). For 6 out of 8 LVT cell lines, relative CLDN18.2 expression levels of more than $1 \times 10^8$ were detected. Only in HAPC-LVT and Suit2-LVT cells, the expression level was above $1 \times 10^5$.

We investigated if CLDN18.2 expression is stable during in vitro cultivation. Patu8988S, Panc05.04 cells and the lentivirally transduced cell lines Suit2-LVT, MiaPaCa2-LVT and Patu8902-LVT were passaged up to 15 times and CLDN18.2 transcript was analyzed (FIG. 12B-D). We observed loss of CLDN18.2 expression in both endogenous and transduced cells with a higher passage number. Loss of expression was highest in the transduced cells. Therefore, early passages were used, wherever possible for the in vitro experiments and expression of CLDN18.2 in tumor xenografts was verified in the below engraftment experiments.

CLDN18.2 Protein Expression in Human Pancreatic Cancer Cell Lines

Detection of CLDN18.2 in Total Cell Lysates

In addition to the transcript analyses, the expression of CLDN18.2 was analyzed on the protein level by Western blot and IF. For Western blot analysis cell lysates of the 26 pancreatic cancer cell lines were investigated by western blotting (WB) using the CLDN18 specific antibody anti-Claudin18 (C-term). Lysates of SKBR-3 cells were again used as negative control, whereas lysates of HEK293 cells stably transfected with CLDN18.2 (HEK293-p740) were used as positive control. Here, we detected high protein expression in Patu8988S, DANG and Panc05.04 cells, confirming the RNA data. Faint bands were detectable in Panc03.27 and BxPC3 cell lysates. YAPC cells, which were identified positive on the RNA level showed a faint band of smaller size in western blots. All other cell lines were negative (FIG. 13).

Cellular Expression of CLDN18 in Pancreatic Cancer Cells

To obtain supportive protein expression data, pancreatic carcinoma cell lines were investigated by immunofluorescence (IF) after fixation and permeabilization of the cells and using antibody 35-22A for detection. IF analyses confirmed previous RNA and protein data showing that most pancreatic cancer cell lines are negative for CLDN18.2 staining (FIG. 14). In a few cell lines (like AsPC1, DANG, HUP-T3, HUP-T4, Panc01) nuclear dots were observed, which most likely represent staining artifacts. DANG, Panc03.27 and BxPC3 cells that were identified to feature low CLDN18.2 on the RNA and/or protein level, were negative in the IF analysis, which has a lower detection sensitivity. In contrast, membranes and cytoplasm of Panc05.04, Patu8988S and KATO-III gastric carcinonoma control cells stained strongly positive for CLDN18.2. Staining intensity was different for each cell and also negative cells were detected within the population (FIGS. 14J and N). In the LVT cell lines we found strong membrane staining of more than 80% of all cells.

Confirmation of CLDN18.2 Expression in Pancreatic Cancer Cells

To confirm expression of CLDN18.2 and to assess amount of this target on the cell surface the endogenous cell lines Panc05.04 and Patu8988S as well as in the LVT cell lines were stained with IMAB362 using a native staining protocol. Although staining of Patu8988S, Panc05.04 and the KATO-III gastric cancer control cells with IMAB362 was less intense and the percentage of positive cells was reduced compared to staining cells with 35-22A (FIG. 16A-F), the IF analysis confirmed that CLDN18.2 is expressed on the surface of pancreatic cancer cells. For the 8 LVT pancreatic cancer cell lines ectopically expressing CLDN18.2, clear membrane staining was observed on almost all cells (as shown for 6 LVT cell lines in FIG. 16G-L).

In conclusion, the CLDN18.2 expression analyses resulted in identification of endogenously expressing pancreatic cancer cell lines Panc05.04 and Patu8988S and all 8 lentivirally transduced cell lines BxPC3-LVT, CAPAN1-LVT, DANG-LVT, MiaPaCa-2-LVT, Suit-2-LVT, Patu8902-LVT and YAPC-LVT as suitable CLDN18.2 positive cell model systems.

Development of Pancreatic Cancer Xenograft and Metastasis Models

Engraftment Studies for Identification of Suitable Subcutaneous Pancreatic Cancer Tumor Models A total of 37 engraftment studies with different pancreatic cancer cell lines were performed to identify suitable subcutaneous xenograft models for testing in vivo efficacy of IMAB362. Of all tested cell lines, the BxPC3-LVT, CAPAN1-LVT, MiaPaCa-2-LVT, HPAC-LVT, DANG-LVT and YAPC-LVT cell lines with ectopic CLDN18.2 expression were selected for subcutaneous xenograft models, showing high engraftment rates and homogeneous tumor growth. In addition, subcutaneous xenograft models with endogenously CLDN18.2 expressing Patu8988S and DANG cell lines were selected for testing IMAB362 efficacy in vivo. S.c. injection of Panc05.04 cells did not result in formation of subcutaneous tumors.

TABLE 17

Summary of tested engraftment conditions for development of s.c. xenograft models for pancreatic cancer.

| Cell line | Engraftment check (EC) | Date | Experimental set-up | Results | Comments |
|---|---|---|---|---|---|
| BxPC3 ATCC | EC1_BxPC3 ATCC | 22.03. 2010 | 1e7 cells subcutaneous into the left flank of 5 female HsdCpb: NMRI-Foxn1nu mice | take rate 40%; median survival 56 days | not recommended |
| BxPC3 ECACC | EC2_BxPC3 ECACC | 23.03. 2010 | 1e7 subcutaneous into the left flank of 5 female HsdCpb: NMRI-Foxn1nu mice | take rate 100%; median survival 63 days | suitable conditions for subcutaneous xenografts |
| BxPC3-LVT | EC3_C179 | 25.03. 2011 | 1e7 cells subcutaneous into the left flank of 10 female HsdCpb: NMRI-Foxn1nu mice | take rate 90%; median survival 64 days | suitable conditions for subcutaneous xenografts |
| CAPAN1 | EC1_CAPAN1 | 26.03. 2010 | 1e7 cells subcutaneous into the left flank of 5 female HsdCpb: NMRI-Foxn1nu mice | take rate 100%; median survival 52 days | suitable conditions for subcutaneous xenografts |
| CAPAN1-LVT | EC1_C186 | 09.08. 2011 | Metastasis assay. 1-2e6 cells in PBS i.v. into 10 female HsdCpb: NMRI-Foxn1nu mice | No metastases in lung and liver detected; analysis 72 days post tumor cell injection | not recommended |
| CAPAN2 | EC1_CAPAN2 | 06.04. 2010 | 1e7 cells subcutaneous into the left flank of 5 female HsdCpb: NMRI-Foxn1nu mice | take rate 100%; median survival 100 days | suitable conditions for subcutaneous xenografts |
| DANG | EC3_C2 | 08.02. 2007 | 1e7 cells subcutaneous into the left flank of 3 athymic mice | take rate 100%; very aggressive tumor growth; median survival 18 days | no adequate conditions for xenograft model |
| DANG | EC4_C2 | 10.10. 2007 | 5e5-1e7 cells subcutaneous into the left flank of 25 athymic mice | take rate 100%; very aggressive tumor growth; median survival 16 to 23 days | no adequate conditions for xenograft model |
| DANG subclone 1C5F2 | EC5_C2 | 01.06. 2010 | 2.5e6 cells subcutaneous into the left flank of 5 female HsdCpb: NMRI-Foxn1nu mice | take rate 100%, cachexia in tumor bearing mice; median survival 17 days | not recommended due to tumor cachexia |
| DANG subclone 1C5F2 | EC6_C2 | 10.02. 2011 | 5e4-2e5 cells subcutaneous into the left flank of 15 female HsdCpb: NMRI-Foxn1nu mice | 5e4 = 40% take rate; 1e5, 2e5 = 100% take rate; median survival 26 to 39 days | not recommended due to tumor cachexia |
| DANG subclone 1C5F2 | EC7_C2 | 02.04. 2011 | 2e5 cells subcutaneous into the left flank of 5 female and 5 male HsdCpb: NMRI-Foxn1nu mice; weight kinetics | take rate 100%; cachexia in tumor bearing mice; median survival 29 days | not recommended due to tumor cachexia |
| DANG-LVT | EC1_C180 | 21.03. 2011 | 5e6 cells subcutaneous into the left flank of 10 female HsdCpb: NMRI-Foxn1nu mice | take rate 100%, cachexia in tumor bearing mice; median survival 28 days | not recommended due to tumor cachexia |
| Patu8902 | EC1_C197 | 25.07. 2011 | 1e7 cells subcutaneous into the left flank of 5 female HsdCpb: NMRI-Foxn1nu mice | take rate 100%, fast tumor growth; median survival 21 days | suitable conditions for xenograft model |

TABLE 17-continued

Summary of tested engraftment conditions for development of s.c. xenograft models for pancreatic cancer.

| Cell line | Engraftment check (EC) | Date | Experimental set-up | Results | Comments |
|---|---|---|---|---|---|
| Patu8902 | EC2_C197 | 25.07.2011 | experimental metastasis assay. Intravenous injection of 1-2e6 cells into 10 female HsdCpb: NMRI-Foxn1nu mice | No metastasis in lung or liver tissues; 8 mice died after tumor cell injection | not recommended for metastasis assay |
| Patu8988S | EC1_C178 | 15.03.2011 | 1e7 cells subcutaneous into the left flank of 5 female HsdCpb: NMRI-Foxn1nu mice | take rate 100%, heterogeneous tumor growth, ulcerating tumors; median survival 55 days | not recommended |
| Patu8988S | EC2_C178 | 05.04.2011 | experimental metastasis assay. Intravenous injection of 1-2e6 cells into 10 female HsdCpb: NMRI-Foxn1nu mice | very slow metastasis model; analysis after 70 days | suitable model for lung metastasis assay |
| Patu8988S | EC3_C178 | 10.06.2011 | 2.5e6-1.5e7 cells subcutaneous into the left flank of 15 female HsdCpb: NMRI-Foxn1nu mice | heterogeneous tumor growth; slow tumor growth; ulcerating tumors; median survival 95.5 days | not recommended |
| Patu8988S (recult.) | EC1_C202 | 11.08.2011 | 5e6 cells subcutaneous into the left flank of 5 female HsdCpb: NMRI-Foxn1nu mice | heterogeneous tumor growth; slow tumor growth; ulcerating tumors; median survival 88 days | not recommended |
| Patu8988S subclone 17 | EC1_C214 | 28.11.2011 | 5e6 cells subcutaneous into the left flank of 5 female HsdCpb: NMRI-Foxn1nu mice | heterogeneous tumor growth; slow tumor growth; ulcerating tumors; median survival 54 days | not recommended |
| Patu8988S subclone 22 | EC1_C215 | 28.11.2011 | 5e6 cells subcutaneous into the left flank of 5 female HsdCpb: NMRI-Foxn1nu mice | take rate 100%, heterogeneous tumor growth; slow tumor growth; ulcerating tumors; median survival 47 days | not recommended due to heterogeneous and ulcerating tumors; best tumor growth curves of tested PATU8988S subclones |
| Patu8988S subclone 30 | EC1_C216 | 28.11.2011 | 5e6 cells subcutaneous into the left flank of 5 female HsdCpb: NMRI-Foxn1nu mice | heterogeneous tumor growth; slow tumor growth; ulcerating tumors; median survival 35 days | not recommended |
| Patu8988S subclone 34 | EC1_C217 | 28.11.2011 | 5e6 cells subcutaneous into the left flank of 5 female HsdCpb: NMRI-Foxn1nu mice | heterogeneous tumor growth; slow tumor growth; ulcerating tumors; median survival 49 days | not recommended |
| Patu8988S subclone 41 | EC1_C218 | 28.11.2011 | 5e6 cells subcutaneous into the left flank of 5 female HsdCpb: NMRI-Foxn1nu mice | heterogeneous tumor growth; slow tumor growth; ulcerating tumors; median survival 108 days | not recommended |
| Patu8988S subclone adM#13 | EC1_C237 | 06.02.2012 | 5e6 cells subcutaneous into the left flank of 5 female HsdCpb: NMRI-Foxn1nu mice | slow tumor growth; bloody cysts, but not ulcerating; median survival 73 days | reasonably model for subcutaneous xenografts |
| Patu8988S subclone adM#19 | EC1_C238 | 06.02.2012 | 5e6 cells subcutaneous into the left flank of 5 female HsdCpb: NMRI-Foxn1nu mice | heterogeneous tumor growth; slow tumor growth; ulcerating tumors; median survival 42 days | not recommended |
| Patu8988S subclone adM#1 | EC1_C239 | 13.02.2012 | 5e6 cells subcutaneous into the left flank of 5 female HsdCpb: NMRI-Foxn1nu mice | heterogeneous tumor growth; slow tumor growth; ulcerating tumors; median survival 77 days | not recommended |
| Patu8988S subclone adM#16 | EC1_C240 | 13.02.2012 | 5e6 cells subcutaneous into the left flank of 5 female HsdCpb: NMRI-Foxn1nu mice | slow tumor growth; bloody cysts, but not ulcerating; median survival 66 days | reasonably model for subcutaneous xenografts |
| Patu8988S subclone adM#9 | EC1_C241 | 13.02.2012 | 5e6 cells subcutaneous into the left flank of 5 female HsdCpb: NMRI-Foxn1nu mice | slow tumor growth; bloody cysts, but not ulcerating; median survival 59 days | reasonably model for subcutaneous xenografts |

TABLE 17-continued

Summary of tested engraftment conditions for development of s.c. xenograft models for pancreatic cancer.

| Cell line | Engraftment check (EC) | Date | Experimental set-up | Results | Comments |
|---|---|---|---|---|---|
| Suit2 | EC1_C196 | 25.07.2011 | 1e7 cells subcutaneous into the left flank of 5 female HsdCpb: NMRI-Foxn1nu mice | take rate 100%; fast tumor growth; ulcerating tumors; median survival 35 days | not recommended |
| Suit2 | EC2_C196 | 25.07.2011 | experimental metastasis assay. Intravenous injection of 2exp6 cells into 10 female HsdCpb: NMRI-Foxn1nu mice | metastases in lung, liver and muscles | suitable model for lung metastasis assay |
| Panc02.03 | EC1_Panc 02.03 | 12.05.2010 | 1e7 cells subcutaneous into the left flank of 5 female HsdCpb: NMRI-Foxn1nu mice | take rate 100%; median survival 54 days | suitable conditions for subcutaneous xenograft model |
| Panc03.27 | EC2_Panc 03.27 | 12.05.2010 | 1e7 cells subcutaneous into the left flank of 5 female HsdCpb: NMRI-Foxn1nu mice | take rate 100%; median survival 91 days | suitable conditions for subcutaneous xenograft model |
| Panc04.03 | EC3_Panc 04.03 | 17.06.2010 | 1e7 cells subcutaneous into the left flank of 5 female HsdCpb: NMRI-Foxn1nu mice | take rate 100%; median survival 39 days | suitable conditions for subcutaneous xenograft model |
| Panc05.04 | EC4_Panc 05.04 | 18.06.2010 | 1e7 cells subcutaneous into the left flank of 5 female HsdCpb: NMRI-Foxn1nu mice | no subcutaneous tumor growth | not recommended |
| Panc05.04 | EC5_Panc 05.04 | 09.05.2011 | 2e7 cells suspended in RPMI subcutaneous into the left flank of 5 female HsdCpb: NMRI-Foxn1nu mice | no subcutaneous tumor growth | not recommended |
| MiaPaCa2 | EC1_C195 | 25.07.2011 | 1e7 cells subcutaneous into the left flank of 5 female HsdCpb: NMRI-Foxn1nu mice | take rate 100%; median survival 42 days | suitable conditions for subcutaneous xenograft model |
| MiaPaCa2-LVT | EC1_C219 | 18.11.2011 | 5e6 or 1e7 cells subcutaneous into the left flank of 10 female HsdCpb: NMRI-Foxn1nu mice | take rate 100%; median survival 40 days | suitable conditions for subcutaneous xenograft model |
| MiaPaCa2 | EC2_C195 | 25.07.2011 | experimental metastasis assay. Intravenous injection of 2e6 cells into 10 female HsdCpb: NMRI-Foxn1nu mice | metastases in lung, liver and lymph nodes | suitable model for lung metastasis assay |
| HPAC | EC1_HPAC | 19.04.2010 | 1.5e7 cells subcutaneous into the left flank of 5 female HsdCpb: NMRI-Foxn1nu mice | take rate 100%; median survival 29 days | suitable conditions for subcutaneous xenograft model |
| YAPC | EC1_YAPC | 10.05.2010 | 1e7 cells subcutaneous into the left flank of 5 female HsdCpb: NMRI-Foxn1nu mice | take rate 100%, very aggressive tumor growth; homogeneous tumor growth; ulcerating tumors; median survival 28 days | limited xenograft model |
| YAPC-LVT | EC2_YAPC | 10.05.2010 | 5e5-7.5e6 cells subcutaneous into the left flank of 20 female HsdCpb: NMRI-Foxn1nu mice | take rate 100%, very aggressive tumor growth; homogeneous tumor growth; ulcerating tumors; median survival 27 days | limited xenograft model |

Engraftment Studies for Identification of Suitable Metastasis Models

To study effects of IMAB362 on metastasis formation, metastatic cancer models were established in nude mice. Pancreatic cancer cell lines were analyzed for their ability to metastasize upon i.v. application. CAPAN1-LVT, MiaPaCa-2, Patu8988S, Patu8902 and Suit-2 cells were injected into tail veins of nude mice as described by Mohanty and Xu 2010. To determine the time point of metastasis engraftment and growth rate, the mice were sacrificed at different time points (Table 18).

TABLE 18

Metastasis engraftment analysis of pancreas cancer cell lines

| Cell line | # of cells | # of mice | Mice analyzed on day (#) | Mice died on day (#) | Organs isolated and stored | Metastasis |
|---|---|---|---|---|---|---|
| Patu8902 | $1 \times 10^6$ | 5 | — | 0(1), 1(3) 4(1) | n.d. | No |
| Patu8902 | $2 \times 10^6$ | 5 | — | 0(1), 1(3), 15 (1) | n.d. | No |

TABLE 18-continued

Metastasis engraftment analysis of pancreas cancer cell lines

| Cell line | # of cells | # of mice | Mice analyzed on day (#) | Mice died on day (#) | Organs isolated and stored | Metastasis |
|---|---|---|---|---|---|---|
| Patu89885 | $1 \times 10^6$ | 7 | 34, 51, 59, 66, 70, 86, 108 | — | Lung/Liver | Lung |
| Patu89885 | $2 \times 10^6$ | 8 | 34, 41, 51, 59, 66, 70, 86, 108 | — | Lung/Liver | Lung |
| Suit-2 | $2 \times 10^6$ | 10 | 36(3), 45(3), 52(2), 59(2) | — | Lung/Liver | Lung/Liver |
| CAPAN1-LVT | $2 \times 10^6$ | 5 | 72(1) | 0(1), 1(3), | n.d. | n.d. |
| CAPAN1-LVT | $1 \times 10^6$ | 5 | 72(4) | 2(1) | Lung/Liver | n.d. |
| MiaPaCa-2 | $2 \times 10^6$ | 10 | 32(2), 52(2), 59(2), 66(2), 73(2) | — | Lung/Liver | No |

Engraftment analysis of Patu8902 cells and CAPAN1-LVT was not feasible, since most mice died almost immediately. In lungs and livers of 5 surviving mice challenged with CAPAN-LVT cells no macroscopically visible metastasis were detected after 72 day. Suit-2 and MiaPaCa2 cell injections, in contrast, were well-tolerated. Lung tissues of these mice were analyzed in IHC analysis at different time points after injection. In mice challenged with MiaPaCa-2 cells no metastases were detected in the lungs after up to 73 days, and therefore this cell line was not selected as an IMAB362 treatment model. Suit-2 cancer cells metastasized into the lungs of the mice. Multiple foci were detected throughout the tissue. Therefore, the lentivirally CLDN18.2 transduced Suit-2-LVT cell line was selected as a model system to analyze the effects of IMAB362 treatment on formation of metastasis.

In addition to Suit-2 also the ability of Patu8988S cells endogenously expressing CLDN18.2 to form metastasis was analyzed. Engraftment checks were performed with 2 different cell numbers ($1 \times 10^6$, $2 \times 10^6$) i.v. injected per mouse. Lungs and livers were isolated at different time points as indicated in Table 18. First, the different tissues obtained were analyzed using Q-PCR. Lungs and livers obtained up to day 70 were analyzed by amplifying human α-satellite DNA of chromosome 17. The results of the lungs show a clear increase in the percentage of human DNA in mouse lungs over time, which was not dependent on the injected cell number. By i.v. application of $1 \times 10^6$ or $2 \times 10^6$ cells 5.8% and 3.7% human DNA could be detected after 70 days, respectively (FIG. 19). In livers, hardly any human DNA was amplified. After 70 days the percentage was slightly increased, but still below 0.005%.

To verify CLDN18.2 expression in the Patu8988S metastasis, lung tissues were immunohistochemically stained using anti-human MHC class I antibodies for detection of human cells in mouse tissue, as well as the anti-Claudin18 (Mid) antibody. MHC-I staining showed that clear metastasis foci were detectable in mouse lung tissue sections, but not in liver sections (FIG. 20). Furthermore, the membranes of the cells in these foci were stained with the anti-Claudin18 (Mid) antibody showing clear expression of the IMAB362 target protein in these cells. Therefore, in addition to the Suit2-LVT model, this endogenous metastasis model was selected for IMAB362 treatment investigation.

Example 4: IMAB362-Mediated Cell Killing Effects

IMAB362 crosslinking induces efficient apoptosis Antibody binding to a cell surface target may initiate aberrant signalling resulting directly in cell death. Such signalling events may depend on the target epitope, the valency of binding and whether binding is associated with cross-linking of the target. For several CD20 positive lymphoma cell lines, for example induction of apoptosis by rituximab is only observed under cross-linking conditions. Such cross-linking may take place in vivo when high affinity Fc-receptor-positive immune cells interact with antibody-coated tumor cells.

Cross-linking of IMAB362 induces direct apoptosis within 18-42 hours in human gastric cancer cells NUGC-4 and KATO-III as measured by the TUNEL assay. The magnitude of apoptosis correlates with the dose of the antibody and level of target expression on the cancer cell. Treatment with gemcitabine leads to cell cycle arrest of tumor cells followed by apoptotic cell death. Apoptosis of gemcitabine treated pancreas tumor cells is shown in FIG. 21.

IMAB362-Mediated ADCC Activity Against Pancreatic Cancer Cells

IMAB362 is highly potent in recruiting and activating Fcγ-receptor-positive immune effector cells, such as natural killer cells. Binding of IMAB362 to target cells, induces antibody-dependent cellular cytotoxicity (ADCC) by granzymes and perforins secreted by the effector cells upon binding of their Fcγ receptors to the antibody. The impact of this mechanism of action was previously shown for luciferase- and CLDN18.2-positive stomach CA cells (like NUGC-4 and KATO-III) by incubation with IMAB362 for 24 hours in the presence of human peripheral blood mononuclear cells (PBMC) (effector to target ratio=40:1). Application of up to 200 μg/ml IMAB362 resulted in maximum lysis rates of 80-100%.

Here, we determined the ADCC activity of IMAB362 against pancreatic cancer cell lines. Increasing concentrations of IMAB362 were incubated with the different cell lines at an E:T ratio of 40:1. PBMCs of different donors were added in each experiment. Results for all cell lines are summarized in Table 19. Of the 5 initially identified CLDN18.2-positive pancreas cell lines, only Patu8988S, Panc05.04 and DANG were efficiently killed by addition of IMAB362 and PBMCs (FIG. 22A). Although CLDN18.2 surface expression was not detectable in FACS for Panc05.04 and DANG, the expression level is significant enough to cause effector cell-dependent killing ($EC_{50}$: Patu8988S: 0.01-1.4 g/ml, DANG/Panc05.04: 0.1-38 μg/ml). From these data it can be concluded that only cells expressing relative RNA levels$>5.5 \times 10^5$ are efficiently lysed.

ADCC analyses were also performed with LVT pancreatic cancer cell lines and their corresponding parental cell lines (FIG. 22B-F). ADCC strictly depends on the specific binding of IMAB362 to the target, since only CLDN18.2 positive target cells are killed by IMAB362 and PBMCs. Half maximum killing and maximum killing rates induced in human pancreatic cancer cells by IMAB362 varied between PBMC donors and were also dependent on passage number of the cells affecting CLDN18.2 expression level.

Figure 22H:
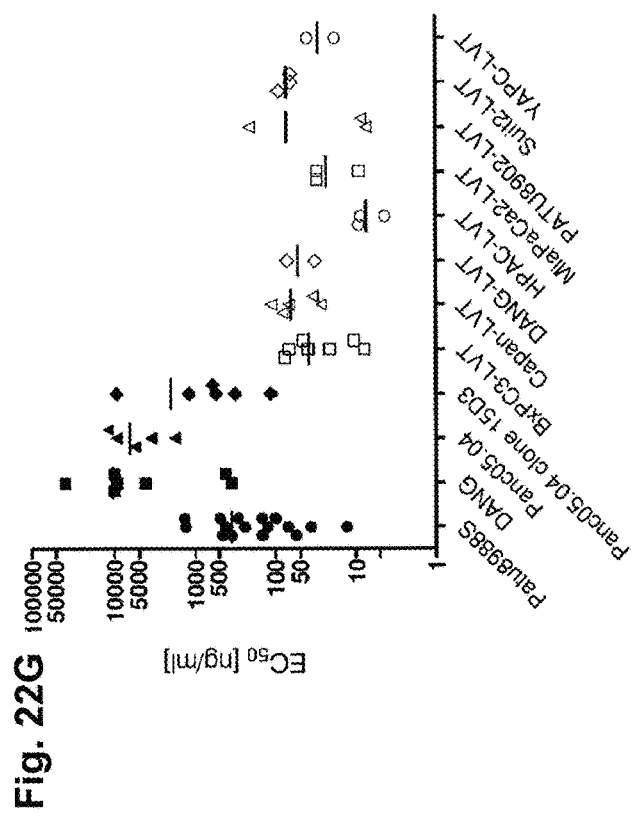

The IMAB362 concentrations causing half maximum killing rates of the target cells as well as the maximum killing rates are shown in FIG. 22G-H. The LVT pancreas CA cell lines were killed upon addition of small amounts of antibody at high rates, whereas for DANG and Panc05 highest antibody concentrations are required to reach a ~50% maximum killing rate. For Panc05.04 results obtained with subclone 15D3 (CLDN18.2 positive clone selected by limited dilution of Panc05.04 and FACS) are included in the figure showing comparable ADCC lysis rates as with the LVT cell lines. Unfortunately, CLDN18.2 expression in this clone is quickly silenced in vitro after subculturing the cells and thus this clone was not used for further experiments.

IMAB362-Mediated CDC Activity Against Pancreatic Cancer Cells

Pancreatic cancer cells, which were killed with IMAB362 in ADCC assays, were analyzed for their sensitivity towards the complement-dependent lytic activity of IMAB362. In addition, the LVT cell lines and the parental strains were tested in CDC.

CDC activity is activated by complexes of antigen and IgM or IgG antibodies (classical pathway) or by microbial surfaces (alternative pathway). In the classical pathway complement C5 is converted to C5b. The anaphyloatoxins C3a, C4a and C5b are released and a membrane attack complex (MAC) is formed by the sequential binding of C5b, C7, C8 and C9. This pathway is inhibited by soluble but also membrane bound proteins (e.g. CR1, DAF, MCP, CD59, CD55, CD46) protect self-tissues.

CHO-K1 cells stably transfected with CLDN18.2 (p740) and luciferase were used as assay positive controls in each assay (FIG. 23A). The cell lines DANG, BxPC3, YAPC, Patu8988S, Panc05.04, CAPAN1 and Suit2 were not lysed by IMAB362 and addition of healthy human serum pool (FIG. 23B). Although DANG, Patu8988S and Panc05.04 cells are CLDN18.2 positive as shown in all the previous experiments, these cells were not lysed in a complement-dependent manner. This is most likely due to the fact that neoplastic cells over-express one or more membrane bound complement inhibitory proteins (e.g. CD46, CD55 and CD59) (Geis et al., Curr Cancer Drug Targets, 2010 10:922-931). However, if expression of these inhibitory proteins on tumor cells affect clinical outcome of an antibody therapy is still contradictory (Dzietczenia et al. Med. Oncol. 2010, 27:743-6; Weng and Levy at al., Blood 2001 98:1352-7). In addition to the endogenous cell lines, all the LVT cell lines were tested in CDC assays. As shown in FIG. 23, IMAB362 and serum addition to MiaPaCa-2-LVT, Suit2-LVT and CAPAN1-LVT resulted in dose-dependent lysis with $EC_{50}$ values ranging from 0.3 to 2.6 µg/ml.

Overview of CLDN18.2 Expression in Human Pancreatic Cancer Cell Lines

TABLE 19

In house in vitro and in vivo characteristics of pancreas cancer cell lines.

| Cell line | CLDN18.2 mRNA level (RT-PCR) | CLDN18 Protein level (WB)[1] | CLDN18 surface expression (FACS)[2] | CLDN18 cellular localization (IF[3]) | ADCC[4] Max. lysis (%) | ADCC[4] $EC_{50}$ (ng/ml) | CDC Max. lysis (%) | CDC $EC_{50}$ (ng/ml) | Selected for IMAB362 treatment studies |
|---|---|---|---|---|---|---|---|---|---|
| AsPC1 | 2E1 | – | 0.14% | Cytoplasm nuclear dots | n.m. | n.m. | n.d. | n.d. | No |
| BxPC3 (ATCC) | 4.3E4 | – | 1.16% | n.d. | n.m. | n.m | n.d. | n.d. | No |
| BxPC3 (ECACC) | 2.9E4 | + | 0.90% | cytoplasm | n.m.-60 | n.m | n.d. | n.d. | Cells able to engraft, used after LVT for in vivo treatments |
| BxPC3 LVT | 6.1E7 | +++ | | cytoplasm + membrane | 90.6 ± 6.4 | 47.7 ± 19.1 | n.m. | n.m. | Cells able to engraft, used for in vivo treatments |
| CAPAN1 | 8.0E2 | – | 0.54% | negative[2] | n.m. | n.m. | n.m. | n.m. | Cells able to engraft, used after LVT for in vivo treatments |
| CAPAN1-LVT | 1.5E5 | +++ | | cytoplasm + membrane | 92.6 ± 5.5 | 65.03 ± 35.1 | 79.1 | 970.1 | Cells able to engraft, used for in vivo treatments |
| CFPAC1 | 1.5E4 | – | 0.55% | negative | 0-1.5 | n.m. | n.d. | n.d. | No |
| DANG | 4.9E5 | ++ | 1.19% | cytoplasm nuclear dots | 52.5 ± 7.8 | 4976.5 ± 4125.4 | n.m. | n.m. | Cells able to engraft, used for in vivo treatments (disadvantage: cachexia) |
| DANG-LVT | 1.8E8 | +++ | | cytoplasm + membrane | 85.9 ± 11.7 | 52.3 ± 27.7 | n.m. | n.m. | Cells able to engraft, used for in vivo treatments |
| HPAFII | 4.2E3 | – | 10.00% | negative | n.m. | n.m. | n.d. | n.d. | Selection of single clones unsuccessful (disadvantage: cachexia) |
| HPAC | 3.6E1 | – | 0.81% | | 0-22.2 | n.m-495.6 | n.d. | n.d. | Cells able to engraft, used after LVT for in vivo treatments |
| HPAC-LVT | 7.0E5 | +++ | | cytoplasm + membrane | 76.2 ± 19.4 | 116.8 ± 105.4 | n.m. | n.m. | Cells able to engraft, used for in vivo treatments |

TABLE 19-continued

In house in vitro and in vivo characteristics of pancreas cancer cell lines.

| Cell line | CLDN18.2 mRNA level (RT-PCR) | CLDN18 Protein level (WB)[1] | CLDN18 surface expression (FACS)[2] | CLDN18 cellular localization (IF[3]) | ADCC[4] Max. lysis (%) | ADCC[4] $EC_{50}$ (ng/ml) | CDC Max. lysis (%) | CDC $EC_{50}$ (ng/ml) | Selected for IMAB362 treatment studies |
|---|---|---|---|---|---|---|---|---|---|
| HUP-T3 | 1.3E4 | – | 0.23% | nuclear dots | n.m. 17.7 | n.m. | n.d. | n.d. | no |
| HUP-T4 | 1.1E2 | – | 5.30% | nuclear dots | n.m. | n.m. | n.d. | n.d. | no |
| KCI-MOH | n.d. | – | n.d. | negative[2] | n.m.-2.8 | n.m. | n.d. | n.d. | no |
| KP-2 | 1 | – | 0.54% | negative | n.d. | n.d. | n.d. | n.d. | no |
| KP-4 | n.d. | – | n.d. | n.d. | n.d. | n.d. | n.d. | n.d. | no |
| MiaPaCa2 | 0 | – | 0.22% | negative | n.m. 8.1 | n.m. | n.m. | n.m. | Cells able to engraft, used after LVT for in vivo treatments |
| MiaPaCa2-LVT | 1.7E8 | +++ | | cytoplasm + membrane | 78.1 ± 6.0 | 23.4 ± 12.3 | 78.4 | 340 | Cells able to engraft, used for in vivo treatments |
| Panc01 | 5.3E1 | – | 65% | nuclear dots | 0-4.5 | n.m. | n.d. | n.d. | no |
| Panc02.03 | n.d. | – | n.d. | negative[2] | n.m. | n.m. | n.d. | n.d. | no |
| Panc03.27 | 2.7E5 | + | 7.30% | cytoplasm | n.m. | n.m. | n.d. | n.d. | Cells engraft, some CLDN18.2 staining observed |
| Panc04.03 | n.d. | – | 1.38% | negative[2] | n.m.-41.4 | n.m. | n.d. | n.d. | No |
| Panc05.04 | 1.2E5 | ++ | 15% | cytoplasm + membrane | 67.1 ± 6.8 | 5728.8 ± 4435.1 | n.m. | n.m. | Selection of single clones unsuccessfull. Cells not able to engraft (standard procedure). |
| Patu8902 | 1.7E3 | – | 0.39% | negative | n.m.-4.2 | n.m. | n.m. | n.m. | Cells able to engraft, used after LVT for engrafments |
| Patu8902-LVT | 1.6E8 | +++ | | cytoplasm + membrane | 74.1 ± 16.4 | 49.2 ± 86.2 | 76.7 | 291.0 | Cells able to engraft s.c., used for metastasis engraftments, mice die upon i.v. application |
| Patu8988S | 3.9E5 | +++ | 81.70% | cytoplasm + membrane | 70.1 ± 22.1 | 174.8 ± 137.9 | n.m. | n.m. | Cells able to engraft, form heterogeous tumors/cysts, used for in vivo treatments (for s.c. tumors and metastasis) |
| Patu8988T | 1.5E1 | – | 6.00% | nuclear dots | n.m.-27.54 | n.m.-470.5 | n.d. | n.d. | No |
| Suit2 | 1.0E4 | – | 0.41% | negative | n.m. | n.m. | n.m. | n.m. | Cells able to engraft, used after LVT for metastasis study |
| Suit2-LVT | 2.0E8 | +++ | | cytoplasm + membrane | 81.2 ± 7.6 | 73.2 ± 14.7 | n.m. | n.m. | Cells able to engraft s.c., used for metastasis assay |
| Su86.86 | 3.2E4 | – | 1.51% | negative | n.m.-14.8 | n.m.-30.4 | n.d. | n.d. | no |
| SW1990 | 1.8E1 | – | 2.53% | negative | n.m. | n.m. | n.d. | n.d. | no |
| YPAC | 1.5E5 | (+) | 0.23% | negative | n.m. | n.m. | n.m. | n.m. | Cells able to engraft, used after LVT for in vivo treatments |
| YAPC-LVT | 2.5E8 | +++ | | cytoplasm + membrane | 91.5 ± 6.3 | 29.5 ± 15.7 | n.m. | n.m. | Cells able to engraft, used for in vivo treatments |

[1]using anti-Claudin18 (C-term) antibody (Zymed)
[2]staining of 2E5 cells/100 μl with 50 μg/ml IMAB362
[3]using antibody 35-22A on fixed and permeabilized cells
[4]Results obtained with at least 2 donors;
n.m.: not measureable;
n.d. not determined.

Example 5: Efficacy of IMAB362 on Pancreatic Cancer Xenograft Models 10 of the 41 tested pancreatic cancer xenograft models were chosen to investigate the efficacy of IMAB362 in vivo. Using pancreatic xenograft models with high expression of CLDN18.2, IMAB362 treatment showed a high antitumoral effect. This was investigated by treatment of mice bearing BxPC3-LVT or MiaPaCa-2-LVT xenografts subcutaneous in the left flank. Treatment was initiated 3 days after tumor inoculation with injections of 200 μg IMAB362 semi-weekly. The IMAB362 treated mice showed significantly inhibited tumor growth compared to mice treated with saline control. In addition tumor growth suppression of IMAB362 treated mice resulted in prolonged median survival (FIG. 24 and FIG. 25). IMAB362 efficacy correlates with the duration of treatment. Initiation of IMAB362 treatment at early time points had an increased effect on tumor growth inhibition than late treatment starts to examine effect on established tumors. Furthermore the antitumoral effect of IMAB362 depended on the amount of CLDN18.2 target expression. IMAB362 mediated growth inhibition of low CLDN18.2 expressing tumors like DANG and Patu8988S xenografts was reduced compared to inhibition of tumor growth using high CLDN18.2 expressing xenograft tumors.

Example 6: Treatment of Pancreatic Metastasis Mouse Models

TABLE 20

Summary of treatments for testing IMAB362 efficacy on pancreatic cancer metastasis

| Cell line | Experiment No. (Date) | Treatment groups | Experimental set-up |
|---|---|---|---|
| Suit2-LVT | ET2_C220 (22.11.2011) | 1. n = 15; 200 µg IMAB362 semi-weekly i.v./i.p.<br>2. n = 15; 200 µg isotype control semi-weekly i.v./i.p.<br>3. n = 15; PBS semi-weekly i.v./i.p. | Injection of 2e6 cells i.v. into the tail vein of female Hsd: Athymic Nude-Foxn1$^{nu}$ mice Initiation of treatment 3 days after tumor cell injection |
| Patu8988S | ET1_C178 (24.05.2011) | 1. n = 10; 200 µg IMAB362 semi-weekly i.v./i.p.<br>2. n = 10; PBS semi-weekly i.v./i.p. | Injection of 2e6 cells i.v. into the tail vein of female Hsd: Athymic Nude-Foxn1$^{nu}$ mice Initiation of treatment 3 days after tumor cell injection |
| Patu8988S | ET1_C178b (03.06.2011) | 1. n = 15; 200 µg IMAB362 semi-weekly i.v./i.p.<br>2. n = 15; isotype control semi-weekly i.v./i.p. | Injection of 2e6 cells i.v. into the tail vein of female Hsd: Athymic Nude-Foxn1$^{nu}$ mice Initiation of treatment 3 days after tumor cell injection |

Suit2-LVT Metastasis Model:

Mice were intravenously injected with $2\times10^6$ Suit2-LVT cells and were treated with 200 µg IMAB362, isotype control antibody (IMAB027), or with PBS as indicated in Table 20. After 35 days the first mouse (isotype control group) died. Consequently, all mice were sacrificed on day 42 and lungs and livers were taken for IHC and Q-PCR analyses.

Q-PCR analysis of human DNA in the lungs of mice was repeated at least twice in triplicate. The calculation of the percentage of human DNA with the obtained Ct values revealed a significant decrease (P<0.05) in Suit2-LVT metastases detected in the lungs, if mice were treated with IMAB362 (FIG. 26A) as compared to both PBS and isotype control treatments. To confirm these results, tissue sections of the lung samples were prepared and stained using MHC-I antibodies. The surface of the positively stained cells in the lung sections was calculated using the ImageJ Program. For IMAB362 treatment significant inhibition (P<0.05) was observed as compared to PBS treatment confirming the results obtained with Q-PCR. For the isotype control antibody however, the differences were not significant (FIG. 26B). This discrepancy is most likely due to differences in tissue processing: IHC processing of tissue sections provides only insight into a very small section of the lung compared to Q-PCR analysis, for which the genomic DNA is extracted from half of the tissue.

In addition to tissue processing, it is possible that the result represents unexpected inhibiting effects of the isotype control antibody targeting CLDN6. To investigate this option, the Suit2-LVT cells were analyzed for CLDN6 expression and IMAB027 binding in FACS. The addition of 200 µg/ml IMAB362 to Suit2-LVT cells confirmed strong binding to the cells, whereas addition of 200 µg/ml IMAB027 resulted in weak binding of the antibody to these target cells, indicating that CLDN6 is indeed weakly expressed on these cells. These results suggest that at least two factors (tissue processing and weak IMAB027 inhibition) resulted in the observed discrepancies with the isotype control antibody.

Patu8988S Metastasis Model

To analyze the effect of IMAB362 treatment on the development and growth of Patu8988S metastasis in vivo, 10 mice per group were injected with $2\times10^6$ Patu8988S cells. The first experiment was performed by comparing IMAB362 treatment to PBS treated mice. In each group 1 mouse died immediately after injection of the cells. In the other 18 mice, the metastasis developed very quickly as compared to the engraftment experiments. After 63 days the first 2 mice in the PBS group were sacrificed due to bad health conditions. All other mice were sacrificed after 65 days. The optical analysis of the lungs revealed large metastasis throughout the lung tissues. The amount of metastasis was analyzed in Q-PCR experiments (FIG. 27). The results show that IMAB362 inhibits the growth of metastasis in lung tissue.

A second experiment with 11 mice per group was performed by comparing IMAB362 treatment with isotype control (Rituximab) control treatment. In this experiment metastasis developed slowly as observed in the engraftments. Nevertheless, for comparability this second experiment was terminated after 65 days. Again lung tissues were analyzed in Q-PCR and again IMAB362 reduced the growth of the metastasis. One mouse of the IMAB362 group was identified as outlier and exclusion of this outlier resulted in almost significant (P=0.0588) inhibition. These data were verified by IHC surface analysis as described for the Suit2-LVT metastasis experiment. Here the same outlier could be identified, and omitting this value in the t-test, the inhibition of IMAB362 is also at the border of being significant (P=0.0691), that values of the same mouse.

Example 7: Primary Pharmacodynamics of IMAB362 in Combination with Chemotherapy

Sensitivity of pancreatic carcinoma cells to gemcitabine and oxaliplatin Pancreatic cancer cell lines constitutively expressing CLDN18.2 (DANG, Patu8988S) and cells stably transduced with CLDN18.2 (MiaPaCa-2-LVT, BxPC3-

LVT) were used to investigate modes of action of IMAB362 in combination with the chemotherapeutic agents oxaliplatin or gemcitabine.

Chemically, gemcitabine (Gemzar, marketed by Eli Lilly&Co) is a nucleoside analog. As with 5-fluorouracil (5-FU) and other analogues of pyrimidines, the triphosphate analogue of gemcitabine replaces one of the building blocks of nucleic acids during DNA replication. The process arrests tumor growth, as only one additional nucleoside can be attached to the "faulty" nucleoside, resulting in apoptosis.

Oxaliplatin functions by forming both inter- and intrastrand cross links in DNA. Cross links in DNA prevent DNA replication and transcription, resulting in cell death. (Graham, Joanne; Mushin, Mohamed; Kirkpatrick, Peter (January 2004). "Oxaliplatin". Nature Reviews Drug Discovery 3 (1): 11-2.)

Dose response curves of gemcitabine and oxaliplatin showed different sensitivities of tested pancreatic tumor cell lines (FIG. 28 and FIG. 29).

TABLE 21

IC50 values of gemcitabine and oxaliplatin for pancreatic carcinoma cell lines.

| Inhibition of Proliferation | IC50 | |
|---|---|---|
| | Gemcitabine | Oxali |
| BxPC3-LVT | ~2 ng/ml | 500-1000 ng/ml |
| Capan1-LVT | ~1 ng/ml | ~100 ng/ml |
| DANG | ~1 ng/ml | ~500 ng/ml |
| Patu8988S-luci#6 | >100 ng/ml | >500 ng/ml |
| MiaPaCa-2-LVT | 50 ng/ml | 50-100 ng/ml |

To inhibit cell proliferation of Patu8988S high concentrations of gemcitabine (IC50>100 ng/ml) or oxaliplatin (IC50>500 ng/ml) are necessary. DANG and BxPC3-LVT reacts very sensitive to gemcitabine but not to oxaliplatin. MiaPaCa-2-LVT cells react most sensitive to oxaliplatin but less sensitive to treatment with gemcitabine (FIG. 28, FIG. 29 and Table 21).

Effect of Chemotherapeutic Agents on CLDN18.2 Expression in Pancreatic Carcinoma Cell Lines Mode of action triggered by IMAB362 binding depends strictly on the presence and cell surface density of its target CLDN18.2. Pretreatment of DANG and Patu8988S cells with gemcitabine (Gem) as well as gemcitabine in combination with oxaliplatin (GemOx) resulted in increased mRNA and protein levels of CLDN18.2 shown by RT-PCR (FIG. 30) and western blot (FIG. 31) analysis of untreated and chemotherapy pretreated cells. Consequently, the amount of CLDN18.2 protein targetable by IMAB362 on the surface of Gem or GemOx pretreated pancreatic cancer cell lines was increased as shown by flow cytometry (FIG. 32). Treatment of DANG and Patu8988S with gemcitabine leads to upregulation of CLDN18.2. Patu8988S show strong upregulation of CLDN18.2 with Gem and lower upregulation with GemOx.

Effect of Chemotherapeutic Compounds on Cell Cycle and CLDN18.2 Expression

Cell cycle progression refers to the sequence of events between one mitotic division and another in a cell. A resting phase (G0/G1) is followed by a DNA synthesis phase (S), then by a phase of cell enlargement (G2) and DNA replication (M) is followed by a division of the cell into two progeny cells. Any interference with the cell machinery may inhibit all cycle progression at any phase of the cell cycle. For example, specific chemotherapeutic agents may block progression in either G2 or M or in both G2 an M (G2/M).

Gemcitabine treatment of DANG or Patu8988S leads to cell cycle arrest in S-Phase (FIG. 33, FIG. 34). Patu8988S cultivated with Gem were analysed. Gemcitabine treatment not only leads to cell cycle arrest it also changes expression of CLDN18.2 (FIG. 34B). The change of CLDN18.2 density after gemcitabine treatment is even higher when comparing proliferating cells in S phase to resting cells in G0/G1 phase (FIG. 34C). In Patu8988S cells, CLDN18.2 is expressed in all phases of the cell cycle. Upon treatment with gemcitabine, its expression is even increased, with the highest levels of CLDN18.2 per cell being found in the S phase cell population.

This perturbation of tumour cell phenotype has a significant impact on the biological effectiveness of therapeutic antibodies. ADCC and CDC are dose-related and therefore an increase of the target structure CLDN18.2 provides synergistic benefit to standard chemotherapeutic regimes.

Kato III cells, a human gastric tumor cell line, was cultivated in RPMI 1640 medium (Invitrogen) containing 20% FCS (Perbio) and 2 mM Glutamax (Invitrogen) at 37° C. and 5% CO2, with or without cytostatic compounds. 5-FU (Neofluor from NeoCorp AG) was tested at a concentration of 10 or 100 ng/ml, and oxaliplatin (Hospira) was tested at a concentration of 50 or 500 ng/ml. $8 \times 10^5$ Kato III cells were cultivated for 96 hours without medium change or for 72 hours followed by 24 hours cultivation in standard medium to release cells from cell cycle arrest in a 6-well tissue culture plate at 37° C., 5% $CO_2$. Cells were harvested with EDTA/trypsin, washed and analysed.

For extracellular detection of CLDN18.2 cells were stained with the monoclonal anti-CLDN18.2 antibody IMAB362 (Ganymed) or an isotyp-matched control antibody (Ganymed). As secondary reagent goat-anti-huIgG-APC from Dianova was used.

Cell cycle stages were determined based on measurement of cellular DNA content. This allows one to discriminate between cells in the G1-, S- or G2-phase of the cell cycle. In the S-phase DNA duplication occurs whereas in the G2-phase cells grow and prepare for mitosis. Cell cycle analysis was done using the CycleTEST PLUS DNA Reagent Kit from BD Biosciences following the manufacturer's protocol. Flow cytometry acquisition and analysis were performed by using BD FACS Cantoll (BD Biosciences) and FlowJo (Tree Star) software.

Figure 35A:
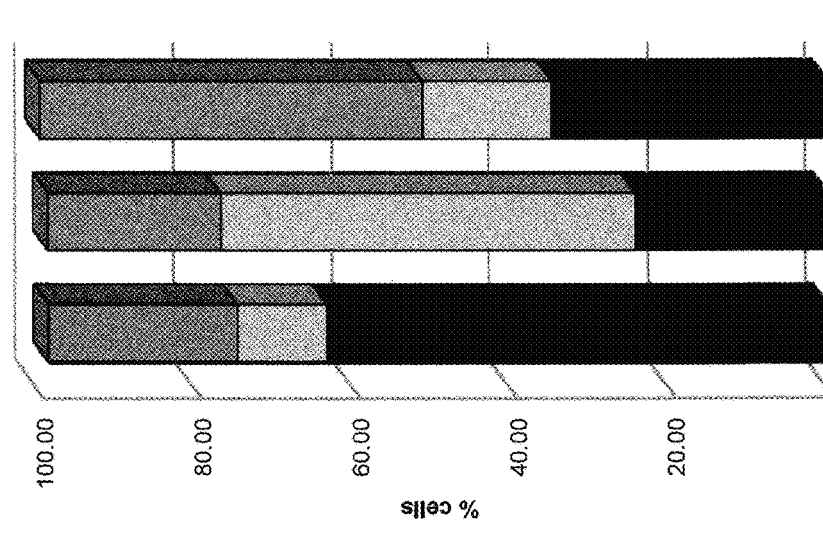

The columns in FIGS. 35a and b show the respective percentage of cells in the G1-, S- or G2-phase of the cell cycle. Medium cultivated Kato III cells show a cell cycle arrest predominantly in the G1-phase. Cells treated with 5-FU are blocked predominantly in the S-phase. Oxaliplatin treated Kato III cells show enrichment of cells predominantly in the G1- and G2-phases. As can be seen in FIG. 35c, a cell cycle arrest in the S-phase or G2-phase results in stabilization or upregulation of CLDN18.2. As soon as cells are released from any phase of the cell cycle (FIG. 35b) the expression of CLDN18.2 on the cell surface of Kato III cells is upregulated (FIG. 35d).

Kato III cells were pretreated for 4 days with Irinotecan or Docetaxel and analysed for CLDN18.2 expression and cell cycle arrest. Treatment of cells with Irinotecan resulted in a dose dependent inhibition of cell growth and a cell cycle arrest in the S/G2-phase (FIG. 36). Treatment of cells with Docetaxel resulted in a dose dependent inhibition of cell growth and a cell cycle arrest in the G2-phase (FIG. 36).

Effect of Chemotherapy on IMAB362 Induced Antibody Dependent Cellular Cytotoxicity (ADCC)

A series of experiments were performed with constitutively CLDN18.2 expressing pancreatic cancer cell lines Patu8988S and DANG. To investigate the effects of gemcitabine (Gem) or gemcitabine+oxaliplatin (GemOx) on IMAB362-mediated ADCC. Dose-response curves for IMAB362 mediated cell lyses of pretreated cells were compared with medium cultivated.

Dose response curves of Gem (1 ng/ml) or GemOx (Gem 1 ng/ml+Ox 10 ng/ml) pretreated DANG (2 days) are shifted upwards and to the left compared to untreated target cells (FIG. 37A). Treatment of tumor cells with Gem or GemOx leads to upregulation of CLDN18.2 and higher susceptibility for IMAB362 mediated ADCC. We could observe a decrease of the EC50 values and higher maximal cell lyses for IMAB362-mediated ADCC (FIG. 37B) in DANG cells after treatment with chemotherapeutic agents.

Peripheral blood mononuclear cells (PBMCs) including NK cells, monocytes, mononuclear cells or other effector cells from healthy human donors were purified by Ficoll Hypaque density centrifugation. Washed effector cells were seeded in X-Vivo medium. Kato III cells which express CLDN18.2 endogenously and are of gastric origin were used as target cells in this setting. Target cells stably expressed luciferase, lucifer yellow, which is oxidized by viable cells only. Purified anti-CLDN18.2 antibody IMAB362 was added at various concentrations and as an isotype control antibody an irrelevant chim huIgG1 antibody was used. Samples were assayed for cytolysis by measuring luminescence resulting from the oxidation of lucifer yellow which is a value for the amount of viable cells left after IMAB362 induced cytotoxicity. Kato III pretreated for 3 days with Irinotecan (1000 ng/ml), Docetaxel (5 ng/ml) or Cisplatin (2000 ng/ml) were compared to untreated medium cultivated target cells and IMAB362 induced ADCC was quantified.

Kato III cells pretreated for 3 days with Irinotecan, Docetaxel or Cisplatin exhibited a lower level of viable cells compared to medium cultivated target cells (FIG. 38a) and claudin18.2 expression in cells pretreated with Irinotecan, Docetaxel or Cisplatin was increased compared to medium cultivated cells (FIG. 38b).

Furthermore, pretreatment of Kato III cells with Irinotecan, Docetaxel or Cisplatin augmented the potency of IMAB362 to induce ADCC (FIG. 38c, d).

Effect of Chemotherapy on IMAB362 Induced CDC

The CDC potency of IMAB362 has been characterized by incubation with target cells in the presence of human serum as source of complement.

Medium cultivated MiaPaCa-2-LVT show EC50 values for IMAB362 specific lyses of 7665 ng/ml. Treatment with Gem leads to decrease of EC50 to 4677 ng/ml compared with increase of max lyses (FIG. 39).

Effects of chemotherapeutic agents on IMAB362-induced CDC were analyzed by pretreating KATO III gastric cancer cells with 10 ng/ml 5-FU and 500 ng/ml oxaliplatin (5-FU+OX) for 48 hours. Representative dose response curves of IMAB362-induced CDC using chemotherapeutic pretreated KATO III cells are shown in FIG. 40. Pretreatment of tumor cells for 48 hours augmented the potency of IMAB362 to induce CDC, resulting in higher maximal cell lysis of pretreated tumor cells compared to untreated cells.

Example 8: Efficacy of IMAB362 in Combination with Chemotherapy in Mouse Tumor Models Antitumoral activity of IMAB362 in combination with Gem or GemOx was examined in subcutaneous pancreatic carcinoma xenograft models, which were used for testing efficacy of IMAB362 as single agent before.

BxPC3-LVT or MiaPaCa-2-LVT tumor bearing nude mice treated with IMAB362 showed significant tumor growth retardation compared to control mice treated with saline control. Chemotherapy with up to 100 mg/kg gemcitabine without additional IMAB362 treatment showed no significant therapeutic effect on BxPC3-LVT or MiaPaCa-2-LVT xenograft. In contrast, the combined treatment with 50-100 mg/kg gemcitabine plus IMAB362 resulted in significantly increased tumor growth inhibition and in prolonged survival of tumor bearing mice compared to mice treated with chemotherapy alone (FIG. 41, FIG. 42, FIG. 43). These observations indicate the existence of synergistic therapeutic effects by combination of gemcitabine and IMAB362 immunotherapy.

When using high doses of gemcitabine with 2×150 mg/kg per week, established MiaPaCa-2-LVT xenograft tumors are strongly inhibited in tumor growth independent from IMAB362 treatment (FIG. 44A). However, mice treated with combined therapy of IMAB362 and gemcitabine showed highly significant prolonged survival compared to mice treated with gemcitabine as single agent (FIG. 44B).

Example 9: ZA/IL-2 Treatment Results in Expansion of High Amounts of Vγ9Vδ2 T-Cells PBMCs were cultivated for 14 days in RPMI medium supplemented with 300 U/ml IL-2 and with or w/o 1 µM zoledronic acid (ZA). The percentage of Vγ9+Vδ2+ T cells within the CD3+ lymphocyte population and the percentage of CD16+ cells within the CD3+Vγ9+Vδ2+ T cell population was determined by multicolor FACS on day 0 and day 14.

IL-2 addition in the PBMC cultures is required for survival and growth of lymphocytes. They efficiently expand in cultures supplied with 300 U/ml IL-2. FACS analysis using Vγ9 and Vδ2 specific antibodies reveal that addition of ZA/IL-2 specifically induces the accumulation of Vγ9Vδ2 T cells. After 14 days, the CD3+ lymphocyte population can comprise up to 80% of Vγ9Vδ2 T cells. A portion of Vγ9Vδ2 T cells express CD16, whereas enrichment of these cells within the CD3+ lymphocyte population is 10-700 fold, dependent on the donor. Enrichment of the CD16+Vγ9+Vδ2+ T cells in the cultures is 10-600 fold higher as compared to cultures grown without ZA. We conclude that ZA/IL-2 treatment of PBMCs in vitro results in the up-regulation of the ADCC-mediating FcγIII receptor CD16 in a significant proportion of γδ T cells.

Similar to NK cells, the ZA/IL-2 expanded Vγ9Vδ2 T cells are positive for CD16, the FcγRIII receptor via which a cell-bound antibody triggers ADCC. To evaluate whether Vγ9Vδ2 T cells are capable of inducing potent ADCC in conjunction with IMAB362 a series of experiments has been performed.

PBMCs derived from 2 different donors (#1 and #2) were cultivated in medium with 300 U/ml IL-2 and with or w/o 1 µM ZA. After 14 days cells were harvested and added with increasing concentrations (0.26 ng/ml-200 µg/ml) of IMAB362 to NUGC-4 cells expressing CLDN18.2. Specific killing was determined in luciferase assays. ADCC assays were performed with 27 donors grown in 300 U/ml IL-2 and either with or w/o ZA wherein NUGC-4 served as target cells. For each donor, the $EC_{50}$ values calculated from the dose-response curves and the maximum specific killing rate at a dose of 200 µg/ml IMAB362 were scored in the scatter plots.

Strong IMAB362-dependent ADCC activity was observed against CLDN18.2-positive NUGC-4 cells using PBMCs cultivated for 14 days with ZA/IL-2. Using ZA/IL-2-treated PBMC cultures, ADCC depends on the presence of Vγ9Vδ2 T cells. If cells are cultured without ZA, ADCC activity is reduced for most donors. In these cultures, residual ADCC activity is NK-cell dependent. By testing more than 20 donors, ADCC assays reveal that ZA/IL-2 treatment of PBMCs improves the $EC_{50}$ and maximum specific killing rates as compared to PBMCs cultured with IL-2 alone.

Example 10: Efficacy of IMAB362 in Combination with Gemcitabine in Mouse Metastasis Model To analyze the effect of IMAB362 in combination with gemcitabine treatment on Patu8988S lung metastases in vivo, 12 Hsd:Athymic Nude-Foxn1$^{nu}$ mice per group were treated with an intravenous injection 2×10$^6$ Patu8988S cells into the tail vein. 14 days post tumor cell injection mice were treated with 200 μg IMAB362 or PBS as control (i.v./i.p.) semi-weekly plus a weekly dose 100 mg/kg gemcitabine i.p. for 4 weeks. Treatment with IMAB362 or PBS was maintained until mice were sacrificed on day 70 post tumor cell injection. Analysis of the xenografted tumor load in the lungs was performed by QPCR of human DNA in the prepared lungs and by an optical analysis of an immunohistological staining with an anti-human MHC-I antibody (clone EPR1394Y). The results show that mice treated with IMAB362 plus gemcitabine have a significantly reduced amount of human DNA in their lungs (FIG. 45A) and that the surface of lung slices stained against human MHC-I complex is significantly smaller than in lungs of mice treated with an irrelevant antibody plus gemcitabine (FIG. 45B). Both methods reveal a reduced tumor load of Patu8988s xenografts in the lungs of IMAB362 plus gemcitabine treated mice, showing that the combination with IMAB362 is significantly superior to a monotherapy with gemcitabine.

---

The invention claimed is:

1. A method of treating pancreatic cancer in a patient in need thereof, wherein the pancreatic cancer is characterized by cells expressing claudin 18 splice variant 2 (CLDN18.2), the method comprising:
   administering an anti-CLDN18.2 antibody to the patient, wherein the antibody comprises a heavy chain variable region (VH) having an amino acid sequence represented by SEQ ID NO: 32 and a light chain variable region (VL) having an amino acid sequence represented by SEQ ID NO: 39, and wherein the antibody has the ability of binding to CLDN18.2 and mediates killing of cells expressing CLDN18.2;
   administering gemcitabine to the patient to increase susceptibility of the cells to killing by the anti-CLDN18.2 antibody; and
   administering a taxane to the patient.

2. The method of claim 1, wherein the taxane is paclitaxel.

3. The method of claim 1, wherein the taxane is albumin-bound paclitaxel.

4. The method of claim 3, wherein the pancreatic cancer is primary pancreatic carcinoma or metastatic pancreatic carcinoma.

5. The method of claim 3, wherein the pancreatic cancer is metastatic pancreatic carcinoma.

6. The method of claim 3, wherein the antibody is administered at a dose of up to 1000 mg/m$^2$.

7. The method of claim 1, wherein gemcitabine is administered intravenously.

8. The method of claim 7, wherein gemcitabine is administered at a dose of 0.8 to 1.5 g/m$^2$ of body surface area.

9. The method of claim 7, wherein gemcitabine is administered repeatedly according to a gemcitabine dosing regimen, wherein the gemcitabine dosing regimen comprises once weekly administration for 3 of 4 weeks.

10. The method of claim 9, wherein gemcitabine is administered at a dose of 1000 mg/m$^2$ of body surface area.

11. The method of claim 10, wherein the pancreatic cancer is primary pancreatic carcinoma or metastatic pancreatic carcinoma.

12. The method of claim 10, wherein the pancreatic cancer is metastatic pancreatic carcinoma.

13. The method of claim 10, wherein the antibody is administered repeatedly according to an antibody dosing regimen, wherein the antibody dosing regimen comprises an initial dose of up to 1000 mg/m$^2$ followed by repeated doses of 300 to 600 mg/m$^2$.

14. A method of treating metastatic pancreatic carcinoma in a patient in need thereof, wherein the pancreatic carcinoma is characterized by cells expressing claudin 18 splice variant 2 (CLDN18.2), the method comprising:
   administering an anti-CLDN18.2 antibody to the patient, wherein the antibody comprises a heavy chain variable region (VH) having an amino acid sequence represented by SEQ ID NO: 32 and a light chain variable region (VL) having an amino acid sequence represented by SEQ ID NO: 39, and wherein the antibody has the ability of binding to CLDN18.2 and mediates killing of cells expressing CLDN18.2; and
   administering a combination of chemotherapeutic agents to the patient, wherein the combination comprises gemcitabine and a taxane and wherein the combination stabilizes or increases expression of CLD18.2.

15. The method of claim 14, wherein the taxane is albumin-bound paclitaxel.

16. The method of claim 15, wherein the combination is administered repeatedly according to a combination dosing regimen, wherein the combination dosing regimen comprises once weekly administration for 3 of 4 weeks.

17. The method of claim 16, wherein the antibody is administered repeatedly according to antibody dosing regimen, wherein the antibody dosing regimen comprises an initial dose of up to 1000 mg/m$^2$ followed by repeated doses of 300 to 600 mg/m$^2$.

18. The method of claim 17, wherein the antibody is a chimeric antibody comprising a human kappa light chain constant region and a human IgG1 heavy chain constant region.

19. The method of claim 18, wherein the human kappa light chain constant region is allotype Km(3) and the human IgG1 heavy chain constant region is allotype G1m(3).

20. The method of claim 17, wherein the anti-CLDN18.2 antibody comprises a heavy chain having an amino acid sequence represented by SEQ ID NO: 17 and a light chain having an amino acid represented by SEQ ID NO: 24.

* * * * *